(12) United States Patent  
Lopez-Girona et al.

(10) Patent No.: US 9,365,640 B2  
(45) Date of Patent: Jun. 14, 2016

(54) METHODS FOR THE TREATMENT OF CANCER AND INFLAMMATORY DISEASES USING CEREBLON AS A PREDICTOR

(75) Inventors: Antonia Lopez-Girona, San Diego, CA (US); Peter H. Schafer, Somerset, NJ (US); Anita Gandhi, Bernardsville, NJ (US); Derek Mendy, San Diego, CA (US); Thomas O. Daniel, La Jolla, CA (US)

(73) Assignee: CELGENE CORPORATION, Summit, NJ (US)

(*) Notice: Subject to any disclaimer, the term of this patent is extended or adjusted under 35 U.S.C. 154(b) by 34 days.

(21) Appl. No.: 13/459,005

(22) Filed: Apr. 27, 2012

(65) Prior Publication Data

US 2012/0322073 A1  Dec. 20, 2012

Related U.S. Application Data

(60) Provisional application No. 61/481,066, filed on Apr. 29, 2011, provisional application No. 61/511,986, filed on Jul. 26, 2011, provisional application No. 61/579,600, filed on Dec. 22, 2011.

(51) Int. Cl.
| | |
|---|---|
| *G01N 33/574* | (2006.01) |
| *C07K 16/18* | (2006.01) |
| *C12Q 1/68* | (2006.01) |
| *G01N 21/64* | (2006.01) |

(52) U.S. Cl.
CPC .............. *C07K 16/18* (2013.01); *C12Q 1/6886* (2013.01); *G01N 33/5743* (2013.01); *G01N 33/57426* (2013.01); *G01N 33/57484* (2013.01); *C12Q 2600/106* (2013.01); *C12Q 2600/156* (2013.01); *C12Q 2600/158* (2013.01); *G01N 21/6428* (2013.01); *G01N 2800/52* (2013.01); *G01N 2800/60* (2013.01)

(58) Field of Classification Search  
None  
See application file for complete search history.

(56) References Cited

U.S. PATENT DOCUMENTS

| | | | |
|---|---|---|---|
| 3,536,809 A | 10/1970 | Applezweig | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 4,008,719 A | 2/1977 | Theeuwes et al. | |
| 4,683,195 A | 7/1987 | Mullis et al. | |
| 4,810,643 A | 3/1989 | Souza | |
| 4,994,443 A | 2/1991 | Folkman et al. | |
| 4,999,291 A | 3/1991 | Souza | |
| 5,001,116 A | 3/1991 | Folkman et al. | |
| 5,059,595 A | 10/1991 | Le Grazie | |
| 5,073,543 A | 12/1991 | Marshall et al. | |
| 5,120,548 A | 6/1992 | McClelland et al. | |
| 5,134,127 A | 7/1992 | Stella et al. | |
| 5,229,496 A | 7/1993 | Deeley et al. | |
| 5,354,556 A | 10/1994 | Sparks et al. | |
| 5,391,485 A | 2/1995 | Deeley et al. | |
| 5,393,870 A | 2/1995 | Deeley et al. | |
| 5,441,050 A | 8/1995 | Thurston et al. | |
| 5,573,758 A | 11/1996 | Adorante et al. | |
| 5,580,755 A | 12/1996 | Souza | |
| 5,582,823 A | 12/1996 | Souza | |
| 5,591,767 A | 1/1997 | Mohr et al. | |
| 5,593,990 A | 1/1997 | D'Amato | |
| 5,629,327 A | 5/1997 | D'Amato | |
| 5,635,517 A | 6/1997 | Muller et al. | |
| 5,639,476 A | 6/1997 | Oshlack et al. | |
| 5,674,533 A | 10/1997 | Santus et al. | |
| 5,698,579 A | 12/1997 | Muller et al. | |
| 5,712,291 A | 1/1998 | D'Amato | |
| 5,733,566 A | 3/1998 | Lewis | |
| 5,798,368 A | 8/1998 | Muller et al. | |
| 5,874,448 A | 2/1999 | Muller et al. | |
| 5,877,200 A | 3/1999 | Muller | |
| 5,929,117 A | 7/1999 | Muller et al. | |
| 5,955,476 A | 9/1999 | Muller et al. | |
| 6,071,948 A | 6/2000 | D'Amato | |
| 6,114,355 A | 9/2000 | D'Amato | |
| 6,281,230 B1 | 8/2001 | Muller et al. | |
| 6,316,471 B1 | 11/2001 | Muller et al. | |
| 6,335,349 B1 | 1/2002 | Muller et al. | |
| 6,380,239 B1 | 4/2002 | Muller et al. | |
| 6,395,754 B1 | 5/2002 | Muller et al. | |
| 6,403,613 B1 | 6/2002 | Man et al. | |
| 6,458,810 B1 | 10/2002 | Muller et al. | |
| 6,476,052 B1 | 11/2002 | Muller et al. | |
| 6,555,554 B2 | 4/2003 | Muller et al. | |
| 6,927,024 B2 | 8/2005 | Dodge et al. | |
| 7,091,353 B2 | 8/2006 | Robarge et al. | |
| 7,101,663 B2 | 9/2006 | Godfrey et al. | |
| 7,122,799 B2 | 10/2006 | Hsieh et al. | |

(Continued)

FOREIGN PATENT DOCUMENTS

| | | |
|---|---|---|
| EP | 2 436 387 A1 | 4/2012 |
| JP | 11-504330 | 4/1999 |

(Continued)

OTHER PUBLICATIONS

Charoenfuprasert et al (Oncogene, 2011, 30:3570-3584) Supplemental Figure 1.*  
English translation of WO/2011/049043 Handa et al, published Apr. 28, 2011.*  
Chow et al (Pharmacological Research, 2006, 53:49-61).*  
ADAPT, Paterson Institute for Cancer Research, probests for CRBN, printed Dec. 2, 2013.*  
Charoenfuprasert et al (Oncogene, 2011, 30:3570-3584, published online Mar. 14, 2011).*  
Charoenfuprasert et al Supplemental Figure 1 (Oncogene, 2011, 30:3570-3584, published online Mar. 14, 2011).*  
Abnova CRBN purified MaxPab mouse polyclonal antibody, printed Mar. 2015.*

(Continued)

*Primary Examiner* — Laura B Goddard  
(74) *Attorney, Agent, or Firm* — Jones Day

(57) ABSTRACT

Uses of the protein cereblon as a predictor of clinical sensitivity to cancer, inflammatory diseases, and patient response to drug treatment.

19 Claims, 62 Drawing Sheets

(56) References Cited

U.S. PATENT DOCUMENTS

Figure 1A:
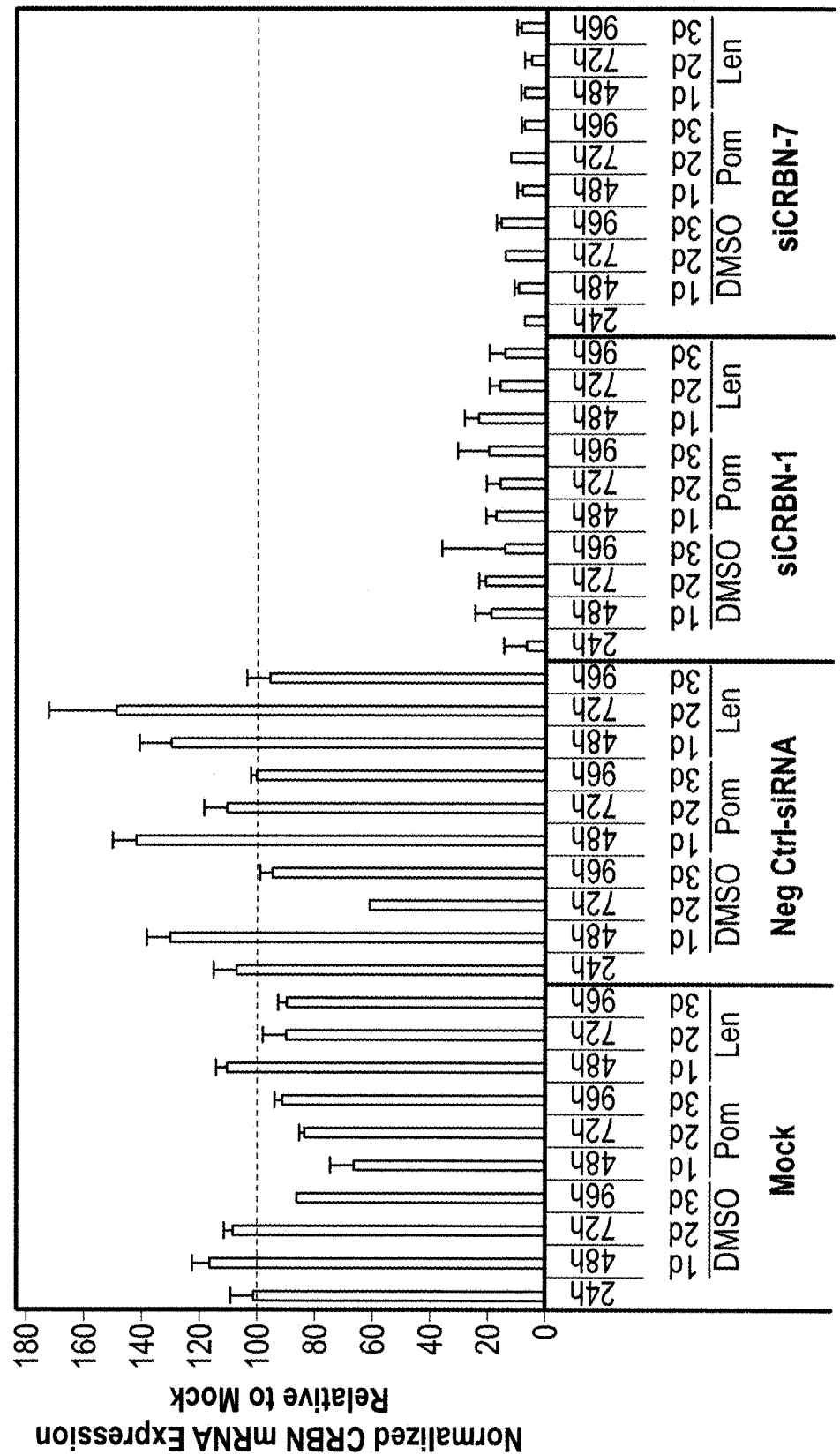

| | | | |
|---|---|---|---|
| 7,186,507 | B2 | 3/2007 | Bacallo et al. |
| 7,244,759 | B2 | 7/2007 | Muller et al. |
| 7,393,862 | B2 | 7/2008 | Zeldis |
| 7,468,363 | B2 | 12/2008 | Zeldis |
| 7,635,700 | B2 | 12/2009 | Muller et al. |
| 8,143,283 | B1 | 3/2012 | D'Amato |
| 2002/0045643 | A1 | 4/2002 | Muller et al. |
| 2003/0045552 | A1 | 3/2003 | Robarge et al. |
| 2003/0096841 | A1 | 5/2003 | Robarge et al. |
| 2004/0029832 | A1 | 2/2004 | Zeldis |
| 2004/0220144 | A1 | 11/2004 | Zeldis |
| 2006/0188475 | A1 | 8/2006 | Xu et al. |
| 2006/0205787 | A1 | 9/2006 | Muller et al. |
| 2007/0015194 | A1 | 1/2007 | Shohat et al. |
| 2007/0049618 | A1 | 3/2007 | Muller et al. |
| 2007/0128636 | A1 | 6/2007 | Baker et al. |
| 2008/0051379 | A1 | 2/2008 | Lerner et al. |
| 2008/0280779 | A1* | 11/2008 | Shaughnessy et al. ......... 506/10 |
| 2009/0148853 | A1 | 6/2009 | Schafer et al. |
| 2010/0021437 | A1 | 1/2010 | Isacson et al. |
| 2010/0284915 | A1 | 11/2010 | Dai et al. |
| 2011/0070218 | A1 | 3/2011 | Teichberg et al. |
| 2011/0196150 | A1 | 8/2011 | Man et al. |
| 2011/0200998 | A1 | 8/2011 | Weichselbaum et al. |
| 2011/0223157 | A1 | 9/2011 | Schafer et al. |
| 2012/0035347 | A1 | 2/2012 | Yver |
| 2012/0077741 | A1 | 3/2012 | Delfani et al. |
| 2012/0134969 | A1 | 5/2012 | Handa et al. |
| 2012/0192297 | A1* | 7/2012 | Handa et al. .................... 800/13 |
| 2012/0230983 | A1* | 9/2012 | Muller et al. .............. 424/133.1 |
| 2012/0322073 | A1 | 12/2012 | Lopez-Girona et al. |
| 2013/0177644 | A1 | 7/2013 | Zeldis |
| 2013/0302323 | A1 | 11/2013 | Zeldis |
| 2014/0051591 | A1 | 2/2014 | O'Donnell et al. |
| 2014/0066480 | A1* | 3/2014 | Stewart ................ A61K 31/454 514/323 |

FOREIGN PATENT DOCUMENTS

| | | |
|---|---|---|
| WO | WO 93/18186 A1 | 9/1993 |
| WO | WO 98/03502 A1 | 1/1998 |
| WO | WO 98/54170 A1 | 3/1998 |
| WO | WO 02/059106 A1 | 8/2002 |
| WO | WO 2007/108968 | 9/2007 |
| WO | WO 2009/075797 A2 | 6/2009 |
| WO | WO 2010/137547 A1 | 12/2010 |
| WO | WO 2011/049043 A1 | 4/2011 |
| WO | WO 2012/125405 A2 | 9/2012 |
| WO | WO 2012/125438 A1 | 9/2012 |
| WO | WO 2012/125459 A1 | 9/2012 |
| WO | WO 2012/125475 A1 | 9/2012 |
| WO | 2012153187 A2 | 11/2012 |
| WO | WO 2012/149299 A2 | 11/2012 |
| WO | WO 2014/028445 A2 | 2/2014 |

OTHER PUBLICATIONS

Galustian et al (Expert Opinion Pharmacother. (2009, 10:125-133).*
Aizawa et al.; "mRNA distribution of the thalidomide binding protein cereblon in adult mouse brain," *Neurosci. Res.*, 69:343-347 (2011).
Akhurst "Taking thalifomide out of rehab," *Nature Med.*, 16(4):370-372 (2010).
Angers et al., "Molecular architecture and assembly of the DDB1-CUL4A ubiquitin ligase machinery," *Nature*, 443:590-5934 (2006).
Anolik et al., "B cell reconstitution after rituximab treatment of lymphoma recapitulates B cell ontogeny," *Clin. Immunol.*, 122:139-145 (2007).
Ausubel et al. (eds.), *Short Protocols in Molecular Biology*, Fifth Edition, John Wiley and Sons, New York, Chapter 11 (2002).
Basel-Vanagaite et al., "The CC2D1A, a member fo a new gene family with C2 domains, is involved in autosomal recessive non-syndromic mental retardation," *J. Med. Genet.*, 43:203-210 (2006).
Basson, "Thalidomide's early effects," *Nature Med.*, 16(4):372 (2010).

Bea et al., "Diffuse large B-cell lymphoma subgroups have distinct genetic profiles that influence tumor biology and improve gene-expression-based survival prediction," *Blood*, 106(9):3183-3190 (2005).
Boyd et al, "High expression levels of the mammalian target of rapamycin inhibitor Deptor are predictive of response to thalidomide in myeloma," *Leukemia & Lymphoma*, 51(11):2126-2129 (2010).
Bruggermann et al., "Designer mice: the production of human antibody repertoires in transgenic animals," *Year Immunol.*, 7:33-40 (1993).
Burlington et al., "Tumor cell gene expression changes following short-term in vivo exposure to single agent chemotherapeutics are related to survival in multiple myeloma," *Clin. Cancer Res.*, 14(15). 4821-4829 (2008).
Cairns et al "Regulation of cancer cell metabolism," *Nature Rev.*, 11:85-95 (2011).
*Cancer: Principles & Practice of Oncology*, Third Edition, J. B. Lippincott Co., Philadelphia, PA, pp. 1843-1847 (1989).
Carstensen, *Drug Stability: Principles & Practices*, Second Edition, Marcel Dekker, New York, NY, pp. 379-380 (1995).
Cerny et al., "Advances in the treatment of non-Hodgkin's lymphoma " *Ann. Oncol.*, 13 Suppl., 4:211-216 (2002).
Chang et al., "What is the functional role of the thalidomide binding protein cereblon," *Int. J. Biochem Mol. Biol.*, 2(3):287-294 (2011).
Chothia et al., "Structural determinants in the sequence of immunoglobulin variable domain," *J. Mol. Biol.*, 278:457-479 (1998).
Christian et at, "p62 (SQSTM1) and cyclic AMP phospodiesterase-4A4 (PDE4A4) locate to a novel, reversible protein aggregate with links to autophagy and proteasome degradation pathways," *Cellular Signaling*, 22:1576-1596 (2010).
Clarke et al., "Changing incidence of non-Hodgkin lymphomas in the United States," *Cancer*, 94(7):2015-2023 (2002).
Corral et al., "Immunomodulation by thalidomide and thalidomide analogues," *Ann. Rheum. Dis.*, 58:(Suppl I)1117-1113 (1999).
Cuoco et al., "Microarray based analysis of an inherited terminal 3p26.3 deletion, containing only the CHL1 gene, from a normal father to his two affected children," *Orphanet J Rare Dis.*, 6:12 (2011).
Dufour-Rainfray et al., "Fetal exposure to teratogens: evidence of genes involved in autism," *Neurosci Biobehav Rev.*, (2011).
Emens et al., "Chemotherapy: friend of foe to cancer vaccines," *Curr. Opin. Mol. Ther.*, 3(1):77-84 (2001).
Ferratuolo et at, "Microarray analysis of the cellular pathways involved in the adaptation to and progression of motor neuron injury in the SOD1 G93A mouse model of familial ALS," *J. Neurosci.*, 27(34):9201-9219 (2007).
Flemming, "Target indentification: Unravelling thalidomide teratogenicity," *Nature Rev. Drug Discov.*, 9:361 (2010).
Folkman et al., "Angiogenesis inhibition and tumor regression caused by heparin or a heparin fragment in the presence of cortisone," *Science*, 221:719-725 (1983).
Galustian et al., "Lenalidomide: a novel anticancer drug with multiple modalities," *Expert Opin. Pharmacother.*, 10(1):125-133 (2009).
Garshasbi et al., "A defect in the *TUSC3* gene is associated with autosomal recessive mental retardation," *Am. I. Hum. Genetics*, 82:1158-1164 (2008).
Geribank Accession No, NP_001166953; GI No. 291045198 (Nov. 24, 2013).
Genbank Accession No. NP_057386; GI No. 39545580 (Sep. 23, 2013).
Gladman et al., *Kelley's Textbook of Rheumatology*, 2 Vols. 6th Edition, ion, W. B. Saunders Company, Chapter 71, pp. 1071-1073 (2001).
Gladman,"Current concepts in psoriatic arthritis," *Curr. Opin. Rheurnatol.*, 14(4):361-366 (2002).
Heintel et al., "High Expression of the thalidomide-binding protein cereblon (CRBN) is associated with improved clinical response in patients with multiple myeloma treated with lenalidomide and dexamethasone," 53rd *ASH Annual Meeting and Exposition*, Abstract 2879 (Dec. 10-13, 2011).

(56) References Cited

OTHER PUBLICATIONS

Hernandez et al., "Thalidomide modu laces mycobacterium leprae-induced NF-κB pathway and lower cytokine response," *Eur. J. Pharmacol.*, 670:272-279 (2011).

Higgins et al., "A mutation in a novel ATP-dependent Lon protease gene in a kindred with mild mental retardation," *Neurology* 63:1927-1931 (2004).

Higgins et al., "Candidate genes for recessive non-syndromic nlentalretardation on chromosome 3p (MRT2A)," *Clin. Genet.*, 65:496-500 (2004).

Higgins et al., "Dysregulation of large-conductance $Ca^{2+}$-activated $K^+$ channel expression in nonsyndromal mental retardation due to a cereblon p.R419X mutation," *Neurogenetics*, 9:219-223 (2008).

Higgins et al., "Temporal and spatial mouse brain expression of cereblon, an ionic channel regulator involved in human intelligence," *J. Neurogenetics*, 24:18-26 (2010).

Hohberger et al., "Cereblon is expressed in the retina and binds to voltagee-gated chloride channels," *FEBS Lett.*, 583:633-637 92009).

Ito et al., "Deciphering the mystery of thalidomide teratogenicity," *Congenital Anomalies*, 52:1-7 (2012).

Ito et al., "Identification of a primary target of thalidomide teratogenicity," *Science*, 327(5971):1345-1350 (2010).

Ito et al,, "Teratogenic effects of thalidomide: molecular mechanisms " *Cell. Mol. Life Sci.*, 68(9):1569-1579 (2011).

Jakobovits et al., "Analysis of homozygous mutant chimeric mice: deletion of the immunoglobulin heavy-chain joining region blocks B-cell development and antibody production," *Proc. Natl. Acad. Sci., USA*, 90:2551-2555 (1993).

Jakobovits et al., "Germ-line transmission and expression of human-derived yeast artificial chromosome," *Nature*, 362(6417):255-258 (1993).

Jalkanen et at, "Cell surface proteoglycan of mouse mammary epithelial cells is shed by cleavage of its matrix-binding ectodomain from its membrane-associated domain," *J. Cell Biol.*, 105(6 Pt 2):3087-3096 (1987).

Jalkanen et al., "Heparan sulfate proteoglycans from mouse mammary epithelial cells: localization on the cell surface with a monoclonal antibody," *J. Cell Biol.*, 101(3):976-984 (1985).

Jemal et al., "Cancer Statistics," *CA Cancer. Clin.*, 57:43-66 (2007).

Jo et al., "Identification and functional characterization of cereblon as a binding protein for large-conductance calcium-activated potassium channel in rat brain." *J. Neurochem.*, 94:1212-1224 (2005).

Jones et al., "Pharmaceutical cocrystals: an emerging approach to physical property enhancement," *MRS Bulletin* 31:875-879 (2006).

Karat et al., "Attempts to locate complementarity-determining residues in the variable positions of light and heavy chains," *Ann. N.Y. Acad. Sci.*, 190:382-393 (1971).

Kantarci et al, "Identification of the genetic basis of nonsyndromic intellectual disability in large consanguineous families by exome sequencing," *Clin. Genet.*, 78(Suppl. 1)103 (2010).

Kim et al, "Thalidomide: the tragedy of birth defects and the effective treatment of disease," *Toxicological Sci.*, 122(1):1-6 (2011).

Kim et al., "Use of absolute lymphocyte counts to predict response to chemotherapy and survival in diffuse large B-cell lymphoma," *J. Clin. Oncology*, ASCO Annual Meeting Proceedings Part I., 25(18S), Jun. 20 Supplement, p. 8082 (2007).

Knobloch et al., Apoptosis induction by thalidomide: critical for limb teratogenicity but therapeutic, *Current Mol. Pharmacol.*, 4:26-61 (2011).

Kohler et al., "Continuous cultures of fused cells secreting antibody of predefined specificity," *Nature*, 256:495-497 (1975).

Lee et al., "Cereblon inhibits proteasome activity by binding to the 20S core proteasome subunit beta type 4,"*Biochem. Biophys. Res. Comm.*, 427:618-622 (2012).

Lee et al., "Embryopathic effects of thalidomide and its hydrolysis p7oducts in rabbit embryo culture: evidence for a prostaglandin H synthase (PHS)-dependent, reactive oxygen species (ROS)-mediated mechanism," *FASEB J.*, 25:2468-2483 (2011).

Lee et al., "Functional modulation of AMP-activated protein kinase by cereblon," *Biochimica Biophysica Acta*, 1813:448-455 (2011).

Lee et al., "Induction of cereblon by NF-E2-related factor 2 in neuroblastoma cells exposed to hypoxia-reoxygenation," *Biochem. Biophys. Res. Comm.*, 399:711-715 (2010).

Lee et al., "Resistance of CD-1 and *oggl* DNA repair-deficient mice to thalidomide and hydrolysis product embryopathies in embryo culture," *Toxicological Sci.*, 122(1):146-156 (2011).

Lenz et al., "Molecular subtypes of diffuse large B-cell lymphoma arise by distinct genetic pathways," *Proc. Natl. Acad. Sci., USA*, 105(36):13520-13525 (2008).

Lenz et al., "Oncogenic CARD11 mutations in human diffuse large B cell lymphoma," *Science*, 319(5870):1676-1679 (2008).

List et al., "The myelodysplastic syndromes: biology and implications for management," *J. Clin. Oncol.*, 8:1424-1441 (1990).

Lopez-Girona et al, "Cereblon is direct protein target for immunomodulatory and antiproliferative acttivities of lenalidomide and pomalidomide," *Leukemia*, 26:23262335 (2012).

Lopez-Girona et al., "Direct binding with cereblon mediates the antiproliferative and immunomodulatory action of lenalidomide and pomalidornide," $53^{rd}$ *ASH Annual Meeting and Exposition*, Abstract 738 (Dec. 10-13, 2011).

Lopez-Girona et al., "Direct binding with cereb on mediates the ant roliterative and immunomodulatory action of lenalidomide and pomalidomide," $53^{rd}$ *ASH Annual Meeting and Exposition*, 738 22 pages (2011).

Lowe et al.., "The PDE IV family of calcium-independent phosphodiesterase enzymes," *Drugs of the Future*, 17(9):799-807 (1992).

Mardis et al., "Recurring mutations found by sequencing an acute myeloid leukemia genome," *N. Engl. J. Med.*, 361(11):1058-1066 (2009).

Marks et al., "By-passing immunization, human antibodies from V-gene libraries displayed on phage," *J. Mol. Biol.*, 222(3):581-597 (1991).

Marriott et al., "Immunotherapeutic and antitumor potential of thalidomide analogues," *Expert Opin. Biol. Ther.*, 1(4):1-8 (2001).

Martiniani et al,, "Biological activity of lenalidomide and its underlying trherapeutic effects in multiple myeloma," *Adv. Hematol.*, 2012:842945.

Mitchell et al., "Physical activity-associated gene expression signature e in nonhuman primate motor cortex," *Obesity*, 20:692-698 (2012).

Muller et al., "Structural modifications of thalidomide produce analogs with enhanced tumor necrosis factor inhibitory activity," *J. Med. Chem.*, 39(17):3238-3240 (1996).

Muller et at, "Thalidomide analogs and PDE4 inhibition," *Bioorg. & Med. Chem. Lett.*, 8:2669-2674 (1998).

Mullis et al., "Specific enzymatic amplification of DNA in vitro: the polvinerve chain reaction," *Cold Spring Harbor Symp. Quant. Biol.*, 51:263-273 (1986).

Neben et al., "High plasma basic fibroblast growth factor concentration is associated with response to thalidomide in progressive multiple myeloma," *Clin. Cancer Res.*, 7(9):2675-2681 (2001).

Nco et al., "Ontogenically active MYD88 mutations in human lymphoma," *Nature*, 470(7332)115-119 (2011).

Offidani et al., "Serum C-reactive protein at diagnosis and response to therapy is the most powerful factor predicting outcome of multiple myeloma treated with thalidomide/anthracycline-based therapy," *Clin. Lymphoma & Myeloma*, 8(5):294-299 (2008).

Parsons et al., "An integrated genomic analysis of human glioblastoma multiforme," *Science*, 321:1807-1812 (2008).

Paul (ed), *Fundamental Immunology*, Second Edition, Raven Press, New York, pp. 332-336 (1989).

Penichet et al., "Antibody-cytokine fusion proteins for the therapy of cancer," *J. Immunol. Methods*, 284:91-101 (2001).

Plückthun, *The Pharmacology of Monoclonal Antibodies*, vol. 113, Springer Verlag, Berlin, pp. 269-315 (1994).

Rajadhyaksha et al., "Behavioral characterization of cereblon forebrain-specific conditional null mice: a model for human non-syndromic intellectual disability," *Behavioural Brain Res.*, 226:428-434 (2012).

Rajpal et al., "A novel panel of protein biorilarkers for predicting response to thalidomide-based therapy in newly diagnosed multiple myeloma patients," *Proteomics*, 11(8):1391-1402 (2011).

(56) References Cited

OTHER PUBLICATIONS

Ren et al., "Oncogenic CUL4A determines the response to thalidomide treatment in prostate cancer," *J. Mol. Med.*, 90(10):1121-1132 (2012).
Ripa et al., "A linear model for the pharmacokinetics of azithromycin in healthy volunteers," *Chemother.*, 42:402-409 (1996).
Roitt et al., *Immunology*, Third Edition, Mosby, St. Louis, MO, 17.1-17.12 (1993).
Schultheiss et al., "Pharmaceutical cocrystals and their physicochemcial properties," *Cryst. Growth Des.*, 9(6):2950-2967 (2009).
Schott et al., "Thalidomide in combination with dexamethasone for pretreated patients with multiple myeloma: serum level of soluble interleukin-2 receptor as a predictive factor for response rate and for survival," *Ann. Hematol.*, 84(9):594-600 (2005).
Shackelford et al., "The LKB1-AMPK pathway: metabolism and growth control in tumour suppression," *Nature Rev.*, 9:563-575 (2009).
Shan et al., "The role of cocrystals in pharmaceutical science," *Drug Discov. Today*, 13(9-10):440-446 (2008).
Sokka et al., "MRI-guieded gas bubble enhanced ultrasound sound heating in in vivo rabbit thigh," *Phys. Med. Biol.*, 48:223-241 (2003).
Stahnke et al., "Activation of apoptosis pathways in peripheral blood lymphocytes by in vivo chemotherapy," *Blood*, 98:3066-3073 (2001).
Staudt, "Gene expression profiling of lymphoid malignancies," *Ann. Rev. Med.*, 53:303-318 (2002).
Taylor et al., "A transgenic mouse that expresses a diversity of human sequence heavy and light chain immunoglobulins," *Nucleic Acids Res.*, 20(23):6287-6295 (1992).
Taylor et al., "Protamine is an inhibitor of angiogenesis," *Nature*, 297:307-312 (1982).
*The Merck Manual*, 17th Edition, Merck & Company, West Point, PA, pp. 448, 944-952 (1999).
Therasse et al., "New guidelines to evaluate the response to treatment in solid tumors," *J. Natl. Cancer Inst.*, 92(3):205-216 (2000).
Thome et al., "Antigen receptor signaling to NF-κK via CARMA1, BCL10, and MALT1," *Cold Spring Harb. Perspect. Biol.*, 2:a003004 (2010).
Tierney et al. (eds), *Current Medical Diagnosis & Treatment 1998*, 37th Edition, Appleton & Lange, Stamford, CT, p. 793 (1998).
Trask, "An overview of pharmaceutical cocrystais as intellectual property," *Mol. Pharm.*, 4(3):301-309 (2007).
Vishweshwar et al., "Pharmaceutical co-crystals," *J. Pharm. Sci.*, 95(3):499-516 (2006).
Wilson et al., "Novel disease targets and management approaches for diffuse large B-cell lymphoma," *Leukemia & Lymphoma*, 51(S1):1-10 (2010).
Wu et al., "Screening and indentification of host factors interacting with UL14 of herpes simplex virus 1," *Med. Microbiol. Immunol.*, 200:203-208 (2011).
Xin et al., "Primary function analysis of human mental retardation related gene CRBN," *Mol. Biol. Rep.*, 35:251-256 (2008).
Yang et al., "Exploiting synthetic lethality for the therapy of ABC diffuse large B cell lymphoma," *Cancer Cell*, 21:723-737 (2012).
Zhu et al., "Molecular mechanism of action of immune-modulaotry drugs thalidomide, lenalidomide and pomalidomide in multiple myeloma," *Leukemia & Lymphoma*, 1-5 (2012).
Zhu et al.; "Cereblon expression is required for the antimyeloma activity of lenalidomide and pomalidomide," *Blood*, 118(18):4771-4779 (2011).
Fukuchi, "Ligand-dependent degradation of Smad3 by a ubiquitin ligase complex of ROC1 and associated proteins," Molecular Biology of The Cell, 12(5): 1059-1524 (2001).
Androutsellis-Theotokis et al, (2009) "Targeting neural precursors in the adult brain rescues injured dopamine neurons," Proc. Natl. Acad. Sci. U.S.A., 106 (32): 13570-5.
Becker et al. (2008) "Adult zebrafish as a model for successful central nervous system regeneration" Restorative Neurol. Neurosci. 26:71-80.
Bonnamain et al., (2012). "Neural stmlprogenitor cells as promising candidates for regenerative therapy of the central nervous system," Frontiers in Cellular Neuroscience, 6: 17.
Bredesen et al., (2006) "Cell death in the nervous system," Nature, 443 (7113): 796-802.
Fleisch et al, (2011) "Investigating regeneration and functional integration of CNS neurons: Lessons from zebrafish genetics and other fish species" Biochim. Biophys. Acta 1812:364-380.
Johansson, (2007) "Regeneration and plasticity in he brain and spinal cord," J Cereb Blood Flow Metab, 27:1417-1430.
Kishimoto et al. (2012) "Neuronal regeneration in zebrafish model of adult brain injury" Disease Models and Mechanisms 5:200-209.
Magavi et al., (2000), "Induction of neurogenesis in the neocortex of adult mice," Nature, 405 (6789): 951-5.
Nakatomi et al., (2002) "Regeneration of Hippocampal Pyramidal Neurons after ischemic Brain Injury by Recruitment of Endogenous Neural Progenitors," Cell, 110 (4): 429-41.
Wu, "Large-Conductance $Ca^{2+}$-Activated K+ Channels: Physiological Role and Pharmacology," Current medicinal Chemistry, 10(8): 649-661 (2003).
English Translation of International Preliminary Report on Patentability Issued in PCT/JP2010/058722 on Dec. 15, 2011.
International Search Report for PCT/JP2010/058722 issued Jun. 22, 2010.
Aklilu et al., "Depletion of normal B cells with rituximab as an adjunct to IL-2 therapy for renal cell carcinoma and melanoma," Annals Oncology, 15:1109-1114 (2004).
Angerer et al., In Genetic Engineering: Principles and Methods, Setlow and Hollaender, Eds., Plenum Press, New York, vol. 7, pp. 43-65 (1985).
Basel-Vanagaite, "Genetics of autosomal recessive non-syndromic mental retardation: recent advances," Clin Genet. 72(3):167-74 (2007).
Bustin et al., "Real-time reverse transcription PCT (qRT-PCR) and its potential use in clinical diagnosis," Clin. Sci., 109:365-379 (2005).
Gall et al., "Nucleic acid hybridization in cytological preparations," Methods Enzymol., 21:470-480 (1981).
Garshasbi et al., "Two independent mutations in the ZC3H14 gene are associated with non-syndromic autosomal recessive mental retardation," Medizinische Genetik, 22(1): 83 (2010).
Gupta D et al., "Adherence of Multiple Myeloma Cells to Bone Marrow Stromal Cells Up Regulates Vascular Endothelial Growth Factor Secretion: Therapeutic Applications," Leukemia, 2001, 15 (12): 1950-1961.
International Searching Authority, "International Search Report for International Application No. PCT/US2013/048510," (mailed Jun. 12, 2014).
Kallioniemi et al., " Comparative genomic hybridization for molecular cytogenetic analysis of solid tumors," Science 258:818-821 (1992).
Kamarch, "Fluorescence-activated cell sorting of hybrid and transfected cells," Methods Enzymol., 151:150-165 (1987).
Kumar et al., "Occurrence of Multiple Myeloma in Both Donor and Recipient After Bone Marrow Transplantation." American Journal of Hematology, 2002, 71: 227-228.
Lee et al., "Cereblon binding modulates AMP-activated protein kinase function," Journal of Neurochemistry, 115(WE03-03): 74 (2010).
Lopez-Girona et al., "Direct Binding with Cereblon Mediates the Antiproliferative and Immunomodulatory Action of Lenalidomide and Pomalidomide," Blood, 2011, 118 (21): 335.
Lu et al., "MaxiK channel partners: Physiological Impact," Journal of Physiology, 570 (1): 65-72 (2006).
Ludwig et al., "IMWG consensus on maintenance therapy in multiple myeloma," Blood, 119(3): 3003-15 (2012).
Michalak et al., "Testis-derived microRNA profiles of African clawed frogs (*Xenopus*) and their sterile hybrids," Genomics, 91(2): 158-64 (2008).
Pohjola et al., "Terminal 3p deletions in two families—correlation between molecular karyotype and phenotype," American Journal of Medical Genetics, Part (2): 441-6 (2010).
Rajkumar, "Multiple myeloma: 2012 update on diagnosis, risk-stratification, and management," Am J Hematol., 87(1):78-88 (2012).

(56) References Cited

OTHER PUBLICATIONS

Rehmann et al., "The rise, fall and subsequent triumph of thalidomide: Lessons learned in drug development," Ther Adv Hematol., 2(5):291-308 (2011).
Takada et al., "Protective effect of thalidomide against N-methyl-D-aspartate-induced retinal neurotoxicity," J Neurosci Res., 89(10):1596-604 (2011).
Vallet et al., "Update on immunomodulatory drugs (IMiDs) in hematologic and solid malignancies," Expert Opinion on Pharmacotherapy, vol. 13, No. 4, pp. 473-494 (2012).
Vanhook, "Thalidomide Target Identified," Sci. Signal., vol. 3, Issue 113, p. ec82 (2010).
Wilen et al., "Strategies in optical resolutions," Tetrahedron, 33:2725-2736 (1977).
Wilen, Tables of Resolving Agents and Optical Resolutions, (E.L. Eliel, Ed.), University of Notre Dame Press, Notre Dame, IN, p. 268 (1972).
Willems, "Cognition genes on autosomes: The paradox," Clinical Genetics, 72(1): 9-12 (2007).
Yamazaki et al., "In vivo formation of a glutathione conjugate derived from thalidomide in humanized uPA-NOG mice," Chem Res Toxicol., 24(3):287-9 (2011).
Zhang et al., "PI3K/Akt signaling pathway is required for neuroprotection of thalidomide on hypoxic-ischemic cortical neurons in vitro," Brain Research, 1357: 157-65 (2010).
Hernandez-Ilizalitrurri et al., Higher Response to Lenalidomide in Relapsed/Refractory Diffuse Large B-Cell lymphoma in Nongerminal Center B-Cell Like Than in Germinal Center B-Cell Like Phenotype, Cancer, pp. 5058-5066 (2011).
Kim et al, Gene Expression Profiles for the Prediction of Progression-free Survival in Diffuse Large B Cell Lymphoma: Results of a DASL Assay, Annals of Hematology, 93 (3): 437-447 (2013).
Altschul et al., "Gapped BLAST and PSI-BLAST: A new generation of protein database search programs," Nucleic Acid Res., 25(17):3389-3402 (1997).
Ando et al., "Efficient transfection strategy for the spatiotemporal control of gene expression in zebrafish," Mar. Biotechnol. (NY), 8(3):295-303 (2006).
Babin et al., "Zebrafish models of human motor neuron diseases: advantages and limitations," Prog. Neurobiol., 118:36-58 (2014).
Bartlett, "Regulation of neural stem cell differentiation in the forebrain," Immunol. Cell Biol., 76(5):414-418 (1998).
Bisht et al., "Brain drug delivery system: a comprehensive review on recent experimental and clinical findings," IJPSR, 2(4):792-806 (2011).
Chamberlain et al., "Structure of the human Cereblon-DDB1-lenalidomide complex reveals basis for responsiveness to thalidomide analogs," Nature Struct. Mol. Biol., 21(9):803-809 (2014).
Hsieh et al., "Review: Critical issues in gene therapy for neurologic disease," Human Gene Ther., 13:579-604 (1998).
Ito et al., "CRBN, a mental retardation-related protein, forms a novel E3 ubiquitin ligase complex with DDB1," Dai 80 Kai the Japanese Society Taikai, Dai 30 Kai The Molecular Biology Society of Japan Nenkai Godo Taikai Koen Yoshishu, pp. 4P-1011 (2007).
Ito et al., "Identification of a primary target of thalidomide teratogenicity," Science, 327:1-28 (2010).
Kobayashi et al., "Overexpression of the forebrain-specific homeobox gene six3 induces rostral forebrain enlargement in zebrafish," Development, 125:2973-2982 (1998).
Medicine, vol. 3, Dale and Federman, eds., Scientific American, Inc., New York, Chapter 12, Section IV and Section X (1998).
Mochida et al., "Genetic basis of developmental malformations of the cerebral cortex," Arch. Neurol., 61:637-640 (2004).
Nakamura et al., "Freud-1/Akil, a Novel PDK1-interacting Protein, Functions as a Scaffold to Activate the PDK1/Akt Pathway in Epidermal Growth Factor Signaling," Mol. Cell. Biol., 28(19):5996-6009 (2008).
Oliver et al., "Immune stimulation in scleroderma patients treated with thalidomide," Clin. Immunol., 97(2):109-120 (2000).
Parman et al., "Free radical-mediated oxidative DNA damage in the mechanism of thalidomide teratogenicity," *Nature Med.*, 5(5):582-585 (1999).
Patent Cooperation Treaty, International Search Report for application PCT/US2013/054663, mailed Aug. 21, 2014.
Razek et al., "Disorders of cortical formation: MR imaging features," AJNR Am. J. Neuroradiol., 30:4-11 (2009).
Santana et al., "Can zebrafish be used as animal model to study Alzheimer's disease," Am. J. Neurodcgener. Dis., 1(1):32-48 (2012).
Science Daily, "How many species on Earth? About 8.7 million, new estimate says," Retrieved online <http://www.sciencedaily.com/releases/2011/08/1108323180459.htm>, retrieved on Apr. 7, 2013.
Shestopalov et al., "Oligonucleotide-based tools for studying zebrafish development," Zebrafish, 7(1):31-40 (2010).
Thomas et al., "Progess and problems with the use of viral vectors for gene," Nat. Rev. Genet., 4(5):346-358 (2003).

* cited by examiner

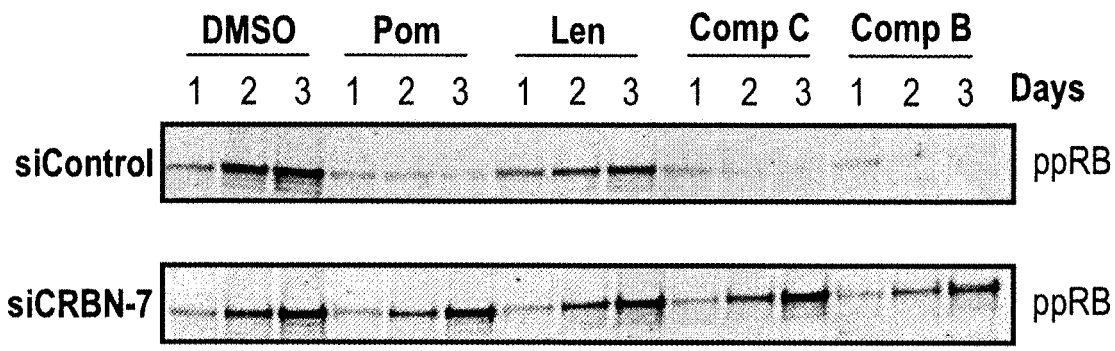
FIG. 4A
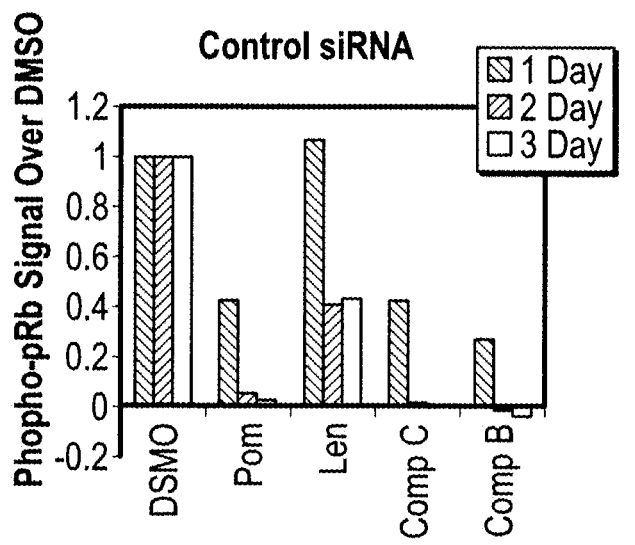
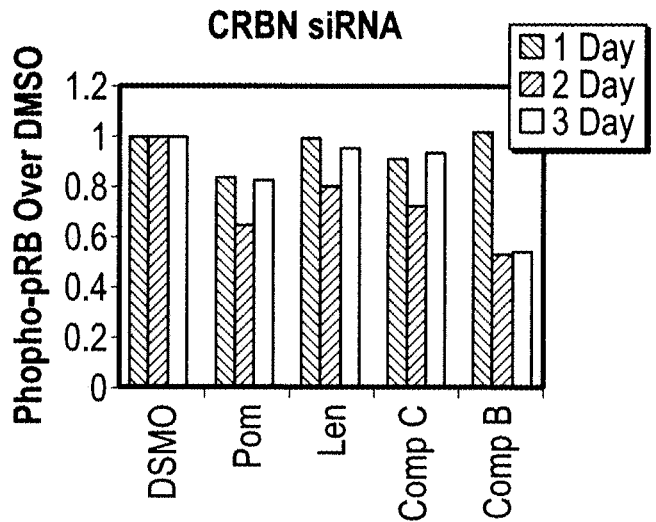
FIG. 4B

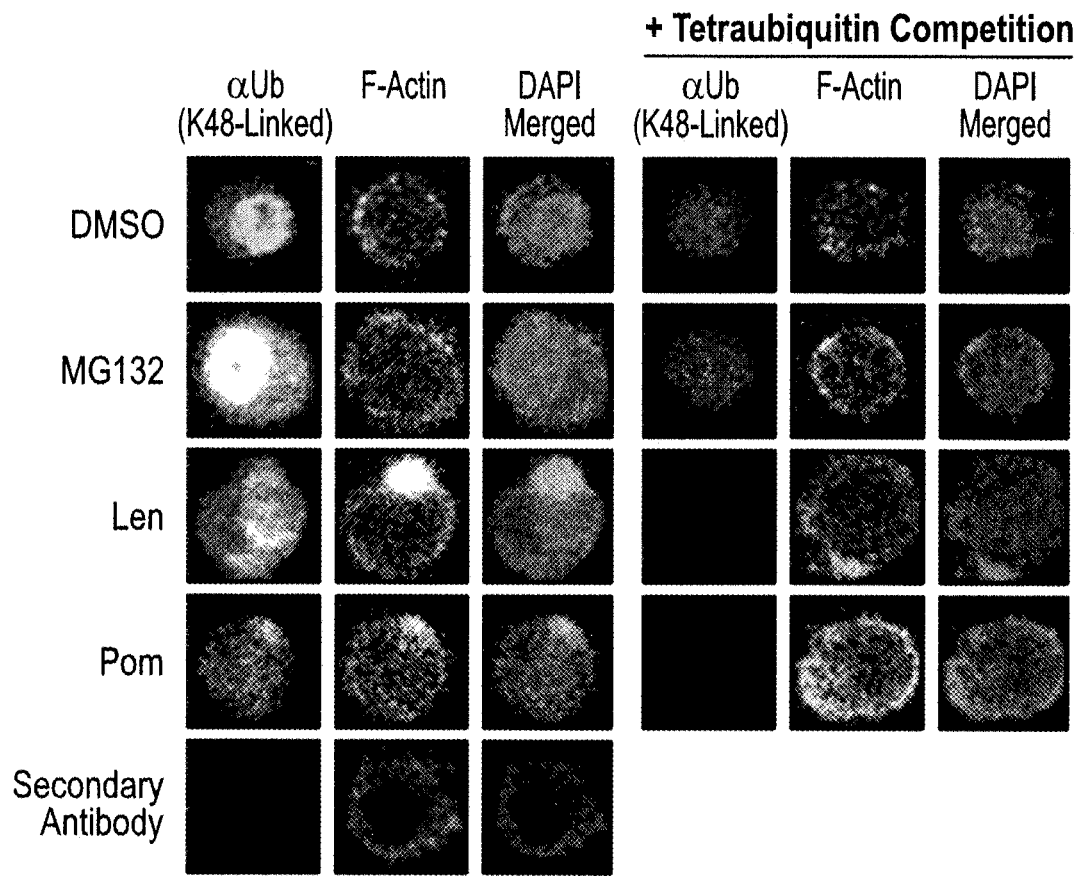
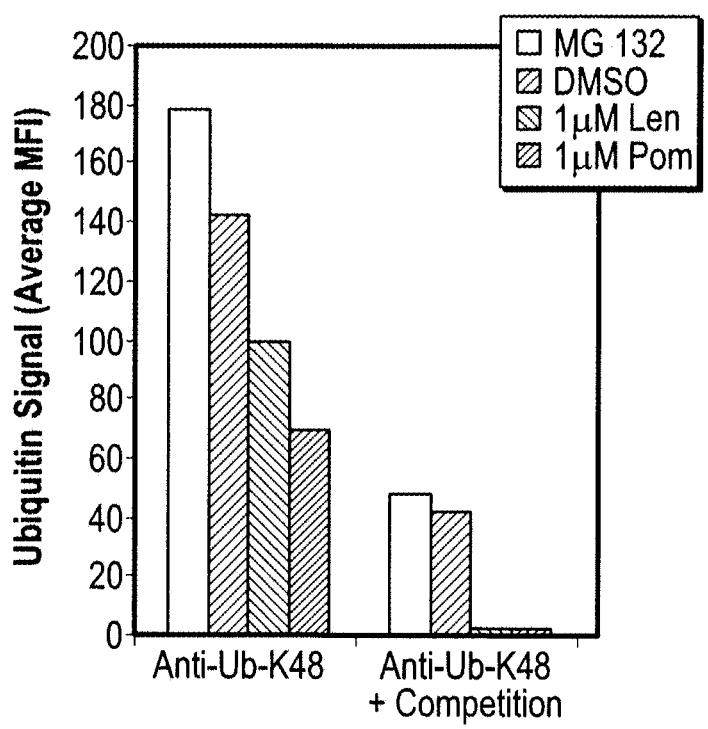
FIG. 7A

| Gene Name | Peptide | Site | Fold Change Pom 1hr | Fold Change Len 1hr |
|---|---|---|---|---|
| UBE2Q1 | ELK*LLESIFHR | 46 | -4.53 | -7.59 |
| G3BP2 | QYYTLLNK*APEYLHR | 25 | -2.19 | -2.07 |
|  |  |  | Pom 4 hr | Len 4 hr |
| GNB2L1 | LK*TNHITGYLNTVTVSPDGSLCASGGK | 185 | -2.08 | -3.98 |

FIG. 21

| Gene Name | Peptide | Site | Pom 1hr Fold Change | Len 1hr Fold Change | Pom 4hr Fold Change | Len 4hr Fold Change | Pom/MG. 1hr Fold Change | Len/MG. 1h Fold Change | Pom/MG. 4h Fold Change | Len/MG. 4hr |
|---|---|---|---|---|---|---|---|---|---|---|
| C7orf42 | QSNPEFCPEK*VA. | 308 | | | -161 | -130 | | | -94 | -107 |
| DUS3L | K*GGGCALM#NR | 404 | -35.5 | -75.7 | | | -37.9 | -132 | | |
| GBA | VGLVASQK*NDLDA | 480 | -53.1 | -113 | -201 | -163 | | | | |
| KLF10 | VDEK*ASAALY | 223 | | | -192 | -155 | | | -145 | -165 |
| LARS | VSELNAGLLK*TDQ.. | 807 | | | -140 | -2.43 | -37.5 | -130 | | |
| UBE2Q1 | **ELK*LLESIFHR | 46 | -4.53 | -7.59 | -3.23 | -2.2** | | | | |
| ALDOA | ..RPEPQVIK*SK | 99 | | | | | 4.09 | 4.85 | | |
| ALDOA | VDK*GVVPLAGT.. | 111 | | | | | | | 4.73 | 4.54 |
| C13orf40 | KPDLRUEQEEK | 6269 | | | 4.98 | 2.17 | | | 4.84 | 4.74 |
| EEF1A1 | | 450 | | | | | | | | |
| EEF1A | | 414 | | | | | | | | |
| eEF1AL3 | AAGAGK*VTK | 450 | | | 2.91 | 2.94 | 11.3 | 3.32 | | |
| | | 389 | | | | | | | | |
| FERMT3 | ETTLSYYK*SQDEAP.. | 385 | | | 108 | 210 | 129 | 174 | | |
| H2AFX | K*TSATVGPK | 120 | | | 2.65 | 2.71 | 7.19 | 3.97 | | |
| HNRNPUL1 | PFSYGYGGTGK*K | 309 | 129 | 79.3 | | | 2.28 | 2.13 | | |
| RPS2 | | 58 | | | | | | | | |
| LOC645018 | AEDK*EWMPVTK | 45 | | | 4.82 | 4.16 | | | 19.4 | 21.8 |

FIG. 22

U266 Multiple Myeloma Cell Ubiscan Data with Lenalidomide and Pomalidomide

| Gene Name | Peptide | Site | Fold Change 1 | Fold Change 2 |
|---|---|---|---|---|
| | | | CC4047.1hr.FC | CC5013.1hr.FC |
| RPL19 | HMGIGK*R | 80 | -18.3 | -26.7 |
| | | | CC4047.4hr.FC | CC5013.4hr.FC |
| GNB2L1 | LK*TNHIGHTGYLNTVTVSPDGSLCASGGK | 185 | -2.08 | -3.98 |
| NEDD8 | QMNDEK*TAADYK | 54 | 2.45 | 2.87 |
| HIST1H1A | GTLVQTK*GTGASGSFK | 100;-100;97;-98;-97 | 2.61 | 2.24 |
| NEDD8 | LIYSGK*QMNDEK | 48 | 2.15 | 2.68 |
| | | | CC4047.MG.1hr.FC | CC5013.MG.1hr.FC |
| PCM1 | LMAAK*QK | 666 | 2.67 | 2.56 |
| HSPA8 | DISENK*R | 257 | 4.01 | 2.83 |
| RPL19 | TLSK*EEETKK | 190 | 2.46 | 2.06 |
| RPL19 | TLSKEEETK*K | 195 | 2.46 | 2.06 |
| RPL19 | TLSKEEETKK* | 196 | 2.46 | 2.06 |
| IKZF3 | SHTVEKPYK*CEFCGR | 147 | 4 | 4.12 |
| | | | CC4047.MG.4hr.FC | CC5013.MG.4hr.FC |
| HNRNPR | IK*ALLER | 128;125 | -9.66 | -35.8 |
| MIB1 | SSEDATDDISSGNIPVLQK*DKDNTNVNADVQK | 936 | -100 | -114 |
| MIB1 | SSEDATDDISSGNIPVLQKDK*DNTNVNADVQK | 938 | -100 | -114 |

FIG. 23A

T Cell Ubiscan Data with Compound B

| | Gene Name | Peptide | Site | CC122.p.val | CC122.FC |
|---|---|---|---|---|---|
| a → | IKZF3 | EYNEYENIK*LER | 100 | 0.00526 | 29.70 |
| a → | RPL19 | KK*LLADQAEAR | 153 | 0.03800 | 18.00 |
| a → | PCM1 | QQNQHPEKPGGK*ER | 1096 | 0.02600 | 3.33 |
| | MIB1 | GQSPLDLCPDPNLCKALAK* | 791 | 0.03400 | 1.96 |
| a → | NEDD8 | VK*TLTGKEIEIDIEPTDKVER | 6 | 0.04240 | 1.57 |
| | HSPA8 | ILDKCNEIINWLDKNQTAEK*EEFEHQQKELEK | 589 | 0.04270 | -1.58 |
| | HSPA8 | ILDKCNEIINWLDKNWTAEKEEFEHQQK*ELEK | 597 | 0.04270 | -1.58 |
| b → | GNB2L1 | LWNTLGVCK*YTVQDESHSEWVSCVR | 139 | 0.04430 | -1.87 |
| | HIST1H1A | SLVSK*GTLVQTK | 93; 93; 90; 91; 90 | 0.03220 | -1.92 |
| | RPL19 | K*PVTVHSR | 53 | 0.02390 | -2.33 |
| b → | HNRNPR | IK*ALLER | 128; 125 | 0.02520 | -2.95 | a: Ub-proteins that are commonly increased in abundance by Rev and Pom in U266 and Compound B in T cells
b: Proteins that are commonly decreased in abundance by Rev and Pom in U266 and Compound B in T cells

FIG. 23B

| | |
|---|---|
| GGGCCGATTTTCAATGTCATTCTTCAGTTTTGGAGACTGATTTCTCTCCAGC | OCI-LY3 |
| GGGCCGATTTTCAATGTCATTCTTCAGTTTTAGAGACTGATTTCTCTCCAGC | U2932 |
| GGGCCGATTTTCAATGTCATTCTTCAGTTTTAGAGACTGATTTCTCTCCAGC | OCI-LY10 |
| GGGCCGATTTTCAATGTCATTCTTCAGTTTTAGAGACTGATTTCTCTCCAGC | RIVA |
| GGGCCGATTTTCAATGTCATTCTTCAGTTTTAGAGACTGATTTCTCTCCAGC | Karpas422 |
| GGGCCGATTTTCAATGTCATTCTTCAGTTTTAGAGACTGATTTCTCTCCAGC | TOLEDO |
| GGGCCGATTTTCAATGTCATTCTTCAGTTTTAGAGACTGATTTCTCTCCAGC | TMD8 |
| GGGCCGATTTTCAATGTCATTCTTCAGTTTTAGAGACTGATTTCTCTCCAGC | OCI-LY19 |
| GGGCCGATTTTCAATGTCATTCTTCAGTTTTAGAGACTGATTTCTCTCCAGC | Karpas1106p |
| GGGCCGATTTTCAATGTCATTCTTCAGTTTTAGAGACTGATTTCTCTCCAGC | SUDHL4 |
| GGGCCGATTTTCAATGTCATTCTTCAGTTTTAGAGACTGATTTCTCTCCAGC | WSU-DLCL2 |
| GGGCCGATTTTCAATGTCATTCTTCAGTTTTAGAGACTGATTTCTCTCCAGC | HBL1 |
| GGGCCGATTTTCAATGTCATTCTTCAGTTTTAGAGACTGATTTCTCTCCAGC | Pfeiffer |
| GGGCCGATTTTCAATGTCATTCTTCAGTTTTAGAGACTGATTTCTCTCCAGC | DB |

FIG. 28

```
CGN-6-1-11-HC    METGLRWLLLVAVLKGVHCQSVEESGGRLVTPGTPLTLTCTVSGFSLSYYGVSWVRQAPG
CGN-6-4-5-HC     METGLRWLLLVAVLKGVQCQSVEESGGRLVTPGTPLTLTCTVSGSSLSRYGVSWVRQAPG
                 *************** ***************************  ** ***********

CGN-6-1-11-HC    KGLEYIGYIYSDSDKTYYATWAKGRFTISKTS-TTVDLKITSPTIEDTATYFCARGTPLA
CGN-6-4-5-HC     KGLEHIGYIYSDPGMTFYATWAKGRFTISKTSSTTVDLKMTSPTIEDTATYFCARGTPLA
                 **** *******  * ***************  ****** *******************

CGN-6-1-11-HC    SYSIWGPGTLVTVSLGQPKAPSVFPLAPCCGDTPSSTVTLGCLVKGYLPEPVTVTWNSGT
CGN-6-4-5-HC     SYSTWGPGTLVTISLGQPKAPSVFPLAPCCGDTPSSTVTLGCLVKGYLPEPVTVTWNSGT
                 *** ******** ***********************************************

CGN-6-1-11-HC    LTNGVRTFPSVRQSSGLYSLSSVVSVTSSSQPVTCNVAHPATNTKVDKTVAPSTCSKPTC
CGN-6-4-5-HC     LTNGVRTFPSVRQSSGLYSLSSVVSVTSSSQPVTCNVAHPATNTKVDKTVAPSTCSKPTC
                 ************************************************************

CGN-6-1-11-HC    PPPELLGGPSVFIFPPKPKDTLMISRTPEVTCVVVDVSQDDPEVQFTWYINNEQVRTARP
CGN-6-4-5-HC     PPPELLGGPSVFIFPPKPKDTLMISRTPEVTCVVVDVSQDDPEVQFTWYINNEQVRTARP
                 ************************************************************

CGN-6-1-11-HC    PLREQQFNSTIRVVSTLPIAHQDWLRGKEFKCKVHNKALPAPIEKTISKARGQPLEPKVY
CGN-6-4-5-HC     PLREQQFNSTIRVVSTLPIAHQDWLRGKEFKCKVHNKALPAPIEKTISKARGQPLEPKVY
                 ************************************************************

CGN-6-1-11-HC    TMGPPREELSSRSVSLTCMINGFYPSDISVEWEKNGKAEDNYKTTPAVLDSDGSYFLYSK
CGN-6-4-5-HC     TMGPPREELSSRSVSLTCMINGFYPSDISVEWEKNGKAEDNYKTTPAVLDSDGSYFLYSK
                 ************************************************************

CGN-6-1-11-HC    LSVPTSEWQRGDVFTCSVMHEALHNHYTQKSISRSPGK-
CGN-6-4-5-HC     LSVPTSEWQRGDVFTCSVMHEALHNHYTQKSISRSPGK-
                 ***************************************
```

FIG. 35

```
CGN-6-1-11-LC   MDTRAPTQLLGLLLLWLPGATFAQVLTQTPASVSAAVGGTVTINCQASQSVYKNNYLSWF
CGN-6-4-5-LC    MDTRAPTQLLGLLLLWLPGATFAQVLTQTPASVSAAVGGTVTINCQSSENIYKNNYLSWF
                ****************************************** :..* ***********

CGN-6-1-11-LC   QQKPGQPPKLLIYEASKLASGVPPRFKGSGFGTQFTFTISDLECDDAAFYYCAGGYYGNI
CGN-6-4-5-LC    QQKPGQPPKLLIYQASTLASGVPSRFKGSGSGTRFSLTISDLECDDAATYYCAGGYSGNI
                *************:**.***** ******* ** * ************ ******.***

CGN-6-1-11-LC   FFFGGGTEVVKGDPVAPTVLIFPPAADQVATGTVTIVCVANKYFPDVTVTWEVDGTTQT
CGN-6-4-5-LC    FTFGGGTEVVKGDPVAPTVLIFPPAADQVATGTVTIVCVANKYFPDVTVTWEVDGTTQT
                * *********************************************************

CGN-6-1-11-LC   TGIENSKTPQNSADCTYNLSSTLTLTSTQYNSHKEYTCKVTQGTTSVVQSFNRGDC-
CGN-6-4-5-LC    TGIENSKTPQNSADCTYNLSSTLTLTSTQYNSHKEYTCKVTQGTTSVVQSFNRGDC-
                *********************************************************
```

FIG. 36

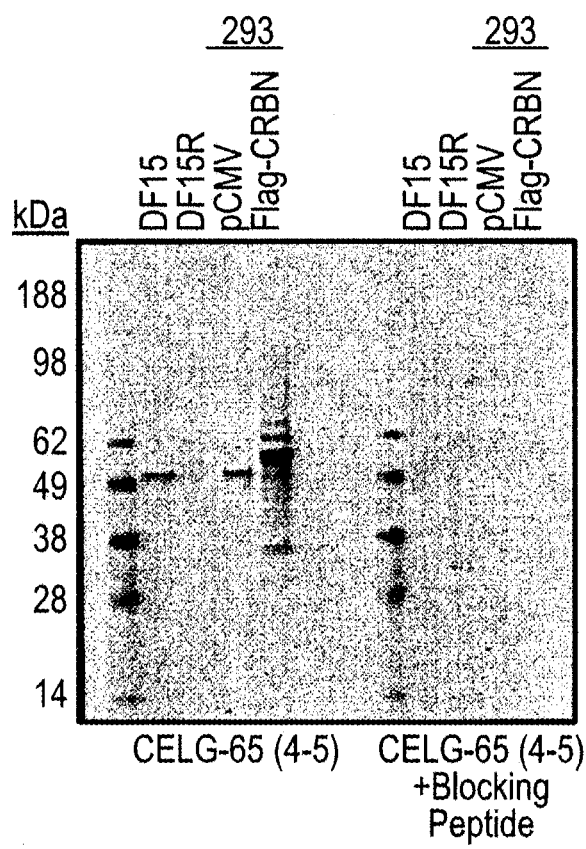
FIG. 38
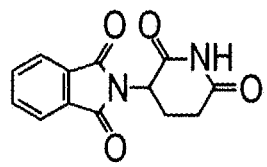
Thalidomide (Thal)
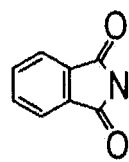
Pthalimide
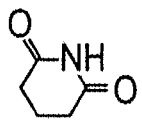
Glutarimide
Bead Elution
FIG. 39A

SEQUENCE LISTING

```
<160> NUMBER OF SEQ ID NOS: 252

<210> SEQ ID NO 1
<211> LENGTH: 13
<212> TYPE: PRT
<213> ORGANISM: Homo sapiens

<400> SEQUENCE: 1

Glu Glu Phe His Gly Arg Thr Leu His Asp Asp Asp Cys
1               5                   10

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcgggcgcgg ctctcggtcc gaaaaggatg tcgtacaact acgtggtaac              50

<210> SEQ ID NO 3
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcttcctttc gggcttattt ttcgaactgc gggtggctcc aatggatccg agttagctcc   60
t                                                                   61

<210> SEQ ID NO 4
<211> LENGTH: 1374
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 4

```
atggagactg ggctgcgctg gcttctcctg gtcgctgtgc tcaaaggtgt ccactgtcag      60
tcagtggagg agtccggggg tcgcctggtc acgcctggga ccccctgac actcacctgt     120
acagtctctg gattctccct cagttactat ggagtgagct gggtccgcca ggctccaggg    180
aaggggctag aatacatcgg atacatttat agtgatagtg ataagacata ctacgcgacc    240
tgggcgaaag gccgattcac catctcccaa acctcgacca cggtggattt gaaaatcacc    300
agtccgacaa tcgaggacac ggccacctat ttctgtgcca gaggtactcc gcttgctagt    360
tatagcatct ggggcccagg caccctggtc accgtctcct tagggcaacc taaggctcca    420
tcagtcttcc cactggcccc ctgctgcggg gacacaccca gctccacggt gaccctgggc    480
tgcctggtca aagggtacct cccggagcca gtgaccgtga cctggaactc gggcacccct    540
accaatgggg tacgcacctt cccgtccgtc cggcagtcct caggcctcta ctcgctgagc    600
agcgtggtga gcgtgacctc aagcagccag cccgtcacct gcaacgtggc ccacccagcc    660
accaacacca agtggacaa gaccgttgcg ccctcgacat gcagcaagcc cacgtgccca    720
cccctgaac tcctgggggg accgtctgtc ttcatcttcc cccaaaaacc caaggacacc    780
ctcatgatct cacgcacccc cgaggtcaca tgcgtggtgg tggacgtgag ccaggatgac    840
cccgaggtgc agttcacatg gtacataaac aacgagcagg tgcgcaccgc ccggccgccg    900
ctacgggagc agcagttcaa cagcacgatc cgcgtggtca gcaccctccc catcgcgcac    960
caggactggc tgaggggcaa ggagttcaag tgcaaagtcc acaacaaggc actcccggcc   1020
cccatcgaga aaaccatctc caaagccaga gggcagcccc tggagccgaa ggtctacacc   1080
atgggccctc ccggggagga gctgagcagc aggtcggtca gcctgacctg catgatcaac   1140
ggcttctacc cttccgacat ctcggtggag tgggagaaga cgggaaggc agaggacaac   1200
tacaagacca cgccggccgt gctggacagc gacggctcct acttcctcta cagcaagctc   1260
tcagtgccca cgagtgagtg gcagcggggc gacgtcttca cctgctccgt gatgcacgag   1320
gccttgcaca accactacac gcagaagtcc atctcccgct ctccgggtaa atga         1374
```

<210> SEQ ID NO 5
<211> LENGTH: 457
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 5

```
Met Glu Thr Gly Leu Arg Trp Leu Leu Leu Val Ala Val Leu Lys Gly
  1               5                  10                  15

Val His Cys Gln Ser Val Glu Glu Ser Gly Gly Arg Leu Val Thr Pro
             20                  25                  30

Gly Thr Pro Leu Thr Leu Thr Cys Thr Val Ser Gly Phe Ser Leu Ser
         35                  40                  45

Tyr Tyr Gly Val Ser Trp Val Arg Gln Ala Pro Gly Lys Gly Leu Glu
     50                  55                  60

Tyr Ile Gly Tyr Ile Tyr Ser Asp Ser Asp Lys Thr Tyr Tyr Ala Thr
 65                  70                  75                  80

Trp Ala Lys Gly Arg Phe Thr Ile Ser Lys Thr Ser Thr Thr Val Asp
                 85                  90                  95

Leu Lys Ile Thr Ser Pro Thr Ile Glu Asp Thr Ala Thr Tyr Phe Cys
```

```
                100                 105                 110
Ala Arg Gly Thr Pro Leu Ala Ser Tyr Ser Ile Trp Gly Pro Gly Thr
            115                 120                 125
Leu Val Thr Val Ser Leu Gly Gln Pro Lys Ala Pro Ser Val Phe Pro
        130                 135                 140
Leu Ala Pro Cys Cys Gly Asp Thr Pro Ser Ser Thr Val Thr Leu Gly
145                 150                 155                 160
Cys Leu Val Lys Gly Tyr Leu Pro Glu Pro Val Thr Val Thr Trp Asn
                165                 170                 175
Ser Gly Thr Leu Thr Asn Gly Val Arg Thr Phe Pro Ser Val Arg Gln
            180                 185                 190
Ser Ser Gly Leu Tyr Ser Leu Ser Ser Val Val Ser Val Thr Ser Ser
        195                 200                 205
Ser Gln Pro Val Thr Cys Asn Val Ala His Pro Ala Thr Asn Thr Lys
    210                 215                 220
Val Asp Lys Thr Val Ala Pro Ser Thr Cys Ser Lys Pro Thr Cys Pro
225                 230                 235                 240
Pro Pro Glu Leu Leu Gly Gly Pro Ser Val Phe Ile Phe Pro Pro Lys
                245                 250                 255
Pro Lys Asp Thr Leu Met Ile Ser Arg Thr Pro Glu Val Thr Cys Val
            260                 265                 270
Val Val Asp Val Ser Gln Asp Asp Pro Glu Val Gln Phe Thr Trp Tyr
        275                 280                 285
Ile Asn Asn Glu Gln Val Arg Thr Ala Arg Pro Pro Leu Arg Glu Gln
    290                 295                 300
Gln Phe Asn Ser Thr Ile Arg Val Val Ser Thr Leu Pro Ile Ala His
305                 310                 315                 320
Gln Asp Trp Leu Arg Gly Lys Glu Phe Lys Cys Lys Val His Asn Lys
                325                 330                 335
Ala Leu Pro Ala Pro Ile Glu Lys Thr Ile Ser Lys Ala Arg Gly Gln
            340                 345                 350
Pro Leu Glu Pro Lys Val Tyr Thr Met Gly Pro Pro Arg Glu Glu Leu
        355                 360                 365
Ser Ser Arg Ser Val Ser Leu Thr Cys Met Ile Asn Gly Phe Tyr Pro
    370                 375                 380
Ser Asp Ile Ser Val Glu Trp Glu Lys Asn Gly Lys Ala Glu Asp Asn
385                 390                 395                 400
Tyr Lys Thr Thr Pro Ala Val Leu Asp Ser Asp Gly Ser Tyr Phe Leu
                405                 410                 415
Tyr Ser Lys Leu Ser Val Pro Thr Ser Glu Trp Gln Arg Gly Asp Val
            420                 425                 430
Phe Thr Cys Ser Val Met His Glu Ala Leu His Asn His Tyr Thr Gln
        435                 440                 445
Lys Ser Ile Ser Arg Ser Pro Gly Lys
    450                 455

<210> SEQ ID NO 6
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
```

```
atggacacga gggcccccac tcagctgctg gggctcctgc tgctctggct cccaggtgcc    60
acatttgccc aggtgctgac ccagactcca gcctcggtgt ctgcagctgt gggaggcaca   120
gtcaccatca attgccaggc cagtcagagt gtttataaga ataactattt atcctggttt   180
cagcagaaac cagggcagcc tcccaagctc ctgatttacg aagcgtccaa actggcatct   240
ggggtccccc gcggttcaa aggcagtgga tttgggacac agttcacttt caccattagc   300
gacctggagt gtgacgatgc tgccttttac tactgtgcag gcggttatta tggtaatatt   360
tttttttcg gcggagggac cgaggtggtg gtcaaaggtg atccagttgc acctactgtc   420
ctcatcttcc caccagctgc tgatcaggtg caactggaa cagtcaccat cgtgtgtgtg   480
gcgaataaat actttcccga tgtcaccgtc acctgggagg tggatggcac cacccaaaca   540
actggcatcg agaacagtaa aacaccgcag aattctgcag attgtaccta caacctcagc   600
agcactctga cactgaccag cacacagtac aacagccaca agagtacac ctgcaaggtg   660
acccagggca cgacctcagt cgtccagagc ttcaataggg gtgactgtta g            711
```

<210> SEQ ID NO 7
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Met Asp Thr Arg Ala Pro Thr Gln Leu Leu Gly Leu Leu Leu Leu Trp
1               5                   10                  15
Leu Pro Gly Ala Thr Phe Ala Gln Val Leu Thr Gln Thr Pro Ala Ser
            20                  25                  30
Val Ser Ala Ala Val Gly Gly Thr Val Thr Ile Asn Cys Gln Ala Ser
        35                  40                  45
Gln Ser Val Tyr Lys Asn Asn Tyr Leu Ser Trp Phe Gln Gln Lys Pro
    50                  55                  60
Gly Gln Pro Pro Lys Leu Leu Ile Tyr Glu Ala Ser Lys Leu Ala Ser
65                  70                  75                  80
Gly Val Pro Pro Arg Phe Lys Gly Ser Gly Phe Gly Thr Gln Phe Thr
                85                  90                  95
Phe Thr Ile Ser Asp Leu Glu Cys Asp Asp Ala Ala Phe Tyr Tyr Cys
            100                 105                 110
Ala Gly Gly Tyr Tyr Gly Asn Ile Phe Phe Phe Gly Gly Gly Thr Glu
        115                 120                 125
Val Val Val Lys Gly Asp Pro Val Ala Pro Thr Val Leu Ile Phe Pro
    130                 135                 140
Pro Ala Ala Asp Gln Val Ala Thr Gly Thr Val Thr Ile Val Cys Val
145                 150                 155                 160
Ala Asn Lys Tyr Phe Pro Asp Val Thr Val Thr Trp Glu Val Asp Gly
                165                 170                 175
Thr Thr Gln Thr Thr Gly Ile Glu Asn Ser Lys Thr Pro Gln Asn Ser
            180                 185                 190
Ala Asp Cys Thr Tyr Asn Leu Ser Ser Thr Leu Thr Leu Thr Ser Thr
        195                 200                 205
Gln Tyr Asn Ser His Lys Glu Tyr Thr Cys Lys Val Thr Gln Gly Thr
    210                 215                 220
Thr Ser Val Val Gln Ser Phe Asn Arg Gly Asp Cys
225                 230                 235
```

<210> SEQ ID NO 8
<211> LENGTH: 1377
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
atggagactg ggctgcgctg gcttctcctg gtcgctgtgc tcaaaggtgt ccagtgtcag      60
tcggtggagg agtccggggg tcgcctggtc acgcctggga ccccctgac actcacctgc     120
acagtctctg gattctccct cagtaggtat ggagtgagct gggtccgcca ggctccaggg    180
aaggggctgg aacacatcgg atacatttat agtgatcctg gtatgacatt ctacgcgacc    240
tgggcgaaag gccgattcac catctccaaa acctcgtcga ccacggtgga tttgaaaatg    300
accagtccga caatcgagga cacggccacc tatttctgtg ccagaggtac tccgcttgct    360
agttatagca cctggggccc aggcaccctg gtcaccatct ccttagggca acctaaggct    420
ccatcagtct tcccactggc ccctgctgc ggggacacac ccagctccac ggtgaccctg    480
ggctgcctgg tcaagggta cctcccggag ccagtgaccg tgacctggaa ctcgggcacc    540
ctcaccaatg gggtacgcac cttcccgtcc gtcggcagt cctcaggcct ctactcgctg    600
agcagcgtgt gagcgtgac ctcaagcagc agcccgtca cctgcaacgt ggcccaccca    660
gccaccaaca ccaaagtgga caagaccgtt gcgccctcga catgcagcaa gcccacgtgc    720
ccaccccctg aactcctggg gggaccgtct gtcttcatct tccccccaaa acccaaggac    780
accctcatga tctcacgcac ccccgaggtc acatgcgtgg tggtggacgt gagccaggat    840
gaccccgagg tgcagttcac atggtacata aacaacgagc aggtgcgcac cgcccggccg    900
ccgctacggg agcagcagtt caacagcacg atccgcgtgg tcagcaccct cccatcgcg    960
caccaggact ggctgagggg caaggagttc aagtgcaaag tccacaacaa ggcactcccg   1020
gcccccatcg agaaaaccat ctccaaagcc agagggcagc cctggagcc aaggtctac    1080
accatgggcc ctccccggga ggagctgagc agcaggtcgg tcagcctgac ctgcatgatc   1140
aacggcttct acccttccga catctcggtg gagtgggaga gaacgggaa gcagaggac    1200
aactacaaga ccacgccggc cgtgctggac agcgacggct cctacttcct ctacagcaag   1260
ctctcagtgc ccacgagtga gtggcagcgg ggcgacgtct tcacctgctc cgtgatgcac   1320
gaggccttgc acaaccacta cacgcagaag tccatctccc gctctccggg taaatga     1377
```

<210> SEQ ID NO 9
<211> LENGTH: 458
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Glu Thr Gly Leu Arg Trp Leu Leu Leu Val Ala Val Leu Lys Gly
1               5                   10                  15

Val Gln Cys Gln Ser Val Glu Glu Ser Gly Gly Arg Leu Val Thr Pro
            20                  25                  30

Gly Thr Pro Leu Thr Leu Thr Cys Thr Val Ser Gly Phe Ser Leu Ser
        35                  40                  45

Arg Tyr Gly Val Ser Trp Val Arg Gln Ala Pro Gly Lys Gly Leu Glu

```
                50                  55                  60
His Ile Gly Tyr Ile Tyr Ser Asp Pro Gly Met Thr Phe Tyr Ala Thr
 65                  70                  75                  80

Trp Ala Lys Gly Arg Phe Thr Ile Ser Lys Thr Ser Thr Thr Val
                 85                  90                  95

Asp Leu Lys Met Thr Ser Pro Thr Ile Glu Asp Thr Ala Thr Tyr Phe
                100                 105                 110

Cys Ala Arg Gly Thr Pro Leu Ala Ser Tyr Ser Thr Trp Gly Pro Gly
                115                 120                 125

Thr Leu Val Thr Ile Ser Leu Gly Gln Pro Lys Ala Pro Ser Val Phe
                130                 135                 140

Pro Leu Ala Pro Cys Cys Gly Asp Thr Pro Ser Ser Thr Val Thr Leu
145                 150                 155                 160

Gly Cys Leu Val Lys Gly Tyr Leu Pro Glu Pro Val Thr Val Thr Trp
                165                 170                 175

Asn Ser Gly Thr Leu Thr Asn Gly Val Arg Thr Phe Pro Ser Val Arg
                180                 185                 190

Gln Ser Ser Gly Leu Tyr Ser Leu Ser Ser Val Val Ser Val Thr Ser
                195                 200                 205

Ser Ser Gln Pro Val Thr Cys Asn Val Ala His Pro Ala Thr Asn Thr
                210                 215                 220

Lys Val Asp Lys Thr Val Ala Pro Ser Thr Cys Ser Lys Pro Thr Cys
225                 230                 235                 240

Pro Pro Pro Glu Leu Leu Gly Gly Pro Ser Val Phe Ile Phe Pro Pro
                245                 250                 255

Lys Pro Lys Asp Thr Leu Met Ile Ser Arg Thr Pro Glu Val Thr Cys
                260                 265                 270

Val Val Val Asp Val Ser Gln Asp Asp Pro Glu Val Gln Phe Thr Trp
                275                 280                 285

Tyr Ile Asn Asn Glu Gln Val Arg Thr Ala Arg Pro Pro Leu Arg Glu
                290                 295                 300

Gln Gln Phe Asn Ser Thr Ile Arg Val Val Ser Thr Leu Pro Ile Ala
305                 310                 315                 320

His Gln Asp Trp Leu Arg Gly Lys Glu Phe Lys Cys Lys Val His Asn
                325                 330                 335

Lys Ala Leu Pro Ala Pro Ile Glu Lys Thr Ile Ser Lys Ala Arg Gly
                340                 345                 350

Gln Pro Leu Glu Pro Lys Val Tyr Thr Met Gly Pro Pro Arg Glu Glu
                355                 360                 365

Leu Ser Ser Arg Ser Val Ser Leu Thr Cys Met Ile Asn Gly Phe Tyr
                370                 375                 380

Pro Ser Asp Ile Ser Val Glu Trp Glu Lys Asn Gly Lys Ala Glu Asp
385                 390                 395                 400

Asn Tyr Lys Thr Thr Pro Ala Val Leu Asp Ser Asp Gly Ser Tyr Phe
                405                 410                 415

Leu Tyr Ser Lys Leu Ser Val Pro Thr Ser Glu Trp Gln Arg Gly Asp
                420                 425                 430

Val Phe Thr Cys Ser Val Met His Glu Ala Leu His Asn His Tyr Thr
                435                 440                 445

Gln Lys Ser Ile Ser Arg Ser Pro Gly Lys
        450                 455

<210> SEQ ID NO 10
```

<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
atggacacga gggcccccac tcagctgctg gggctcctgc tgctctggct cccaggtgcc      60
acatttgctc aagtgctgac ccagactcca gcctccgtgt ctgcagctgt gggaggcaca     120
gtcaccatca attgccagtc cagtgagaat atttataaga caactacttt atcctggttt     180
cagcagaaac cagggcagcc tcccaagctc ctgatctatc aggcatccac tctggcatct     240
ggggtcccat cgcggttcaa aggcagtgga tctgggacac gattcagtct caccatcagc     300
gacctggagt gtgacgatgc tgccacttac tactgtgcag gcggttatag tggtaatatt     360
tttactttcg gcggagggac cgaggtggtg gtcaaaggtg atccagttgc acctactgtc     420
ctcatcttcc caccagctgc tgatcaggtg gcaactggaa cagtcaccat cgtgtgtgtg     480
gcgaataaat actttcccga tgtcaccgtc acctgggagg tggatggcac cacccaaaca     540
actggcatcg agaacagtaa aaccccgcag aattctgcag attgtaccta caacctcagc     600
agcactctga cactgaccag cacacagtac aacagccaca agagtacac ctgcaaggtg     660
acccagggca cgacctcagt cgtccagagc ttcaataggg gtgactgtta g             711
```

<210> SEQ ID NO 11
<211> LENGTH: 236
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

```
Met Asp Thr Arg Ala Pro Thr Gln Leu Leu Gly Leu Leu Leu Leu Trp
  1               5                  10                  15

Leu Pro Gly Ala Thr Phe Ala Gln Val Leu Thr Gln Thr Pro Ala Ser
             20                  25                  30

Val Ser Ala Ala Val Gly Gly Thr Val Thr Ile Asn Cys Gln Ser Ser
         35                  40                  45

Glu Asn Ile Tyr Lys Asn Asn Tyr Leu Ser Trp Phe Gln Gln Lys Pro
     50                  55                  60

Gly Gln Pro Pro Lys Leu Leu Ile Tyr Gln Ala Ser Thr Leu Ala Ser
 65                  70                  75                  80

Gly Val Pro Ser Arg Phe Lys Gly Ser Gly Ser Gly Thr Arg Phe Ser
                 85                  90                  95

Leu Thr Ile Ser Asp Leu Glu Cys Asp Asp Ala Ala Thr Tyr Tyr Cys
            100                 105                 110

Ala Gly Gly Tyr Ser Gly Asn Ile Phe Thr Phe Gly Gly Gly Thr Glu
        115                 120                 125

Val Val Val Lys Gly Asp Pro Val Ala Pro Thr Val Leu Ile Phe Pro
    130                 135                 140

Pro Ala Ala Asp Gln Val Ala Thr Gly Thr Val Thr Ile Val Cys Val
145                 150                 155                 160

Ala Asn Lys Tyr Phe Pro Asp Val Thr Val Thr Trp Glu Val Asp Gly
                165                 170                 175

Thr Thr Gln Thr Thr Gly Ile Glu Asn Ser Lys Thr Pro Gln Asn Ser
            180                 185                 190
```

```
Ala Asp Cys Thr Tyr Asn Leu Ser Ser Thr Leu Thr Leu Thr Ser Thr
        195                 200                 205

Gln Tyr Asn Ser His Lys Glu Tyr Thr Cys Lys Val Thr Gln Gly Thr
210                 215                 220

Thr Ser Val Val Gln Ser Phe Asn Arg Gly Asp Cys
225                 230                 235

<210> SEQ ID NO 12
<211> LENGTH: 442
<212> TYPE: PRT
<213> ORGANISM: Homo sapiens

<400> SEQUENCE: 12

Met Ala Gly Glu Gly Asp Gln Gln Asp Ala Ala His Asn Met Gly Asn
1               5                   10                  15

His Leu Pro Leu Leu Pro Ala Glu Ser Glu Glu Glu Asp Glu Met Glu
            20                  25                  30

Val Glu Asp Gln Asp Ser Lys Glu Ala Lys Lys Pro Asn Ile Ile Asn
        35                  40                  45

Phe Asp Thr Ser Leu Pro Thr Ser His Thr Tyr Leu Gly Ala Asp Met
50                  55                  60

Glu Glu Phe His Gly Arg Thr Leu His Asp Asp Asp Ser Cys Gln Val
65                  70                  75                  80

Ile Pro Val Leu Pro Gln Val Met Met Ile Leu Ile Pro Gly Gln Thr
                85                  90                  95

Leu Pro Leu Gln Leu Phe His Pro Gln Glu Val Ser Met Val Arg Asn
            100                 105                 110

Leu Ile Gln Lys Asp Arg Thr Phe Ala Val Leu Ala Tyr Ser Asn Val
        115                 120                 125

Gln Glu Arg Glu Ala Gln Phe Gly Thr Thr Ala Glu Ile Tyr Ala Tyr
    130                 135                 140

Arg Glu Glu Gln Asp Phe Gly Ile Glu Ile Val Lys Val Lys Ala Ile
145                 150                 155                 160

Gly Arg Gln Arg Phe Lys Val Leu Glu Leu Arg Thr Gln Ser Asp Gly
                165                 170                 175

Ile Gln Gln Ala Lys Val Gln Ile Leu Pro Glu Cys Val Leu Pro Ser
            180                 185                 190

Thr Met Ser Ala Val Gln Leu Glu Ser Leu Asn Lys Cys Gln Ile Phe
        195                 200                 205

Pro Ser Lys Pro Val Ser Arg Glu Asp Gln Cys Ser Tyr Lys Trp Trp
    210                 215                 220

Gln Lys Tyr Gln Lys Arg Lys Phe His Cys Ala Asn Leu Thr Ser Trp
225                 230                 235                 240

Pro Arg Trp Leu Tyr Ser Leu Tyr Asp Ala Glu Thr Leu Met Asp Arg
                245                 250                 255

Ile Lys Lys Gln Leu Arg Glu Trp Asp Glu Asn Leu Lys Asp Asp Ser
            260                 265                 270

Leu Pro Ser Asn Pro Ile Asp Phe Ser Tyr Arg Val Ala Ala Cys Leu
        275                 280                 285

Pro Ile Asp Asp Val Leu Arg Ile Gln Leu Leu Lys Ile Gly Ser Ala
    290                 295                 300

Ile Gln Arg Leu Arg Cys Glu Leu Asp Ile Met Asn Lys Cys Thr Ser
305                 310                 315                 320

Leu Cys Cys Lys Gln Cys Gln Glu Thr Glu Ile Thr Thr Lys Asn Glu
```

```
            325                 330                 335
Ile Phe Ser Leu Ser Leu Cys Gly Pro Met Ala Ala Tyr Val Asn Pro
            340                 345                 350

His Gly Tyr Val His Glu Thr Leu Thr Val Tyr Lys Ala Cys Asn Leu
            355                 360                 365

Asn Leu Ile Gly Arg Pro Ser Thr Glu His Ser Trp Phe Pro Gly Tyr
        370                 375                 380

Ala Trp Thr Val Ala Gln Cys Lys Ile Cys Ala Ser His Ile Gly Trp
385                 390                 395                 400

Lys Phe Thr Ala Thr Lys Lys Asp Met Ser Pro Gln Lys Phe Trp Gly
                405                 410                 415

Leu Thr Arg Ser Ala Leu Leu Pro Thr Ile Pro Asp Thr Glu Asp Glu
                420                 425                 430

Ile Ser Pro Asp Lys Val Ile Leu Cys Leu
                435                 440
```

<210> SEQ ID NO 13
<211> LENGTH: 441
<212> TYPE: PRT
<213> ORGANISM: Homo sapiens

<400> SEQUENCE: 13

```
Met Ala Gly Glu Gly Asp Gln Gln Asp Ala Ala His Asn Met Gly Asn
1               5                   10                  15

His Leu Pro Leu Pro Glu Ser Glu Glu Asp Glu Met Glu Val
            20                  25                  30

Glu Asp Gln Asp Ser Lys Glu Ala Lys Lys Pro Asn Ile Ile Asn Phe
            35                  40                  45

Asp Thr Ser Leu Pro Thr Ser His Thr Tyr Leu Gly Ala Asp Met Glu
        50                  55                  60

Glu Phe His Gly Arg Thr Leu His Asp Asp Ser Cys Gln Val Ile
65                  70                  75                  80

Pro Val Leu Pro Gln Val Met Met Ile Leu Ile Pro Gly Gln Thr Leu
                85                  90                  95

Pro Leu Gln Leu Phe His Pro Gln Glu Val Ser Met Val Arg Asn Leu
                100                 105                 110

Ile Gln Lys Asp Arg Thr Phe Ala Val Leu Ala Tyr Ser Asn Val Gln
            115                 120                 125

Glu Arg Glu Ala Gln Phe Gly Thr Thr Ala Glu Ile Tyr Ala Tyr Arg
        130                 135                 140

Glu Glu Gln Asp Phe Gly Ile Glu Ile Val Lys Val Lys Ala Ile Gly
145                 150                 155                 160

Arg Gln Arg Phe Lys Val Leu Glu Leu Arg Thr Gln Ser Asp Gly Ile
                165                 170                 175

Gln Gln Ala Lys Val Gln Ile Leu Pro Glu Cys Val Leu Pro Ser Thr
                180                 185                 190

Met Ser Ala Val Gln Leu Glu Ser Leu Asn Lys Cys Gln Ile Phe Pro
            195                 200                 205

Ser Lys Pro Val Ser Arg Glu Asp Gln Cys Ser Tyr Lys Trp Trp Gln
        210                 215                 220

Lys Tyr Gln Lys Arg Lys Phe His Cys Ala Asn Leu Thr Ser Trp Pro
225                 230                 235                 240

Arg Trp Leu Tyr Ser Leu Tyr Asp Ala Glu Thr Leu Met Asp Arg Ile
                245                 250                 255
```

```
Lys Lys Gln Leu Arg Glu Trp Asp Glu Asn Leu Lys Asp Asp Ser Leu
                260                 265                 270

Pro Ser Asn Pro Ile Asp Phe Ser Tyr Arg Val Ala Ala Cys Leu Pro
            275                 280                 285

Ile Asp Asp Val Leu Arg Ile Gln Leu Leu Lys Ile Gly Ser Ala Ile
290                 295                 300

Gln Arg Leu Arg Cys Glu Leu Asp Ile Met Asn Lys Cys Thr Ser Leu
305                 310                 315                 320

Cys Cys Lys Gln Cys Gln Glu Thr Glu Ile Thr Thr Lys Asn Glu Ile
                325                 330                 335

Phe Ser Leu Ser Leu Cys Gly Pro Met Ala Ala Tyr Val Asn Pro His
                340                 345                 350

Gly Tyr Val His Glu Thr Leu Thr Val Tyr Lys Ala Cys Asn Leu Asn
            355                 360                 365

Leu Ile Gly Arg Pro Ser Thr Glu His Ser Trp Phe Pro Gly Tyr Ala
370                 375                 380

Trp Thr Val Ala Gln Cys Lys Ile Cys Ala Ser His Ile Gly Trp Lys
385                 390                 395                 400

Phe Thr Ala Thr Lys Lys Asp Met Ser Pro Gln Lys Phe Trp Gly Leu
                405                 410                 415

Thr Arg Ser Ala Leu Leu Pro Thr Ile Pro Asp Thr Glu Asp Glu Ile
                420                 425                 430

Ser Pro Asp Lys Val Ile Leu Cys Leu
                435                 440

<210> SEQ ID NO 14
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtgccgcgtg gctccatgat ggccggcgaa ggagatca                              38

<210> SEQ ID NO 15
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcttcctttc gggcttatta caagcaaagt attactt                               37

<210> SEQ ID NO 16
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ubiquitinated Lys

<400> SEQUENCE: 16

Gln Tyr Tyr Thr Leu Leu Asn Lys Ala Pro Glu Tyr Leu His Arg
1               5                   10                  15
```

```
<210> SEQ ID NO 17
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ubiquitinated Lys
<220> FEATURE:
<221> NAME/KEY: MOD_RES
<222> LOCATION: (17)..(17)
<223> OTHER INFORMATION: Oxidized Met

<400> SEQUENCE: 17

Gln Val Cys Glu Ile Ile Glu Ser Pro Leu Phe Leu Lys Leu Asn Pro
1               5                   10                  15

Met Thr Lys

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Oxidized Met
<220> FEATURE:
<221> NAME/KEY: MOD_RES
<222> LOCATION: (19)..(19)
<223> OTHER INFORMATION: Ubiquitinated Lys

<400> SEQUENCE: 18

Gln Val Cys Glu Ile Ile Glu Ser Pro Leu Phe Leu Lys Leu Asn Pro
1               5                   10                  15

Met Thr Lys

<210> SEQ ID NO 19
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Ubiquitinated Lys

<400> SEQUENCE: 19

Val Gly Asp Val Gln Gly Gln Glu Ser Glu Ser Gln Leu Pro Thr Lys
1               5                   10                  15

Ile Ile Leu Thr Gly Gln Lys
            20

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (9)..(9)
<223> OTHER INFORMATION: Oxidized Met
<220> FEATURE:
<221> NAME/KEY: MOD_RES
<222> LOCATION: (12)..(12)
<223> OTHER INFORMATION: Ubiquitinated Lys

<400> SEQUENCE: 20

Phe Phe Gly Asp Ser Ala Ala Ser Met Ala Ile Lys Asn Pro Lys
1               5                   10                  15

<210> SEQ ID NO 21
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ubiquitinated Lys

<400> SEQUENCE: 21

Phe Leu Gln Glu Phe Tyr Gln Asp Asp Glu Leu Gly Lys Lys
1               5                   10

<210> SEQ ID NO 22
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(3)
<223> OTHER INFORMATION: Oxidized Met
<220> FEATURE:
<221> NAME/KEY: MOD_RES
<222> LOCATION: (4)..(4)
<223> OTHER INFORMATION: Ubiquitinated Lys
<220> FEATURE:
<221> NAME/KEY: MOD_RES
<222> LOCATION: (15)..(15)
<223> OTHER INFORMATION: Oxidized Met

<400> SEQUENCE: 22

Ser Met Met Lys Met Leu Leu Asp Pro Met Gly Gly Ile Val Met Thr
1               5                   10                  15

Asn Asp Gly Asn Ala Ile Leu Arg
            20

<210> SEQ ID NO 23
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ubiquitinated Lys

<400> SEQUENCE: 23

Leu Ser Ser Asp Gln Asn Asp Lys Ala Ala Ser Ala Ala Arg
1               5                   10
```

```
<210> SEQ ID NO 24
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Ubiquitinated Lys

<400> SEQUENCE: 24

Leu Ser Pro Tyr Leu Glu Asp Val Ser Gly Gly Met Trp Pro Val Val
1               5                   10                  15

His Ile Gln Lys Lys Asn Thr Lys
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Ubiquitinated Lys

<400> SEQUENCE: 25

Ala Thr Gly Asp Pro Tyr Tyr Leu Glu Val Gly Lys Thr Leu Ile Glu
1               5                   10                  15

Asn Leu Asn Lys
            20

<210> SEQ ID NO 26
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ubiquitinated Lys
<220> FEATURE:
<221> NAME/KEY: MOD_RES
<222> LOCATION: (14)..(14)
<223> OTHER INFORMATION: Oxidized Met

<400> SEQUENCE: 26

Val Val Lys Ala Asp Ile Val Asn Tyr Asn Gln Glu Pro Met Ser Arg
1               5                   10                  15

<210> SEQ ID NO 27
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Ubiquitinated Lys

<400> SEQUENCE: 27

Ile Gly Trp Ser Leu Asp Ser Cys Ser Thr Gln Leu Gly Glu Glu Pro
```

```
                1               5                   10                  15
Phe Ser Tyr Gly Tyr Gly Gly Thr Gly Lys Lys
                20                  25

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ubiquitinated Lys

<400> SEQUENCE: 28

Tyr Gly Leu Thr Gly Lys Gln Gln Val Ser Pro Ile Arg
1               5                   10

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Ubiquitinated Lys

<400> SEQUENCE: 29

Ala Leu Pro His Leu Ile Gln Asp Ala Gly Gln Phe Tyr Ala Lys Tyr
1               5                   10                  15

Lys

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Ubiquitinated Lys
<220> FEATURE:
<221> NAME/KEY: MOD_RES
<222> LOCATION: (20)..(20)
<223> OTHER INFORMATION: Oxidized Met

<400> SEQUENCE: 30

Val Leu Thr Ser Gly Ile Phe Glu Thr Lys Phe Gln Val Asp Lys Val
1               5                   10                  15

Asn Phe His Met Phe Asp Val Gly Gly Gln Arg Asp Glu Arg
                20                  25                  30

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
```

```
<223> OTHER INFORMATION: Ubiquitinated Lys

<400> SEQUENCE: 31

Ala Ser Leu Glu Lys Ala Gly Lys
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ubiquitinated Lys

<400> SEQUENCE: 32

His Met Gly Ile Gly Lys Arg
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 33

Ala Met Glu Leu Leu Lys Val Ser Lys
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ubiquitinated Lys

<400> SEQUENCE: 34

Met Phe Ala Pro Thr Lys Thr Trp Arg
1               5

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ubiquitinated Lys

<400> SEQUENCE: 35

Glu Leu Lys Leu Leu Glu Ser Ile Phe His Arg
1               5                   10
```

```
<210> SEQ ID NO 36
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ubiquitinated Lys
<220> FEATURE:
<221> NAME/KEY: MOD_RES
<222> LOCATION: (23)..(23)
<223> OTHER INFORMATION: Oxidized Met

<400> SEQUENCE: 36

Asn Leu Val Ala His Gly Gln Ala Phe Ser Lys Pro Ile Leu Asp Leu
1               5                   10                  15

Gly Ala Glu Ala Leu Ile Met Gln Ala Arg
            20                  25

<210> SEQ ID NO 37
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: Ubiquitinated Lys

<400> SEQUENCE: 37

Ile Ser Val Asn Ser Asn Asn Val Gln Ser Leu Leu Asp Ala Ala Asn
1               5                   10                  15

Gln Tyr Gln Ile Glu Pro Val Lys Lys
            20                  25

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 38

Phe Cys Thr Ser Ala Ala Asp Met Lys Ile Arg
1               5                   10

<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ubiquitinated Lys

<400> SEQUENCE: 39
```

```
Val Val Thr Ser Ala Gln Gln Lys Ala Gly Arg
1               5                   10
```

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Oxidized Met
<220> FEATURE:
<221> NAME/KEY: MOD_RES
<222> LOCATION: (4)..(4)
<223> OTHER INFORMATION: Ubiquitinated Lys

<400> SEQUENCE: 40

```
Ile Met Leu Lys Gly Asp Asn Ile Thr Leu Leu Gln Ser Val Ser Asn
1               5                   10                  15
```

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys

<400> SEQUENCE: 41

```
Lys Ala Ser Ser Lys Gly Pro Lys
1               5
```

<210> SEQ ID NO 42
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ubiquitinated Lys

<400> SEQUENCE: 42

```
Ala Tyr Gln Asp Tyr Ile Leu Ala Asp Cys Lys Ala Ser Glu Val Gln
1               5                   10                  15
Glu Phe Thr Ala Glu Phe Leu Glu Lys
            20                  25
```

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 43

```
Met Lys Gly Asp Tyr His Arg
1               5

<210> SEQ ID NO 44
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ubiquitinated Lys

<400> SEQUENCE: 44

Glu Thr Thr Leu Ser Tyr Tyr Lys Ser Gln Asp Glu Ala Pro Gly Asp
1               5                   10                  15

Pro Ile Gln Gln Leu Asn Leu Lys
            20

<210> SEQ ID NO 45
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ubiquitinated Lys
<220> FEATURE:
<221> NAME/KEY: MOD_RES
<222> LOCATION: (17)..(17)
<223> OTHER INFORMATION: Oxidized Met

<400> SEQUENCE: 45

Gln Val Cys Glu Ile Ile Glu Ser Pro Leu Phe Leu Lys Leu Asn Pro
1               5                   10                  15

Met Thr Lys

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Oxidized Met
<220> FEATURE:
<221> NAME/KEY: MOD_RES
<222> LOCATION: (19)..(19)
<223> OTHER INFORMATION: Ubiquitinated Lys

<400> SEQUENCE: 46

Gln Val Cys Glu Ile Ile Glu Ser Pro Leu Phe Leu Lys Leu Asn Pro
1               5                   10                  15

Met Thr Lys

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (5)..(5)
<223> OTHER INFORMATION: Ubiquitinated Lys

<400> SEQUENCE: 47

Leu Met Ala Ala Lys Gln Lys
1               5

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ubiquitinated Lys

<400> SEQUENCE: 48

Ser Val Ala Val Asn Pro Lys Glu Ile Ala Ser Lys
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys

<400> SEQUENCE: 49

Lys Ile Gln Glu Gln Asp Ile Ile Asn Phe Arg
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 50

Ser Ala Val Glu Asp Glu Gly Leu Lys Gly Lys
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ubiquitinated Lys

<400> SEQUENCE: 51
```

```
Asp Ile Ser Glu Asn Lys Arg
1               5

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 52

Asp Asn Arg Gly Gly Ile Lys Ser Lys
1               5

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (27)..(27)
<223> OTHER INFORMATION: Ubiquitinated Lys

<400> SEQUENCE: 53

Ile Phe Tyr Pro Glu Ile Glu Glu Val Gln Ala Leu Asp Asp Thr Glu
1               5                   10                  15

Arg Gly Ser Gly Gly Phe Gly Ser Thr Gly Lys Asn
            20                  25

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys

<400> SEQUENCE: 54

Lys Gly Asn Tyr Ala Glu Arg
1               5

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys

<400> SEQUENCE: 55

Lys Thr Ser Ala Thr Val Gly Pro Lys
1               5
```

```
<210> SEQ ID NO 56
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ubiquitinated Lys

<400> SEQUENCE: 56

Thr Leu Glu Gly Glu Leu His Asp Leu Arg Gly Gln Val Ala Lys Leu
1               5                   10                  15

Glu Ala Ala Leu Gly Glu Ala Lys
            20

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys

<400> SEQUENCE: 57

Lys Leu Glu Ser Thr Glu Ser Arg
1               5

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ubiquitinated Lys

<400> SEQUENCE: 58

Asp Val Asn Ala Ala Ile Ala Thr Ile Lys Thr Lys
1               5                   10

<210> SEQ ID NO 59
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ubiquitinated Lys
<220> FEATURE:
<221> NAME/KEY: MOD_RES
<222> LOCATION: (13)..(13)
<223> OTHER INFORMATION: Oxidized Met

<400> SEQUENCE: 59

Leu Thr Glu Gln Pro Glu Leu Ala Asn Lys Val Asp Met Val Trp Ile
1               5                   10                  15
```

```
Val Gly Gly Ser Ser Val Tyr Lys
            20

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ubiquitinated Lys

<400> SEQUENCE: 60

Glu Val Asp Asp Leu Gly Pro Glu Val Gly Asp Ile Lys Ile Ile Pro
1               5                   10                  15

Leu Tyr Ser Thr Leu Pro Pro Gln Gln Gln Gln Arg
            20                  25

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ubiquitinated Lys

<400> SEQUENCE: 61

Leu Leu Leu Pro His Trp Ala Lys Val Val Leu Thr Asp Pro Glu Ala
1               5                   10                  15

Ala Lys

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ubiquitinated Lys

<400> SEQUENCE: 62

Asn Thr Gly Lys Ser Ile Ala Asn Lys
1               5

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ubiquitinated Lys

<400> SEQUENCE: 63

Cys Gly Leu Pro Tyr Val Glu Val Leu Cys Lys Asn Arg
1               5                   10
```

```
<210> SEQ ID NO 64
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ubiquitinated Lys

<400> SEQUENCE: 64

Gly Gln Gln Lys Thr Val
1               5

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ubiquitinated Lys

<400> SEQUENCE: 65

Val Leu Lys Tyr His Leu Leu Leu Gln Glu Leu Val Lys
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ubiquitinated Lys

<400> SEQUENCE: 66

Ile Asp Gly Glu Leu Lys Ile Thr Ser Val Glu Arg
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 67

Val Leu Thr Ser Glu Gln Lys Ala Lys
1               5

<210> SEQ ID NO 68
<211> LENGTH: 14
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Ubiquitinated Lys

<400> SEQUENCE: 68

Ala Asp Asp Gly Arg Pro Phe Pro Gln Val Ile Lys Ser Lys
1               5                   10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ubiquitinated Lys

<400> SEQUENCE: 69

Ala Phe Gly Gly Gln Ser Leu Lys Phe Gly Lys
1               5                   10

<210> SEQ ID NO 70
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Ubiquitinated Lys

<400> SEQUENCE: 70

Ala Ile Thr Val Phe Ser Pro Asp Gly His Leu Phe Gln Val Glu Tyr
1               5                   10                  15

Ala Gln Glu Ala Val Lys Lys
            20

<210> SEQ ID NO 71
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Ubiquitinated Lys

<400> SEQUENCE: 71

Ala Ile Thr Val Phe Ser Pro Asp Gly His Leu Phe Gln Val Glu Tyr
1               5                   10                  15

Ala Gln Glu Ala Val Lys Lys
            20

<210> SEQ ID NO 72
<211> LENGTH: 21
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (11)..(11)
<223> OTHER INFORMATION: Ubiquitinated Lys

<400> SEQUENCE: 72

Cys Pro Ile Pro Ala Phe Pro Asp Ser Val Lys Pro Glu Lys Pro Leu
1               5                   10                  15

Ala Ala Ser Val Arg
            20

<210> SEQ ID NO 73
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Ubiquitinated Lys

<400> SEQUENCE: 73

Asn Ile Leu Glu Glu Ser Leu Cys Glu Leu Val Ala Lys Gln Leu Lys
1               5                   10                  15

<210> SEQ ID NO 74
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Ubiquitinated Lys

<400> SEQUENCE: 74

Gly His Asp Glu Arg Glu His Pro Phe Leu Val Lys Gly Gly Glu Asp
1               5                   10                  15

Leu Arg

<210> SEQ ID NO 75
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(26)
<223> OTHER INFORMATION: Ubiquitinated Lys

<400> SEQUENCE: 75

Ile Gly Trp Ser Leu Asp Ser Cys Ser Thr Gln Leu Gly Glu Glu Pro
1               5                   10                  15

Phe Ser Tyr Gly Tyr Gly Gly Thr Gly Lys Lys
            20                  25

<210> SEQ ID NO 76
<211> LENGTH: 18
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Ubiquitinated Lys

<400> SEQUENCE: 76

Leu Val Val Pro Ala Ser Gln Cys Gly Ser Leu Ile Gly Lys Gly Gly
1               5                   10                  15

Cys Lys

<210> SEQ ID NO 77
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Ubiquitinated Lys

<400> SEQUENCE: 77

Val Ala Glu Thr Ala Asn Glu Glu Glu Val Lys Lys
1               5                   10

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ubiquitinated Lys

<400> SEQUENCE: 78

Val Leu Ala Gly Lys Ser Lys
1               5

<210> SEQ ID NO 79
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Oxidized Met
<220> FEATURE:
<221> NAME/KEY: MOD_RES
<222> LOCATION: (19)..(19)
<223> OTHER INFORMATION: Ubiquitinated Lys

<400> SEQUENCE: 79

Ile Gly Val Gly Ala Met Thr Trp Ser Pro Leu Ala Cys Gly Ile Val
1               5                   10                  15

Ser Gly Lys Tyr Asp Ser Gly Ile Pro Pro Tyr Ser Arg
                20                  25

<210> SEQ ID NO 80
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ubiquitinated Lys

<400> SEQUENCE: 80

Asp Lys Pro Ile Asp Ile Ser Gln Leu Thr Lys Gln Arg
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ubiquitinated Lys

<400> SEQUENCE: 81

Val Cys Lys Asn Asp Val Gly Gly Glu Lys
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 82

Phe Gln Ala Leu Gln Asp Asn Cys Lys Lys
1               5                   10

<210> SEQ ID NO 83
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 83

Ile Lys Ser Glu His Pro Gly Leu Ser Ile Gly Asp Thr Ala Lys
1               5                   10                  15

<210> SEQ ID NO 84
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

<223> OTHER INFORMATION: Ubiquitinated Lys

<400> SEQUENCE: 84

Lys Lys Glu Val Asp Ala Thr Ser Pro Ala Pro Ser Thr Ser Ser Thr
1               5                   10                  15

Val Lys

<210> SEQ ID NO 85
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys

<400> SEQUENCE: 85

Lys Ile Leu Gly Gln Glu Gly Asp Ala Ser Tyr Leu Ala Ser Glu Ile
1               5                   10                  15

Ser Thr Trp Asp Gly Val Ile Val Thr Pro Ser Glu Lys
            20                  25

<210> SEQ ID NO 86
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ubiquitinated Lys

<400> SEQUENCE: 86

Gln Trp Leu Ile Asp Gln Ile Asp Ser Gly Lys Tyr Pro Gly Leu Val
1               5                   10                  15

Trp Glu Asn Glu Glu Lys
            20

<210> SEQ ID NO 87
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ubiquitinated Lys

<400> SEQUENCE: 87

Asn Ile Leu Phe Val Ile Thr Lys Pro Asp Val Tyr Lys Ser Pro Ala
1               5                   10                  15

Ser Asp Thr Tyr Ile Val Phe Gly Glu Ala Lys
            20                  25

<210> SEQ ID NO 88
<211> LENGTH: 36
<212> TYPE: PRT
<213> ORGANISM: Artificial Sequence
<220> FEATURE:
<223> OTHER INFORMATION: Description of Artificial Sequence: Synthetic -continued

```
      polypeptide
<220> FEATURE:
<221> NAME/KEY: MOD_RES
<222> LOCATION: (28)..(28)
<223> OTHER INFORMATION: Ubiquitinated Lys

<400> SEQUENCE: 88

Ser Ser Val Gly Glu Thr Val Tyr Gly Gly Ser Asp Glu Leu Ser Asp
1               5                   10                  15

Asp Ile Thr Gln Gln Gln Leu Leu Pro Gly Val Lys Asp Pro Asn Leu
            20                  25                  30

Trp Thr Val Lys
        35

<210> SEQ ID NO 89
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 89

Gly Lys Asp Val Glu Phe Pro Asn Asp Tyr Pro Ser Gly Cys Leu Leu
1               5                   10                  15

Gly Cys Val Asp Leu Ile Asp Cys Leu Ser Gln Lys
            20                  25

<210> SEQ ID NO 90
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Oxidized Met
<220> FEATURE:
<221> NAME/KEY: MOD_RES
<222> LOCATION: (28)..(28)
<223> OTHER INFORMATION: Oxidized Met
<220> FEATURE:
<221> NAME/KEY: MOD_RES
<222> LOCATION: (32)..(32)
<223> OTHER INFORMATION: Ubiquitinated Lys

<400> SEQUENCE: 90

Ile Gly Tyr Asn Pro Asp Thr Val Ala Phe Val Pro Ile Ser Gly Trp
1               5                   10                  15

Asn Gly Asp Asn Met Leu Glu Pro Ser Ala Asn Met Pro Trp Phe Lys
            20                  25                  30

Gly Trp Lys
        35

<210> SEQ ID NO 91
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MOD_RES
<222> LOCATION: (21)..(21)
<223> OTHER INFORMATION: Oxidized Met
<220> FEATURE:
<221> NAME/KEY: MOD_RES
<222> LOCATION: (28)..(28)
<223> OTHER INFORMATION: Oxidized Met
<220> FEATURE:
<221> NAME/KEY: MOD_RES
<222> LOCATION: (35)..(35)
<223> OTHER INFORMATION: Ubiquitinated Lys

<400> SEQUENCE: 91

Ile Gly Tyr Asn Pro Asp Thr Val Ala Phe Val Pro Ile Ser Gly Trp
1               5                   10                  15

Asn Gly Asp Asn Met Leu Glu Pro Ser Ala Asn Met Pro Trp Phe Lys
            20                  25                  30

Gly Trp Lys
        35

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ubiquitinated Lys

<400> SEQUENCE: 92

Ala Ala Gly Ala Gly Lys Val Thr Lys
1               5

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ubiquitinated Lys

<400> SEQUENCE: 93

Thr Leu Ser Lys Glu Glu Glu Thr Lys Lys
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 94

Thr Leu Ser Lys Glu Glu Glu Thr Lys Lys
1               5                   10

<210> SEQ ID NO 95
```

-continued

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ubiquitinated Lys

<400> SEQUENCE: 95

Thr Leu Ser Lys Glu Glu Glu Thr Lys Lys
1               5                   10

<210> SEQ ID NO 96
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ubiquitinated Lys

<400> SEQUENCE: 96

Leu Val Ser Lys His Arg
1               5

<210> SEQ ID NO 97
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (4)..(4)
<223> OTHER INFORMATION: Oxidized Met
<220> FEATURE:
<221> NAME/KEY: MOD_RES
<222> LOCATION: (17)..(17)
<223> OTHER INFORMATION: Ubiquitinated Lys
<220> FEATURE:
<221> NAME/KEY: MOD_RES
<222> LOCATION: (19)..(19)
<223> OTHER INFORMATION: Oxidized Met

<400> SEQUENCE: 97

Leu Lys Ala Met Asp Gln Glu Ile Thr Val Asn Pro Gln Phe Val Gln
1               5                   10                  15

Lys Ser Met Gly Ser Gln Glu Asp Asp Ser Gly Asn Lys Pro Ser Ser
            20                  25                  30

Tyr Ser

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ubiquitinated Lys

<400> SEQUENCE: 98
```

```
Ile Leu Lys Ala His Gly Glu Lys
1               5
```

<210> SEQ ID NO 99
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Ubiquitinated Lys

<400> SEQUENCE: 99

```
Ile Asp Leu Ala Val Leu Leu Gly Lys Thr Pro Ser Thr Met Glu Asn
1               5                   10                  15

Asp Ser Ser Asn Leu Asp Pro Ser Gln Ala Pro Ser Leu Ala Gln Pro
            20                  25                  30

Leu Val Phe Ser Asn Ser Lys
        35
```

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ubiquitinated Lys

<400> SEQUENCE: 100

```
Gly Thr Thr Val Thr Pro Asp Lys Arg
1               5
```

<210> SEQ ID NO 101
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 101

```
Ala Lys Ser Glu Glu Asn Thr Lys Glu Glu Lys Pro Asp Ser Lys
1               5                   10                  15
```

<210> SEQ ID NO 102
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ubiquitinated Lys

<400> SEQUENCE: 102

Val Leu Lys Gln Tyr Asp Tyr Asp Ser Ser Thr Ile Arg
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ubiquitinated Lys

<400> SEQUENCE: 103

Phe Val Tyr His Leu Ser Asp Leu Cys Lys Lys
1               5                   10

<210> SEQ ID NO 104
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 104

Ser His Thr Val Glu Lys Pro Tyr Lys Cys Glu Phe Cys Gly Arg
1               5                   10                  15

<210> SEQ ID NO 105
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 105

Glu Gly Asp Lys His Thr Leu Ser Lys Lys
1               5                   10

<210> SEQ ID NO 106
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ubiquitinated Lys

<400> SEQUENCE: 106

Lys Tyr Asp Thr Pro Lys Thr Lys
1               5

<210> SEQ ID NO 107
<211> LENGTH: 13
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 107

Ser Lys Ala Phe Asp Asp Ile Ala Thr Tyr Phe Ser Lys
1               5                   10

<210> SEQ ID NO 108
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 108

Leu Lys Val Val Pro Thr Thr Asp His Ile Asp Thr Glu Lys Leu Lys
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ubiquitinated Lys
<220> FEATURE:
<221> NAME/KEY: MOD_RES
<222> LOCATION: (13)..(13)
<223> OTHER INFORMATION: Oxidized Met

<400> SEQUENCE: 109

Arg Glu Pro Phe Ala Val Val Lys Thr Ala Ser Glu Met Glu Arg
1               5                   10                  15

<210> SEQ ID NO 110
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (17)..(17)
<223> OTHER INFORMATION: Ubiquitinated Lys
<220> FEATURE:
<221> NAME/KEY: MOD_RES
<222> LOCATION: (26)..(26)
<223> OTHER INFORMATION: Oxidized Met

<400> SEQUENCE: 110

Ala Leu Gln Gln Tyr Thr Leu Glu Pro Ser Glu Lys Pro Phe Asp Leu
1               5                   10                  15

Lys Ser Val Pro Leu Ala Thr Ala Pro Met Ala Glu Gln Arg
            20                  25                  30
```

```
<210> SEQ ID NO 111
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
<223> OTHER INFORMATION: Ubiquitinated Lys

<400> SEQUENCE: 111

Gly Lys Asp Ala Ala Ser Ser Thr Lys Val Asp Ala Ala Pro Gly Ile
1               5                   10                  15

Pro Pro Ala Val Glu Ser Ile Gln Asp Ser Pro Leu Pro Lys
            20                  25                  30

<210> SEQ ID NO 112
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Ubiquitinated Lys

<400> SEQUENCE: 112

Gly Lys Asp Ala Ala Ser Ser Thr Lys Val Asp Ala Ala Pro Gly Ile
1               5                   10                  15

Pro Pro Ala Val Glu Ser Ile Gln Asp Ser Pro Leu Pro Lys
            20                  25                  30

<210> SEQ ID NO 113
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 113

Leu Lys Thr Asn His Ile Gly His Thr Gly Tyr Leu Asn Thr Val Thr
1               5                   10                  15

Val Ser Pro Asp Gly Ser Leu Cys Ala Ser Gly Gly Lys
            20                  25

<210> SEQ ID NO 114
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Ubiquitinated Lys

<400> SEQUENCE: 114

Leu Leu His Pro Pro Ser His Trp Pro Leu Ile Lys Ala Thr Val Gly
```

```
1               5                   10                  15

Leu Ile Arg

<210> SEQ ID NO 115
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ubiquitinated Lys

<400> SEQUENCE: 115

Thr Tyr Asp Met Leu Lys Ala Gly Thr Thr Ala Thr Tyr Glu Gly Arg
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ubiquitinated Lys

<400> SEQUENCE: 116

Asn Leu Gly Thr Ile Ala Lys Ser Gly Thr Ser Glu Phe Leu Asn Lys
1               5                   10                  15

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 117

Lys Thr Glu Ser His Lys Pro Gly Lys Asn Lys
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ubiquitinated Lys

<400> SEQUENCE: 118

Lys Thr Glu Ser His Lys Pro Gly Lys Asn Lys
1               5                   10

<210> SEQ ID NO 119
<211> LENGTH: 20
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (20)..(20)
<223> OTHER INFORMATION: Ubiquitinated Lys

<400> SEQUENCE: 119

Gly Leu Ile Gly Tyr Val Leu Asp Thr Asp Phe Val Glu Ser Leu Pro
1               5                   10                  15

Val Lys Val Lys
            20

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ubiquitinated Lys

<400> SEQUENCE: 120

Ser Phe Glu Glu Lys Val Glu Asn Leu Lys
1               5                   10

<210> SEQ ID NO 121
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(22)
<223> OTHER INFORMATION: Oxidized Met
<220> FEATURE:
<221> NAME/KEY: MOD_RES
<222> LOCATION: (35)..(35)
<223> OTHER INFORMATION: Ubiquitinated Lys

<400> SEQUENCE: 121

Arg Tyr Cys Val Arg Pro Asn Ser Gly Ile Ile Asp Pro Gly Ser Thr
1               5                   10                  15

Val Thr Val Ser Val Met Leu Gln Pro Phe Asp Tyr Asp Pro Asn Glu
            20                  25                  30

Lys Ser Lys
        35

<210> SEQ ID NO 122
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ubiquitinated Lys
<220> FEATURE:
<221> NAME/KEY: MOD_RES
<222> LOCATION: (9)..(9)
```

<223> OTHER INFORMATION: Oxidized Met

<400> SEQUENCE: 122

Leu Leu Leu Asn Asn Gly Ala Lys Met Pro Ile Leu Gly Leu Gly Thr
1               5                   10                  15

Trp Lys

<210> SEQ ID NO 123
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Ubiquitinated Lys

<400> SEQUENCE: 123

Ser Ala Leu Thr Ala His Pro Val Arg Asp Pro Val His Met Tyr Gln
1               5                   10                  15

Leu His Lys Ala Phe Ala Arg
            20

<210> SEQ ID NO 124
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Oxidized Met
<220> FEATURE:
<221> NAME/KEY: MOD_RES
<222> LOCATION: (21)..(21)
<223> OTHER INFORMATION: Ubiquitinated Lys

<400> SEQUENCE: 124

Ala Thr Asn Glu Gly Leu Ser Leu Met Leu Ile Gly Pro Glu Asp Val
1               5                   10                  15

Ile Asn Phe Lys Lys
            20

<210> SEQ ID NO 125
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Ubiquitinated Lys

<400> SEQUENCE: 125

Asp Gly Leu Leu Glu Asn Gln Thr Pro Glu Phe Phe Gln Asp Val Cys
1               5                   10                  15

Lys Pro Lys

<210> SEQ ID NO 126
<211> LENGTH: 15
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys

<400> SEQUENCE: 126

Lys Ala Ala Leu Glu Gln Asp Leu Ala Phe Trp Tyr Gly Pro Arg
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Ubiquitinated Lys

<400> SEQUENCE: 127

Gln Leu Leu Pro Cys Glu Met Ala Cys Asn Glu Lys Leu Gly Lys
1               5                   10                  15

<210> SEQ ID NO 128
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ubiquitinated Lys

<400> SEQUENCE: 128

Ile Gly Glu Ala Thr Lys Pro Asp Gly Thr Val Glu Gln Ile Gly His
1               5                   10                  15

Ile Leu Val Ser Trp Leu Pro Arg
            20

<210> SEQ ID NO 129
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (19)..(19)
<223> OTHER INFORMATION: Ubiquitinated Lys

<400> SEQUENCE: 129

Lys Leu Glu Leu Ser Asp Asn Ile Ile Ser Gly Gly Leu Glu Val Leu
1               5                   10                  15

Ala Glu Lys Cys Pro Asn Leu Thr Tyr Leu Asn Leu Ser Gly Asn Lys
            20                  25                  30

<210> SEQ ID NO 130
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Ubiquitinated Lys

<400> SEQUENCE: 130

Ser Leu Asn Gln Tyr Pro Ala Leu Tyr Tyr Pro Glu Leu Tyr Ile Leu
1               5                   10                  15

Lys Gly Gly Tyr Arg
            20

<210> SEQ ID NO 131
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 131

Ala Lys Tyr Gln Tyr Gly Gly Leu Asn Ser Gly Arg Pro Val Thr Pro
1               5                   10                  15

Pro Arg

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Oxidized Met
<220> FEATURE:
<221> NAME/KEY: MOD_RES
<222> LOCATION: (14)..(14)
<223> OTHER INFORMATION: Ubiquitinated Lys

<400> SEQUENCE: 132

Met Cys Gly Thr Leu Pro Tyr Val Ala Pro Glu Leu Leu Lys Arg
1               5                   10                  15

<210> SEQ ID NO 133
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ubiquitinated Lys

<400> SEQUENCE: 133

Leu Phe Leu Ile Asp Phe Gly Leu Ala Lys Lys
1               5                   10

<210> SEQ ID NO 134
<211> LENGTH: 15
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Ubiquitinated Lys

<400> SEQUENCE: 134

Gly Thr Leu Ala Tyr Leu Pro Glu Glu Tyr Ile Lys Thr Gly Arg
1               5                   10                  15

<210> SEQ ID NO 135
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys
<220> FEATURE:
<221> NAME/KEY: MOD_RES
<222> LOCATION: (13)..(14)
<223> OTHER INFORMATION: Ubiquitinated Lys
<220> FEATURE:
<221> NAME/KEY: MOD_RES
<222> LOCATION: (19)..(19)
<223> OTHER INFORMATION: Ubiquitinated Lys

<400> SEQUENCE: 135

Lys Lys Asp Val Ser Ser Pro Gly Gly Ser Gly Gly Lys Lys Asn Ala
1               5                   10                  15

Ser Gln Lys

<210> SEQ ID NO 136
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Oxidized Met
<220> FEATURE:
<221> NAME/KEY: MOD_RES
<222> LOCATION: (30)..(30)
<223> OTHER INFORMATION: Ubiquitinated Lys

<400> SEQUENCE: 136

Val Asn Cys Tyr Met Pro Ala Asn Gly Glu Thr Val Thr Leu Pro Thr
1               5                   10                  15

Ser Pro Ser Ile Pro Val Gly Ile Ser Leu Gly Leu Leu Lys Arg
            20                  25                  30

<210> SEQ ID NO 137
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
```

<223> OTHER INFORMATION: Ubiquitinated Lys

<400> SEQUENCE: 137

Ser Asp Gly Gly Tyr Thr Tyr Asp Thr Ser Asp Leu Ala Ala Ile Lys
1               5                   10                  15

Gln Arg

<210> SEQ ID NO 138
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ubiquitinated Lys

<400> SEQUENCE: 138

Gln Ser Asn Pro Glu Phe Cys Pro Glu Lys Val Ala Leu Ala Glu Ala
1               5                   10                  15

<210> SEQ ID NO 139
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ubiquitinated Lys

<400> SEQUENCE: 139

Ser Glu Val Ile Lys Asn Asn Leu Asn Pro Thr Trp Lys
1               5                   10

<210> SEQ ID NO 140
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Ubiquitinated Lys

<400> SEQUENCE: 140

Ile Tyr Ser Leu Arg Glu Pro Gln Thr Pro Thr Asn Val Ile Ile Leu
1               5                   10                  15

Ser Glu Ala Glu Glu Glu Ser Leu Val Leu Asn Lys Gly Arg
                20                  25                  30

<210> SEQ ID NO 141
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ubiquitinated Lys -continued

<400> SEQUENCE: 141

Gln Glu Glu Asn Lys Ala Gly Leu Leu Asp Leu Pro Asp Ala Ser Val
1               5                   10                  15

Asn Gly Trp Ser Ser Asp Glu Glu Lys
            20                  25

<210> SEQ ID NO 142
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys
<220> FEATURE:
<221> NAME/KEY: MOD_RES
<222> LOCATION: (4)..(5)
<223> OTHER INFORMATION: Oxidized Met

<400> SEQUENCE: 142

Lys Ser Pro Met Met Pro Glu Asn Ala Glu Asn Glu Gly Asp Ala Leu
1               5                   10                  15

Leu Gln Phe Thr Ala Glu Phe Ser Ser Arg
            20                  25

<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ubiquitinated Lys

<400> SEQUENCE: 143

Ile Thr Gly Asp Ala Phe Lys Val Gln Gln Ala Arg
1               5                   10

<210> SEQ ID NO 144
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Oxidized Met
<220> FEATURE:
<221> NAME/KEY: MOD_RES
<222> LOCATION: (16)..(16)
<223> OTHER INFORMATION: Ubiquitinated Lys

<400> SEQUENCE: 144

Leu Ala Gly Pro Gln Leu Val Gln Met Phe Ile Gly Asp Gly Ala Lys
1               5                   10                  15

Leu Val Arg

<210> SEQ ID NO 145
<211> LENGTH: 12
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ubiquitinated Lys

<400> SEQUENCE: 145

Ala Ser Leu Ile Ser Ala Val Ser Asp Lys Leu Arg
1               5                   10

<210> SEQ ID NO 146
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Ubiquitinated Lys

<400> SEQUENCE: 146

Ala Asp Ile Glu Val Ala Cys Tyr Gly Tyr Glu Gly Ile Asp Ala Val
1               5                   10                  15

Lys Glu Ala Leu Arg
            20

<210> SEQ ID NO 147
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys

<400> SEQUENCE: 147

Lys Phe Leu Asp Gly Ile Tyr Val Ser Glu Lys
1               5                   10

<210> SEQ ID NO 148
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ubiquitinated Lys

<400> SEQUENCE: 148

Ala Glu Asp Lys Glu Trp Met Pro Val Thr Lys
1               5                   10

<210> SEQ ID NO 149
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (6)..(6)
<223> OTHER INFORMATION: Ubiquitinated Lys

<400> SEQUENCE: 149

Cys Ile Asn Ile Thr Lys Gln Thr Pro Ser Phe Trp Ile Leu Ala Arg
1               5                   10                  15

<210> SEQ ID NO 150
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Ubiquitinated Lys

<400> SEQUENCE: 150

Lys Pro Asp Leu Arg Ile Ile Glu Gln Glu Glu Lys
1               5                   10

<210> SEQ ID NO 151
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Oxidized Met
<220> FEATURE:
<221> NAME/KEY: MOD_RES
<222> LOCATION: (22)..(22)
<223> OTHER INFORMATION: Ubiquitinated Lys

<400> SEQUENCE: 151

Leu Glu Val Ala Ala Ala Pro Gly Thr Pro Ala Gln Pro Val Ala Met
1               5                   10                  15

Ser Leu Ser Ala Asp Lys Phe Gln Val Leu Leu Ala Glu Leu Lys
            20                  25                  30

<210> SEQ ID NO 152
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Ubiquitinated Lys

<400> SEQUENCE: 152

Gly Ala Leu Leu Asp Val Cys Val Glu Gln Gly Lys Ser Cys His Ser
1               5                   10                  15

Val Gly Gln Leu Ala Leu Asp Pro Ser Leu Val Pro Thr Phe
            20                  25                  30

<210> SEQ ID NO 153
<211> LENGTH: 14
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ubiquitinated Lys

<400> SEQUENCE: 153

Thr Pro Val Phe Ser Phe Leu Asp Leu Thr Tyr Trp Lys Arg
1               5                   10

<210> SEQ ID NO 154
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ubiquitinated Lys

<400> SEQUENCE: 154

Gly Tyr Glu Gln Phe Ala Tyr Asp Gly Lys Asp Tyr Leu Thr Leu Asn
1               5                   10                  15

Glu Asp Leu Arg
            20

<210> SEQ ID NO 155
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ubiquitinated Lys
<220> FEATURE:
<221> NAME/KEY: MOD_RES
<222> LOCATION: (10)..(10)
<223> OTHER INFORMATION: Oxidized Met

<400> SEQUENCE: 155

Ala Arg Glu Pro Val Thr Lys Ala Glu Met Leu Gly Ser Val Val Gly
1               5                   10                  15

Asn Trp Gln Tyr Phe Phe Pro Val Ile Phe Ser Lys
            20                  25

<210> SEQ ID NO 156
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 156

Ile Lys Ala Asp Pro Asp Gly Pro Glu Ala Gln Ala Glu Ala Cys Ser
1               5                   10                  15

Gly Glu Arg
```

```
<210> SEQ ID NO 157
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ubiquitinated Lys

<400> SEQUENCE: 157

Leu Trp Thr Ile Lys Asn Asn Glu Cys Val Arg
1               5                   10

<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ubiquitinated Lys

<400> SEQUENCE: 158

Gln Met Asn Asp Glu Lys Thr Ala Ala Asp Tyr Lys
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ubiquitinated Lys

<400> SEQUENCE: 159

Tyr Leu Ala Glu Val Ala Ala Gly Asp Asp Lys Lys
1               5                   10

<210> SEQ ID NO 160
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Oxidized Met
<220> FEATURE:
<221> NAME/KEY: MOD_RES
<222> LOCATION: (14)..(14)
<223> OTHER INFORMATION: Ubiquitinated Lys

<400> SEQUENCE: 160

Ser Gln Pro Pro Tyr Asn Pro Ala Tyr Met Asp Ala Pro Lys Ala Ala
1               5                   10                  15

Leu
```

```
<210> SEQ ID NO 161
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ubiquitinated Lys

<400> SEQUENCE: 161

Gly Thr Leu Val Gln Thr Lys Gly Thr Gly Ala Ser Gly Ser Phe Lys
1               5                   10                  15

<210> SEQ ID NO 162
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Ubiquitinated Lys

<400> SEQUENCE: 162

Leu Ile Tyr Ser Gly Lys Gln Met Asn Asp Glu Lys
1               5                   10

<210> SEQ ID NO 163
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys
<220> FEATURE:
<221> NAME/KEY: MOD_RES
<222> LOCATION: (5)..(5)
<223> OTHER INFORMATION: Ubiquitinated Lys

<400> SEQUENCE: 163

Lys Ile Gln Asp Lys Glu Gly Ile Pro Pro Asp Gln Gln Arg
1               5                   10

<210> SEQ ID NO 164
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ubiquitinated Lys
<220> FEATURE:
<221> NAME/KEY: MOD_RES
<222> LOCATION: (10)..(10)
<223> OTHER INFORMATION: Oxidized Met

<400> SEQUENCE: 164

Phe Ile Ile Asp Asn Thr Lys Gly Gln Met Leu Gly Leu Gly Asn Pro
1               5                   10                  15
```

Ser Phe Ser Asp Pro Phe Thr Gly Gly Gly Arg
            20                  25

<210> SEQ ID NO 165
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 165

Ala Cys Gly Gln Ile Phe Cys Gly Lys Cys Ser Ser Lys
1               5                   10

<210> SEQ ID NO 166
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ubiquitinated Lys

<400> SEQUENCE: 166

Ala Cys Gly Gln Ile Phe Cys Gly Lys Cys Ser Ser Lys
1               5                   10

<210> SEQ ID NO 167
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ubiquitinated Lys

<400> SEQUENCE: 167

Val Gly Gln Gly Tyr Pro His Asp Pro Pro Lys Val Lys
1               5                   10

<210> SEQ ID NO 168
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ubiquitinated Lys

<400> SEQUENCE: 168

Val Gly Gln Gly Tyr Pro His Asp Pro Pro Lys Val Lys
1               5                   10

<210> SEQ ID NO 169
<211> LENGTH: 10
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ubiquitinated Lys

<400> SEQUENCE: 169

Gly Asp Lys Glu Glu Leu Thr Pro Gln Lys
1               5                   10

<210> SEQ ID NO 170
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Oxidized Met
<220> FEATURE:
<221> NAME/KEY: MOD_RES
<222> LOCATION: (3)..(3)
<223> OTHER INFORMATION: Ubiquitinated Lys

<400> SEQUENCE: 170

Ala Met Lys Gly Phe Gly Thr Asp Glu Gln Ala Ile Val Asp Val Val
1               5                   10                  15

Ala Asn Arg

<210> SEQ ID NO 171
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Ubiquitinated Lys
<220> FEATURE:
<221> NAME/KEY: MOD_RES
<222> LOCATION: (18)..(18)
<223> OTHER INFORMATION: Ubiquitinated Lys

<400> SEQUENCE: 171

Asn Lys Met Leu Gly Thr Ser Ser Lys Glu Ser Glu Glu Leu Leu Lys
1               5                   10                  15

Ser Lys

<210> SEQ ID NO 172
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Oxidized Met
<220> FEATURE:
<221> NAME/KEY: MOD_RES
<222> LOCATION: (26)..(26)
<223> OTHER INFORMATION: Ubiquitinated Lys
```

```
<400> SEQUENCE: 172

Ile Phe Gly Gly Leu Asp Met Leu Ala Glu Lys Leu Pro Asn Leu Thr
1               5                   10                  15

His Leu Asn Leu Ser Gly Asn Lys Leu Lys
            20                  25

<210> SEQ ID NO 173
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys
<220> FEATURE:
<221> NAME/KEY: MOD_RES
<222> LOCATION: (14)..(14)
<223> OTHER INFORMATION: Oxidized Met

<400> SEQUENCE: 173

Phe Phe Phe Asp Val Gly Ser Asn Lys Tyr Gly Val Phe Met Arg
1               5                   10                  15

<210> SEQ ID NO 174
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ubiquitinated Lys

<400> SEQUENCE: 174

Lys Ala Phe Glu Glu Ala Glu Lys Asn Ala Pro Ala Ile Ile Phe Ile
1               5                   10                  15

Asp Glu Leu Asp Ala Ile Ala Pro Lys Arg
            20                  25

<210> SEQ ID NO 175
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Ubiquitinated Lys

<400> SEQUENCE: 175

Glu Leu Gln Glu Leu Val Gln Tyr Pro Val Glu His Pro Asp Lys Phe
1               5                   10                  15

Leu Lys

<210> SEQ ID NO 176
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Ubiquitinated Lys

<400> SEQUENCE: 176

Asp Ile Lys Glu Lys Leu Cys Tyr Val Ala Leu Asp Phe Glu Gln Glu
1               5                   10                  15

Met Ala Thr Ala Ala Ser Ser Ser Leu Glu Lys
            20                  25

<210> SEQ ID NO 177
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Oxidized Met
<220> FEATURE:
<221> NAME/KEY: MOD_RES
<222> LOCATION: (8)..(8)
<223> OTHER INFORMATION: Ubiquitinated Lys

<400> SEQUENCE: 177

Gln Glu Met Leu Leu Ser Leu Lys Pro Ser Glu Ala Pro Glu Leu Asp
1               5                   10                  15

Glu Asp Glu Gly Phe Gly Asp Trp Ser Gln Arg Pro Glu Gln Arg
            20                  25                  30

<210> SEQ ID NO 178
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 178

Thr Ser Leu Ser Phe Gln Asp Pro Lys Leu Glu Leu Gln Phe Pro Arg
1               5                   10                  15

<210> SEQ ID NO 179
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Ubiquitinated Lys

<400> SEQUENCE: 179

Phe Pro Ser Ser Gly Pro Val Thr Pro Gln Pro Thr Ala Leu Thr Phe
1               5                   10                  15

Ala Lys Ser Ser Trp Ala Arg
            20

<210> SEQ ID NO 180
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ubiquitinated Lys

<400> SEQUENCE: 180

Gly Tyr Ala Trp Gly Leu Asn Glu Leu Lys Pro Ile Ser Lys
1               5                   10

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys

<400> SEQUENCE: 181

Lys Gly Ser Gly Pro Ala Ala Leu Arg
1               5

<210> SEQ ID NO 182
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Oxidized Met
<220> FEATURE:
<221> NAME/KEY: MOD_RES
<222> LOCATION: (32)..(32)
<223> OTHER INFORMATION: Ubiquitinated Lys

<400> SEQUENCE: 182

Tyr Cys Val Arg Pro Asn Ser Gly Ile Ile Asp Pro Gly Ser Thr Val
1               5                   10                  15

Thr Val Ser Val Met Leu Gln Pro Phe Asp Tyr Asp Pro Asn Glu Lys
            20                  25                  30

Ser Lys

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 183

Val Ser Phe Glu Leu Phe Ala Asp Lys Val Pro Lys
1               5                   10
```

<210> SEQ ID NO 184
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (19)..(19)
<223> OTHER INFORMATION: Ubiquitinated Lys

<400> SEQUENCE: 184

Glu Leu Ala Ser Gln Pro Asp Val Asp Gly Phe Leu Val Gly Gly Ala
1               5                   10                  15

Ser Leu Lys Pro Glu Phe Val Asp Ile Ile Asn Ala Lys Gln
            20                  25                  30

<210> SEQ ID NO 185
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Ubiquitinated Lys

<400> SEQUENCE: 185

Lys Gln Ser Leu Gly Glu Leu Ile Gly Thr Leu Asn Ala Ala Lys Val
1               5                   10                  15

Pro Ala Asp Thr Glu Val Val Cys Ala Pro Pro Thr Ala Tyr Ile Asp
            20                  25                  30

Phe Ala Arg
        35

<210> SEQ ID NO 186
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ubiquitinated Lys

<400> SEQUENCE: 186

Val Asp Lys Gly Val Val Pro Leu Ala Gly Thr Asn Gly Glu Thr Thr
1               5                   10                  15

Thr Gln Gly Leu Asp Gly Leu Ser Glu Arg
            20                  25

<210> SEQ ID NO 187
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Ubiquitinated Lys

```
<400> SEQUENCE: 187

Phe Thr Gly Ala Pro Leu Lys Val His Lys Ile Ser Asn Pro Trp Gln
1               5                   10                  15

Ser Pro Ser Gly Thr Leu Pro Ala Leu Arg
            20                  25

<210> SEQ ID NO 188
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (29)..(29)
<223> OTHER INFORMATION: Ubiquitinated Lys

<400> SEQUENCE: 188

Thr Gln Ile Ala Pro Gly Ser Gln Thr Val Leu Gly Ile Gly Pro Gly
1               5                   10                  15

Pro Ala Asp Leu Ile Asp Lys Val Thr Gly His Leu Lys Leu Tyr
            20                  25                  30

<210> SEQ ID NO 189
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ubiquitinated Lys

<400> SEQUENCE: 189

Val Phe Asp Lys Glu Gly Asn Gly Thr Val Met Gly Ala Glu Ile Arg
1               5                   10                  15

<210> SEQ ID NO 190
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 190

His Leu Thr Glu Tyr Phe Thr Phe Lys Gln Glu Cys Lys
1               5                   10

<210> SEQ ID NO 191
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Ubiquitinated Lys

<400> SEQUENCE: 191
```

```
Ser Gln Ala Thr Gly Phe Pro Ser Leu Ile Thr Ile Phe Ser Ala Pro
1               5                   10                  15

Asn Tyr Leu Asp Val Tyr Asn Asn Lys Ala Ala Val Leu Lys
            20                  25                  30
```

<210> SEQ ID NO 192
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (16)..(16)
<223> OTHER INFORMATION: Ubiquitinated Lys

<400> SEQUENCE: 192

```
Thr Leu Ala Glu His Gln Gln Leu Ile Pro Leu Val Glu Lys Ala Lys
1               5                   10                  15
```

<210> SEQ ID NO 193
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ubiquitinated Lys

<400> SEQUENCE: 193

```
Gly Pro Ser Thr Pro Asn Val Lys Asn Ser Asn Tyr Cys Leu Pro Ser
1               5                   10                  15

Tyr Thr Ala Tyr Lys
            20
```

<210> SEQ ID NO 194
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys
<220> FEATURE:
<221> NAME/KEY: MOD_RES
<222> LOCATION: (17)..(17)
<223> OTHER INFORMATION: Ubiquitinated Lys
<220> FEATURE:
<221> NAME/KEY: MOD_RES
<222> LOCATION: (25)..(25)
<223> OTHER INFORMATION: Oxidized Met

<400> SEQUENCE: 194

```
Lys Pro Glu Pro His Gln Pro Gly Pro Gly Ser Thr Gly Ile Pro His
1               5                   10                  15

Lys Glu Asp Pro Leu Met Leu Asp Met Val Arg
            20                  25
```

<210> SEQ ID NO 195
<211> LENGTH: 22
<212> TYPE: PRT

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Ubiquitinated Lys

<400> SEQUENCE: 195

Lys Thr Thr Gln Ser Gly Gln Met Ser Gly Glu Gly Lys Ala Gly Pro
1               5                   10                  15

Pro Gly Gly Ser Ser Arg
            20

<210> SEQ ID NO 196
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 196

Ile Lys Ala Leu Leu Glu Arg
1               5

<210> SEQ ID NO 197
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Oxidized Met
<220> FEATURE:
<221> NAME/KEY: MOD_RES
<222> LOCATION: (29)..(29)
<223> OTHER INFORMATION: Ubiquitinated Lys

<400> SEQUENCE: 197

Ser Thr Asn Gln Gln Thr Ala Thr Asp Val Ser Thr Ser Ser Asn Ile
1               5                   10                  15

Glu Glu Ser Val Asn His Met Asp Gly Glu Ser Leu Lys Leu Arg
            20                  25                  30

<210> SEQ ID NO 198
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 198

Val Val Cys Asp Glu Asn Gly Ser Lys Gly Tyr Gly Phe Val His Phe
1               5                   10                  15

Glu Thr Gln Glu Ala Ala Glu Arg
```

```
<210> SEQ ID NO 199
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ubiquitinated Lys

<400> SEQUENCE: 199

Ser Thr Ala Leu Lys Ile Leu Ala Gly Lys
1               5                   10

<210> SEQ ID NO 200
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys

<400> SEQUENCE: 200

Lys Gly Ser Met Ser Asp Ser Ala Asn Ile Leu Asp Glu Val Pro Phe
1               5                   10                  15

Pro Ala Arg

<210> SEQ ID NO 201
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Ubiquitinated Lys

<400> SEQUENCE: 201

Thr Ala Glu Pro Ala Glu Ser Ser Val Pro Pro Val Thr Ser Ile Gly
1               5                   10                  15

Ile Asp Asn Leu Gly Leu Lys Leu Glu Glu Asn Leu Gln Glu Thr His
            20                  25                  30

Ser Ala Val Leu
        35

<210> SEQ ID NO 202
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (25)..(25)
<223> OTHER INFORMATION: Oxidized Met
<220> FEATURE:
<221> NAME/KEY: MOD_RES
<222> LOCATION: (32)..(32)
```

```
<223> OTHER INFORMATION: Ubiquitinated Lys

<400> SEQUENCE: 202

Lys His Asn Leu Gly Ile Asn Asn Asn Ile Leu Gln Pro Val Asp
1               5                   10                  15

Ser Lys Ile Gln Glu Ile Glu Tyr Met Glu Asn His Ile Asn Ser Lys
            20                  25                  30

<210> SEQ ID NO 203
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Ubiquitinated Lys

<400> SEQUENCE: 203

Cys Phe Thr Cys Gly Lys Ile Val Gly Asn Lys Trp Glu Ala Tyr Leu
1               5                   10                  15

Gly Leu Leu Gln Ala Glu Tyr Thr Glu Gly Asp Ala Leu Asp Ala Leu
            20                  25                  30

Gly Leu Lys Arg
        35

<210> SEQ ID NO 204
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 204

Ala Gln Ile Asp Pro Val Leu Leu Lys Asn Ser Ser Gln Gln Asp Asn
1               5                   10                  15

Ser Ser Arg

<210> SEQ ID NO 205
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 205

Met Lys Glu Ser Pro Gly Ser Gln Gln Cys Cys Gln Glu Ser Glu Val
1               5                   10                  15

Leu Glu Arg

<210> SEQ ID NO 206
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 206

Asp Lys Leu Ala Gln Gln Gln Ala Ala Ala Ala Ala Ala Ala Ala
1               5                   10                  15

Ala Ala Ser Gln Gln Gly Ser Ala Lys
            20                  25

<210> SEQ ID NO 207
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (9)..(9)
<223> OTHER INFORMATION: Oxidized Met
<220> FEATURE:
<221> NAME/KEY: MOD_RES
<222> LOCATION: (12)..(12)
<223> OTHER INFORMATION: Ubiquitinated Lys
<220> FEATURE:
<221> NAME/KEY: MOD_RES
<222> LOCATION: (31)..(31)
<223> OTHER INFORMATION: Ubiquitinated Lys

<400> SEQUENCE: 207

Lys Ser Glu Ile Glu Tyr Tyr Ala Met Leu Ala Lys Thr Gly Val His
1               5                   10                  15

His Tyr Ser Gly Asn Asn Ile Glu Leu Gly Thr Ala Cys Gly Lys Tyr
            20                  25                  30

Tyr Arg

<210> SEQ ID NO 208
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Oxidized Met
<220> FEATURE:
<221> NAME/KEY: MOD_RES
<222> LOCATION: (11)..(11)
<223> OTHER INFORMATION: Ubiquitinated Lys

<400> SEQUENCE: 208

Gln Phe Met Ile Phe Thr Gln Ser Ser Glu Lys Thr Ala Val Ser Cys
1               5                   10                  15

Leu Ser Gln Asn Asp Trp Lys
            20

<210> SEQ ID NO 209
<211> LENGTH: 18
<212> TYPE: PRT
<213> ORGANISM: Artificial Sequence
<220> FEATURE:
<223> OTHER INFORMATION: Description of Artificial Sequence: Synthetic
```

```
                          peptide
<220> FEATURE:
<221> NAME/KEY: MOD_RES
<222> LOCATION: (18)..(18)
<223> OTHER INFORMATION: Ubiquitinated Lys

<400> SEQUENCE: 209

Glu Asn Trp Leu Pro Glu Asp Lys Gly Lys Asp Lys Gly Glu Ile Ser
1               5                   10                  15

Glu Lys

<210> SEQ ID NO 210
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (19)..(19)
<223> OTHER INFORMATION: Ubiquitinated Lys

<400> SEQUENCE: 210

Ser Ser Glu Asp Ala Thr Asp Asp Ile Ser Ser Gly Asn Ile Pro Val
1               5                   10                  15

Leu Gln Lys Asp Lys Asp Asn Thr Asn Val Asn Ala Asp Val Gln Lys
            20                  25                  30

<210> SEQ ID NO 211
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (21)..(21)
<223> OTHER INFORMATION: Ubiquitinated Lys

<400> SEQUENCE: 211

Ser Ser Glu Asp Ala Thr Asp Asp Ile Ser Ser Gly Asn Ile Pro Val
1               5                   10                  15

Leu Gln Lys Asp Lys Asp Asn Thr Asn Val Asn Ala Asp Val Gln Lys
            20                  25                  30

<210> SEQ ID NO 212
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (19)..(19)
<223> OTHER INFORMATION: Ubiquitinated Lys

<400> SEQUENCE: 212

Ser Thr Asp Ser Gln Cys Gly Thr Val Ile Asp Val Asn Ile Asp Cys
1               5                   10                  15

Ala Val Lys Leu Ile Gly Thr Asn Cys Ile Ile Tyr Pro Val Asn Ser
            20                  25                  30

Lys
```

```
<210> SEQ ID NO 213
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Oxidized Met
<220> FEATURE:
<221> NAME/KEY: MOD_RES
<222> LOCATION: (9)..(9)
<223> OTHER INFORMATION: Ubiquitinated Lys

<400> SEQUENCE: 213

Leu Thr Leu Asp Leu Met Lys Pro Lys
1               5

<210> SEQ ID NO 214
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ubiquitinated Lys

<400> SEQUENCE: 214

Gln Lys Thr Glu Asp Glu Val Leu Thr Ser Lys Gly Asp Ala Trp Ala
1               5                   10                  15

Lys

<210> SEQ ID NO 215
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (17)..(17)
<223> OTHER INFORMATION: Ubiquitinated Lys

<400> SEQUENCE: 215

Gln Lys Thr Glu Asp Glu Val Leu Thr Ser Lys Gly Asp Ala Trp Ala
1               5                   10                  15

Lys

<210> SEQ ID NO 216
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Ubiquitinated Lys

<400> SEQUENCE: 216

Leu Ala Gly Lys Asp Ser Glu Ile Thr Ala Asn Ala Leu Lys
1               5                   10
```

<210> SEQ ID NO 217
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ubiquitinated Lys

<400> SEQUENCE: 217

Lys Pro Val Ala Gly Ala Leu Asp Val Ser Phe Asn Lys Phe Ile Pro
1               5                   10                  15

Leu Ser Glu Pro Ala Pro Val Pro Pro Ile Pro Asn Glu Gln Gln Leu
            20                  25                  30

Ala Arg

<210> SEQ ID NO 218
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys

<400> SEQUENCE: 218

Lys Leu Tyr Ser Ser Glu Gln Leu Leu Ile Glu Glu Cys
1               5                   10

<210> SEQ ID NO 219
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Ubiquitinated Lys

<400> SEQUENCE: 219

Ser Val Leu Thr Gly Gly Leu Asp Ala Leu Glu Phe Ile Gly Lys
1               5                   10                  15

<210> SEQ ID NO 220
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ubiquitinated Lys

<400> SEQUENCE: 220

Ala Met Gln Gln Gln Val Gln Lys Leu Lys
1               5                   10

<210> SEQ ID NO 221

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 221

Gly Ala Val Thr Gly Ser Val Glu Lys Thr Lys
1               5                   10

<210> SEQ ID NO 222
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ubiquitinated Lys

<400> SEQUENCE: 222

Gly Ala Val Thr Gly Ser Val Glu Lys Thr Lys
1               5                   10

<210> SEQ ID NO 223
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Oxidized Met
<220> FEATURE:
<221> NAME/KEY: MOD_RES
<222> LOCATION: (7)..(7)
<223> OTHER INFORMATION: Oxidized Met
<220> FEATURE:
<221> NAME/KEY: MOD_RES
<222> LOCATION: (8)..(8)
<223> OTHER INFORMATION: Ubiquitinated Lys

<400> SEQUENCE: 223

Met Val Leu Leu Pro Val Met Lys Phe Pro Thr Tyr Pro Val Pro His
1               5                   10                  15

Tyr Ser Phe Phe
            20

<210> SEQ ID NO 224
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ubiquitinated Lys

<400> SEQUENCE: 224

Met Val Lys Val Asp Pro Glu Thr Arg
```

<210> SEQ ID NO 225
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ubiquitinated Lys

<400> SEQUENCE: 225

Asn Leu Gln Ser Glu Val Glu Gly Val Lys Asn Ile Met Thr Gln Asn
1               5                   10                  15

Val Glu Arg

<210> SEQ ID NO 226
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys

<400> SEQUENCE: 226

Lys Ala Leu Ala Ala Ala Gly Tyr Asp Val Glu Lys Asn Asn Ser Arg
1               5                   10                  15

<210> SEQ ID NO 227
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ubiquitinated Lys

<400> SEQUENCE: 227

Ile Asn Ser Leu Gln Asp Met Val Thr Lys Tyr Gln Lys Arg
1               5                   10

<210> SEQ ID NO 228
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ubiquitinated Lys

<400> SEQUENCE: 228

Leu Thr Leu Ser Lys Ala Gly Gln Glu His Leu Leu Arg
1               5                   10

<210> SEQ ID NO 229
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 229

Ile Lys Val Ala Glu Asp Glu Ala Glu Ala Ala Ala Ala Ala Ala Lys
1               5                   10                  15

<210> SEQ ID NO 230
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 230

His His His His His His
1               5

<210> SEQ ID NO 231
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 231

Leu Lys Thr Asn His Ile Thr Gly Tyr Leu Asn Thr Val Thr Val Ser
1               5                   10                  15

Pro Asp Gly Ser Leu Cys Ala Ser Gly Gly Lys
            20                  25

<210> SEQ ID NO 232
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ubiquitinated Lys

<400> SEQUENCE: 232

Gln Ser Asn Pro Glu Phe Cys Pro Glu Lys Val Ala
1               5                   10

<210> SEQ ID NO 233
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
```

<223> OTHER INFORMATION: Ubiquitinated Lys
<220> FEATURE:
<221> NAME/KEY: MOD_RES
<222> LOCATION: (7)..(7)
<223> OTHER INFORMATION: Oxidized Met

<400> SEQUENCE: 233

Lys Gly Gly Cys Ala Leu Met Asn Arg
1               5

<210> SEQ ID NO 234
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ubiquitinated Lys

<400> SEQUENCE: 234

Val Gly Leu Val Ala Ser Gln Lys Asn Asp Leu Asp Ala
1               5                   10

<210> SEQ ID NO 235
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ubiquitinated Lys

<400> SEQUENCE: 235

Val Asp Glu Lys Ala Ser Ala Ala Leu Tyr
1               5                   10

<210> SEQ ID NO 236
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ubiquitinated Lys

<400> SEQUENCE: 236

Val Ser Glu Leu Asn Ala Gly Ile Ile Lys Thr Asp Gln
1               5                   10

<210> SEQ ID NO 237
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ubiquitinated Lys

<400> SEQUENCE: 237

```
Arg Pro Phe Pro Gln Val Ile Lys Ser Lys
1               5                   10

<210> SEQ ID NO 238
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Ubiquitinated Lys

<400> SEQUENCE: 238

Val Asp Lys Gly Val Val Pro Leu Ala Gly Thr
1               5                   10

<210> SEQ ID NO 239
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Ubiquitinated Lys

<400> SEQUENCE: 239

Glu Thr Thr Leu Ser Tyr Tyr Lys Ser Gln Asp Glu Ala Pro
1               5                   10

<210> SEQ ID NO 240
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: Ubiquitinated Lys

<400> SEQUENCE: 240

Pro Phe Ser Tyr Gly Tyr Gly Gly Thr Gly Lys Lys
1               5                   10

<210> SEQ ID NO 241
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 241

Glu Tyr Asn Glu Tyr Glu Asn Ile Lys Leu Glu Arg
1               5                   10

<210> SEQ ID NO 242
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 242

Lys Lys Leu Leu Ala Asp Gln Ala Glu Ala Arg
1               5                   10

<210> SEQ ID NO 243
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Ubiquitinated Lys

<400> SEQUENCE: 243

Gln Gln Asn Gln His Pro Glu Lys Pro Gly Gly Lys Glu Arg
1               5                   10

<210> SEQ ID NO 244
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (19)..(19)
<223> OTHER INFORMATION: Ubiquitinated Lys

<400> SEQUENCE: 244

Gly Gln Ser Pro Leu Asp Leu Cys Pro Asp Pro Asn Leu Cys Lys Ala
1               5                   10                  15

Leu Ala Lys

<210> SEQ ID NO 245
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ubiquitinated Lys

<400> SEQUENCE: 245

Val Lys Thr Leu Thr Gly Lys Glu Ile Glu Ile Asp Ile Glu Pro Thr
1               5                   10                  15

Asp Lys Val Glu Arg
            20

<210> SEQ ID NO 246
<211> LENGTH: 32
<212> TYPE: PRT
<213> ORGANISM: Artificial Sequence
```

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Ubiquitinated Lys

<400> SEQUENCE: 246

Ile Leu Asp Lys Cys Asn Glu Ile Ile Asn Trp Leu Asp Lys Asn Gln
1               5                   10                  15

Thr Ala Glu Lys Glu Glu Phe Glu His Gln Gln Lys Glu Leu Glu Lys
            20                  25                  30

<210> SEQ ID NO 247
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (28)..(28)
<223> OTHER INFORMATION: Ubiquitinated Lys

<400> SEQUENCE: 247

Ile Leu Asp Lys Cys Asn Glu Ile Ile Asn Trp Leu Asp Lys Asn Gln
1               5                   10                  15

Thr Ala Glu Lys Glu Glu Phe Glu His Gln Gln Lys Glu Leu Glu Lys
            20                  25                  30

<210> SEQ ID NO 248
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: Ubiquitinated Lys

<400> SEQUENCE: 248

Leu Trp Asn Thr Leu Gly Val Cys Lys Tyr Thr Val Gln Asp Glu Ser
1               5                   10                  15

His Ser Glu Trp Val Ser Cys Val Arg
            20                  25

<210> SEQ ID NO 249
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ubiquitinated Lys

<400> SEQUENCE: 249

Ser Leu Val Ser Lys Gly Thr Leu Val Gln Thr Lys
1               5                   10

<210> SEQ ID NO 250
<211> LENGTH: 8
```

```
-continued

<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ubiquitinated Lys

<400> SEQUENCE: 250

Lys Pro Val Thr Val His Ser Arg
1               5

<210> SEQ ID NO 251
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 251
gggccgattt tcaatgtcat tcttcagttt tggagactga tttctctcca gc          52

<210> SEQ ID NO 252
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 252
gggccgattt tcaatgtcat tcttcagttt tagagactga tttctctcca gc          52
```

METHODS FOR THE TREATMENT OF CANCER AND INFLAMMATORY DISEASES USING CEREBLON AS A PREDICTOR

The present application claims priority to U.S. Provisional Patent Application Nos. 61/481,066, filed Apr. 29, 2011; 61/511,986, filed Jul. 26, 2011; and 61/579,600, filed Dec. 22, 2011; the entirety of each of which is incorporated herein by reference.

SEQUENCE LISTING

The instant application contains a Sequence Listing which has been submitted in ASCII format via EFS-Web and is hereby incorporated by reference in its entirety. Said ASCII copy, created on Jul. 5, 2012, is named 12827227.txt and is 119,198 bytes in size.

1. FIELD

Provided herein are uses of the protein cereblon as a predictor of clinical sensitivity to cancer and inflammatory diseases, and patient response to drug treatment.

2. BACKGROUND

2.1 Pathobiology of Cancer

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J and Kale, D., *Immunology*, 17.1-17.12 (3rd ed., Mosby, St. Louis, Mo., 1993).

There is an enormous variety of cancers which are described in detail in the medical literature. Examples include cancers of the lung, colon, rectum, prostate, breast, brain, blood and intestine. The incidence of cancer continues to climb as the general population ages, as new cancers develop, and as susceptible populations (e.g., people infected with AIDS or excessively exposed to sunlight) grow. However, options for the treatment of cancer are limited. For example, in the case of blood cancers (e.g., multiple myeloma), few treatment options are available, especially when conventional chemotherapy fails and bone-marrow transplantation is not an option. A tremendous demand therefore exists for new methods and compositions that can be used to treat patients with cancer.

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties. Examples of these cytokines include acidic and basic fibroblastic growth factor (a,b-FGF), angiogenin, vascular endothelial growth factor (VEGF), and TNF-α. Alternatively, tumor cells can release angiogenic peptides through the production of proteases and the subsequent breakdown of the extracellular matrix where some cytokines are stored (e.g., b-FGF). Angiogenesis can also be induced indirectly through the recruitment of inflammatory cells (particularly macrophages) and their subsequent release of angiogenic cytokines (e.g., TNF-α, b-FGF).

Lymphoma refers to cancers that originate in the lymphatic system. Lymphoma is characterized by malignant neoplasms of lymphocytes—B lymphocytes and T lymphocytes (i.e., B-cells and T-cells). Lymphoma generally starts in lymph nodes or collections of lymphatic tissue in organs including, but not limited to, the stomach or intestines. Lymphoma may involve the marrow and the blood in some cases. Lymphoma may spread from one site to other parts of the body. The treatment of various forms of lymphomas are described, for example, in U.S. Pat. No. 7,468,363, the entirety of which is incorporated herein by reference. Such lymphomas include, but are not limited to, Hodgkin's lymphoma, non-Hodgkin's lymphoma, cutaneous B-cell lymphoma, activated B-cell lymphoma, diffuse large B-cell lymphoma (DLBCL), mantle cell lymphoma (MCL), follicular center lymphoma, transformed lymphoma, lymphocytic lymphoma of intermediate differentiation, intermediate lymphocytic lymphoma (ILL), diffuse poorly differentiated lymphocytic lymphoma (PDL), centrocytic lymphoma, diffuse small-cleaved cell lymphoma (DSCCL), peripheral T-cell lymphomas (PTCL), cutaneous T-Cell lymphoma and mantle zone lymphoma and low grade follicular lymphoma.

Non-Hodgkin's lymphoma (NHL) is the fifth most common cancer for both men and women in the United States, with an estimated 63,190 new cases and 18,660 deaths in 2007. Jemal A, et al., *CA Cancer J Clin* 2007; 57(1):43-66. The probability of developing NHL increases with age and the incidence of NHL in the elderly has been steadily increasing in the past decade, causing concern with the aging trend of the US population. Id. Clarke C A, et al., *Cancer* 2002; 94(7):2015-2023.

Diffuse large B-cell lymphoma (DLBCL) accounts for approximately one-third of non-Hodgkin's lymphomas. While some DLBCL patients are cured with traditional chemotherapy, the remainder die from the disease. Anticancer drugs cause rapid and persistent depletion of lymphocytes, possibly by direct apoptosis induction in mature T and B cells. See K. Stahnke. et al., *Blood* 2001, 98:3066-3073. Absolute lymphocyte count (ALC) has been shown to be a prognostic factor in follicular non-Hodgkin's lymphoma and recent results have suggested that ALC at diagnosis is an important prognostic factor in diffuse large B-cell lymphoma. The diffuse large-B-cell lymphomas (DLBCL) can be divided into distinct molecular subtypes according to their gene profiling patterns: germinal-center B-cell-like DLBCL (GCB-DLBCL), activated B-cell-like DLBCL (ABC-DLBCL), and primary mediastinal B-cell lymphoma (PMBL) or unclassified type. These subtypes are characterized by distinct differences in survival, chemo-responsiveness, and signaling pathway dependence, particularly the NF-κB pathway. See D. Kim et al., *Journal of Clinical Oncology*, 2007 ASCO Annual Meeting Proceedings Part I. Vol 25, No. 18S (June 20 Supplement), 2007: 8082. See Bea S, et al., *Blood* 2005; 106: 3183-90; Ngo V. N. et al., *Nature* 2011; 470: 115-9. Such differences have prompted the search for more effective and subtype-specific treatment strategies in DLBCL.

Leukemia refers to malignant neoplasms of the blood-forming tissues. Various forms of leukemias are described, for example, in U.S. Pat. No. 7,393,862 and U.S. provisional patent application No. 60/380,842, filed May 17, 2002, the entireties of which are incorporated herein by reference. Although viruses reportedly cause several forms of leukemia in animals, causes of leukemia in humans are to a large extent unknown. *The Merck Manual*, 944-952 (17th ed. 1999).

Transformation to malignancy typically occurs in a single cell through two or more steps with subsequent proliferation and clonal expansion. In some leukemias, specific chromosomal translocations have been identified with consistent leukemic cell morphology and special clinical features (e.g., translocations of 9 and 22 in chronic myelocytic leukemia, and of 15 and 17 in acute promyelocytic leukemia). Acute leukemias are predominantly undifferentiated cell populations and chronic leukemias more mature cell forms.

Acute leukemias are divided into lymphoblastic (ALL) and non-lymphoblastic (ANLL) types. *The Merck Manual*, 946-949 ($17^{th}$ ed. 1999). They may be further subdivided by their morphologic and cytochemical appearance according to the French-American-British (FAB) classification or according to their type and degree of differentiation. The use of specific B- and T-cell and myeloid-antigen monoclonal antibodies are most helpful for classification. ALL is predominantly a childhood disease which is established by laboratory findings and bone marrow examination. ANLL, also known as acute myelogenous leukemia or acute myeloid leukemia (AML), occurs at all ages and is the more common acute leukemia among adults; it is the form usually associated with irradiation as a causative agent.

Chronic leukemias are described as being lymphocytic (CLL) or myelocytic (CML). *The Merck Manual*, 949-952 ($17^{th}$ ed. 1999). CLL is characterized by the appearance of mature lymphocytes in blood, bone marrow, and lymphoid organs. The hallmark of CLL is sustained, absolute lymphocytosis (>5,000/μL) and an increase of lymphocytes in the bone marrow. Most CLL patients also have clonal expansion of lymphocytes with B-cell characteristics. CLL is a disease of middle or old age. In CML, the characteristic feature is the predominance of granulocytic cells of all stages of differentiation in blood, bone marrow, liver, spleen, and other organs. In the symptomatic patient at diagnosis, the total white blood cell (WBC) count is usually about 200,000/μL, but may reach 1,000,000/μL. CML is relatively easy to diagnose because of the presence of the Philadelphia chromosome.

Bone marrow stromal cells are well known to support CLL disease progression and resistance to chemotherapy. Disrupting the interactions between CLL cells and stromal cells is an additional target of CLL chemotherapy.

In addition to the acute and chronic categorization, neoplasms are also categorized based upon the cells giving rise to such disorder into precursor or peripheral. See e.g., U.S. patent publication no. 2008/0051379, the disclosure of which is incorporated herein by reference in its entirety. Precursor neoplasms include ALLs and lymphoblastic lymphomas and occur in lymphocytes before they have differentiated into either a T- or B-cell. Peripheral neoplasms are those that occur in lymphocytes that have differentiated into either T- or B-cells. Such peripheral neoplasms include, but are not limited to, B-cell CLL, B-cell prolymphocytic leukemia, lymphoplasmacytic lymphoma, mantle cell lymphoma, follicular lymphoma, extranodal marginal zone B-cell lymphoma of mucosa-associated lymphoid tissue, nodal marginal zone lymphoma, splenic marginal zone lymphoma, hairy cell leukemia, plasmacytoma, diffuse large B-cell lymphoma and Burkitt lymphoma. In over 95 percent of CLL cases, the clonal expansion is of a B cell lineage. See Cancer: Principles & Practice of Oncology (3rd Edition) (1989) (pp. 1843-1847). In less than 5 percent of CLL cases, the tumor cells have a T-cell phenotype. Notwithstanding these classifications, however, the pathological impairment of normal hematopoiesis is the hallmark of all leukemias.

Multiple myeloma (MM) is a cancer of plasma cells in the bone marrow. Normally, plasma cells produce antibodies and play a key role in immune function. However, uncontrolled growth of these cells leads to bone pain and fractures, anemia, infections, and other complications.

Multiple myeloma is the second most common hematological malignancy, although the exact causes of multiple myeloma remain unknown. Multiple myeloma causes high levels of proteins in the blood, urine, and organs, including but not limited to M-protein and other immunoglobulins (antibodies), albumin, and beta-2-microglobulin. M-protein, short for monoclonal protein, also known as paraprotein, is a particularly abnormal protein produced by the myeloma plasma cells and can be found in the blood or urine of almost all patients with multiple myeloma.

Skeletal symptoms, including bone pain, are among the most clinically significant symptoms of multiple myeloma. Malignant plasma cells release osteoclast stimulating factors (including IL-1, IL-6 and TNF) which cause calcium to be leached from bones causing lytic lesions; hypercalcemia is another symptom. The osteoclast stimulating factors, also referred to as cytokines, may prevent apoptosis, or death of myeloma cells. Fifty percent of patients have radiologically detectable myeloma-related skeletal lesions at diagnosis. Other common clinical symptoms for multiple myeloma include polyneuropathy, anemia, hyperviscosity, infections, and renal insufficiency.

Bone marrow stromal cells are well known to support multiple myeloma disease progression and resistance to chemotherapy. Disrupting the interactions between multiple myeloma cells and stromal cells is an additional target of multiple myeloma chemotherapy.

Myelodysplastic syndrome (MDS) refers to a diverse group of hematopoietic stem cell disorders. MDS is characterized by a cellular marrow with impaired morphology and maturation (dysmyelopoiesis), peripheral blood cytopenias, and a variable risk of progression to acute leukemia, resulting from ineffective blood cell production. See The Merck Manual 953 (17th ed. 1999) and List et al., 1990, *J Clin. Oncol.* 8:1424. The treatment of MDS using immunomodulatory compounds is described in U.S. Patent Publication No. 2004/0220144, the entirety of which is hereby incorporated by reference.

Solid tumors are abnormal masses of tissue that may, but usually do not contain cysts or liquid areas. Solid tumors may be benign (not cancer), or malignant (cancer). Different types of solid tumors are named for the type of cells that form them. Examples of types solid tumors include, but are not limited to malignant melanoma, adrenal carcinoma, breast carcinoma, renal cell cancer, carcinoma of the pancreas, non-small-cell lung carcinoma (NSCLC) and carcinoma of unknown primary. Drugs commonly administered to patients with various types or stages of solid tumors include, but are not limited to, celebrex, etoposide, cyclophosphamide, docetaxel, apecitabine, IFN, tamoxifen, IL-2, GM-CSF, or a combination thereof.

While patients who achieve a complete remission after initial therapy have a good chance for cure, less than 10% of those who do not respond or relapse achieve a cure or a response lasting longer than 3 years. See Cerny T, et al., *Ann Oncol* 2002; 13 Suppl 4:211-216.

Rituximab is known to deplete normal host B cells. See M. Aklilu et al., Annals of Oncology 15:1109-1114, 2004. The long-term immunologic effects of B cell depletion with rituximab and the characteristics of the reconstituting B cell pool in lymphoma patients are not well defined, despite the widespread usage of this therapy. See Jennifer H. Anolik et al., *Clinical Immunology*, vol. 122, issue 2, February 2007, pages 139-145.

The approach for patients with relapsed or refractory disease relies heavily on experimental treatments followed by stem cell transplantation, which may not be appropriate for patients with a poor performance status or advanced age. Therefore, a tremendous demand exists for new methods that can be used to treat patients with NHL.

The link between cancer an altered cellular metabolism has been well established. See Cairns, R. A., et al. *Nature Rev.*, 2011, 11:85-95. Understanding tumor cell metabolism and the associated genetic changes thereof may lead to the identification of improved methods of cancer treatment. Id. For example, tumor cell survival and proliferation via increased glucose metabolism has been linked to the PIK3 pathway, whereby mutations in tumor suppressor genes such as PTEN activate tumor cell metabolism. Id. AKT1 (a.k.a., PKB) stimulates glucose metabolism associated with tumor cell growth by various interactions with PFKFB3, ENTPD5, mTOR and TSC2 (a.k.a., tuberin). Id.

Transcription factors HIF1 and HIF2 are largely responsible for cellular response to low oxygen conditions often associated with tumors. Id. Once activated, HIF1 promotes tumor cell capacity to carry out glycolysis. Id. Thus, inhibition of HIF1 may slow or reverse tumor cell metabolism. Activation of HIF1 has been linked to PI3K, tumor suppressor proteins such as VHL, succinate dehydrogenase (SDH) and fumarate hydratase. Id. The oncogenic transcription factor MYC has also been linked to tumor cell metabolism, specifically glycolysis. Id. MYC also promotes cell proliferation by glutamine metabolic pathways. Id.

AMP-activated protein kinase (AMPK) functions as a metabolic check point which tumor cells must overcome in order to proliferate. Id. Several mutations have been identified which suppress AMPK signaling in tumor cells. See Shackelford, D. B. & Shaw, R. J., *Nature Rev. Cancer*, 2009, 9: 563-575. STK11 has been identified as a tumor suppressor gene related to the role of AMPK. See Cairns, R. A., et al. *Nature Rev.*, 2011, 11:85-95.

The transcription factor p53, a tumor suppressor, also has an important role in the regulation of cellular metabolism. Id. The loss of p53 in tumor cells may be a significant contributor to changes in tumor cell metabolism to the glycolytic pathway. Id. The OCT1 transcription factor, another potential target for chemotherapeutics, may cooperate with p53 in regulating tumor cell metabolism. Id.

Pyruvate kinate M2 (PKM2) promotes changes in cellular metabolism which confer metabolic advantages to cancer cells by supporting cell proliferation. Id. For example, lung cancer cells which express PKM2 over PKM1 have been found to have such an advantage. Id. In the clinic, PKM2 has been identified as being overexpressed in a number of cancer types. Id. Thus PKM2 may be a useful biomarker for the early detection of tumors.

Mutations in isocitrate dehydrogenases IDH1 and IDH2 have been linked to tumorigenesis, specifically, in glioblastoma and acute myeloid leukemia. See Mardis, E. R. et al., *N. Engl. J. Med.*, 2009, 361: 1058-1066; Parsons, D. W. et al., *Science*, 2008, 321: 1807-1812.

The incidence of cancer continues to climb as the general population ages, as new cancers develop, and as susceptible populations (e.g., people infected with AIDS, the elderly or excessively exposed to sunlight) grow. A tremendous demand therefore exists for new methods, treatments and compositions that can be used to treat patients with cancer including but not limited to those with lymphoma, NHL, multiple myeloma, AML, leukemias, and solid tumors.

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, fibrosis, arthritis and autoimmune diseases. Examples of such diseases and conditions include, but are not limited to: diabetic retinopathy; retinopathy of prematurity; corneal graft rejection; neovascular glaucoma; retrolental fibroplasia; and proliferative vitreoretinopathy.

Accordingly, compounds that can control and/or inhibit unwanted angiogenesis or inhibit the production of certain cytokines, including TNF-α, may be useful in the treatment and prevention of various diseases and conditions.

2.2 Inflammatory Diseases

Inflammation plays a fundamental role in host defenses and the progression of immune-mediated diseases. The inflammatory response is initiated in response to injury (e.g., trauma, ischemia, and foreign particles) and infection (e.g., bacterial or viral infection) by a complex cascade of events, including chemical mediators (e.g., cytokines and prostaglandins) and inflammatory cells (e.g., leukocytes). The inflammatory response is characterized by increased blood flow, increased capillary permeability, and the influx of phagocytic cells. These events result in swelling, redness, warmth (altered heat patterns), and pus formation at the site of injury or infection.

Cytokines and prostaglandins control the inflammatory response, and are released in an ordered and self-limiting cascade into the blood or affected tissues. This release of cytokines and prostaglandins increases the blood flow to the area of injury or infection, and may result in redness and warmth. Some of these chemicals cause a leak of fluid into the tissues, resulting in swelling. This protective process may stimulate nerves and cause pain. These changes, when occurring for a limited period in the relevant area, work to the benefit of the body.

Tumor necrosis factor alpha (TNF-α) is a cytokine that is released primarily by mononuclear phagocytes in response to immunostimulators. TNF-α is capable of enhancing most cellular processes, such as differentiation, recruitment, proliferation, and proteolytic degradation. At low levels, TNF-α confers protection against infective agents, tumors, and tissue damage. But TNF-α also has a role in many diseases. When administered to mammals or humans, TNF-α causes or aggravates inflammation, fever, cardiovascular effects, hemorrhage, coagulation, and acute phase responses similar to those seen during acute infections and shock states. Enhanced or unregulated TNF-α production has been implicated in a number of diseases and medical conditions, for example, cancers, such as solid tumors and blood-borne tumors; heart disease, such as congestive heart failure; and viral, genetic, inflammatory, allergic, and autoimmune diseases.

Adenosine 3',5'-cyclic monophosphate (cAMP) also plays a role in many diseases and conditions, such as but not limited to asthma and inflammation, and other conditions (Lowe and Cheng, *Drugs of the Future*, 17(9), 799-807, 1992). It has been shown that the elevation of cAMP in inflammatory leukocytes inhibits their activation and the subsequent release of inflammatory mediators, including TNF-α and NF-κB. Increased levels of cAMP also leads to the relaxation of airway smooth muscle.

A delicate well-balanced interplay between the humoral and cellular immune elements in the inflammatory response enables the elimination of harmful agents and the initiation of the repair of damaged tissue. When this delicately balanced interplay is disrupted, the inflammatory response may result in considerable damage to normal tissue and may be more harmful than the original insult that initiated the reaction. In these cases of uncontrolled inflammatory responses, clinical intervention is needed to prevent tissue damage and organ dysfunction. Diseases such as psoriasis, rheumatoid arthritis, osteoarthritis, psoriatic arthritis, Crohn's disease, asthma, allergies or inflammatory bowel disease, are characterized by chronic inflammation. Inflammatory diseases such as arthritis, related arthritic conditions (e.g., osteoarthritis, rheumatoid arthritis, and psoriatic arthritis), inflammatory bowel disease (e.g., Crohn's disease and ulcerative colitis), sepsis, psoriasis, atopic dermatitis, contact dermatitis, and chronic obstructive pulmonary disease, chronic inflammatory pulmonary diseases are also prevalent and problematic ailments. Enhanced or unregulated TNF-α production plays a central role in the inflammatory response and the administration of their antagonists block chronic and acute responses in animal models of inflammatory disease.

Arthritis is a systemic autoimmune disease that can refer to a group of conditions involving damage to the joints of the body. There are over 100 different forms of arthritis. The most common form is osteoarthritis (degenerative joint disease) and other arthritis forms are rheumatoid arthritis, psoriatic arthritis, and related autoimmune diseases such as lupus and gout. Rheumatoid arthritis is characterized by a chronic inflammation of the joints. Both synovial tissue and fluid are invaded by inflammatory cells which lead to cytokine production. T cells and monocytes infiltrating the joints display an increased activation of Type 1 and 2 immune response markers.

Psoriatic arthritis is a chronic inflammatory arthritic condition affecting the skin, the joints, the insertion sites of tendons, ligaments, and fascia. Gladman, *Current Opinion in Rheumatology*, "Current concepts in psoriatic arthritis," 2002, 14:361-366, and Ruddy et al., *Rheumatology*, vol. 2., chapter 71, page 1071, 6th ed., 2001. Psoriatic arthritis is commonly associated with psoriasis. Id. Approximately 7% of patients with psoriasis develop psoriatic arthritis. The Merck Manual, 448 (17th ed., 1999). Psoriatic arthritis may appear in a variety of clinical patterns. There are five general patterns of psoriatic arthritis: arthritis of the distal interphalangeal joints, destructive arthritis, symmetric polyarthritis indistinguishable from rheumatoid arthritis, asymmetric oligoarthritis, and spondyloarthropathy. Ruddy et al., page 1073. Psoriasis appears to precede the onset of psoriatic arthritis in 60-80% of patients. Occasionally, arthritis and psoriasis appear simultaneously. Cutaneous eruptions may be preceded by the arthropathy.

Psoriasis is a chronic systemic autoimmune disease that appears on the skin. There are five types of psoriasis: plaque, guttate, inverse, pustular and erythrodermic. The most common form, plaque psoriasis, is commonly seen as red and white hues of scaly patches appearing on the top first layer of the epidermis. Some patients, though, have no dermatological symptoms. In plaque psoriasis, skin rapidly accumulates at these sites, which gives it a silvery-white appearance. Plaques frequently occur on the skin of the elbows and knees, but can affect any area, including the scalp, palms of hands and soles of feet, and genitals. In contrast to eczema, psoriasis is more likely to be found on the outer side of the joint. The disorder is a chronic recurring condition that varies in severity from minor localized patches to complete body coverage. Fingernails and toenails are frequently affected (psoriatic nail dystrophy) and can be seen as an isolated symptom. Psoriasis can also cause inflammation of the joints, which is known as psoriatic arthritis. In psoriasis, one hypothesis is that T cells become active, migrate to the dermis and trigger the release of cytokines, TNF-α in particular, which causes inflammation and the rapid proliferation of keratinocytes.

2.3 Compounds

A number of studies have been conducted with the aim of providing compounds that can safely and effectively be used to treat diseases associated with abnormal production of TNF-α. See, e.g., Marriott, J. B., et al., *Expert Opin. Biol. Ther.*, 2001, 1(4): 1-8; G. W. Muller, et al., *J Med Chem.*, 1996, 39(17): 3238-3240; and G. W. Muller, et al., *Bioorg & Med Chem Lett.*, 1998, 8: 2669-2674. Some studies have focused on a group of compounds selected for their capacity to potently inhibit TNF-α production by LPS stimulated PBMC. L. G. Corral, et al., *Ann. Rheum. Dis.*, 1999, 58: (Suppl I) 1107-1113. These compounds show not only potent inhibition of TNF-α but also marked inhibition of LPS induced monocyte IL1β and IL12 production. LPS induced IL6 is also inhibited by such compounds, albeit partially. These compounds are potent stimulators of LPS induced IL10. Id.

Compounds for the methods provided herein include, but are not limited to, the substituted 2-(2,6-dioxopiperidin-3-yl) phthalimides and substituted 2-(2,6-dioxopiperidin-3-yl)-1-oxoisoindoles described in U.S. Pat. Nos. 6,281,230 and 6,316,471, both to G. W. Muller, et al. Still other specific compounds disclosed herein belong to a class of isoindole-imides disclosed in U.S. Pat. Nos. 6,395,754, 6,555,554, 7,091,353, U.S. patent publication no. 2004/0029832, and International Publication No. WO 98/54170, each of which is incorporated herein by reference. Thalidomide, lenalidomide and pomalidomide have shown remarkable responses in patients with multiple myeloma, lymphoma and other hematological diseases such as myelodysplastic syndrome. See Galustian C, et al., *Expert Opin Pharmacother.*, 2009, 10:125-133. These drugs display a broad spectrum of activity, including anti-angiogenic properties, modulation of pro-inflammatory cytokines, co-stimulation of T cells, increased NK cell toxicity, direct anti-tumor effects and modulation of stem cell differentiation.

For example, thalidomide and lenalidomide have emerged as important options for the treatment of multiple myeloma in newly diagnosed patients, in patients with advanced disease who have failed chemotherapy or transplantation, and in patients with relapsed or refractory multiple myeloma. Lenalidomide in combination with dexamethasone has been approved for the treatment of patients with multiple myeloma who have received at least one prior therapy. Pomalidomide may also be administered in combination with dexamethasone. U.S. Patent Publication No. 2004/0029832 A1, the disclosure of which is hereby incorporated in its entirety, discloses the treatment of multiple myeloma.

Another compound provided herein is 3-(5-amino-2-methyl-4-oxo-4H-quinazolin-3-yl)-piperidine-2,6-dione ("Compound B"), which has the following structure:

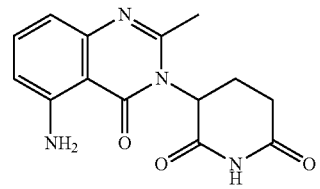 [SMILES: Cc1nc2cccc(N)c2c(=O)n1C1CCC(=O)NC1=O]

or an enantiomer or a mixture of enantiomers thereof; or a pharmaceutically acceptable salt, solvate, hydrate, co-crystal, clathrate, or polymorph thereof.

Compound B can be prepared according to the methods described in the Examples provided herein or as described in U.S. Pat. No. 7,635,700, the disclosure of which is incorporated herein by reference in its entirety. The compound can be also synthesized according to other methods apparent to those of skill in the art based upon the teaching herein. In certain embodiments, Compound B is in a crystalline form described in U.S. Provisional Pat. App. No. 61/451,806, filed Mar. 11, 2011, which is incorporated herein by reference in its entirety. In some embodiments, the hydrochloride salt of Compound B is used in the methods provided herein. Methods of treating, preventing and/or managing cancers and other diseases using Compound B are described in U.S. Provisional Pat. App. No. 61/451,995, filed Mar. 11, 2011, which is incorporated herein by reference in its entirety.

2.4 Cereblon

The protein Cereblon (CRBN) is a 442-amino acid protein conserved from plant to human. In humans, the CRBN gene has been identified as a candidate gene of an autosomal recessive nonsyndromic mental retardation (ARNSMR). See Higgins, J. J. et al., *Neurology*, 2004, 63:1927-1931. CRBN was initially characterized as an RGS-containing novel protein that interacted with a calcium-activated potassium channel protein (SLO1) in the rat brain, and was later shown to interact with a voltage-gated chloride channel (CIC-2) in the retina with AMPK7 and DDB1. See Jo, S. et al., *J. Neurochem*, 2005, 94:1212-1224; Hohberger B. et al., *FEBS Lett*, 2009, 583:633-637; Angers S. et al., *Nature*, 2006, 443:590-593. DDB1 was originally identified as a nucleotide excision repair protein that associates with damaged DNA binding protein 2 (DDB2). Its defective activity causes the repair defect in the patients with xeroderma pigmentosum complementation group E (XPE). DDB1 also appears to function as a component of numerous distinct DCX (DDB1-CUL4-X-box) E3 ubiquitin-protein ligase complexes which mediate the ubiquitination and subsequent proteasomal degradation of target proteins. CRBN has also been identified as a target for the development of therapeutic agents for diseases of the cerebral cortex. See WO 2010/137547 A1.

Cereblon has recently been identified as a key molecular target that binds to thalidomide to cause birth defects. See Ito, T. et al., *Science*, 2010, 327:1345-1350. DDB1 was found to interact with CRBN and, thus, was indirectly associated with thalidomide. Moreover, thalidomide was able to inhibit autoubiquitination of CRBN in vitro, suggesting that thalidomide is an E3 ubiquitin-ligase inhibitor. Id. Importantly, this activity was inhibited by thalidomide in wild-type cells, but not in cells with mutated CRBN binding sites that prevent thalidomide binding. Id. The thalidomide binding site was mapped to a highly conserved C-terminal 104 amino acid region in CRBN. Id. Individual point mutants in CRBN, Y384A and W386A were both defective for thalidomide binding, with the double point mutant having the lowest thalidomide-binding activity. Id. A link between CRBN and the teratogenic effect of thalidomide was confirmed in animal models of zebra-fish and chick embryos. Id.

Whether binding to CRBN, the CRBN E3 ubiquitin-ligase complex, or one or more substrates of CRBN, is required for the beneficial effects of thalidomide and other drugs is yet to be established. Understanding these interactions with thalidomide and other drug targets will allow the definition of the molecular mechanisms of efficacy and/or toxicity and may lead to drugs with improved efficacy and toxicity profiles.

2.5 Methods of Treating Cancer

Current cancer therapy may involve surgery, chemotherapy, hormonal therapy and/or radiation treatment to eradicate neoplastic cells in a patient (see, for example, Stockdale, 1998, *Medicine*, vol. 3, Rubenstein and Federman, eds., Chapter 12, Section IV). Recently, cancer therapy could also involve biological therapy or immunotherapy. All of these approaches may pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells. Certain biological and other therapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A number of cancer chemotherapeutics act by inhibiting DNA synthesis, either directly or indirectly by inhibiting the biosynthesis of deoxyribonucleotide triphosphate precursors, to prevent DNA replication and concomitant cell division. Gilman et al., *Goodman and Gilman's: The Pharmacological Basis of Therapeutics*, Tenth Ed. (McGraw Hill, New York).

Despite availability of a variety of chemotherapeutic agents, chemotherapy has many drawbacks. Stockdale, *Medicine*, vol. 3, Rubenstein and Federman, eds., ch. 12, sect. 10, 1998. Almost all chemotherapeutic agents are toxic, and chemotherapy causes significant and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as multidrug resistance. Because of the drug resistance, many cancers prove refractory to standard chemotherapeutic treatment protocols.

Other diseases or conditions associated with, or characterized by, undesired angiogenesis are also difficult to treat. However, some compounds such as protamine, hepain and steroids have been proposed to be useful in the treatment of certain specific diseases associated with, or characterized by, undesired angiogenesis. Taylor et al., *Nature* 297:307 (1982); Folkman et al., *Science* 221:719 (1983); and U.S. Pat. Nos. 5,001,116 and 4,994,443. Thalidomide and certain thalidomide derivatives based on their multiple activities have also been proposed for the treatment of such diseases and conditions. U.S. Pat. Nos. 5,593,990, 5,629,327, 5,712,291, 6,071, 948 and 6,114,355 to D'Amato.

Still, there is a significant need for safe and effective methods of treating, preventing and managing cancer and other diseases that are refractory to standard treatments, such as surgery, radiation therapy, chemotherapy and hormonal therapy, while reducing or avoiding the toxicities and/or side effects associated with the conventional therapies.

2.6 Methods of Treating Inflammatory Diseases

Current treatments for inflammatory diseases and disorders involve symptomatic medications and immunosuppressive agents to control symptoms. For example, nonsteroidal anti-inflammatory drugs (NSAIDs) such as aspirin, ibuprofen, fenoprofen, naproxen, tolmetin, sulindac, meclofenamate sodium, piroxicam, flurbiprofen, diclofenac, oxaprozin, nabumetone, etodolac, and ketoprofen have analgesic and anti-inflammatory effects. However, NSAIDs are believed not to be capable of altering progression of the disease. (Tierney et al. (eds), *Current Medical Diagnosis & Treatment,* 37 ed., Appleton & Lange (1998), p 793). Moreover, NSAIDs frequently cause gastrointestinal side effects, affect the lower intestinal tract causing perforation or aggravating inflammatory bowel disease, produce renal toxicity, and prolong bleeding time. Corticosteroids are another class of drugs that are commonly used to control inflammatory symptoms. Corticosteroids, like NSAIDs, do not alter the natural progression of the disease, and thus, clinical manifestations of active disease commonly reappear when the drug is discontinued. The serious problem of untoward reactions resulting from prolonged corticosteroid therapy (e.g., osteoporosis, increased risk of infection, increased appetite, hypertension, edema, peptic ulcers, psychoses) greatly limits its long-term use.

Low doses of immunosuppressive agents such as cytotoxic agents may be used for the treatment of inflammatory disorders. For example, some treatments for psoriasis and arthritis are based on disease-modifying anti-rheumatic drugs (DMARDs such as cyclosporine A and methotrexate), anti-inflammatory agents (TNF-α inhibitors such as etanercept), and analgesics. New treatments for inflammatory and autoimmune disorders are constantly being sought.

In particular, any new treatment that reduces the dosage and/or frequency of administration of agents currently being used, or is capable of making a currently used treatment more effective is constantly being sought.

3. SUMMARY OF THE INVENTION

Provided herein are uses of the protein cereblon (CRBN) as a predictor of clinical sensitivity to cancer and inflammatory diseases, and patient response to treatment with the compounds provided herein. In certain embodiments, the compounds provided herein bind directly to CRBN-DDB1.

Also provided herein are methods for the treatment or management of cancer and inflammatory diseases using CRBN as a predictive or prognostic factor for the compounds provided herein. In certain embodiments, provided herein are methods for screening or identifying cancer patients, e.g., multiple myeloma, DLBCL, mantle cell lymphoma, follicular lymphoma, acute myeloblastic leukemia, chronic lymphocytic leukemia, and/or MDS patients, for treatment with thalidomide, lenalidomide and/or pomalidomide, using CRBN levels as a predictive or prognostic factor. In some embodiments, provided herein are methods for selecting patients having a higher response rate to therapy with thalidomide, lenalidomide and/or pomalidomide, using CRBN levels as a predictive or prognostic factor.

In one embodiment, provided herein is a method of predicting patient response to treatment of cancer or an inflammatory disease with thalidomide, lenalidomide and/or pomalidomide, the method comprising obtaining biological material from the patient, and measuring the presence or absence of CRBN.

In one embodiment, the mRNA or protein is purified from the tumor and the presence or absence of a biomarker is measured by gene or protein expression analysis. In certain embodiments, the presence or absence of a biomarker is measured by quantitative real-time PCR (QRT-PCR), microarray, flow cytometry or immunofluorescence. In other embodiments, the presence or absence of a biomarker is measured by enzyme-linked immunosorbent assay-based methodologies (ELISA) or other similar methods known in the art. Biomarkers associated with non-Hodgkin's lymphomas are described, for example, in U.S. Patent Publication No. 2011/0223157, the entirety of which is incorporated by reference in its entirety.

In another embodiment, provided herein is a method of predicting patient response to treatment in a cancer patient, the method comprising obtaining cancer cells from the patient, culturing the cells in the presence or absence of a compound provided herein, purifying protein or RNA from the cultured cells, and measuring the presence or absence of a biomarker by, e.g., protein or gene expression analysis. The expression monitored may be, for example, mRNA expression or protein expression. In one embodiment, the cancer patient is a lymphoma, leukemia, multiple myeloma, solid tumor, non-Hodgkin's lymphoma, DLBCL, mantle cell lymphoma, follicular lymphoma, acute myeloblastic leukemia, chronic lymphocytic leukemia, MDS or melanoma patient.

In another embodiment, provided herein is a method of monitoring tumor response to compound (e.g., drug) treatment in a cancer patient. The method comprises obtaining a biological sample from the patient, measuring the expression of a biomarker in the biological sample, administering one or more compounds (e.g., drugs) to the patient, thereafter obtaining a second biological sample from the patient, measuring biomarker expression in the second biological sample, and comparing the levels of expression, where an increased level of biomarker expression after treatment indicates the likelihood of an effective tumor response. In one embodiment, the cancer patient is a lymphoma, leukemia, multiple myeloma, solid tumor, non-Hodgkin's lymphoma, DLBCL, mantle cell lymphoma, follicular lymphoma, acute myeloblastic leukemia, chronic lymphocytic leukemia, MDS or melanoma patient.

In one embodiment, a decreased level of biomarker expression after treatment indicates the likelihood of effective tumor response. The biomarker expression monitored can be, for example, mRNA expression or protein expression. The expression in the treated sample can increase, for example, by about 1.5×, 2.0×, 3×, 5×, or more. In one embodiment, the tumor is a lymphoma, leukemia, multiple myeloma, solid tumor, non-Hodgkin's lymphoma, DLBCL or melanoma.

In another embodiment, provided herein is a method of predicting the sensitivity to compound (e.g., drug) treatment in a cancer patient, specifically, a multiple myeloma or non-Hodgkin's lymphoma patient (e.g., DLBCL). The method comprises obtaining a biological sample from the patient, optionally isolating or purifying mRNA from the biological sample, amplifying the mRNA transcripts by, e.g., RT-PCR, where a higher baseline level of a specific biomarker indicates a higher likelihood that the cancer will be sensitive to treatment with a compound (e.g., drug). In certain embodiments, the biomarker is a gene or protein associated with multiple myeloma or non-Hodgkin's lymphoma (e.g., DLBCL). In one embodiment, the genes are selected from the group consisting of DDB1, DDB2, GSK3B, CUL4A, CUL4B, XBP-1, FAS1, RANBP6, DUS3L, PHGDH, AMPK, IRF4 and NFκB.

In one embodiment, identifying a patient having lymphoma, leukemia, multiple myeloma, solid tumor, non-Hodgkin's lymphoma, DLBCL, mantle cell lymphoma, follicular lymphoma, acute myeloblastic leukemia, chronic lymphocytic leukemia, MDS or melanoma sensitive to treatment with thalidomide, lenalidomide, pomalidomide and/or 3-(5-amino-2-methyl-4-oxo-4H-quinazolin-3-yl)-piperidine-2,6-dione, comprises identifying a gene or protein associated with CRBN. In one embodiment, the gene or protein associated with CRBN is selected from the group consisting of DDB1, DDB2, GSK3B, CUL4A, CUL4B, XBP-1, FAS1, RANBP6, DUS3L, PHGDH, AMPK, IRF4 and NFκB.

In one embodiment, identifying a patient having lymphoma, leukemia, multiple myeloma, a solid tumor, non-Hodgkin's lymphoma, DLBCL or melanoma sensitive to treatment with thalidomide, lenalidomide, pomalidomide and/or 3-(5-amino-2-methyl-4-oxo-4H-quinazolin-3-yl)-piperidine-2,6-dione comprises measuring the level of CRBN activity in the patient. In another embodiment, measuring the level of CRBN activity in the patient comprises measuring DDB1, DDB2, GSK3B, CUL4A, CUL4B, XBP-1, FAS1, RANBP6, DUS3L, PHGDH, AMPK, IRF4 and/or NFκB in cells obtained from the patient.

In still other embodiments, provided herein are methods of predicting the sensitivity to compound (e.g., drug) treatment in a patient having a disease or disorder selected from systemic lupus erythematosus, ANCA-induced vasculitis, glomerulonephritis, acute Wegener's granulomatosis, Myasthenia Gravis, Sjogren Syndrome, anti-phospholipid syndrome, rheumatoid arthritis and fibrotic conditions such as systemic sclerosis. The method comprises obtaining a biological sample from the patient, optionally isolating or purifying mRNA from the biological sample, amplifying the mRNA transcripts by, e.g., RT-PCR, where a higher baseline level of a specific biomarker indicates a higher likelihood that the disease or disorder will be sensitive to treatment with a compound (e.g., drug). In certain embodiments, the biomarker is a gene or protein selected from the group consisting of DDB1, DDB2, GSK3B, CUL4A, CUL4B, XBP-1, FAS1, RANBP6, DUS3L, PHGDH, AMPK, IRF4 and NFκB.

In one embodiment, identifying a patient having systemic lupus erythematosus, ANCA-induced vasculitis, glomerulonephritis, acute Wegener's granulomatosis, Myasthenia Gravis, Sjogren Syndrome, anti-phospholipid syndrome, rheumatoid arthritis or systemic sclerosis and sensitive to treatment with thalidomide, lenalidomide, pomalidomide and/or 3-(5-amino-2-methyl-4-oxo-4H-quinazolin-3-yl)-piperidine-2,6-dione, comprises identifying a gene or protein associated with CRBN. In one embodiment, the gene or protein associated with CRBN is selected from the group consisting of DDB1, DDB2, GSK3B, CUL4A, CUL4B, XBP-1, FAS1, RANBP6, DUS3L, PHGDH, AMPK, IRF4 and NFκB.

In one embodiment, identifying a patient having systemic lupus erythematosus, ANCA-induced vasculitis, glomerulonephritis, acute Wegener's granulomatosis, Myasthenia Gravis, Sjogren Syndrome, anti-phospholipid syndrome, rheumatoid arthritis or systemic sclerosis sensitive to treatment with thalidomide, lenalidomide, pomalidomide and/or 3-(5-amino-2-methyl-4-oxo-4H-quinazolin-3-yl)-piperidine-2,6-dione comprises measuring the level of CRBN activity in the patient. In another embodiment, measuring the level of CRBN activity in the patient comprises measuring DDB1, DDB2, GSK3B, CUL4A, CUL4B, XBP-1, FAS1, RANBP6, DUS3L, PHGDH, AMPK, IRF4 and/or NFκB in cells obtained from the patient.

In one embodiment, the compound is thalidomide.
In another embodiment, the compound is lenalidomide.
In another embodiment, the compound is pomalidomide.
In another embodiment, the compound is 3-(5-amino-2-methyl-4-oxo-4H-quinazolin-3-yl)-piperidine-2,6-dione, or an enantiomer thereof, or a pharmaceutically acceptable salt, polymorph, solvate or hydrate thereof.

Also provided herein are kits useful for predicting the likelihood of an effective lymphoma, leukemia, multiple myeloma, a solid tumor, non-Hodgkin's lymphoma, diffuse large B-cell lymphoma mantle cell lymphoma, follicular lymphoma, acute myeloblastic leukemia, chronic lymphocytic leukemia, MDS or melanoma treatment or for monitoring the effectiveness of a treatment with one or more compounds (e.g., drugs). The kit comprises a solid support, and a means for detecting the protein expression of at least one biomarker in a biological sample. Such a kit may employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an oral tissue, gastrointestinal tissue, an organ, an organelle, a biological fluid, a blood sample, a urine sample, or a skin sample. The biological sample can be, for example, a lymph node biopsy, a bone marrow biopsy, or a sample of peripheral blood tumor cells.

In another embodiment, the kit comprises a solid support, nucleic acids contacting the support, where the nucleic acids are complementary to at least 20, 50, 100, 200, 350, or more bases of mRNA, and a means for detecting the expression of the mRNA in a biological sample.

In certain embodiments, the kits provided herein employ means for detecting the expression of a biomarker by quantitative real-time PCR (QRT-PCR), microarray, flow cytometry or immunofluorescence. In other embodiments, the expression of the biomarker is measured by ELISA-based methodologies or other similar methods known in the art.

In still other embodiments, the kits provided herein are useful for predicting the likelihood of an effective treatment of a disease or disorder selected from systemic lupus erythematosus, ANCA-induced vasculitis, glomerulonephritis, acute Wegener's granulomatosis, Myasthenia Gravis, Sjogren Syndrome, anti-phospholipid syndrome, rheumatoid arthritis and fibrotic conditions such as systemic sclerosis.

In addition to the methods described above, a compound provided herein is administered in combination with a therapy conventionally used to treat, prevent or manage a disease or disorder described herein. Examples of such conventional therapies include, but are not limited to, surgery, chemotherapy, radiation therapy, hormonal therapy, biological therapy and immunotherapy.

Also provided herein are pharmaceutical compositions, single unit dosage forms, dosing regimens and kits which comprise a compound provided herein, or a pharmaceutically acceptable salt, solvate, hydrate, stereoisomer, clathrate, or prodrug thereof, and a second, or additional, active agent. Second active agents include specific combinations, or "cocktails," of drugs.

4. BRIEF DESCRIPTION OF THE FIGURES

Figure 1B:
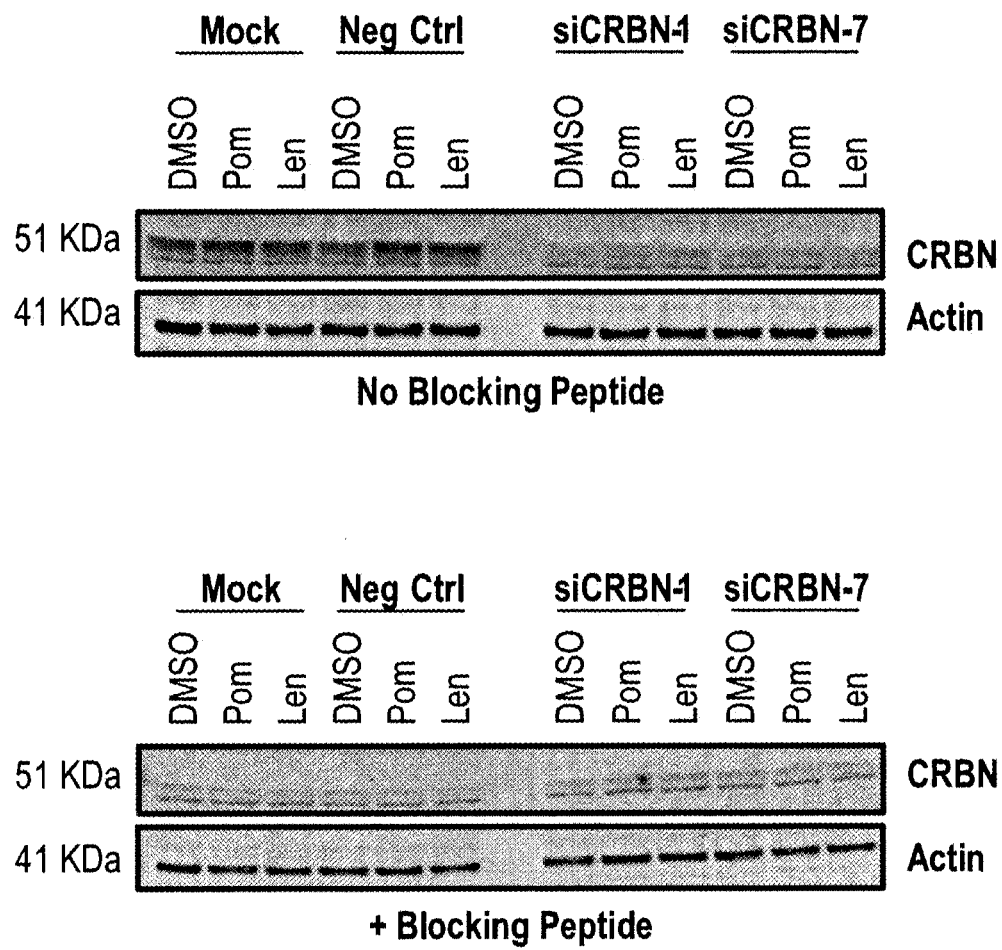

FIGS. 1A & 1B: Confirmation of CRBN knockdown by siRNAs in H929 and U266 multiple myeloma cells.

Figure 2A:
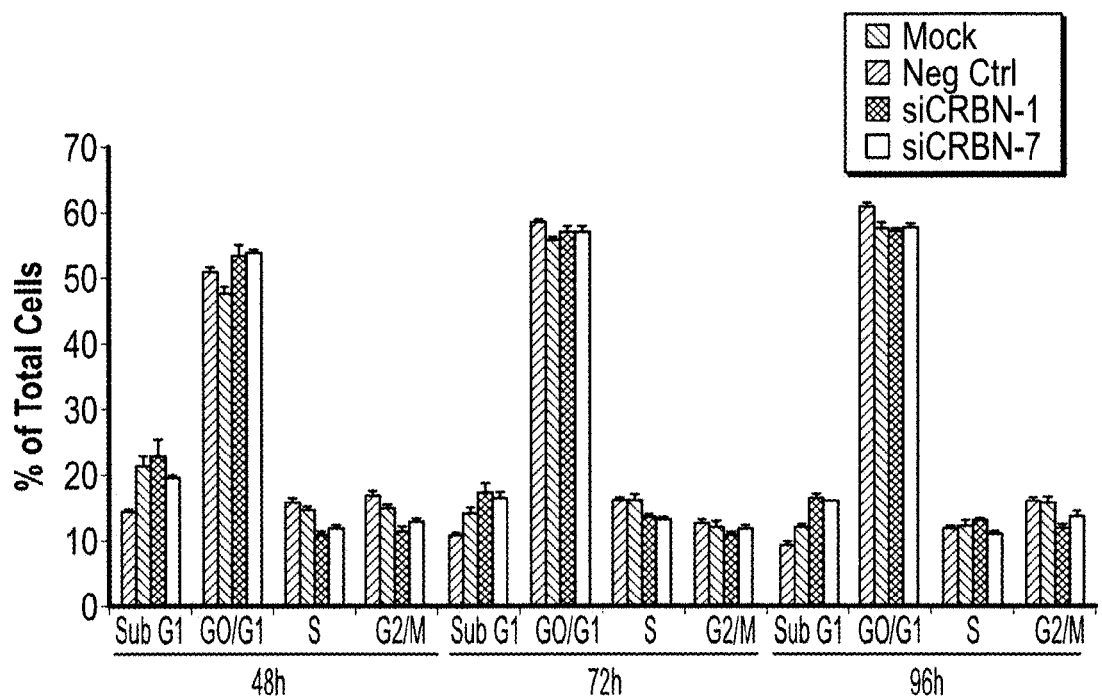
Figure 2B:
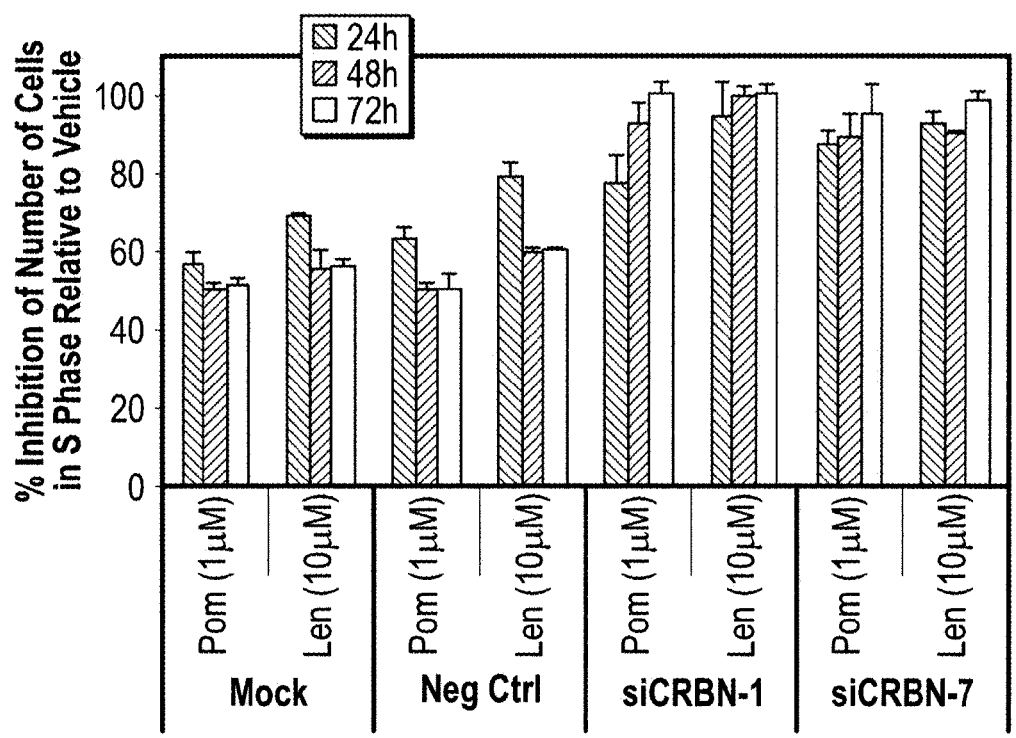
Figure 2C:
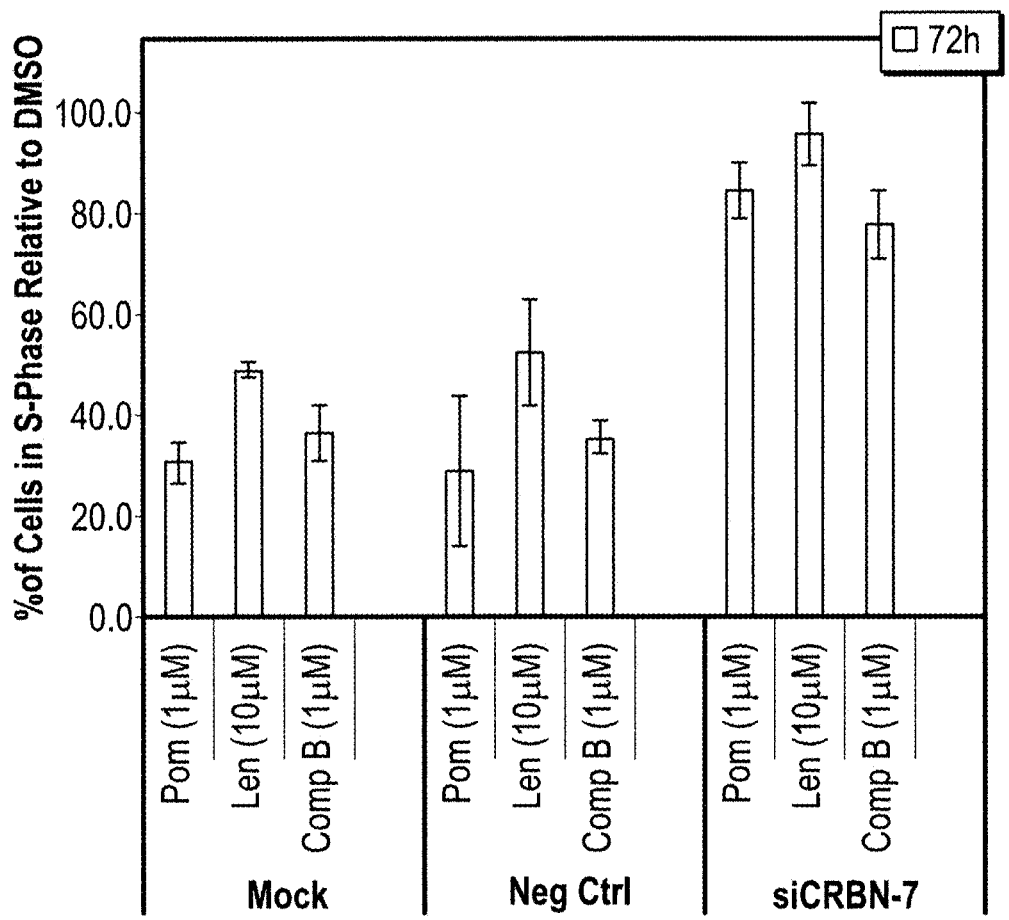

FIGS. 2A-2C: Knockdown of CRBN abrogated G1 arrest induced by lenalidomide ("Len"), pomalidomide ("Pom") and Compound B.

Figure 3A:
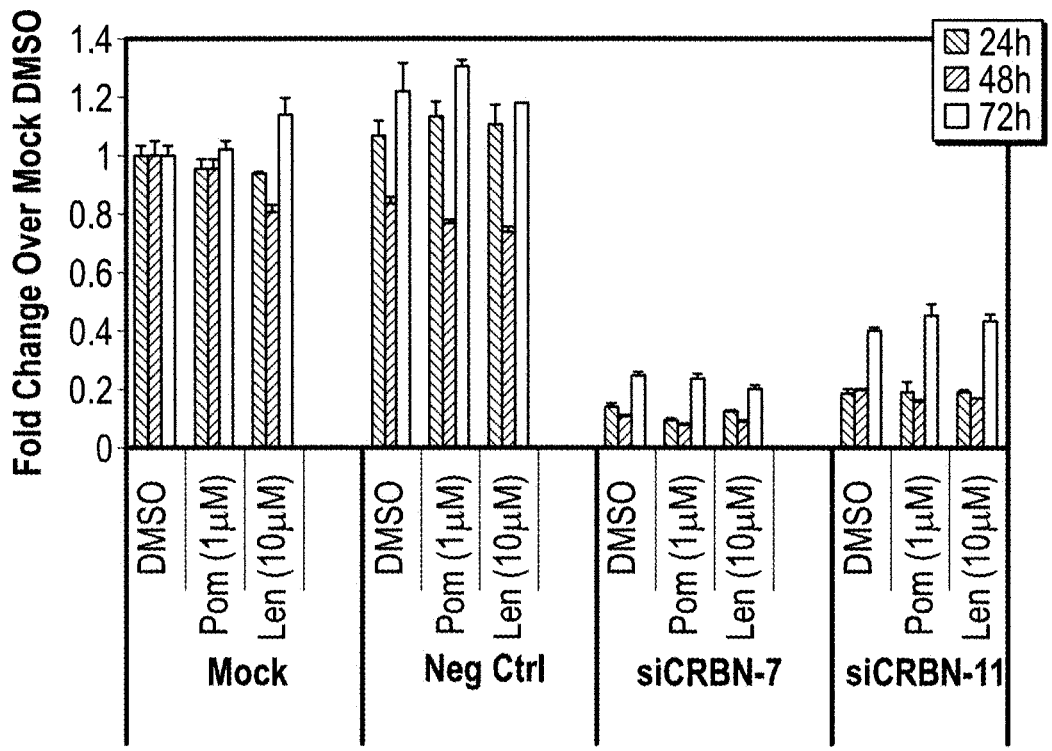

FIG. 3A: CRBN knockdown in U266B1 cells confirmed by RT-PCR.

Figure 3B:
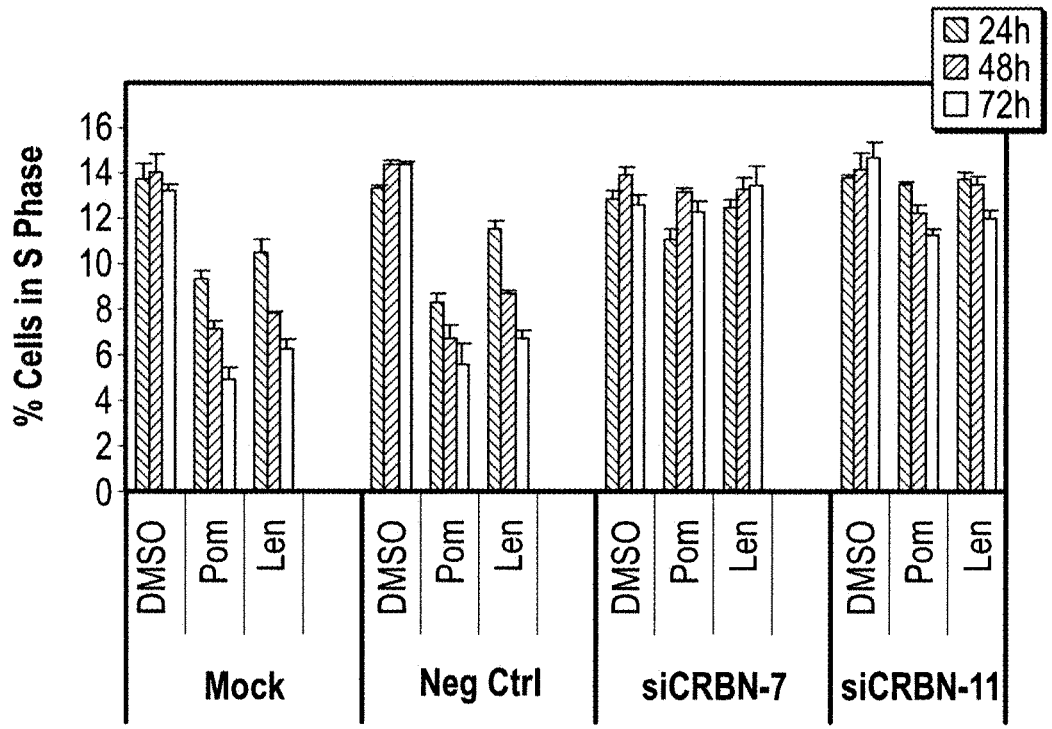

FIG. 3B: CRBN knockdown abrogates lenalidomide and pomalidomide effect on cell cycle in U266 cells.

Figure 3C:
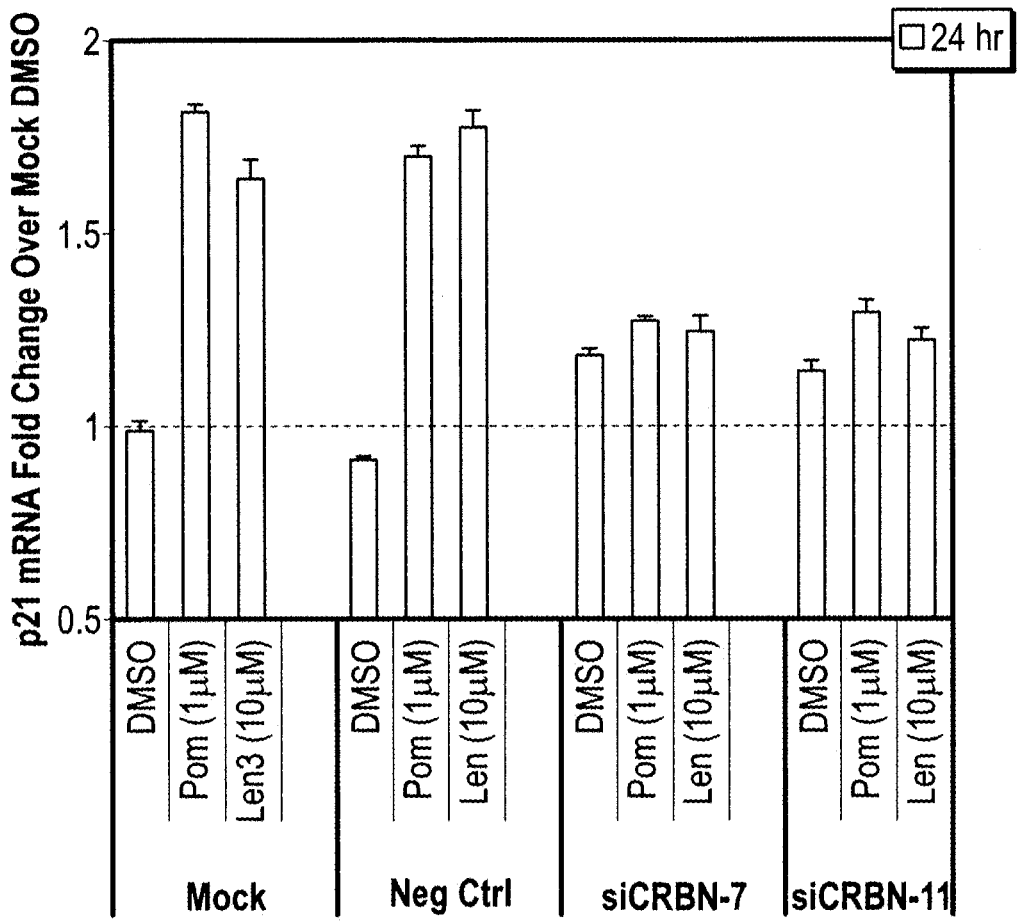
Figure 3D:
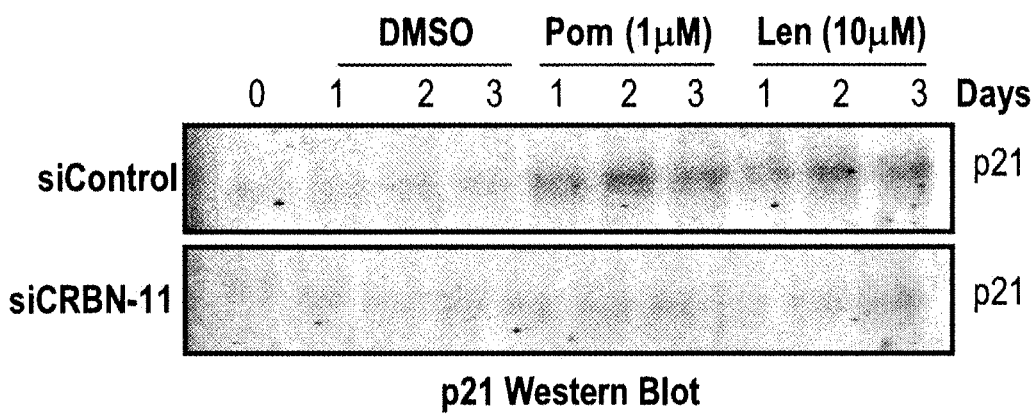

FIGS. 3C & 3D: Knockdown of CRBN prevents increase of p21$^{WAF1}$ in lenalidomide and pomalidomide treated U266 cells as detected by RT-PCR and Western blot analysis.

FIGS. 4A-4D: CRBN knockdown abrogates drug effect on phosphorylation of pRb and IRF-4 in H929 cells.

Figure 5A:
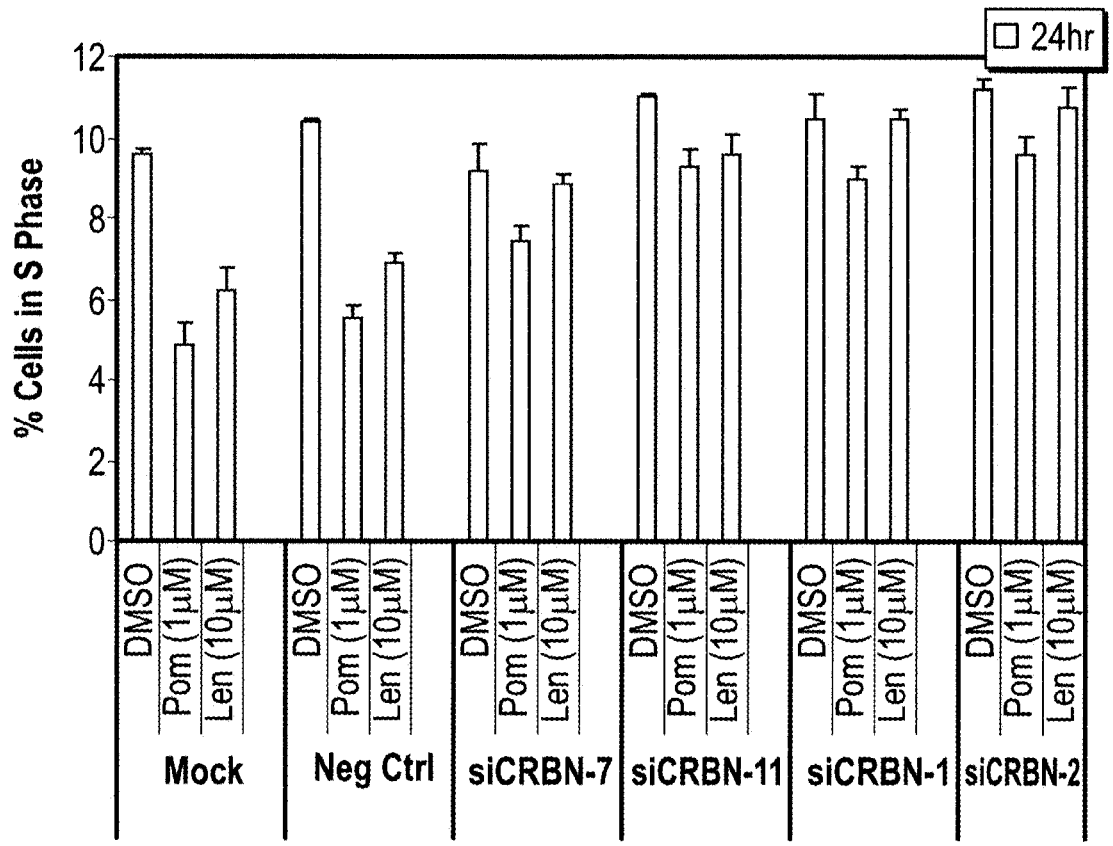
Figure 5B:
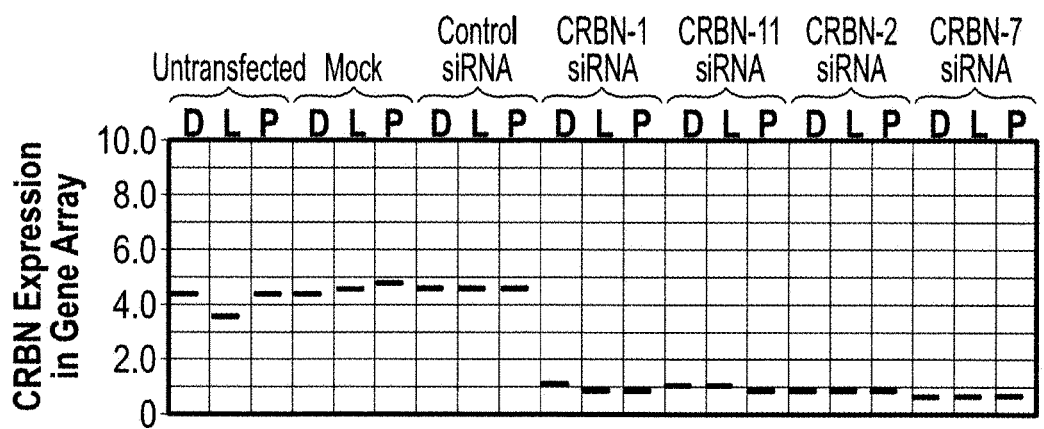
Figure 5C:
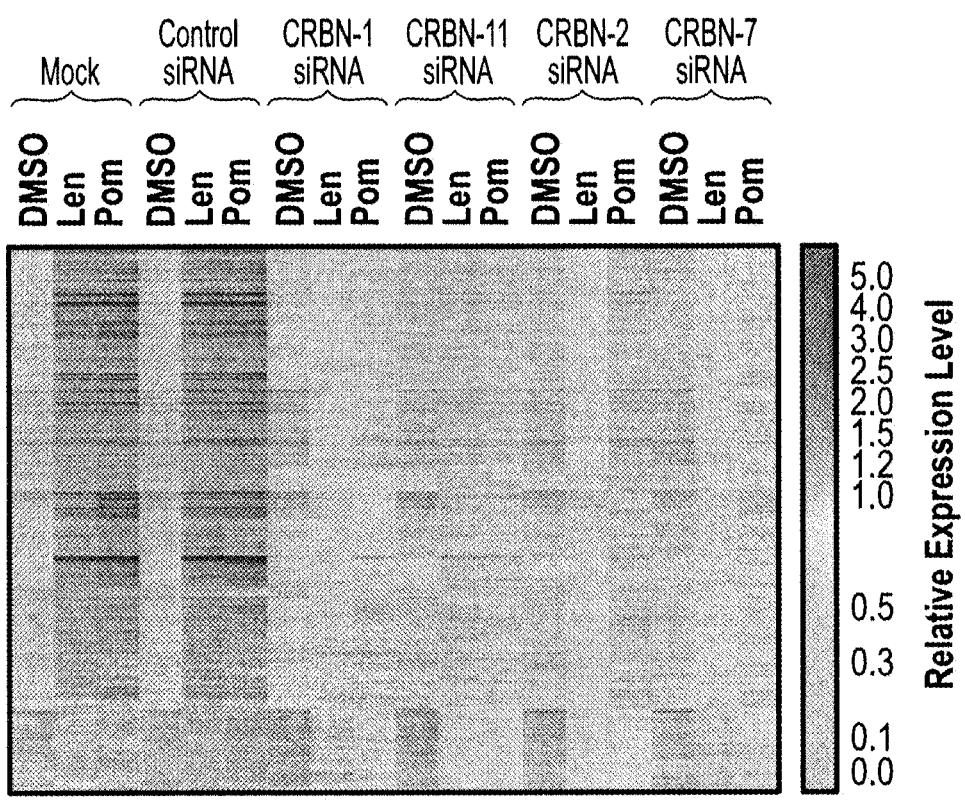
Figure 6A:
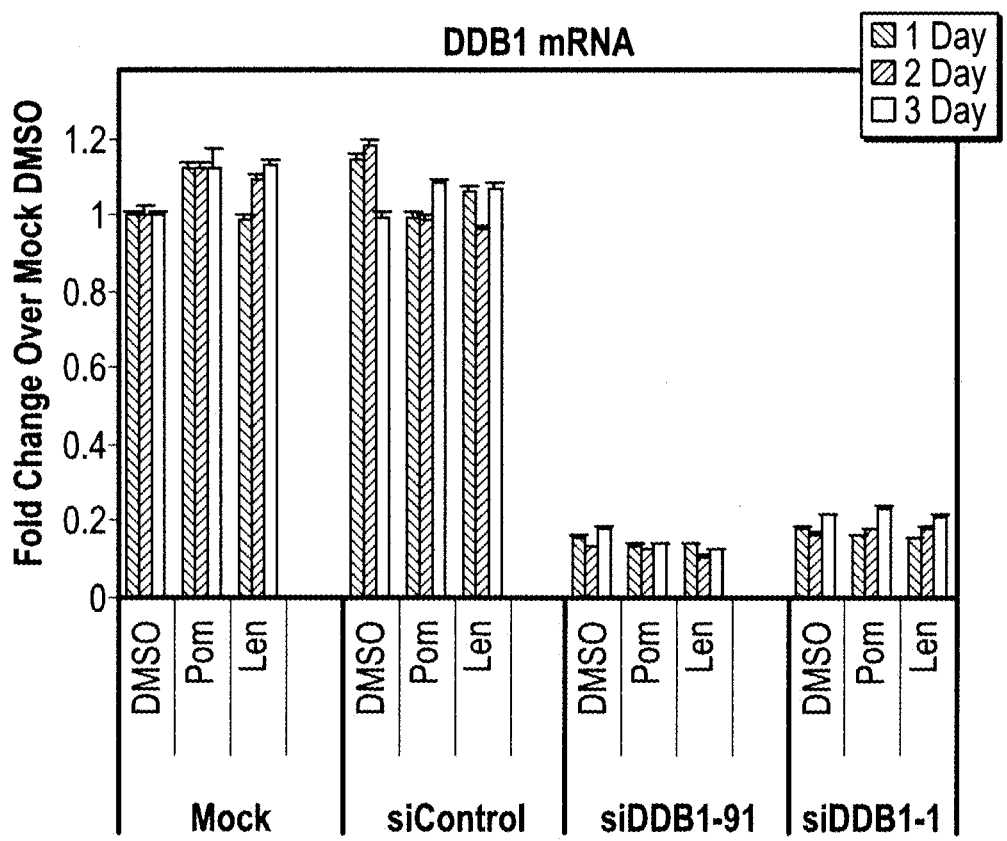
Figure 6B:
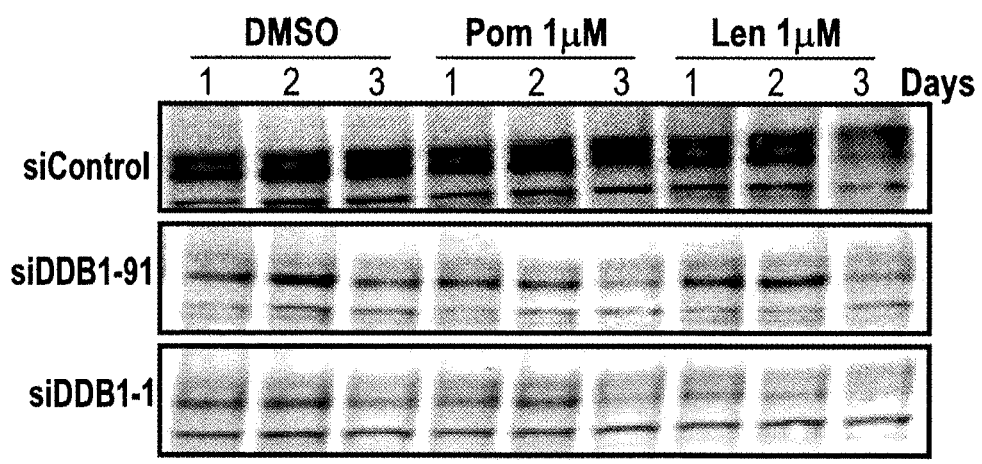
Figure 6C:
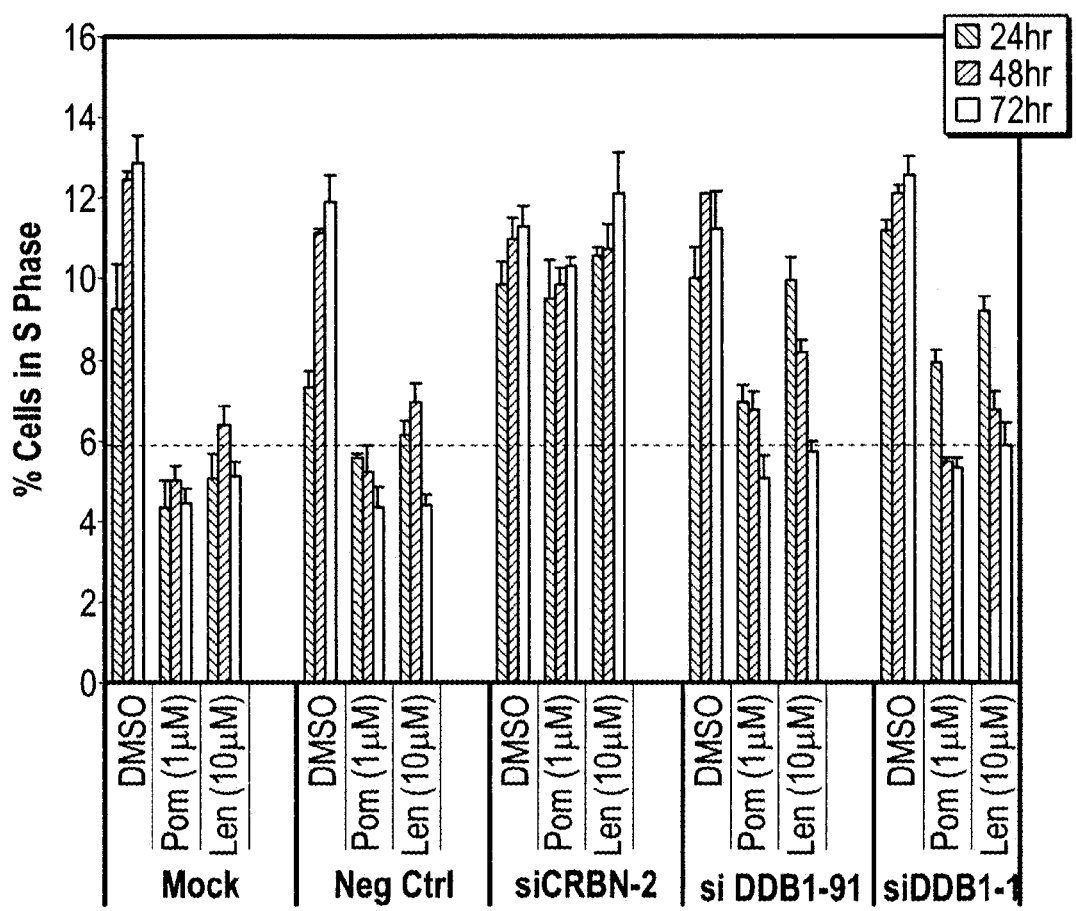
Figure 6D:
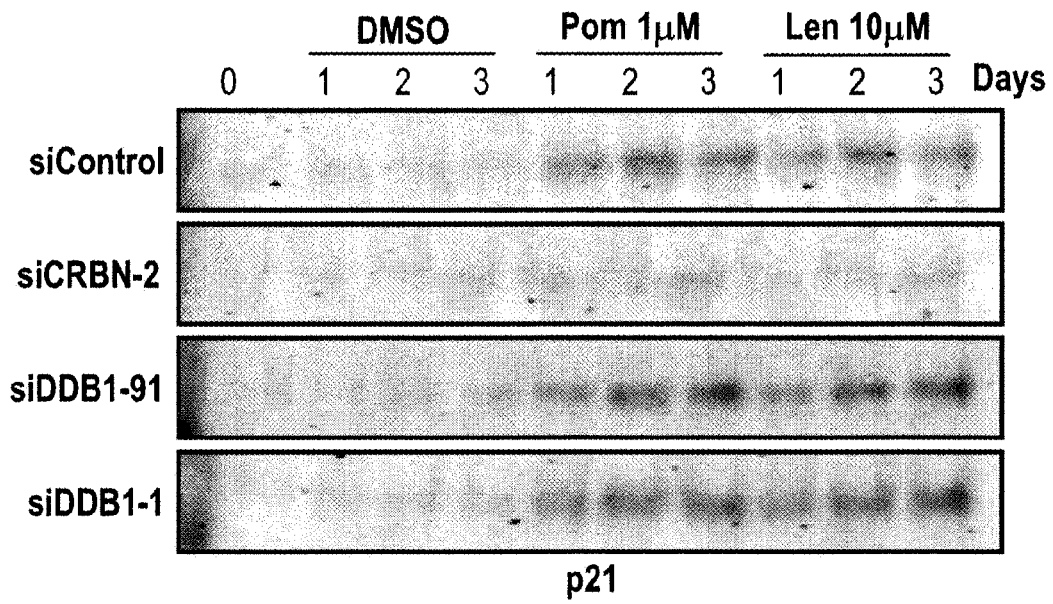

FIGS. 5A-5C: Cell cycle and gene expression profiles in U266B1 cells transfected with CRBN-siRNA.

FIGS. 6A-6D: DDB1 knockdown only partially affected cell cycle delay induced by lenalidomide and pomalidomide in U266 cells.

Figure 7B:
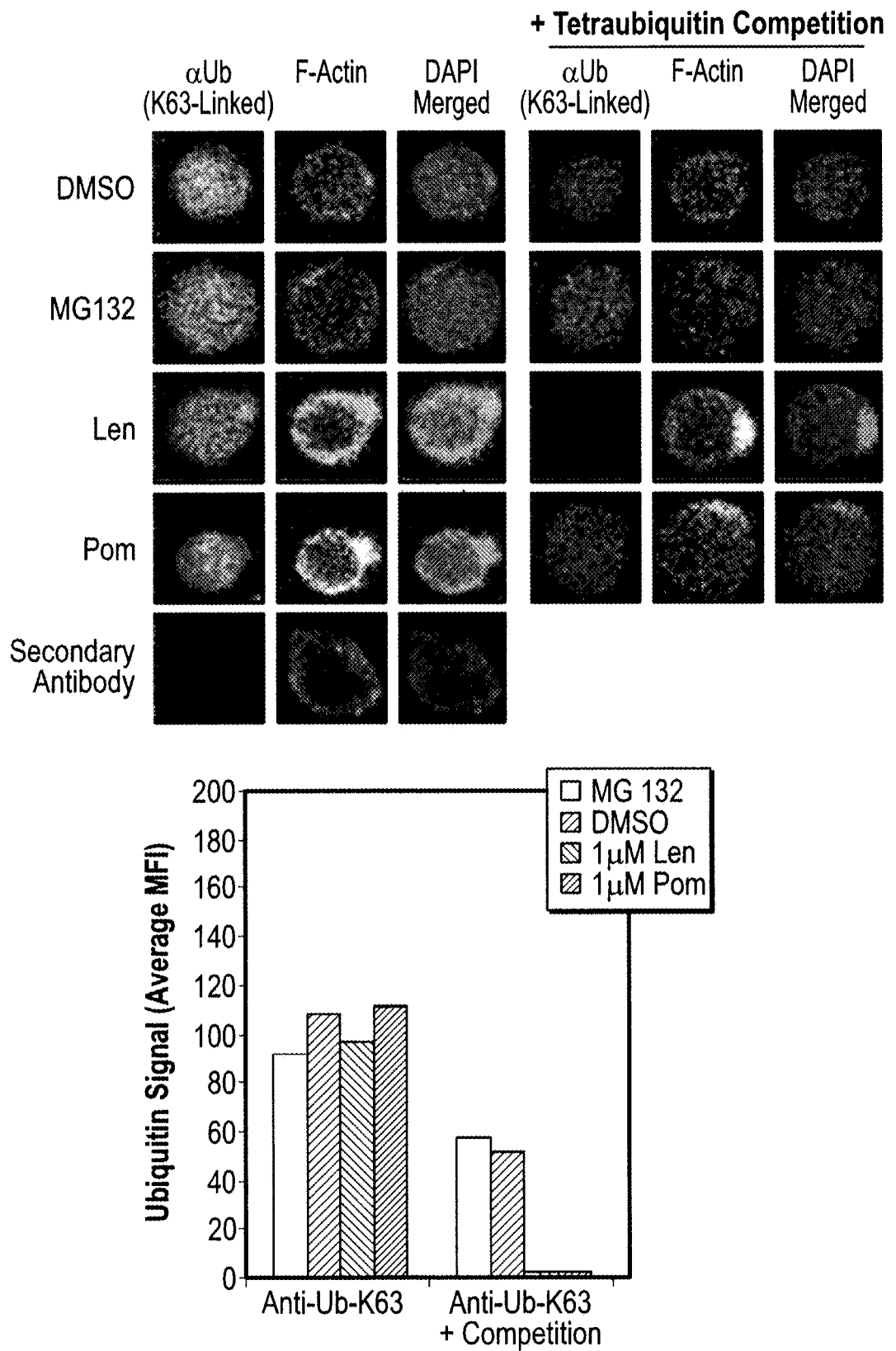

FIGS. 7A & 7B: Lenalidomide and pomalidomide decrease total K48-linked polyubiquitination but not K-63-linked ubiquitination in H929.

Figure 8:

FIG. 8: 1 hour up-regulated ubiquitination, no MG132.

Figure 9A:
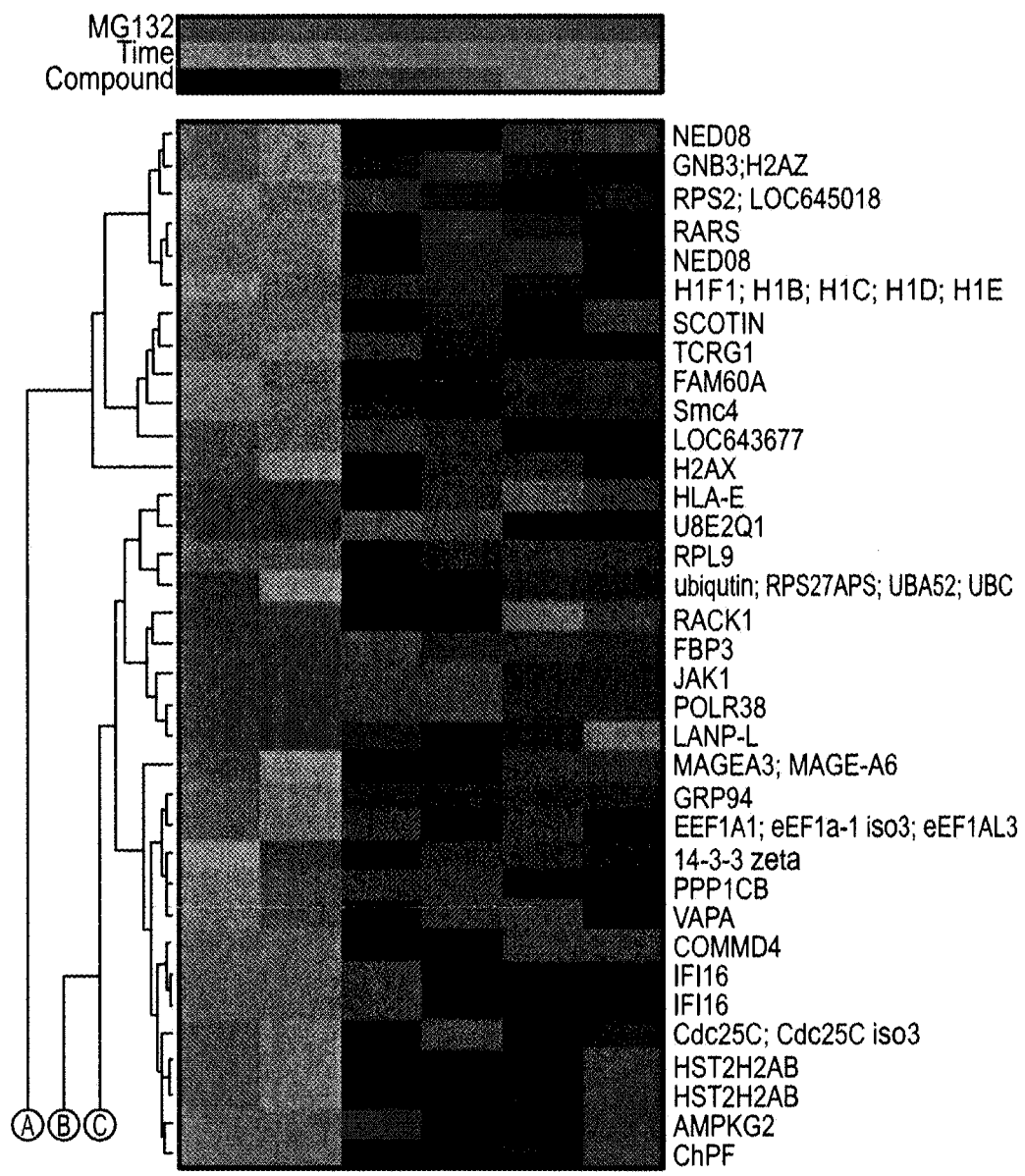
Figure 9B:
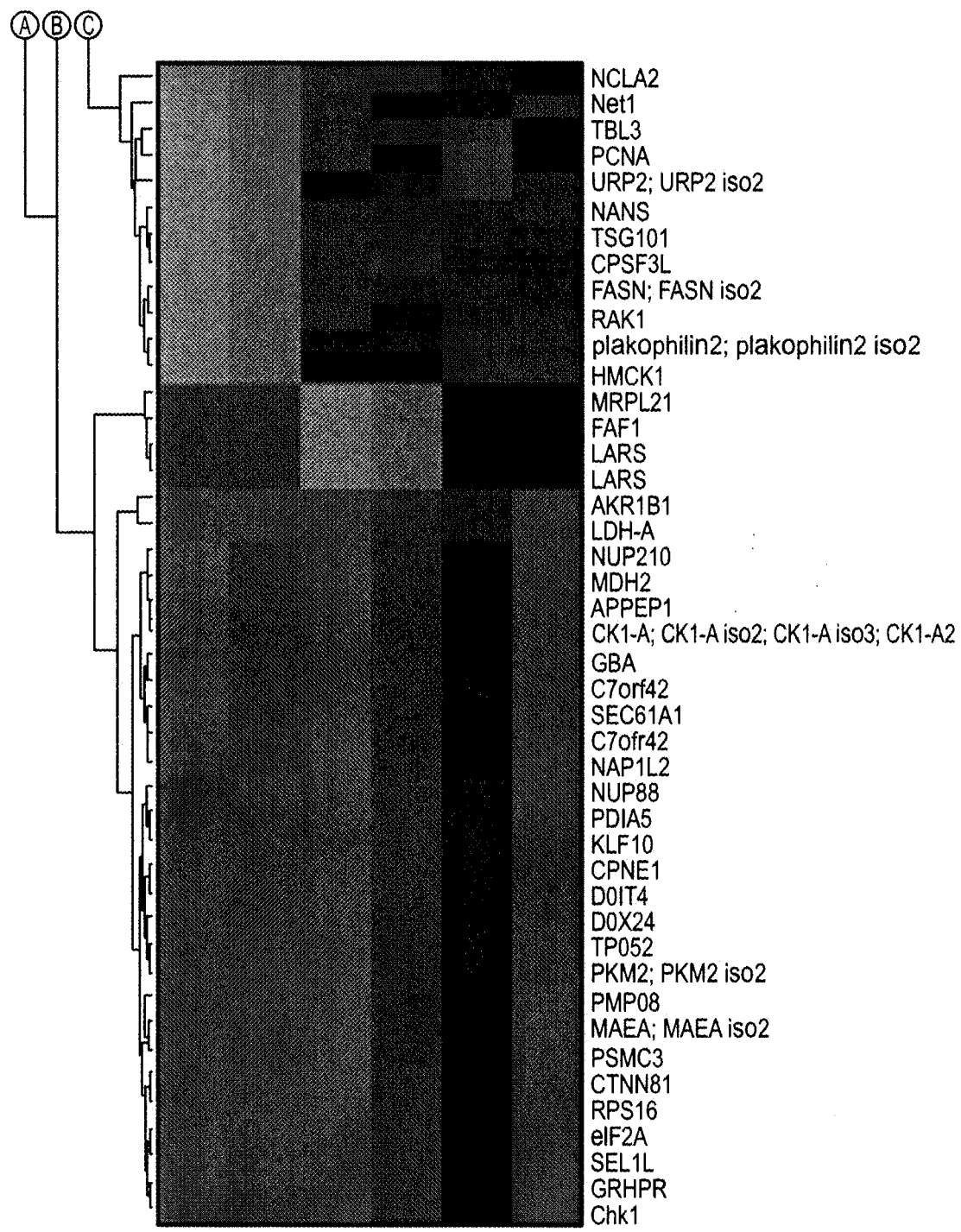

FIG. 9: 4 hour up-regulated ubiquitination, no MG132.

Figure 10A:
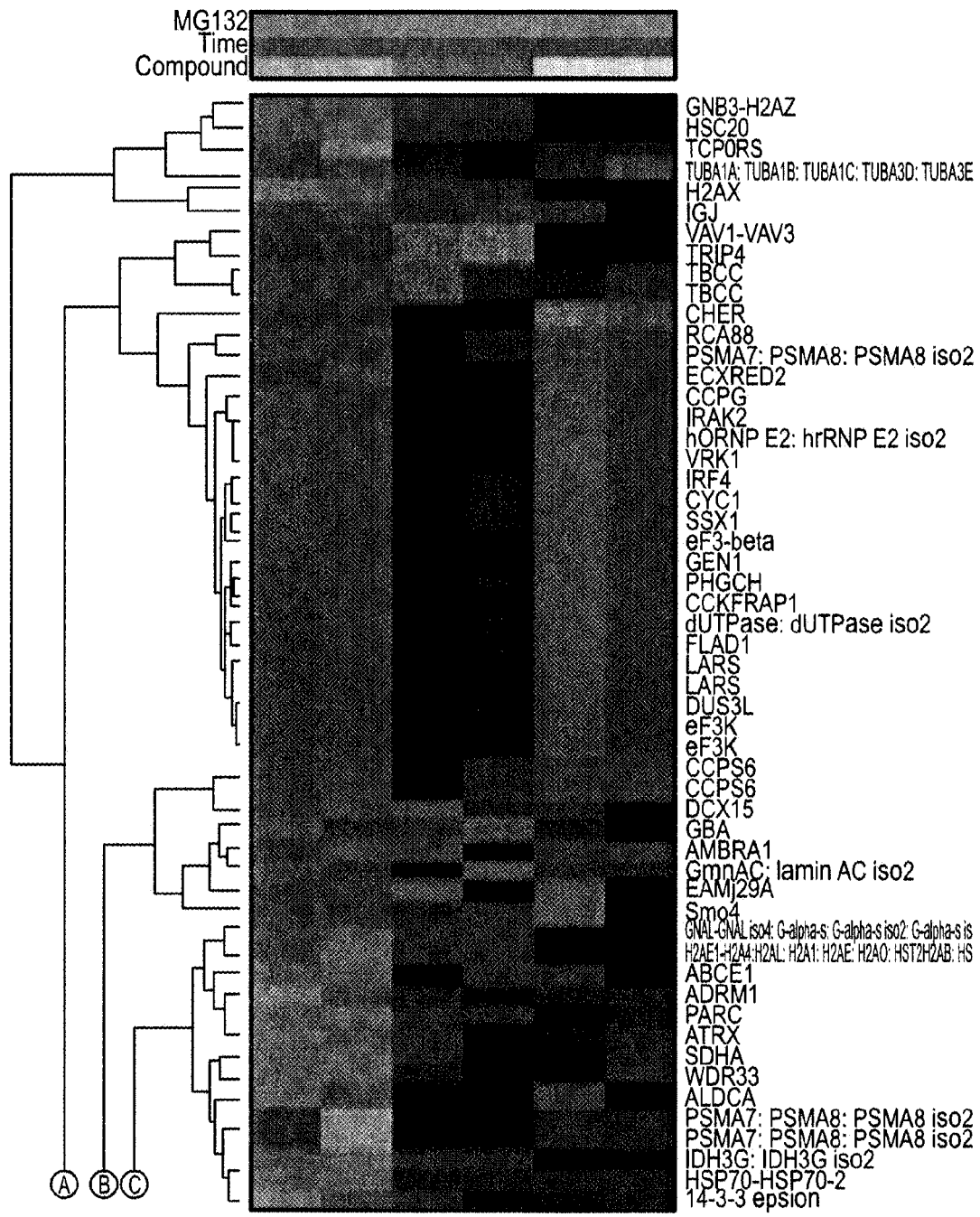
Figure 10B:
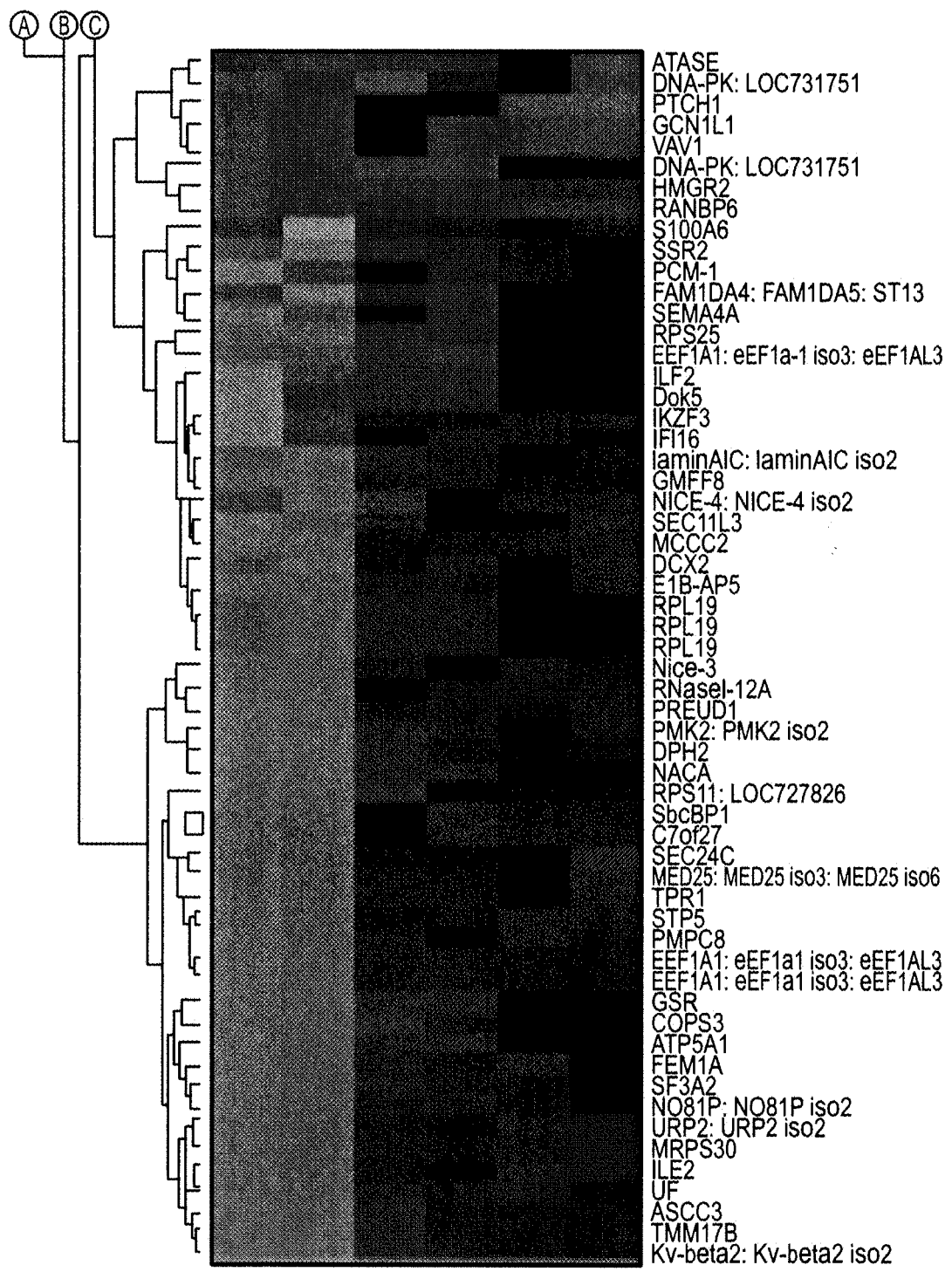

FIG. 10: 1 hour up-regulated ubiquitination, MG132.

Figure 11A:
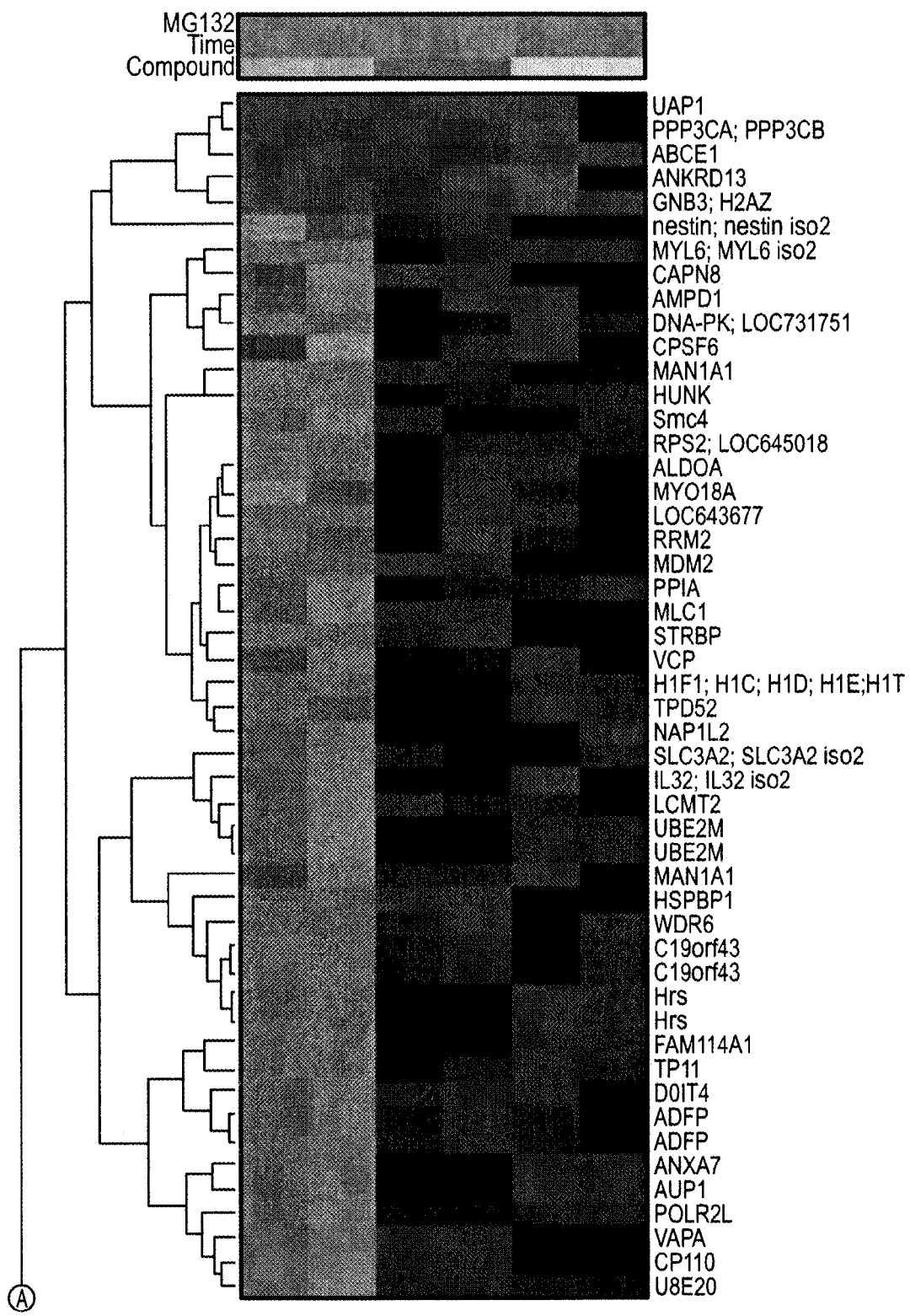
Figure 11B:
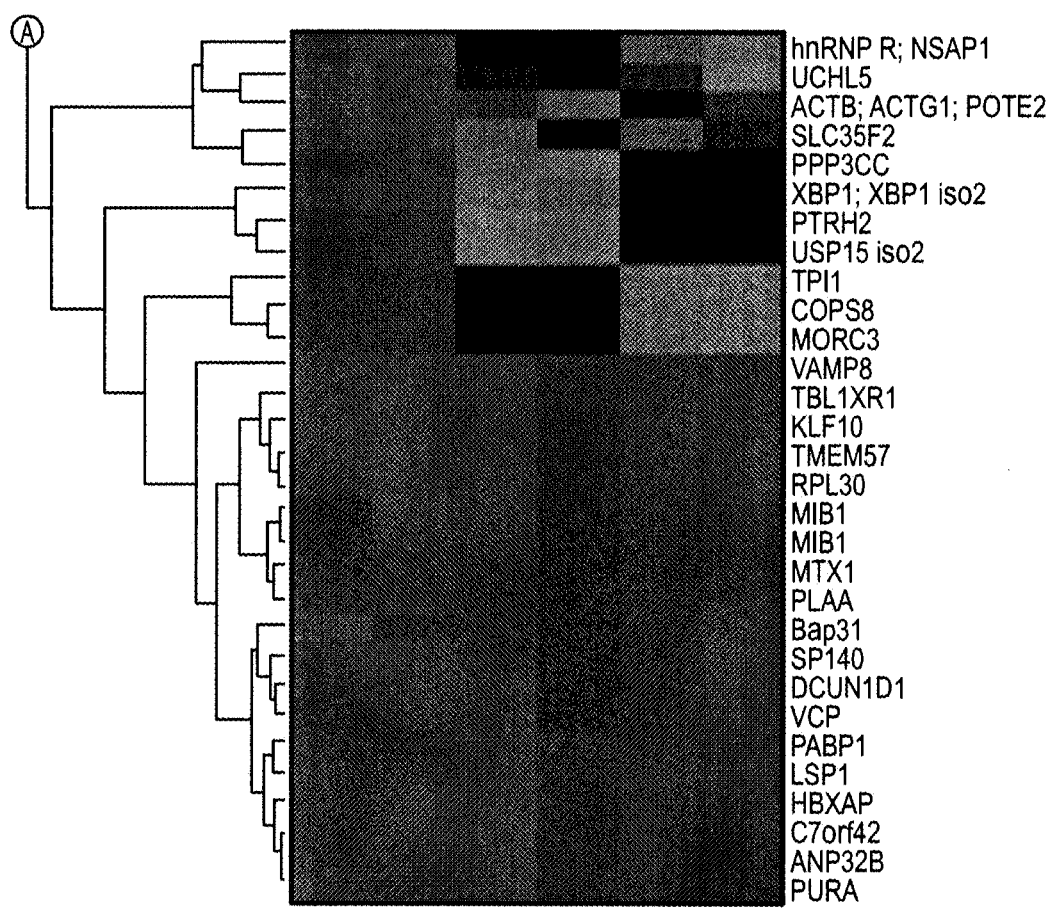
Figure 12A:
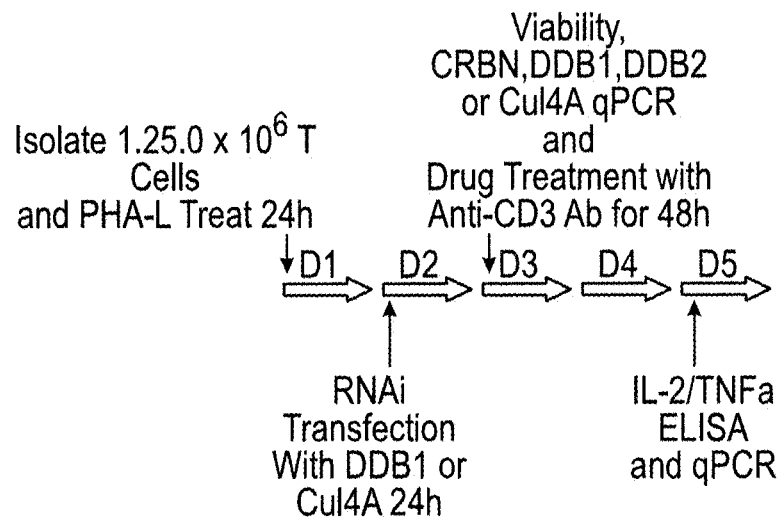
Figure 12B:
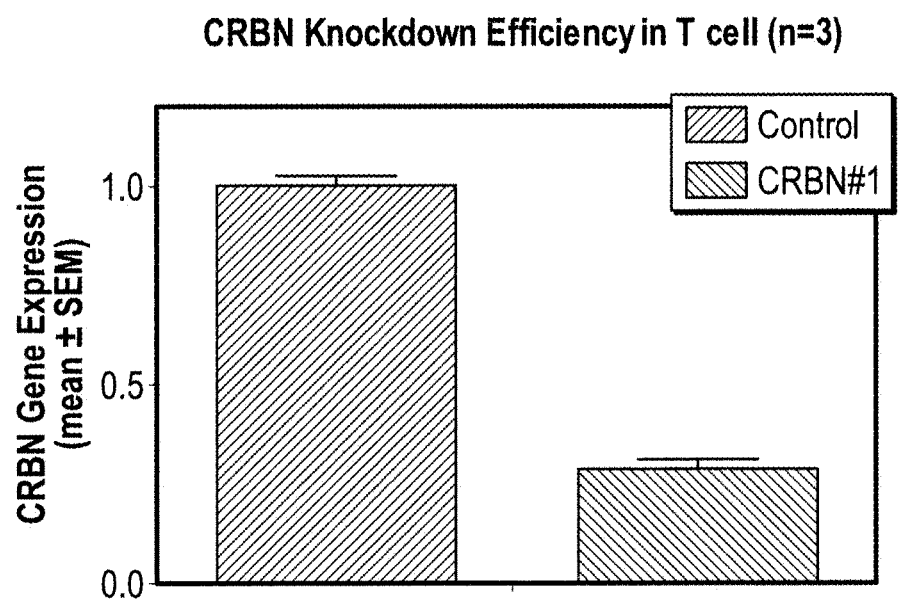
Figure 12C:
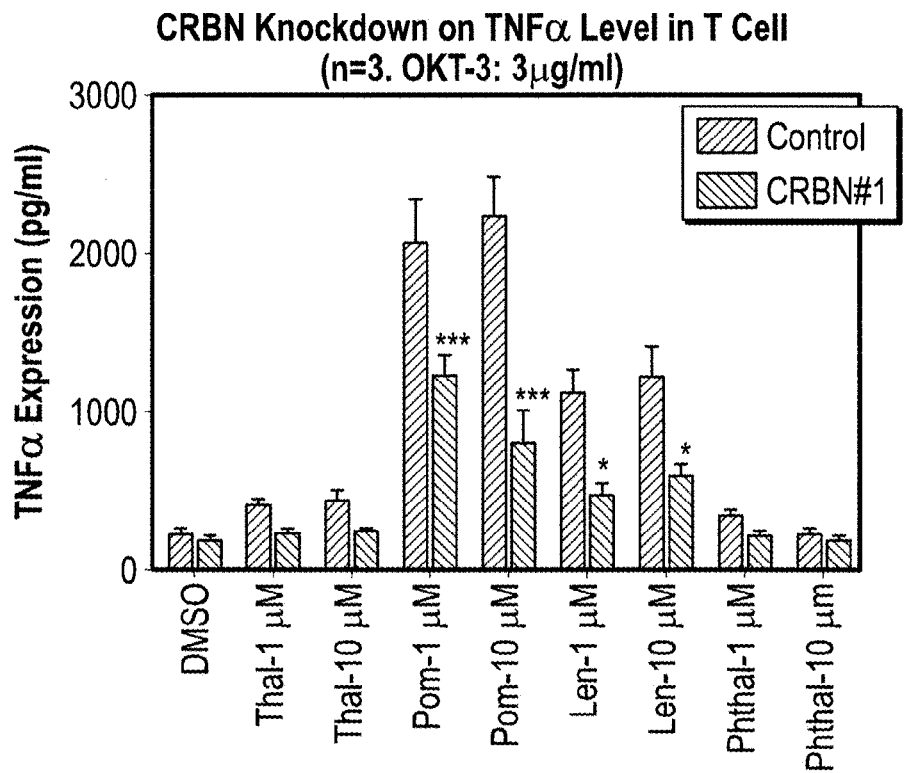
Figure 12D:
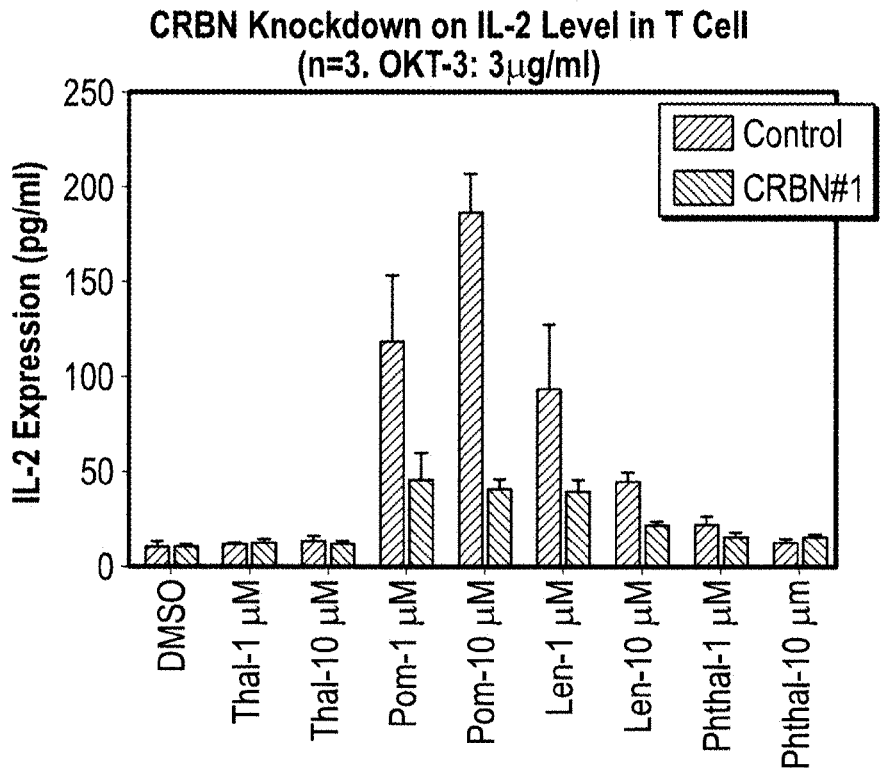

FIG. 11: 4 hour up-regulated ubiquitination, MG132.

FIGS. 12A-12D: Effect of CRBN knockdown on TNFα and IL-2 levels in T cells.

Figure 13A:
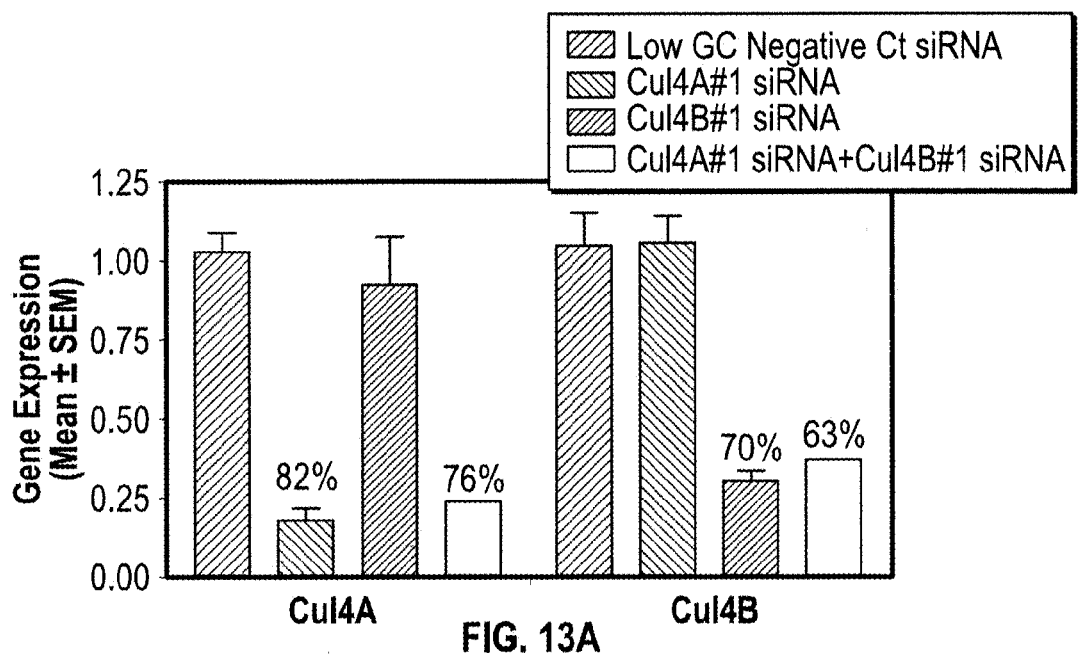
Figure 13B:
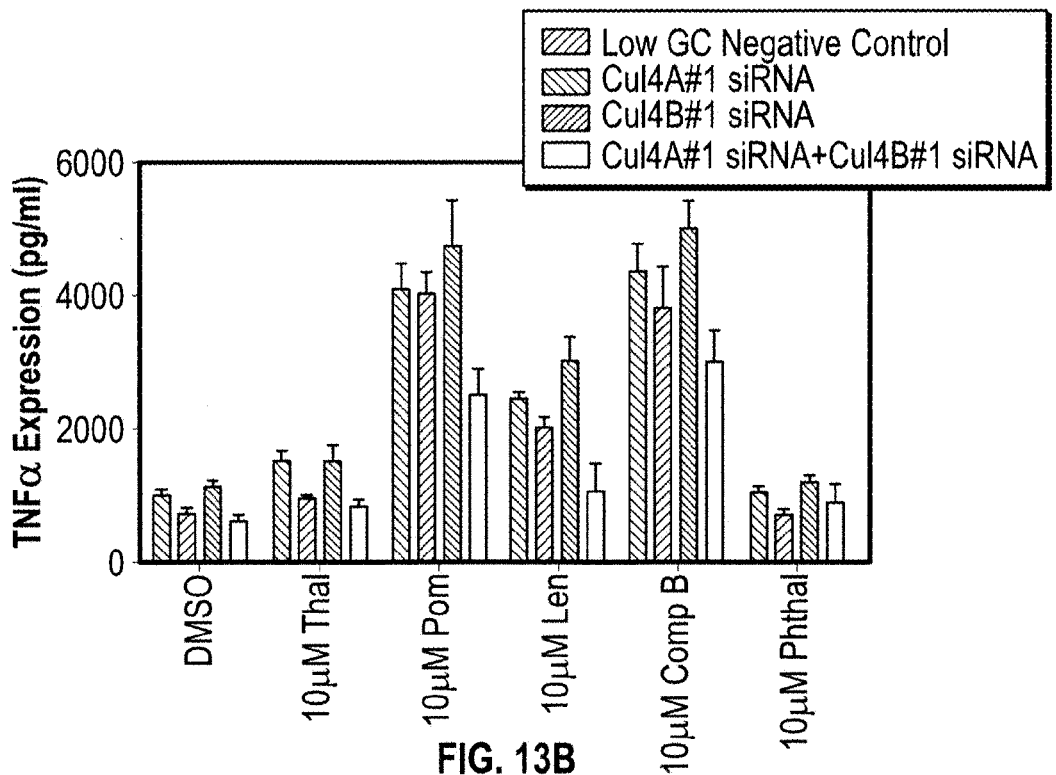
Figure 13C:
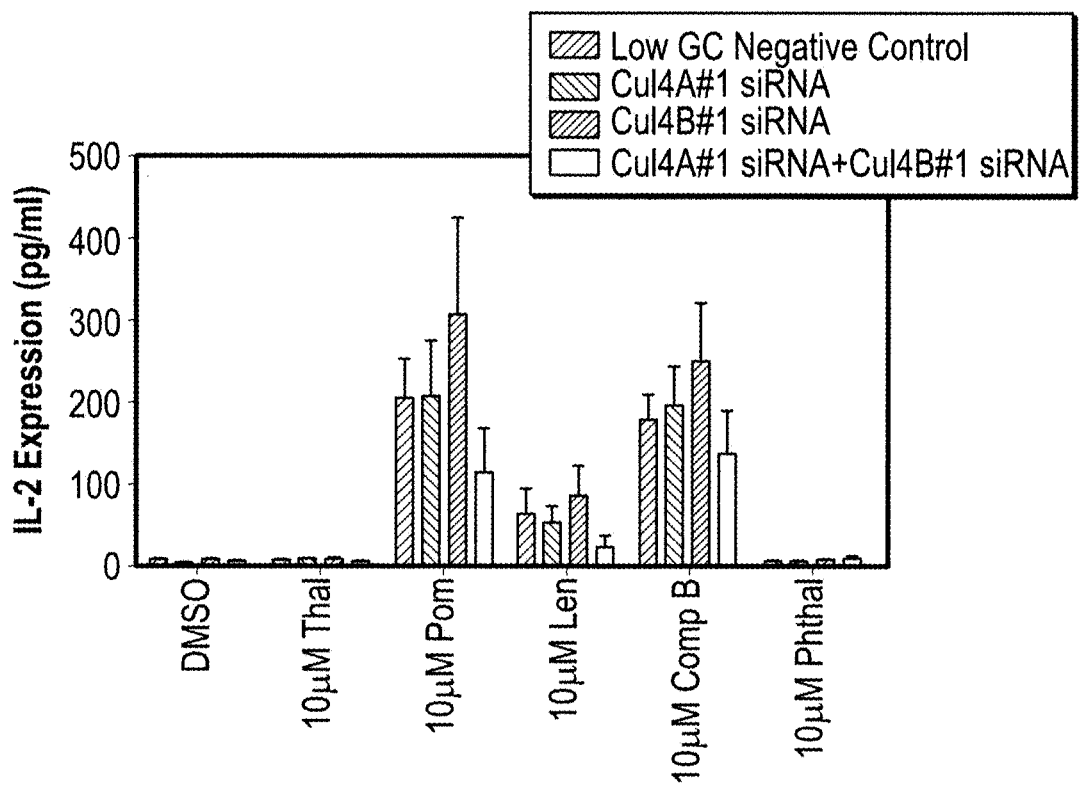

FIGS. 13A-13C: Effect of CUL4A and CUL4A knockdown on TNFα and IL-2 levels in T cells.

Figure 14:
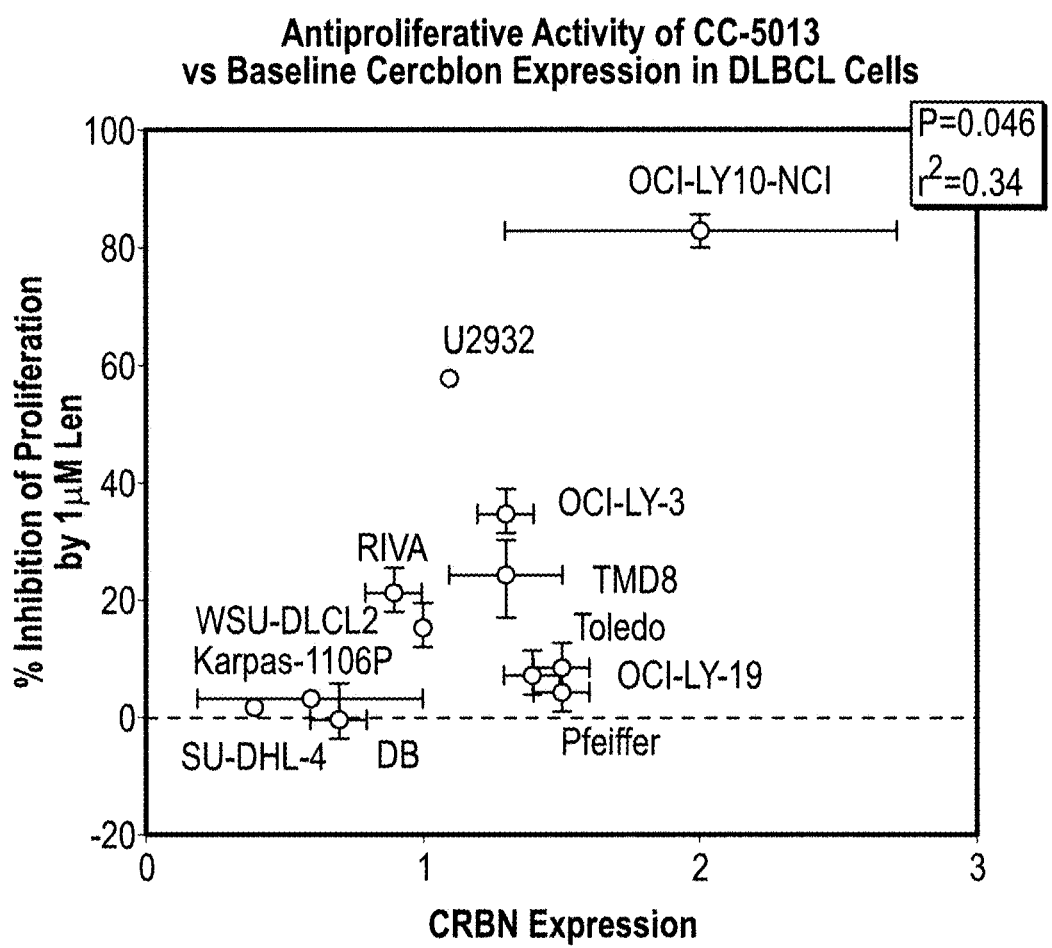

FIG. 14: Antiproliferative activity of lenalidomide vs. CRBN expression in DLBCL cells.

Figure 15A:
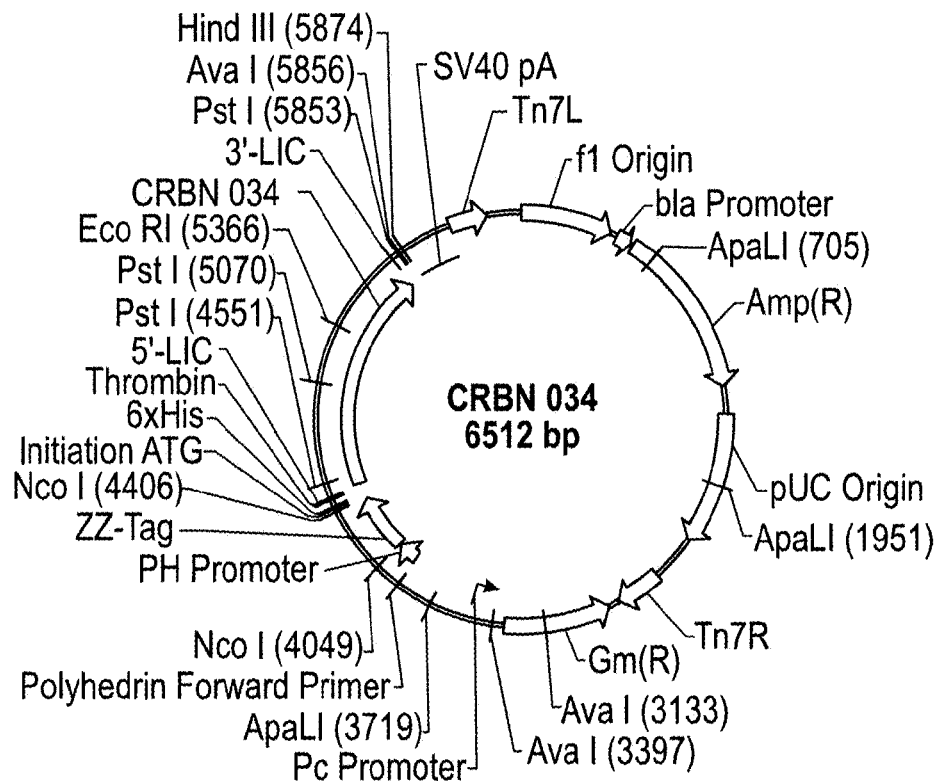

FIG. 15A: Map of CRBN_034 clone. FIG. 15A discloses "6xHis" as SEQ ID NO: 230.

Figure 15B:
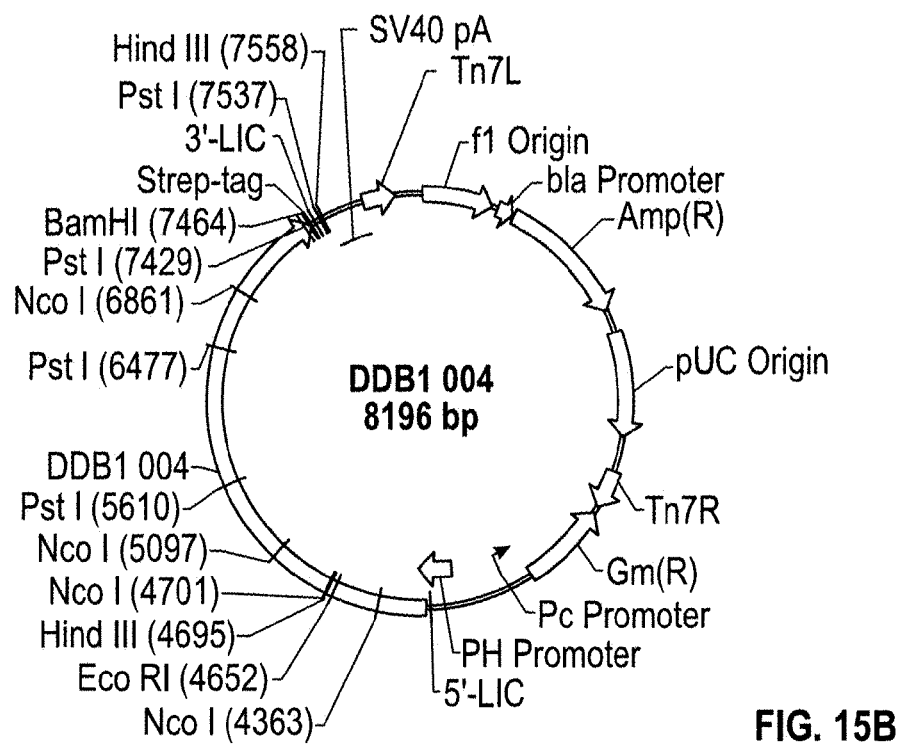

FIG. 15B: Map of DDB1_004 clone.

Figure 16A:
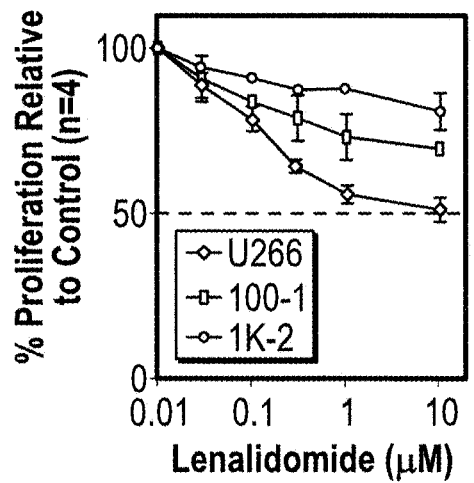

FIG. 16A: Antiproliferative activity of lenalidomide in CRBN-sensitive myeloma cells.

Figure 16B:
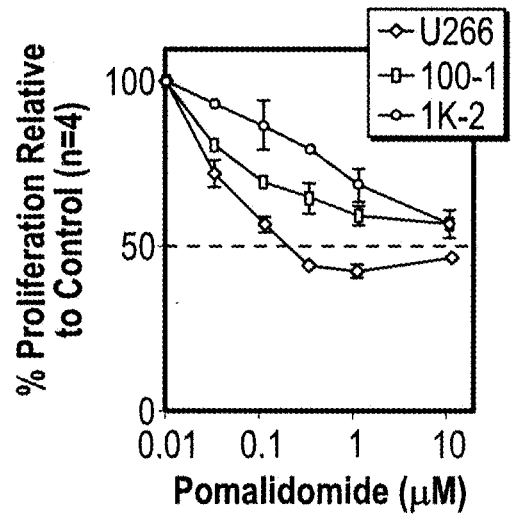

FIG. 16B: Antiproliferative activity of pomalidomide in CRBN-sensitive myeloma cells.

Figure 16C:
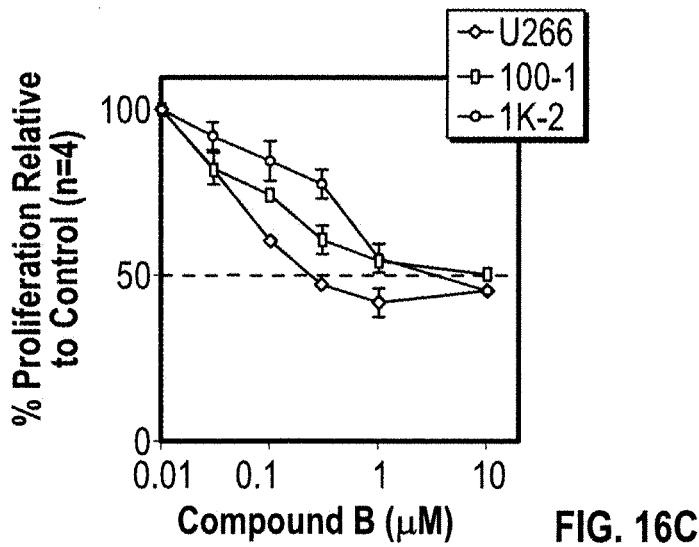

FIG. 16C: Antiproliferative activity of Compound B in CRBN-sensitive myeloma cells.

Figure 17:
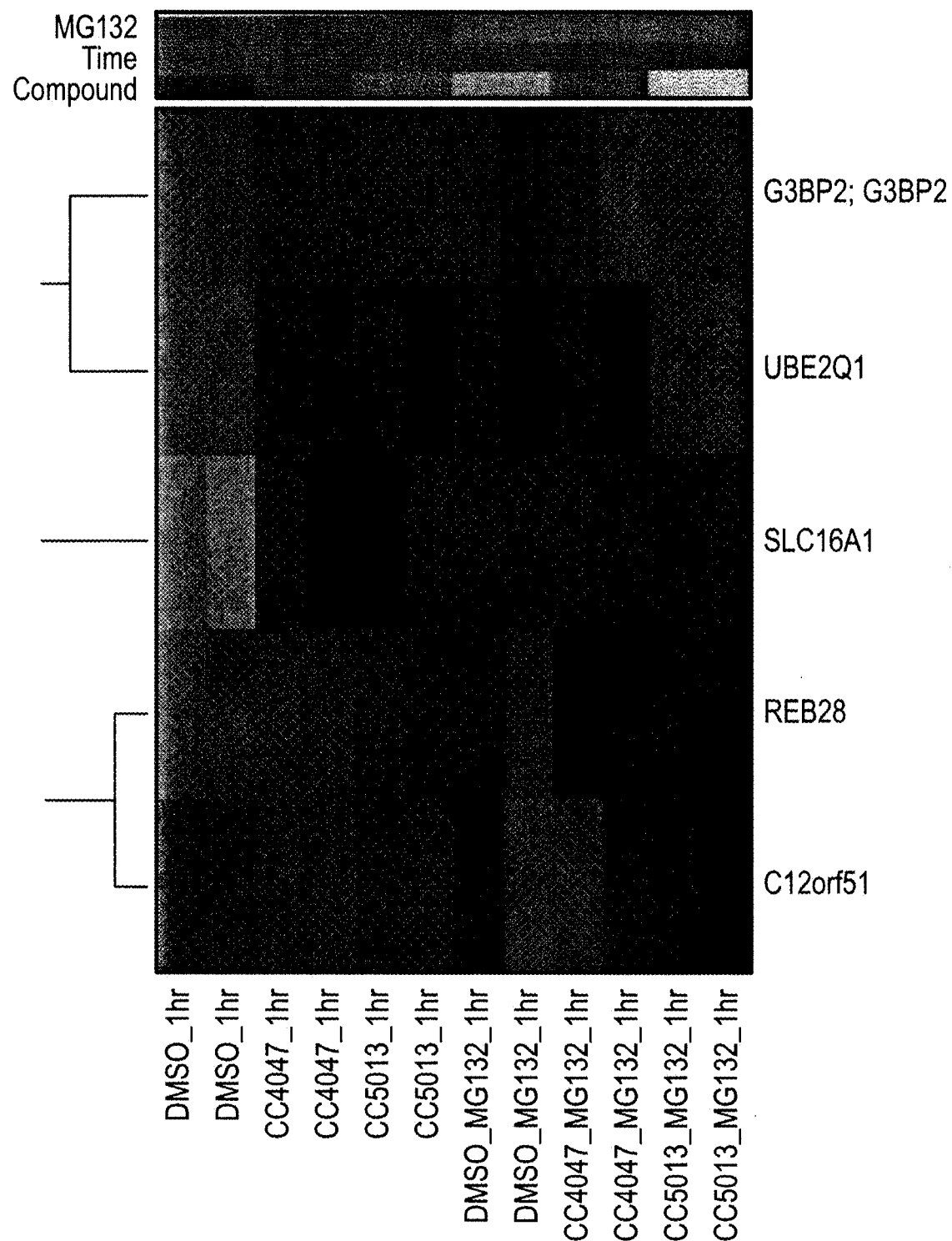

FIG. 17: Peptides regulated by lenalidomide ("Len") and pomalidomide ("Pom") without MG132 in 1 hour ubiquitination experiments.

Figure 18:
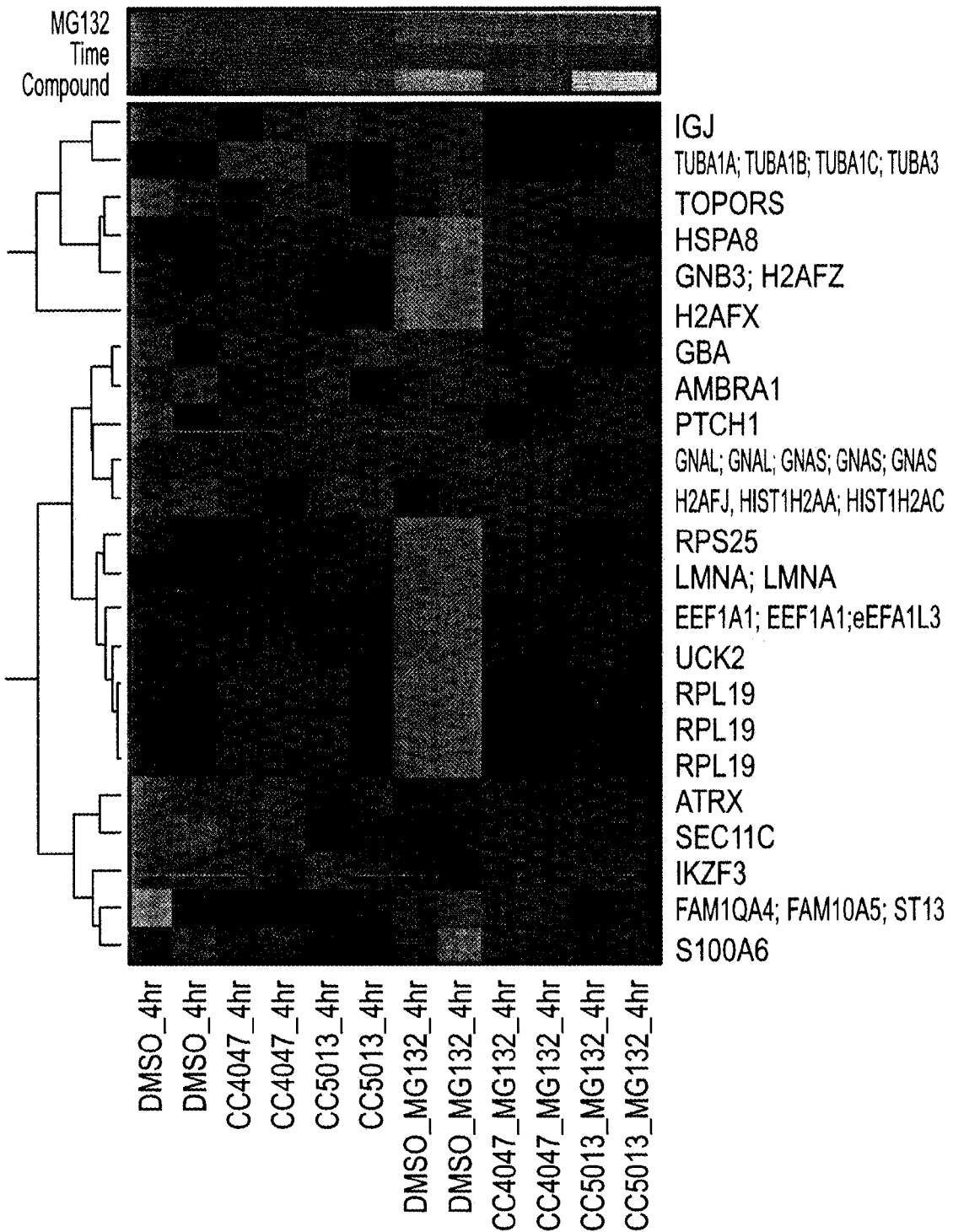

FIG. 18: Peptides regulated by lenalidomide ("Len") and pomalidomide ("Pom") with MG132 in 1 hour ubiquitination experiments.

Figure 19:
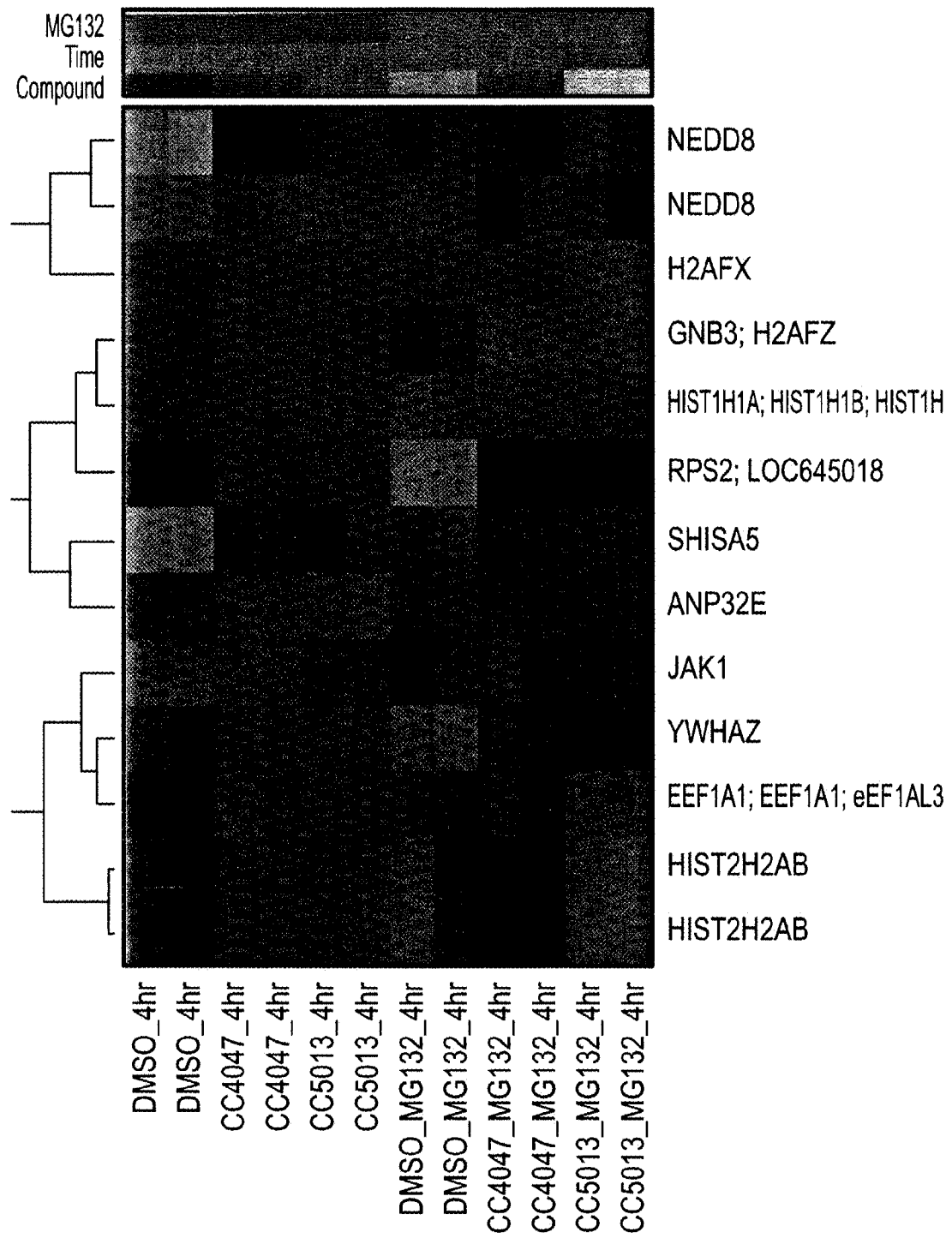

FIG. 19: Peptides regulated by lenalidomide ("Len") and pomalidomide ("Pom") without MG132 in 4 hour ubiquitination experiments.

Figure 20:
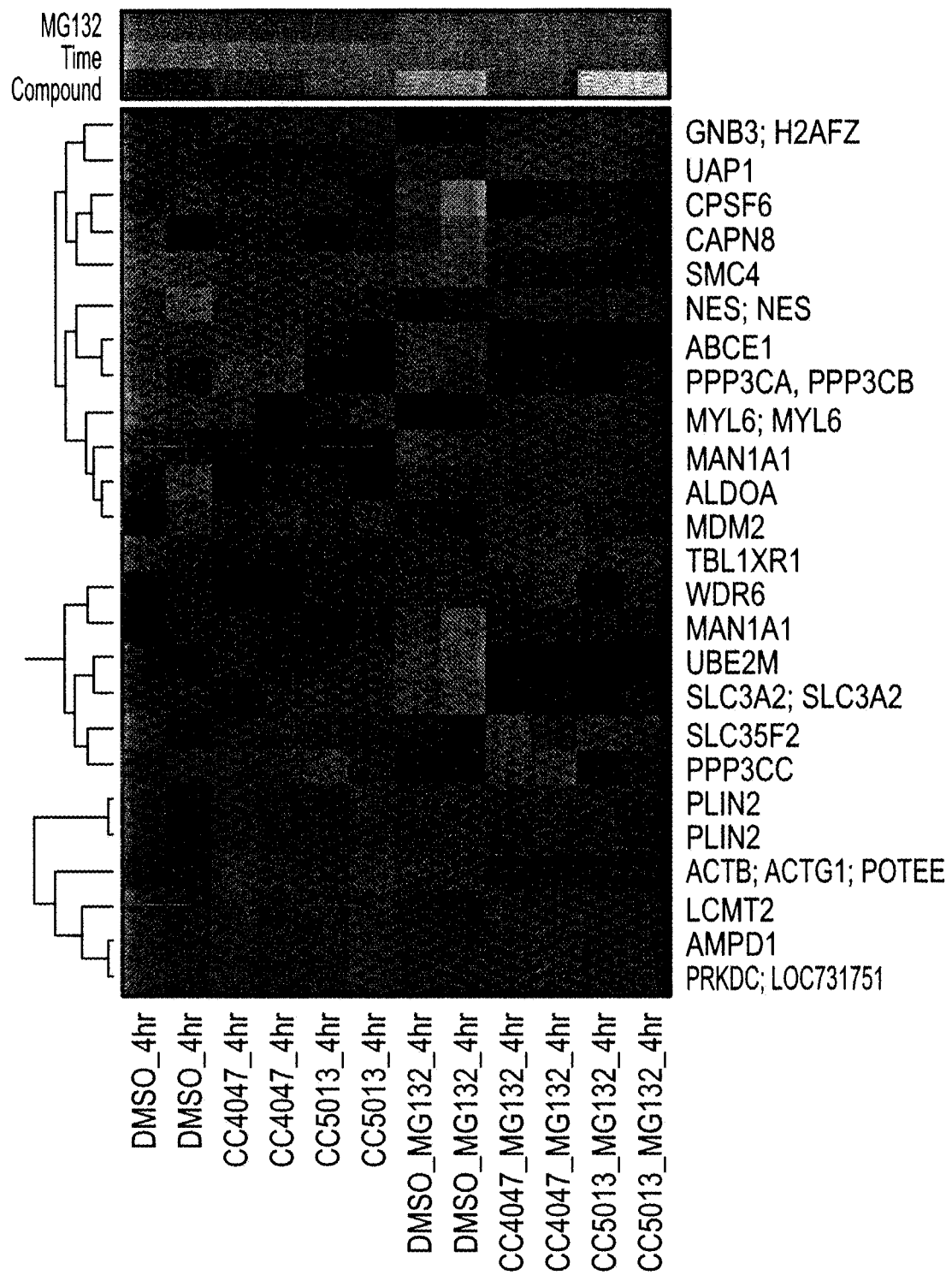

FIG. 20: Peptides regulated by lenalidomide ("Len") and pomalidomide ("Pom") with MG132 in 4 hour ubiquitination experiments.

FIG. 21: Table of common peptides (SEQ ID NOS 35, 16 and 231, respectively, in order of appearance) between lenalidomide ("Len") and pomalidomide ("Pom") in ubiquitination experiments.

FIG. 22: Table of common hits in multiple lenalidomide ("Len") and pomalidomide ("Pom") ubiquitination experiments. FIG. 22 discloses SEQ ID NOS 232-236, 35, 237-238, 150, 92, 239, 55, 240 and 148, respectively, in order of appearance.

FIG. 23: Ubiscan data for lenalidomide ("Len" or "Rev"), pomalidomide ("Pom"), and Compound B. FIG. 23 discloses SEQ ID NOS 32, 113, 158, 161-162, 47, 51, 93-95, 104, 193, 210-211, 241-250 and 196, respectively, in order of appearance.

Figure 24A:
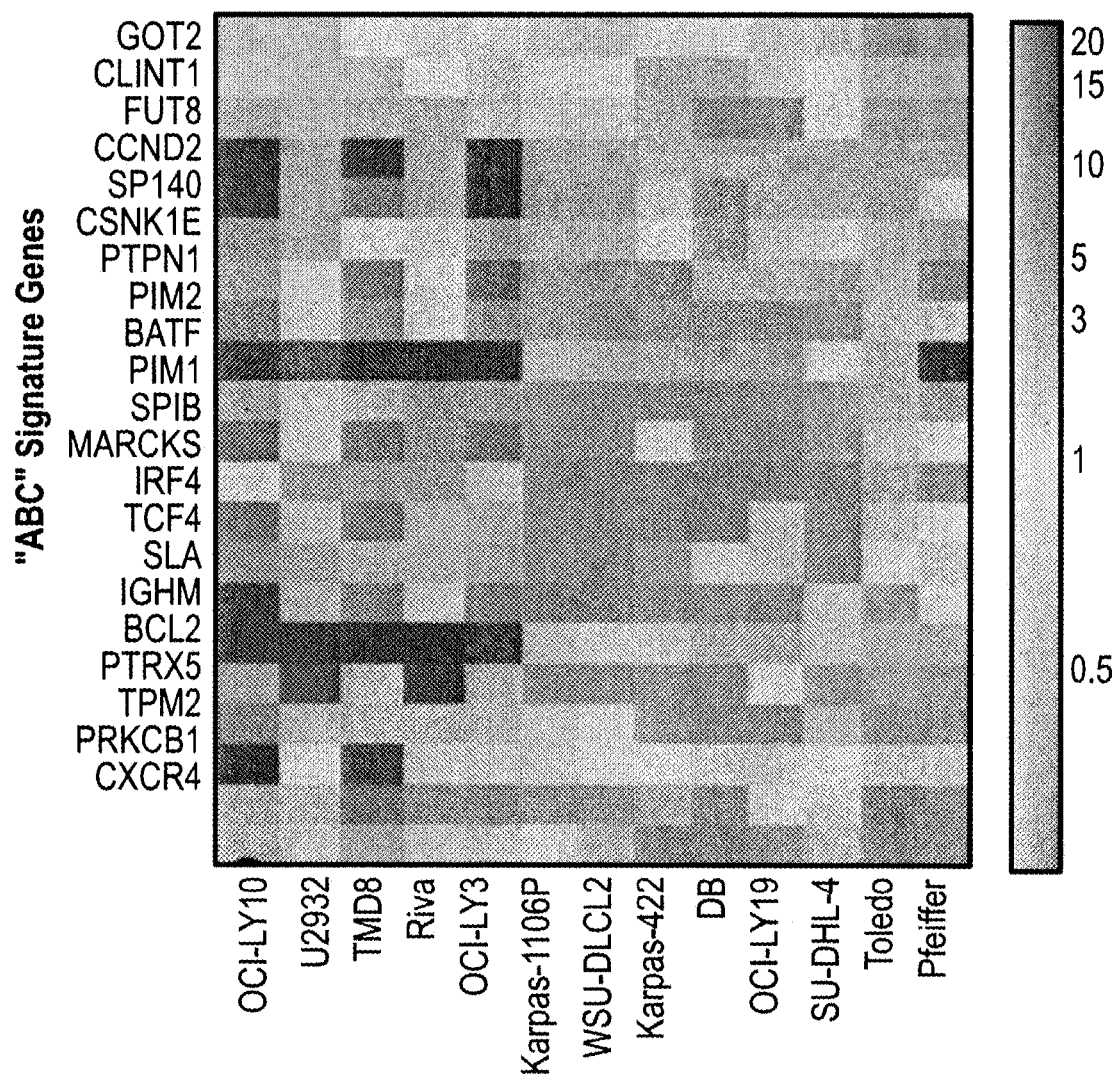

FIG. 24A: ABC-DLBCL signature genes.

Figure 24B:
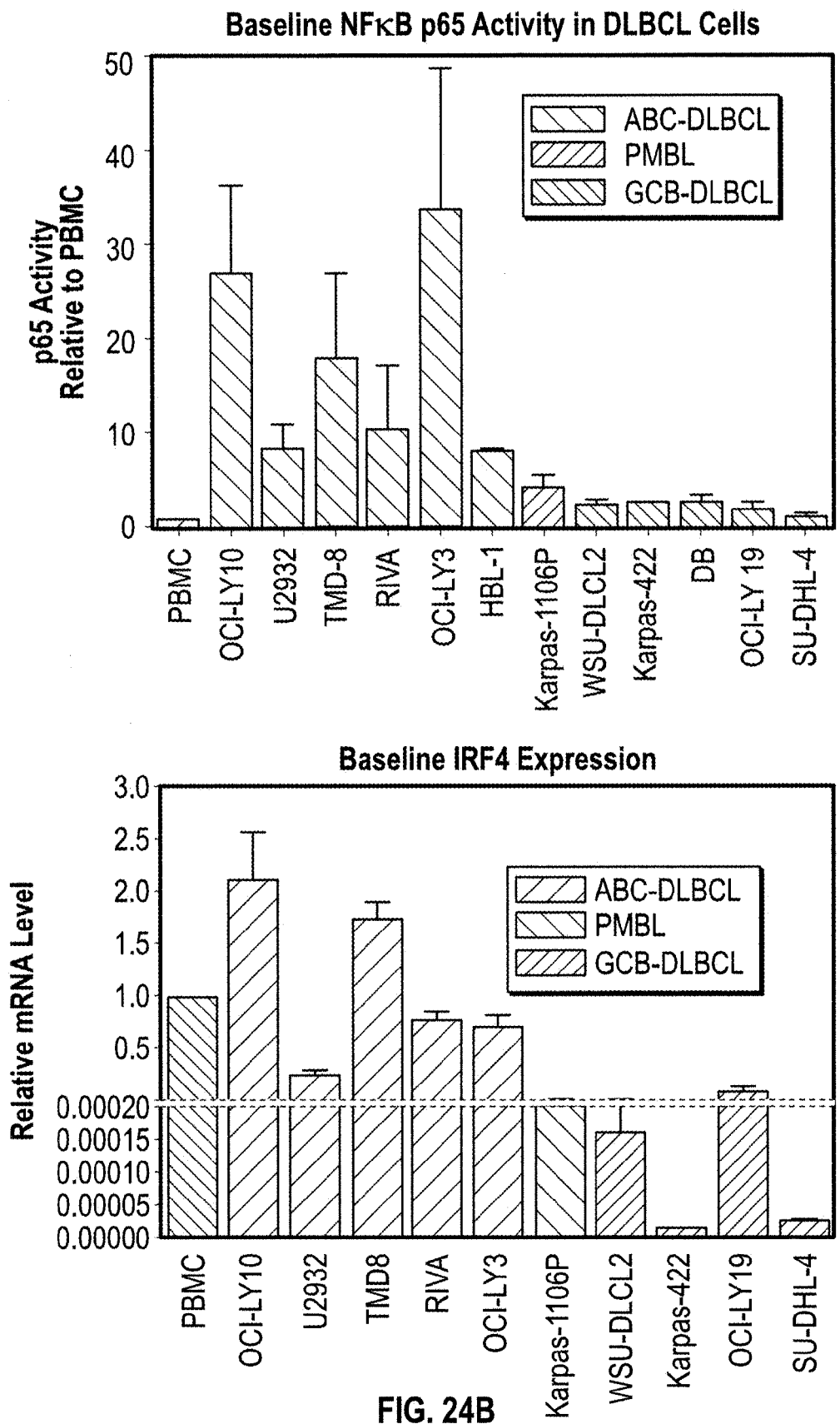

FIG. 24B: NF-κB activity and IRF4 activity in DLBCL cells.

Figure 24C:
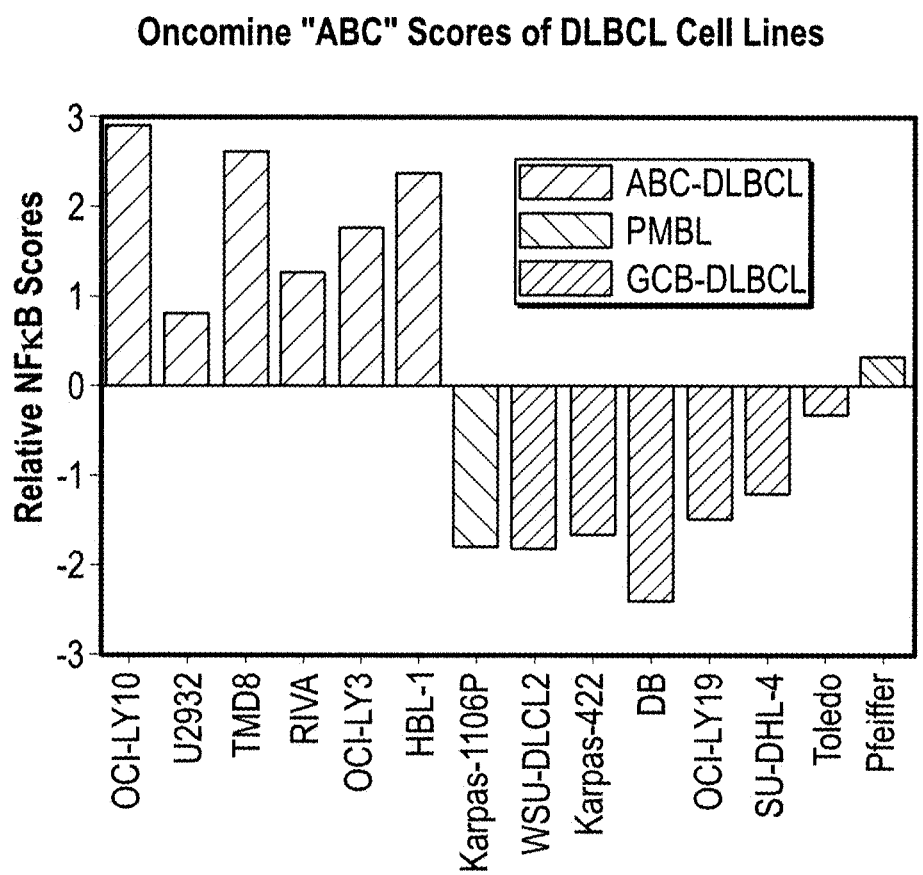

FIG. 24C: "ABC Scores" of DLBCL cell lines.

Figure 25:
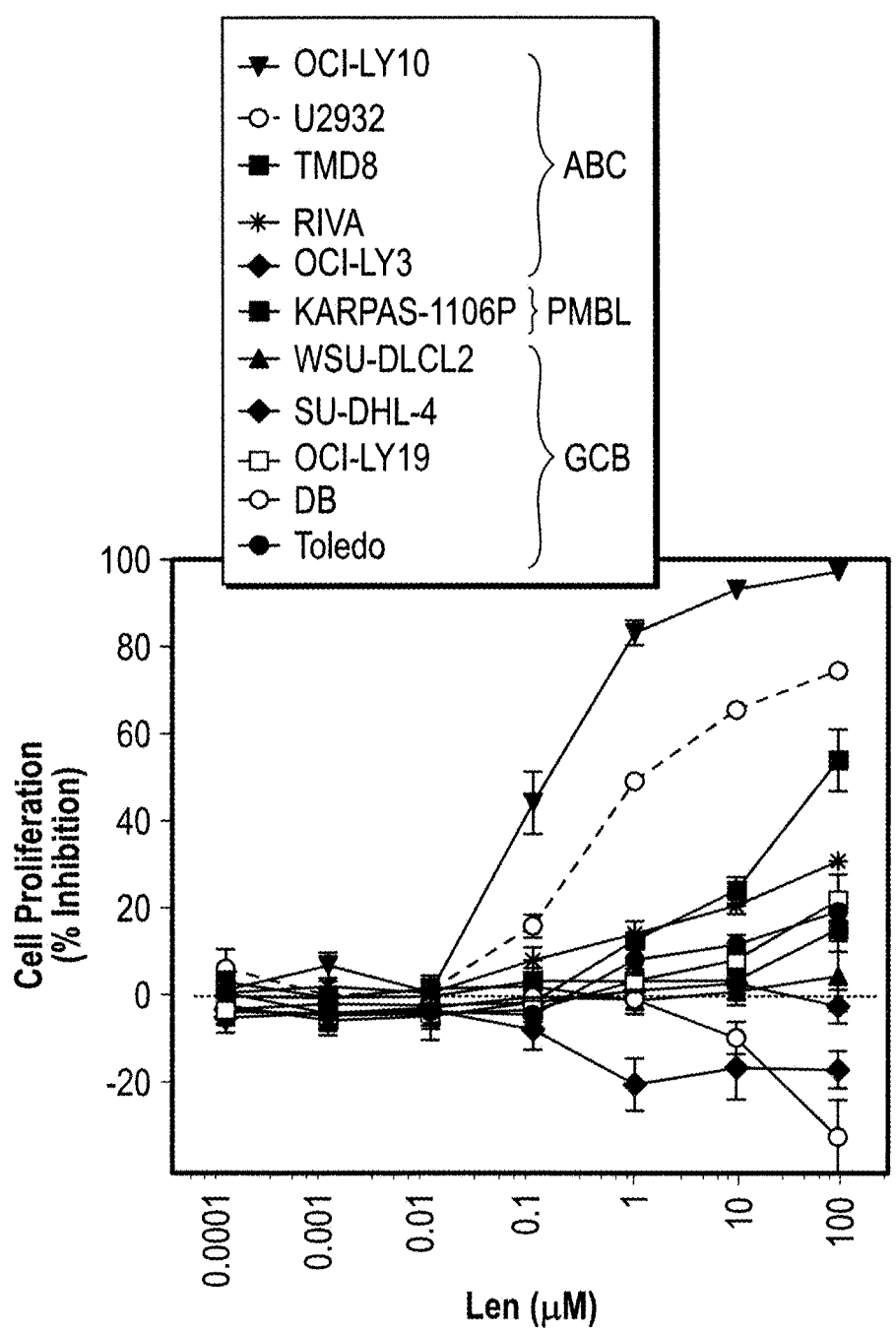

FIG. 25: Lenalidomide inhibits proliferation of ABC-DLBCL cells in vitro.

Figure 26:
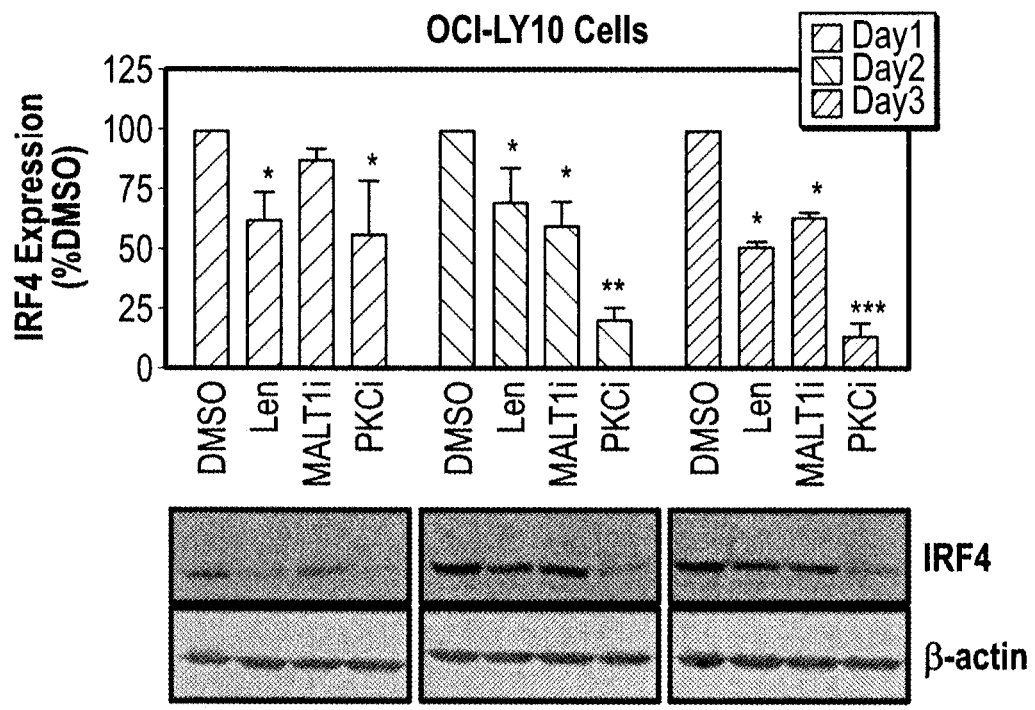

FIG. 26: Lenalidomide treatment also induced apoptosis of sensitive cell lines such as OCI-Ly10.

Figure 27A:
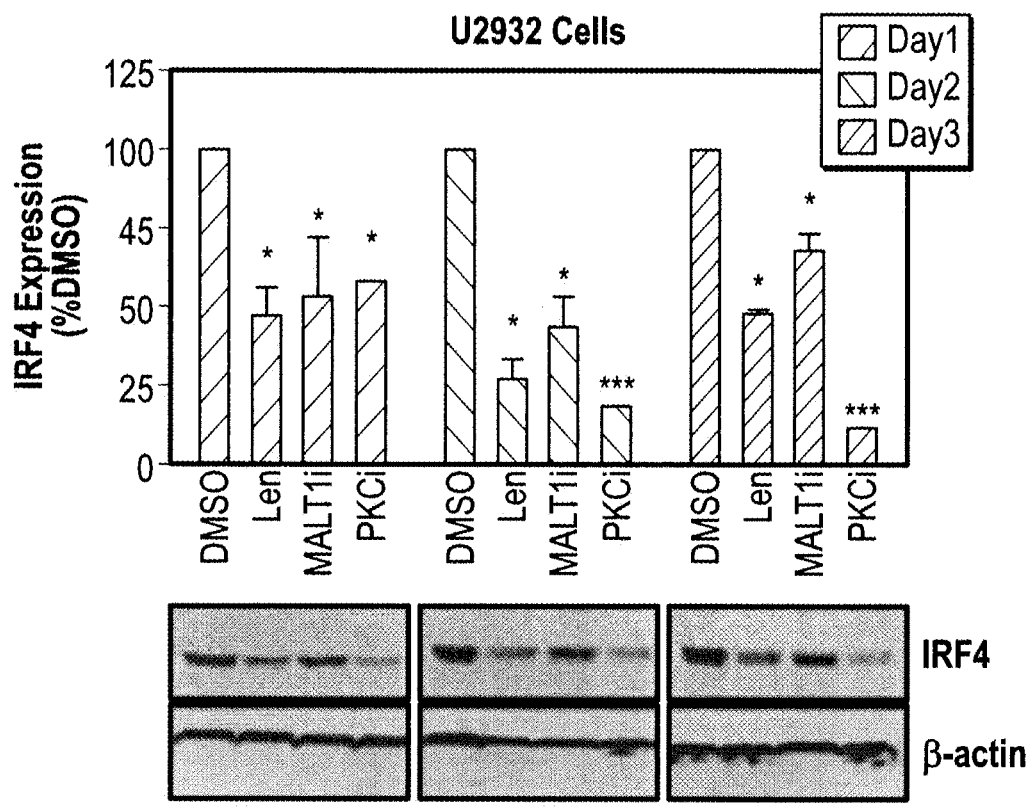
Figure 27B:
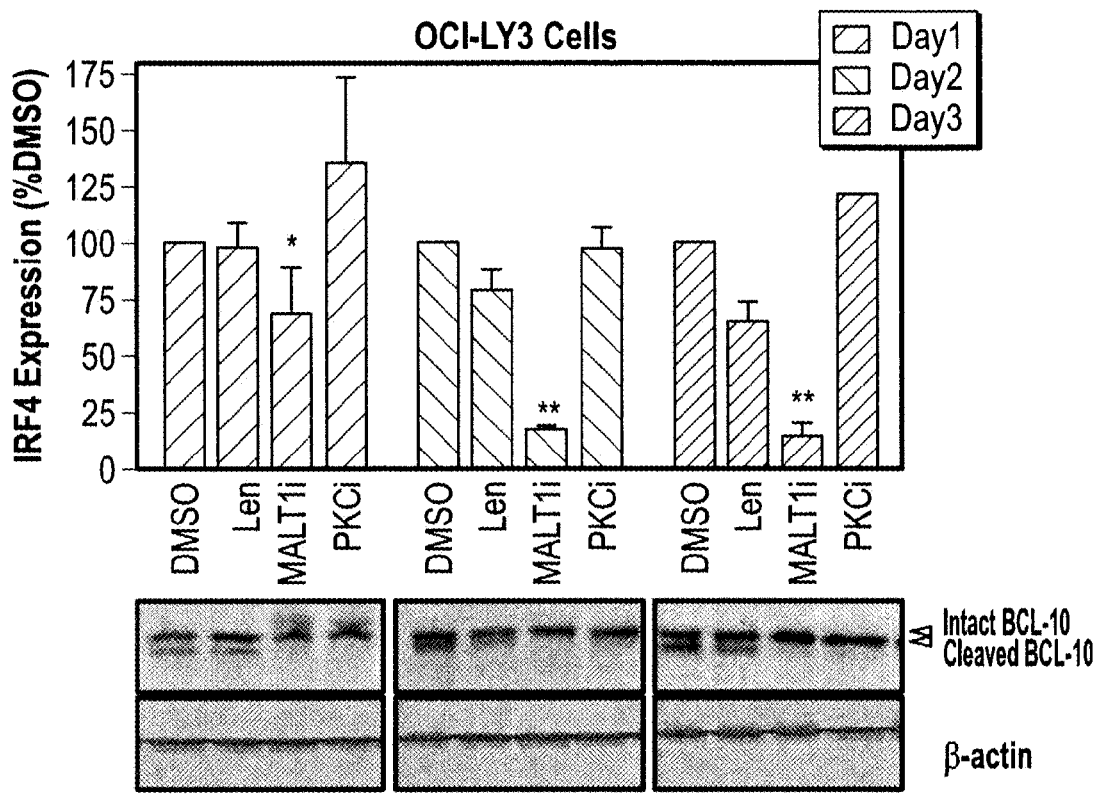
Figure 27C:
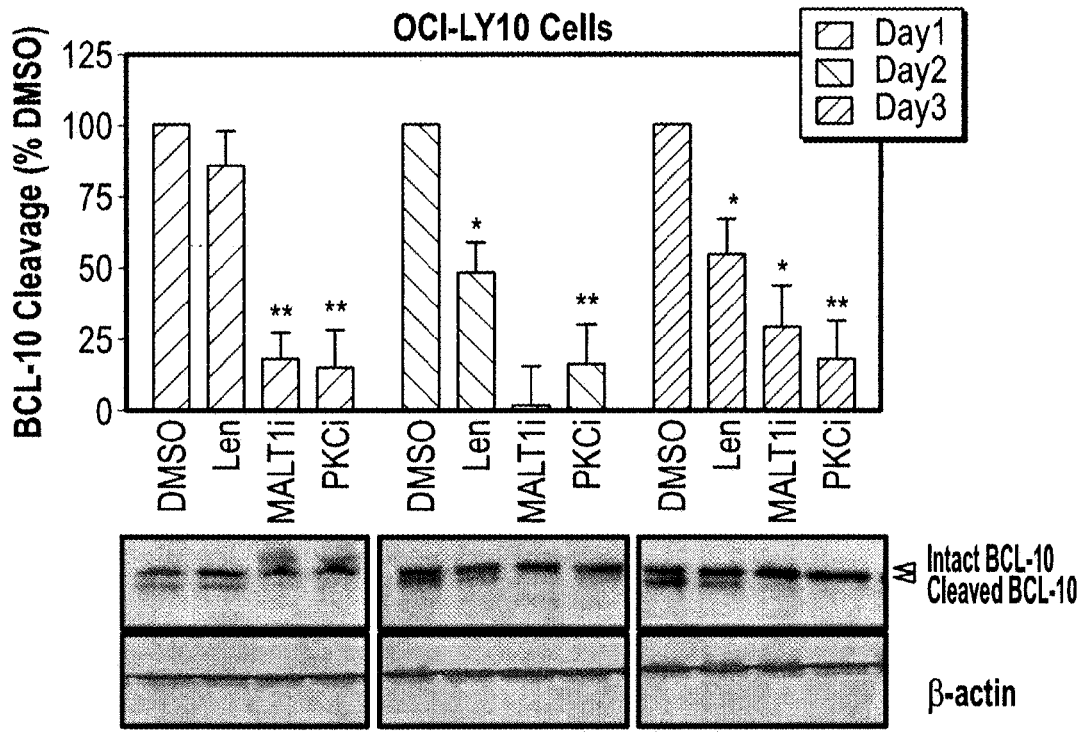

FIGS. 27A-27C: Effect of Lenalidomide on IRF4 expression in ABC-DLBCL cell lines.

FIG. 28: Mutation analysis of CARD11 coiled-coil domain 1 in DLBCL cell lines. FIG. 28 discloses SEQ ID NOS 251, 252, 252, 252, 252, 252, 252, 252, 252, 252, 252, 252 and 252, respectively, in order of appearance.

Figure 29A:
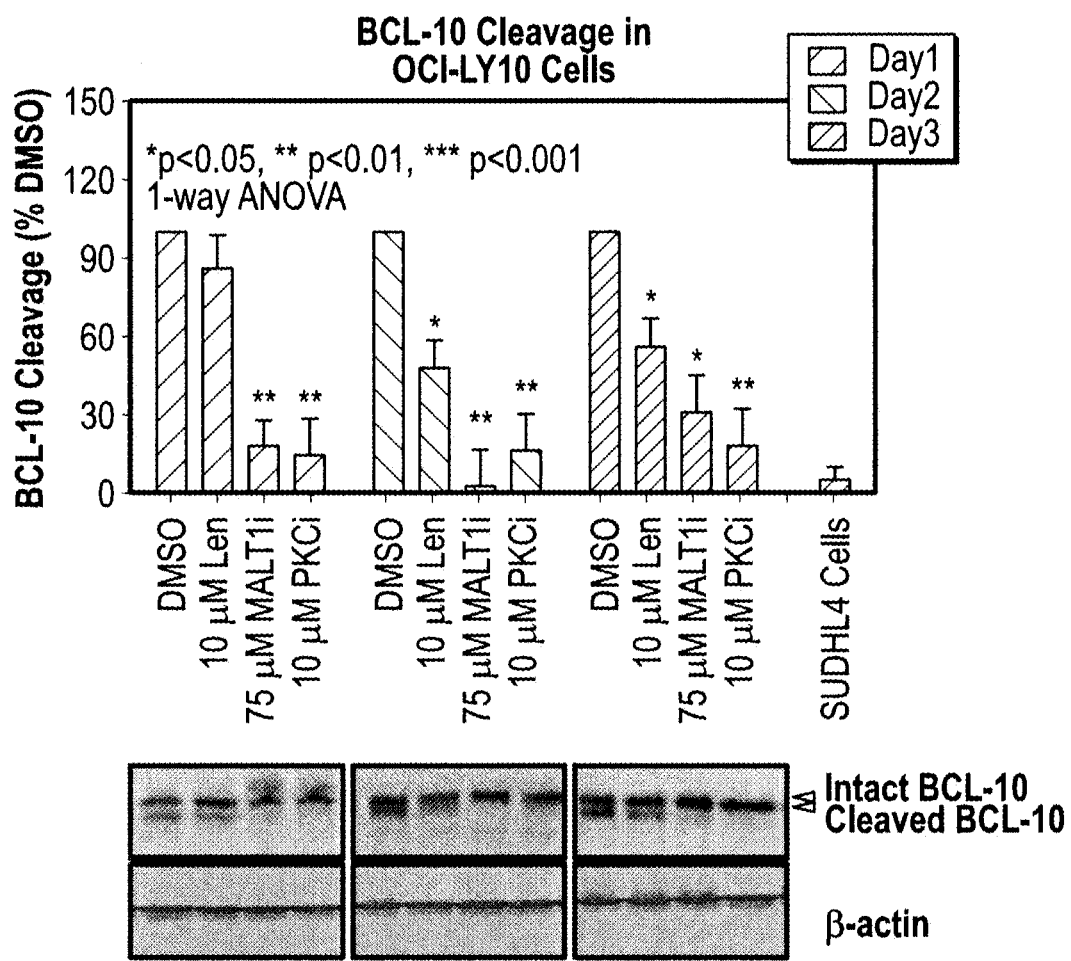
Figure 29B:
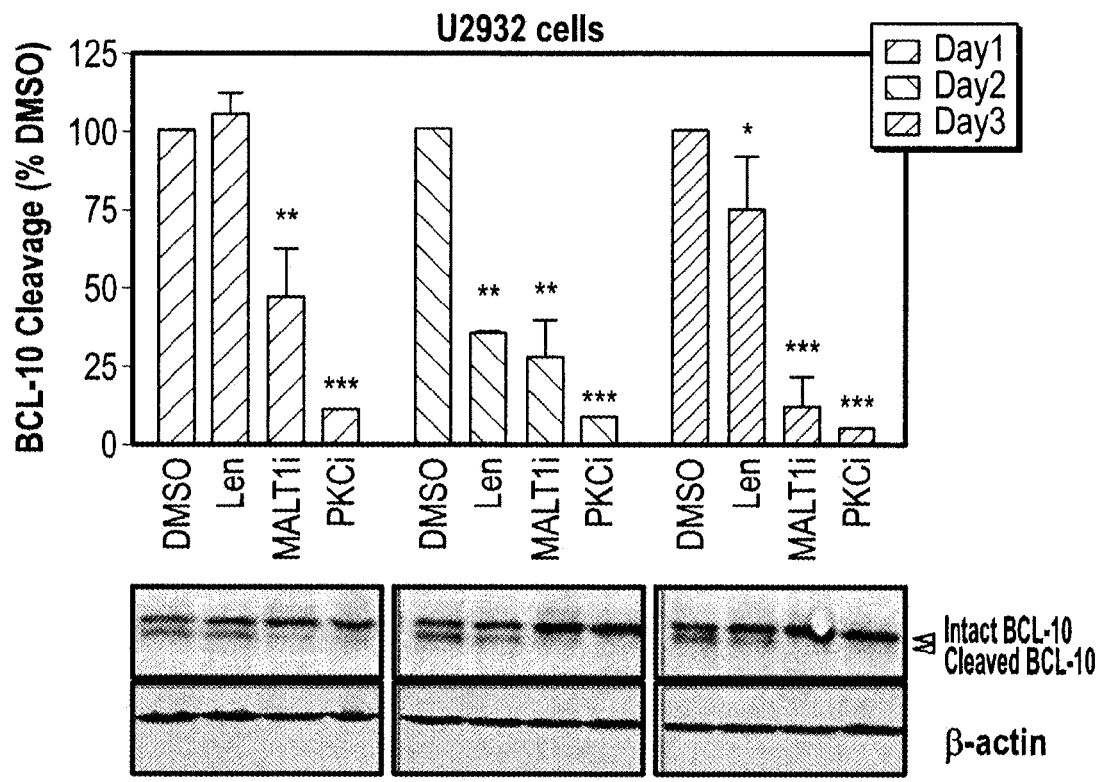
Figure 29C:
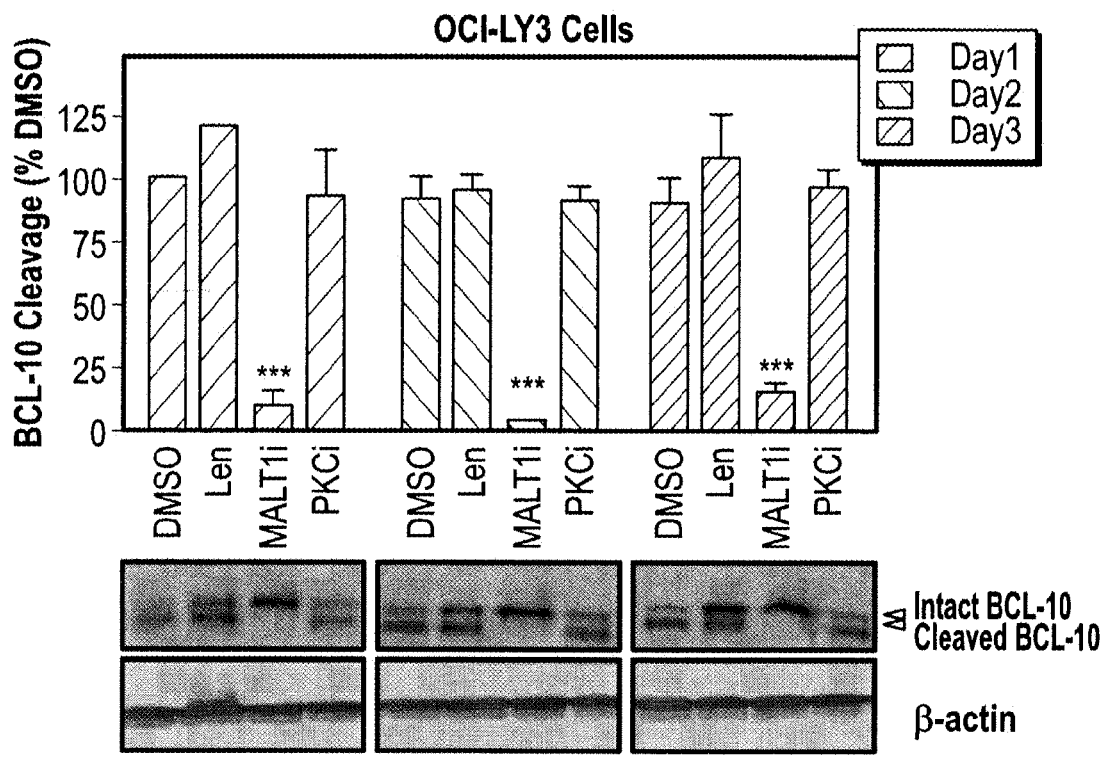

FIGS. 29A-29C: Lenalidomide inhibits activation of CARD11-Bcl-10-MALT1 complex in sensitive DLBCL cell lines.

Figure 30A:
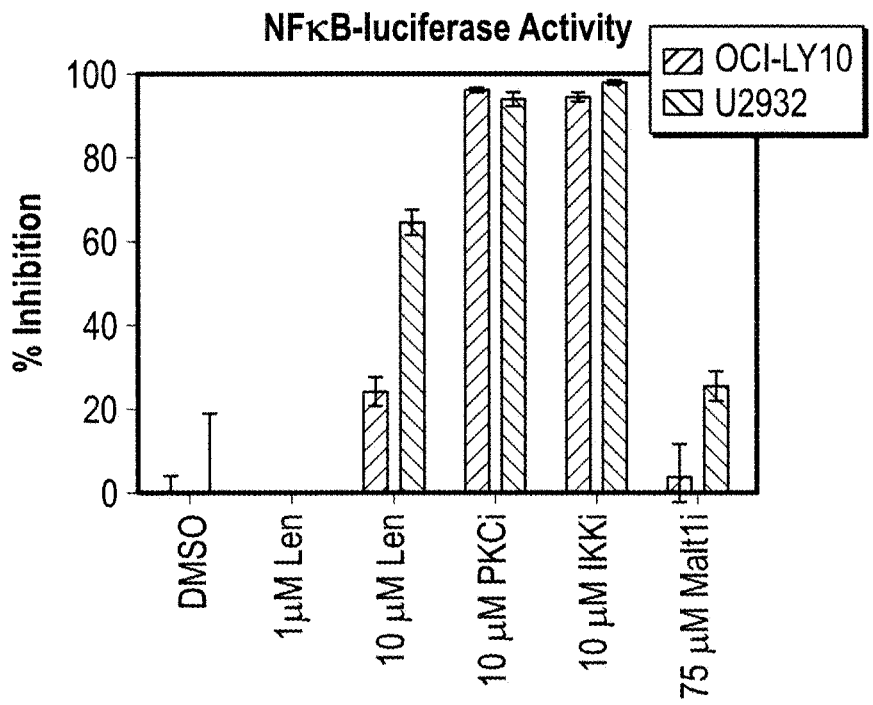
Figure 30B:
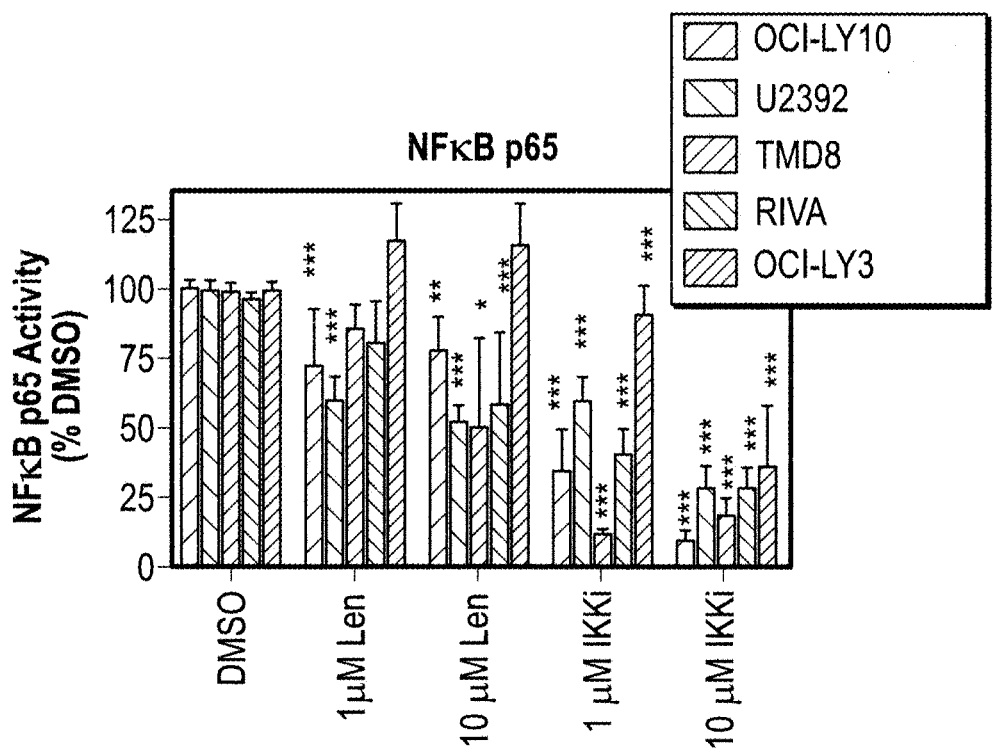
Figure 30C:
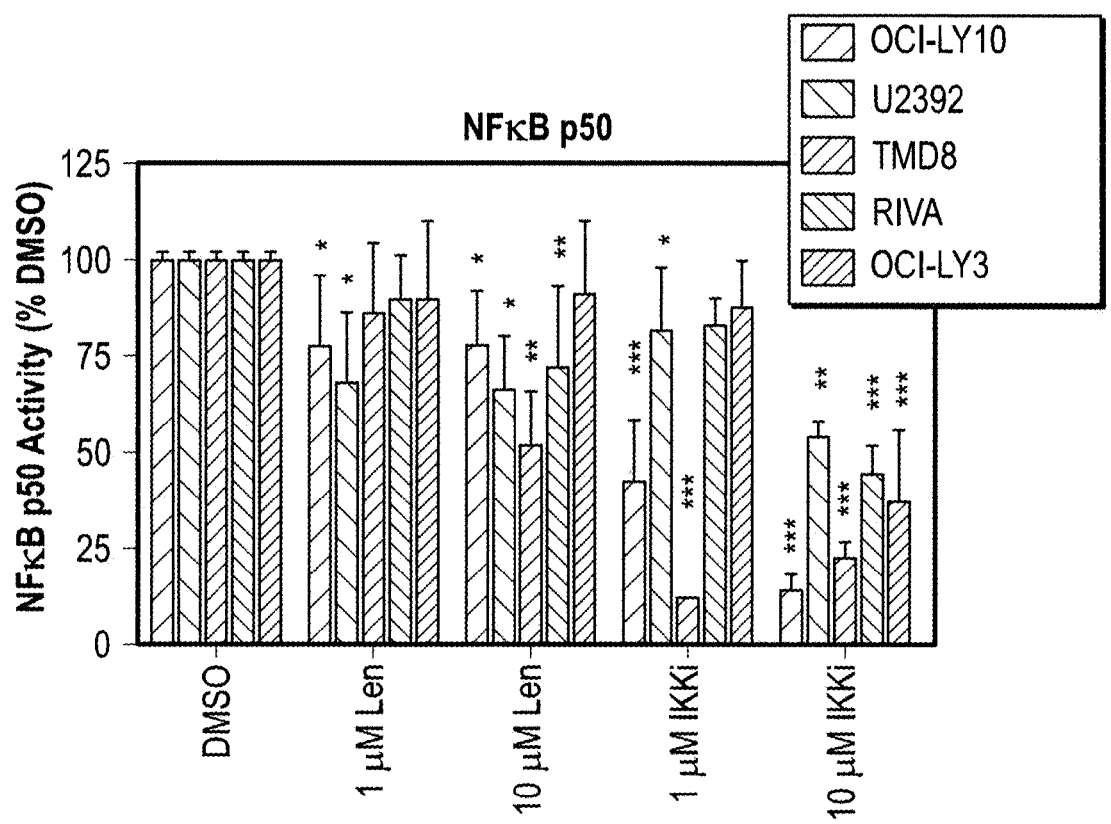
Figure 31A:
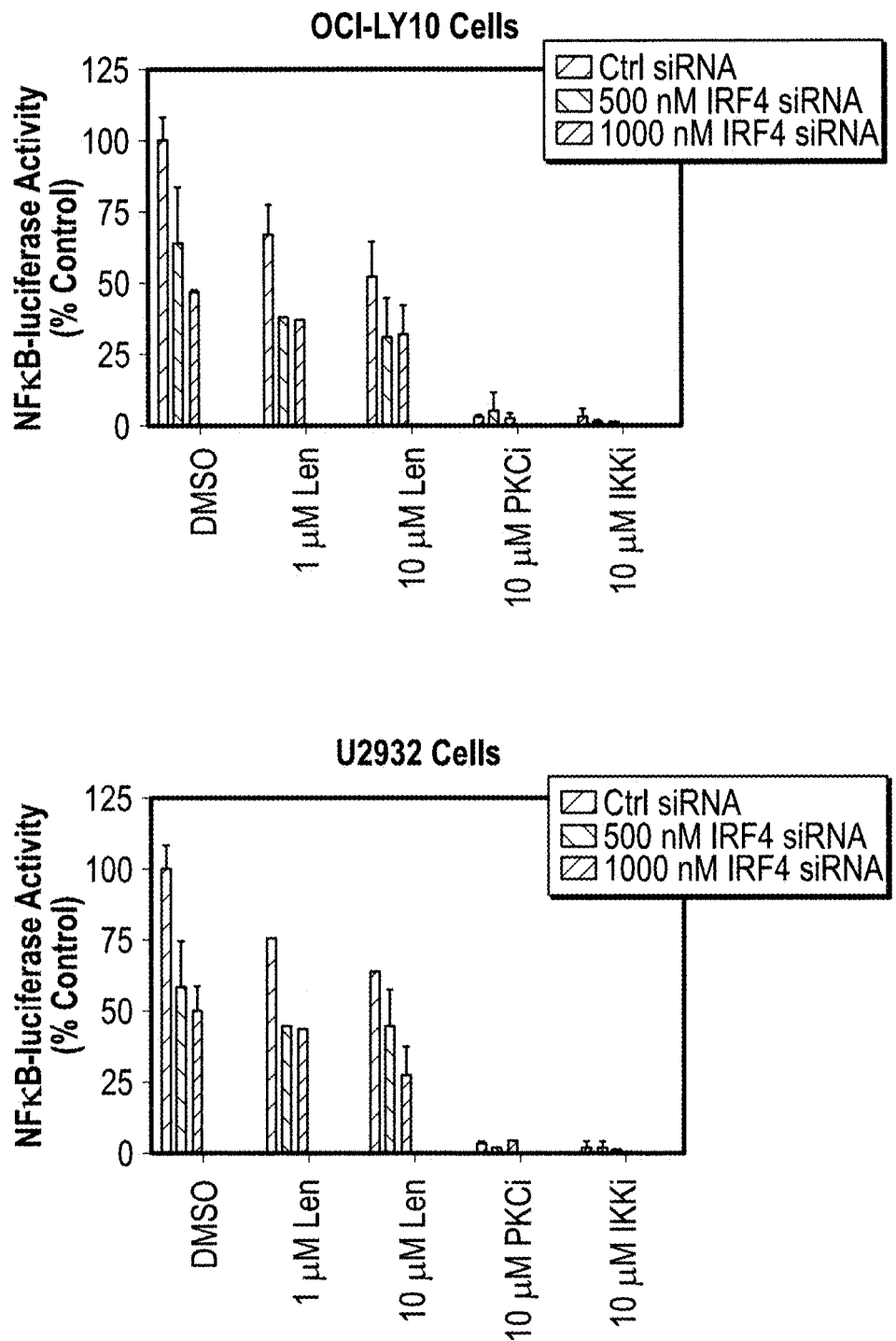
Figure 31B:
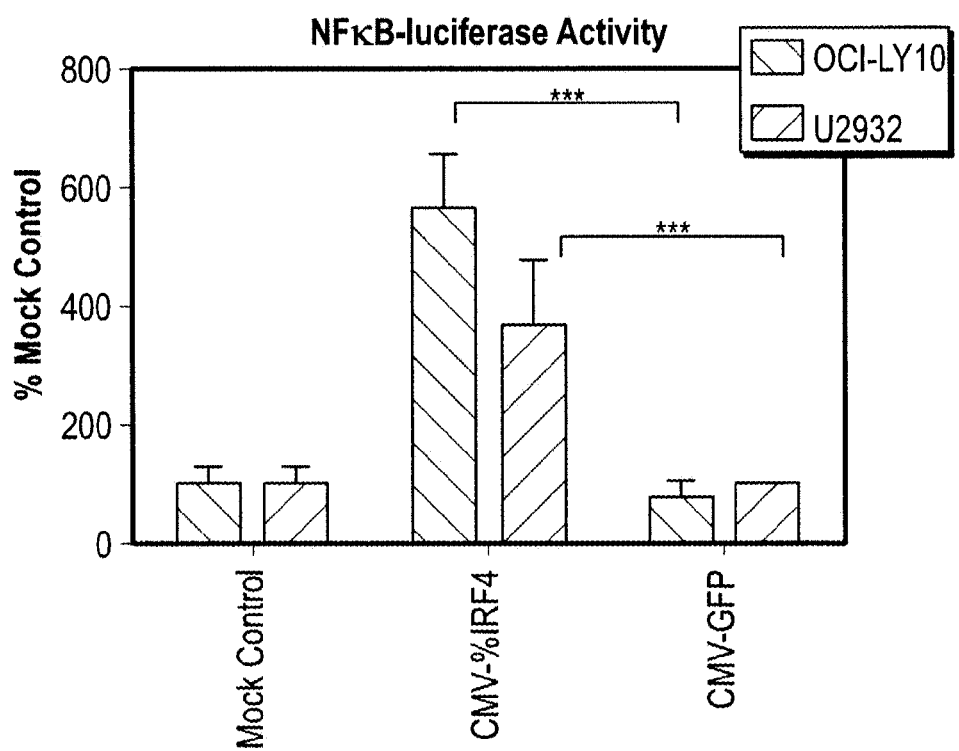
Figure 31C:
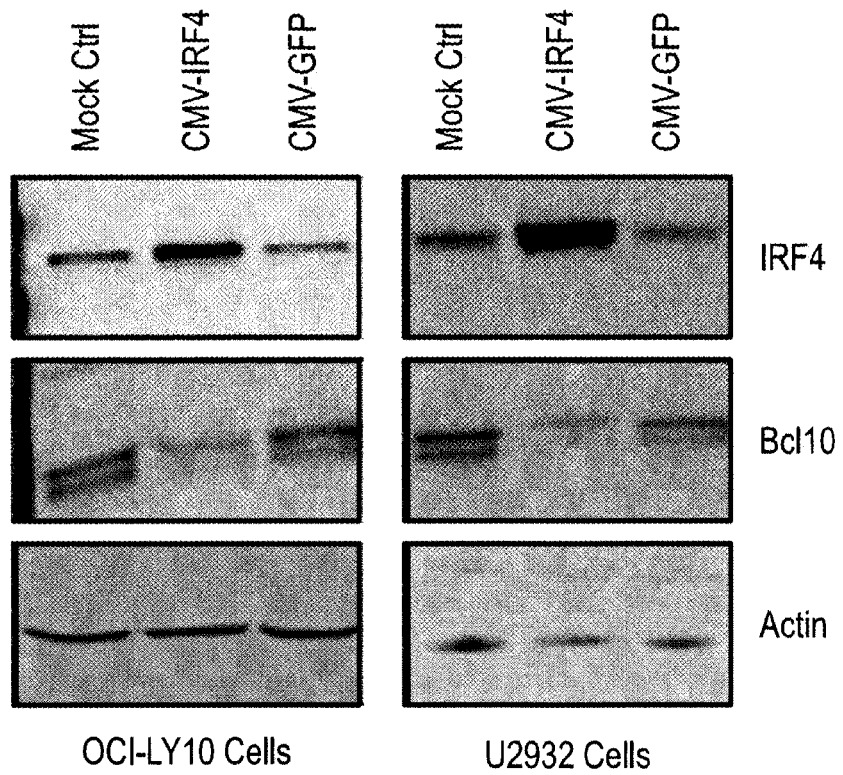
Figure 31D:
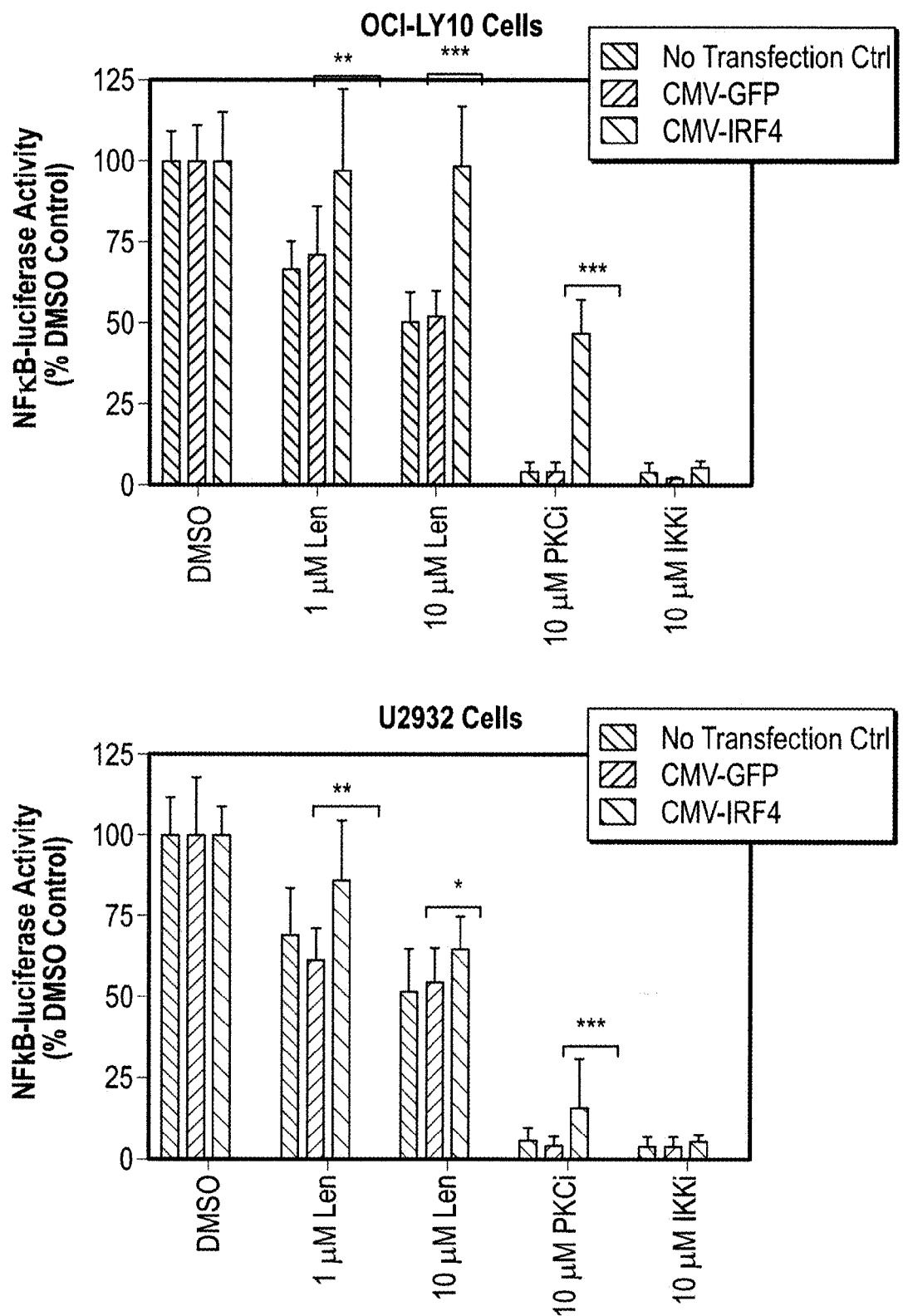
Figure 32A:
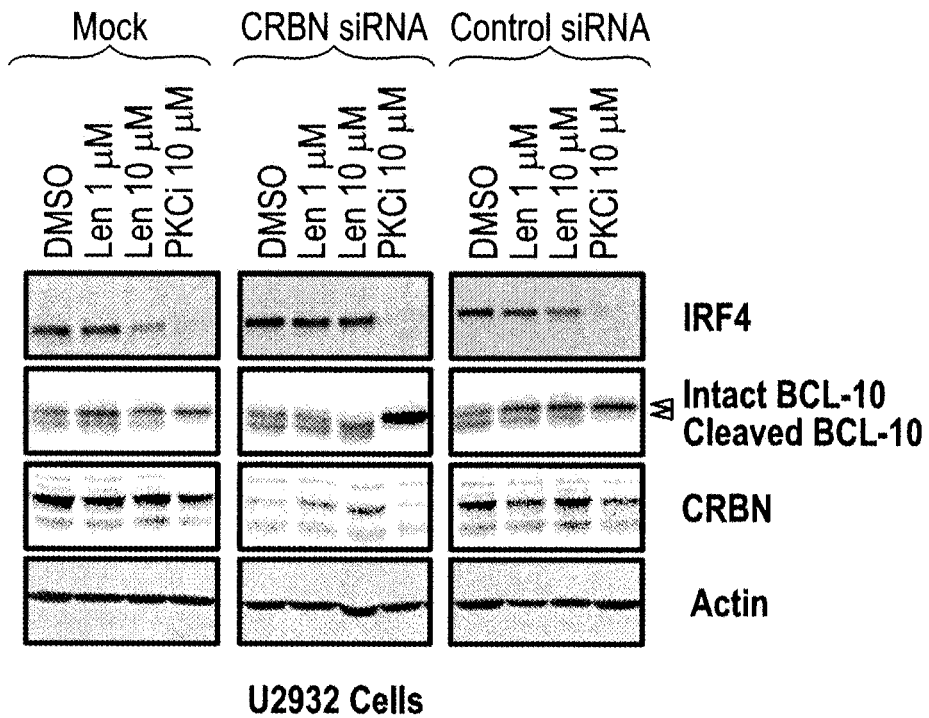
Figure 32B:
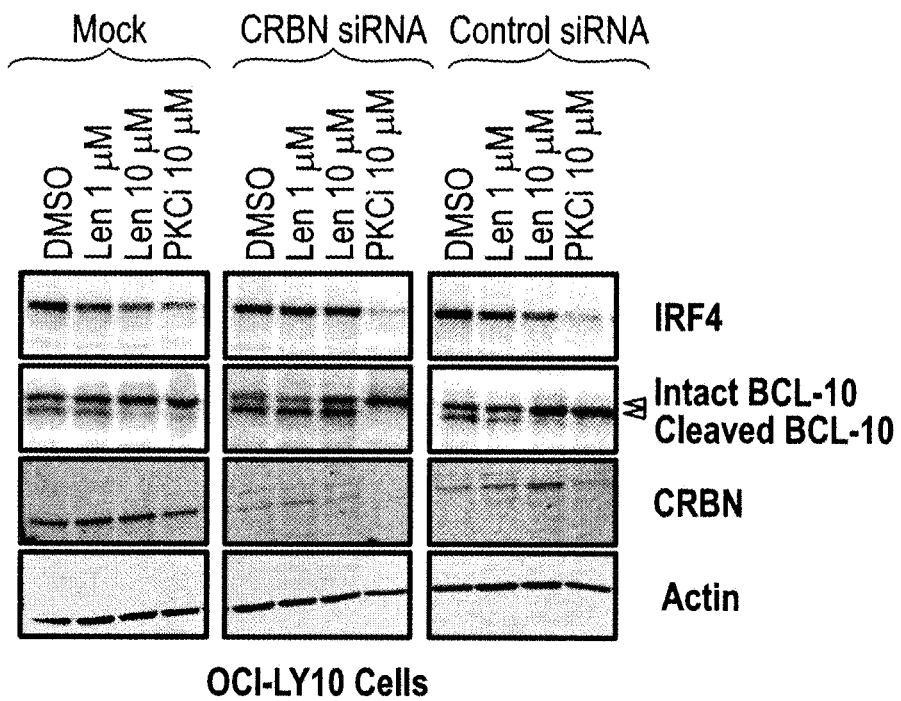
Figure 32C:
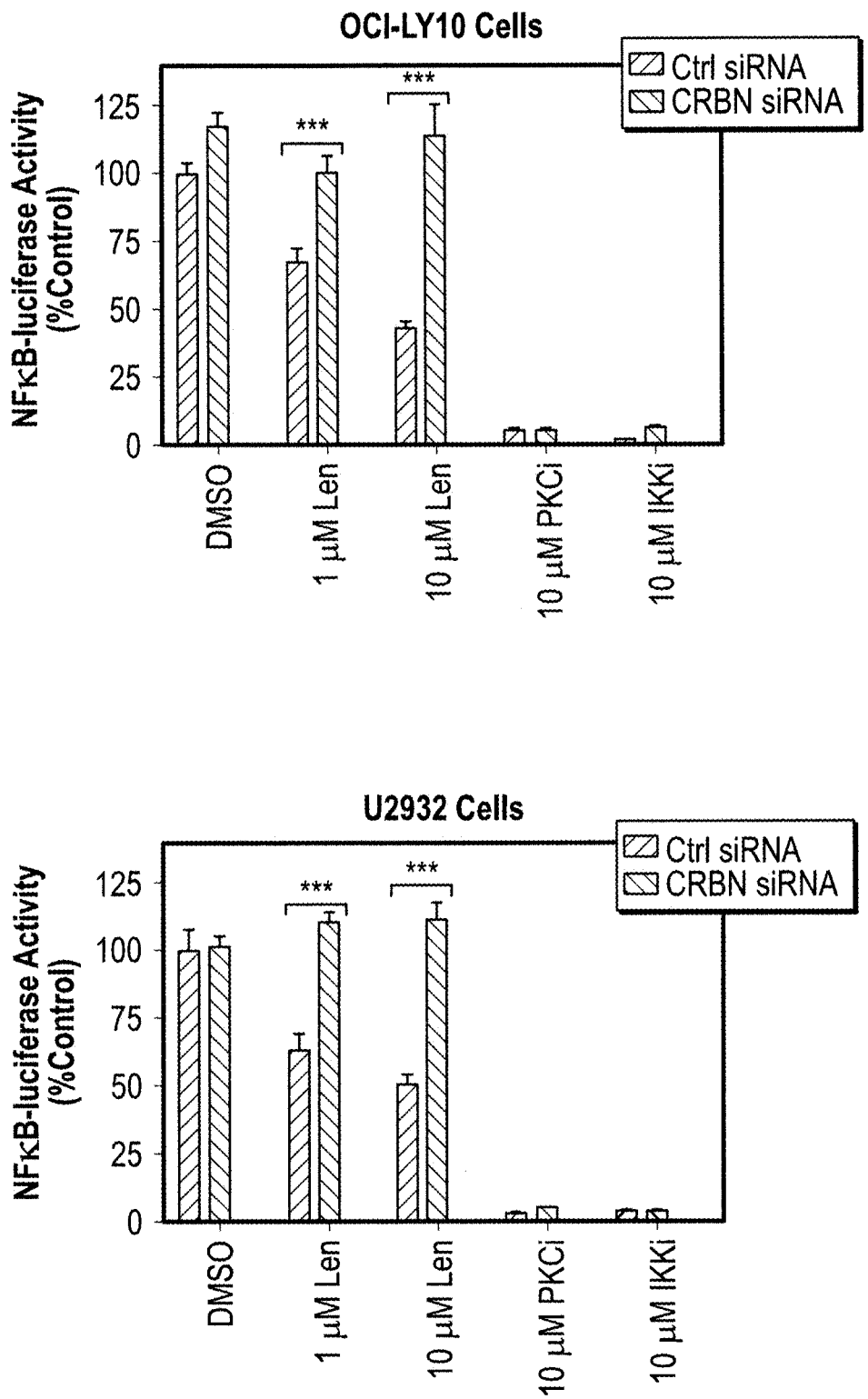
Figure 32D:
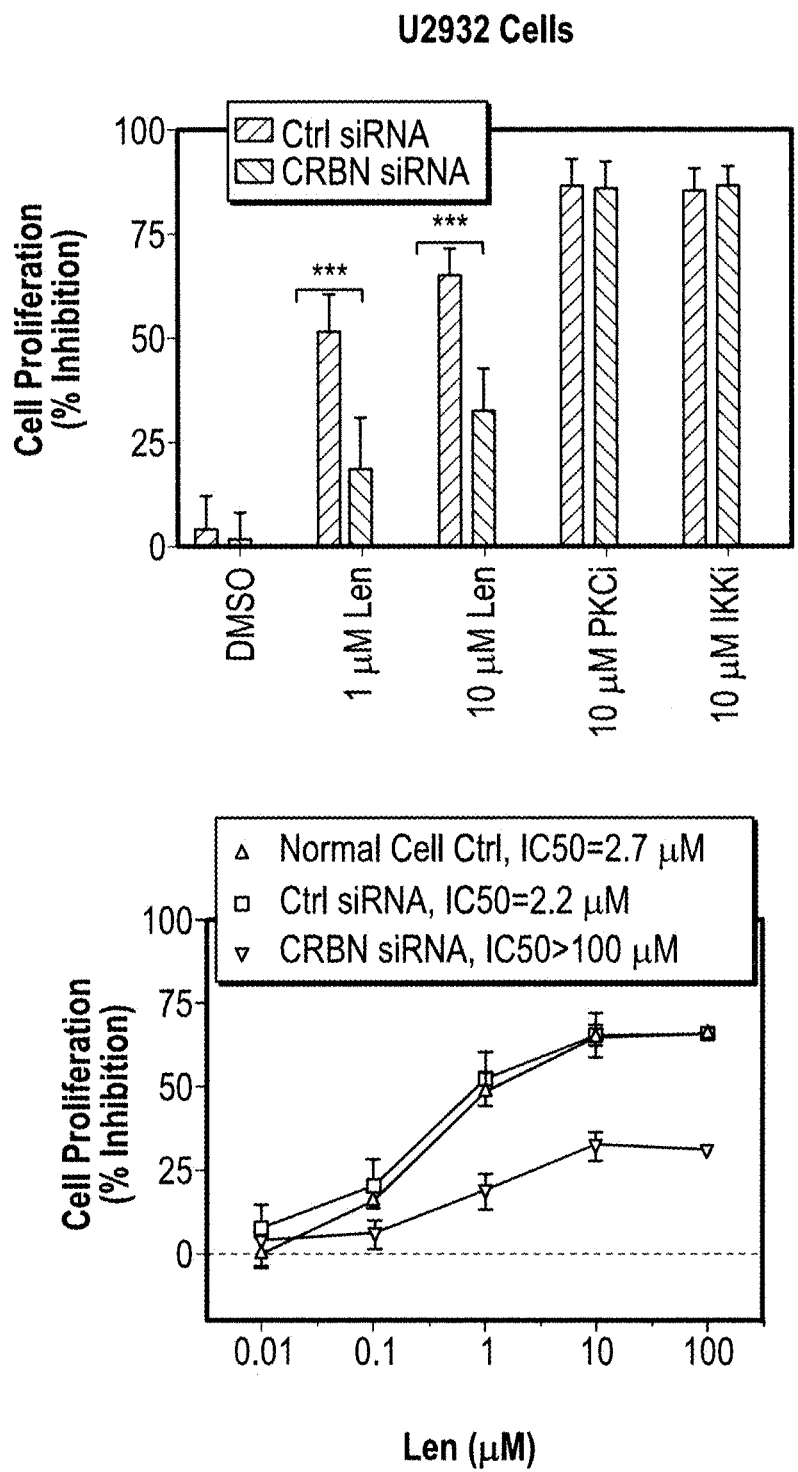

FIGS. 30A-30C: Lenalidomide inhibits NF-κB activity in ABC-DLBCL cells.

FIGS. 31A-31D: Alteration of IRF4 expression in ABC-DLBCL cells affects cell sensitivity to lenalidomide.

FIGS. 32A-32D: Downregulation of IRF4, NF-κB and proliferation by lenalidomide requires the presence of cereblon.

Figure 33A:
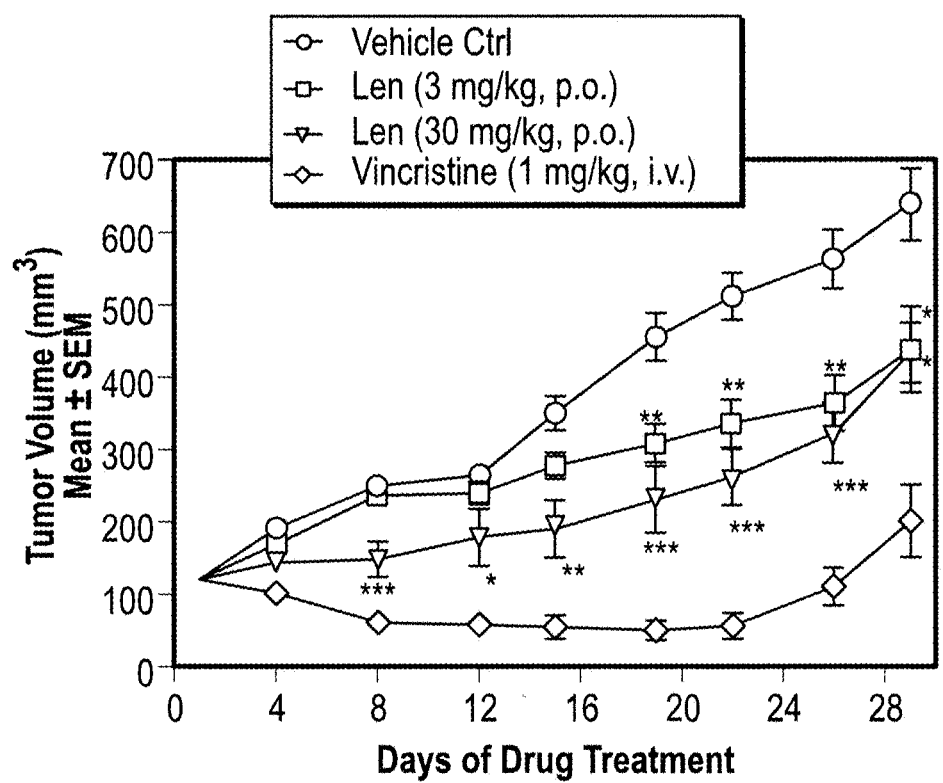
Figure 33B:
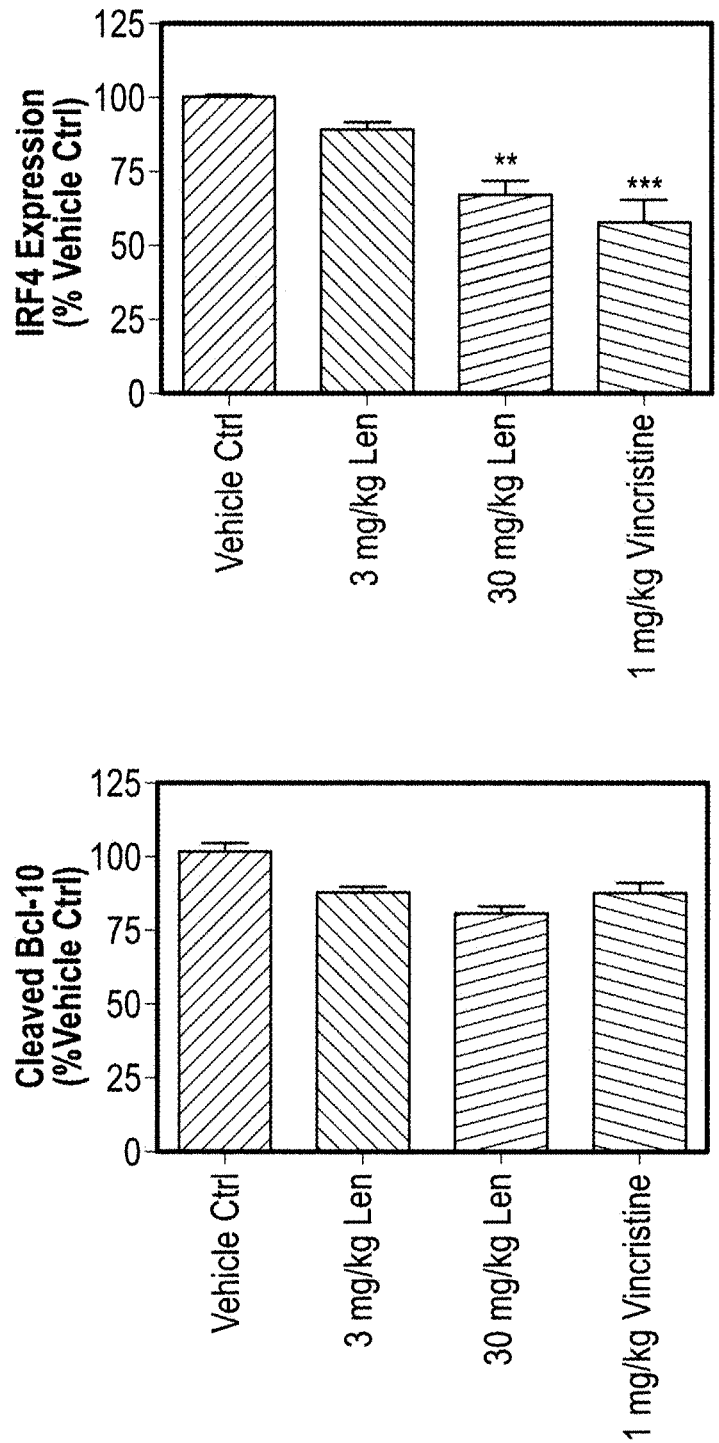

FIGS. 33A-33B: Lenalidomide inhibits tumor growth in mouse xenograft model with OCI-Ly10 ABC-DLBCL.

Figure 34A:
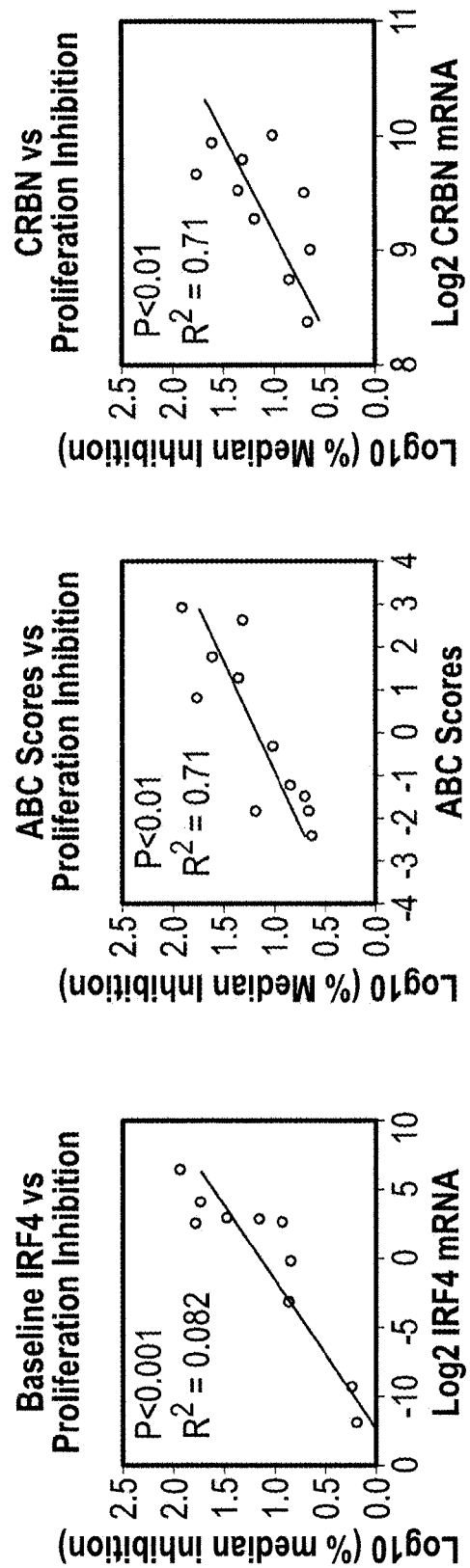
Figure 34B:
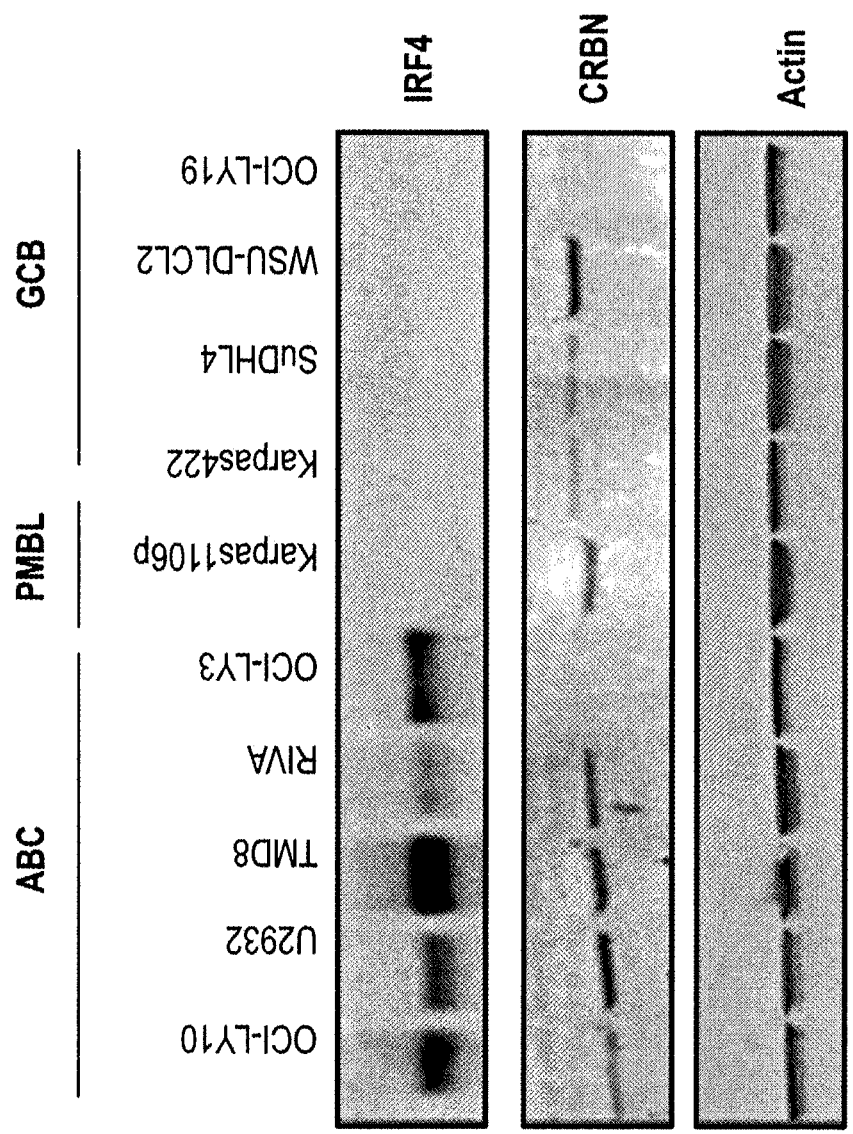

FIGS. 34A-34B: "ABC scores" and baseline IRF4/CRBN levels correlate lenalidomide sensitivity of DLBCL cells.

FIG. 35: Alignment between heavy chain amino acid sequences of antibodies CGN-6-1-11 (top; SEQ ID NO:5) and CGN-6-4-5 (bottom; SEQ ID NO:9).

FIG. 36: Alignment between light chain amino acid sequences of antibodies CGN-6-1-11 (top; SEQ ID NO:7) and CGN-6-4-5 (bottom; SEQ ID NO:11).

Figures 37A, 37B:
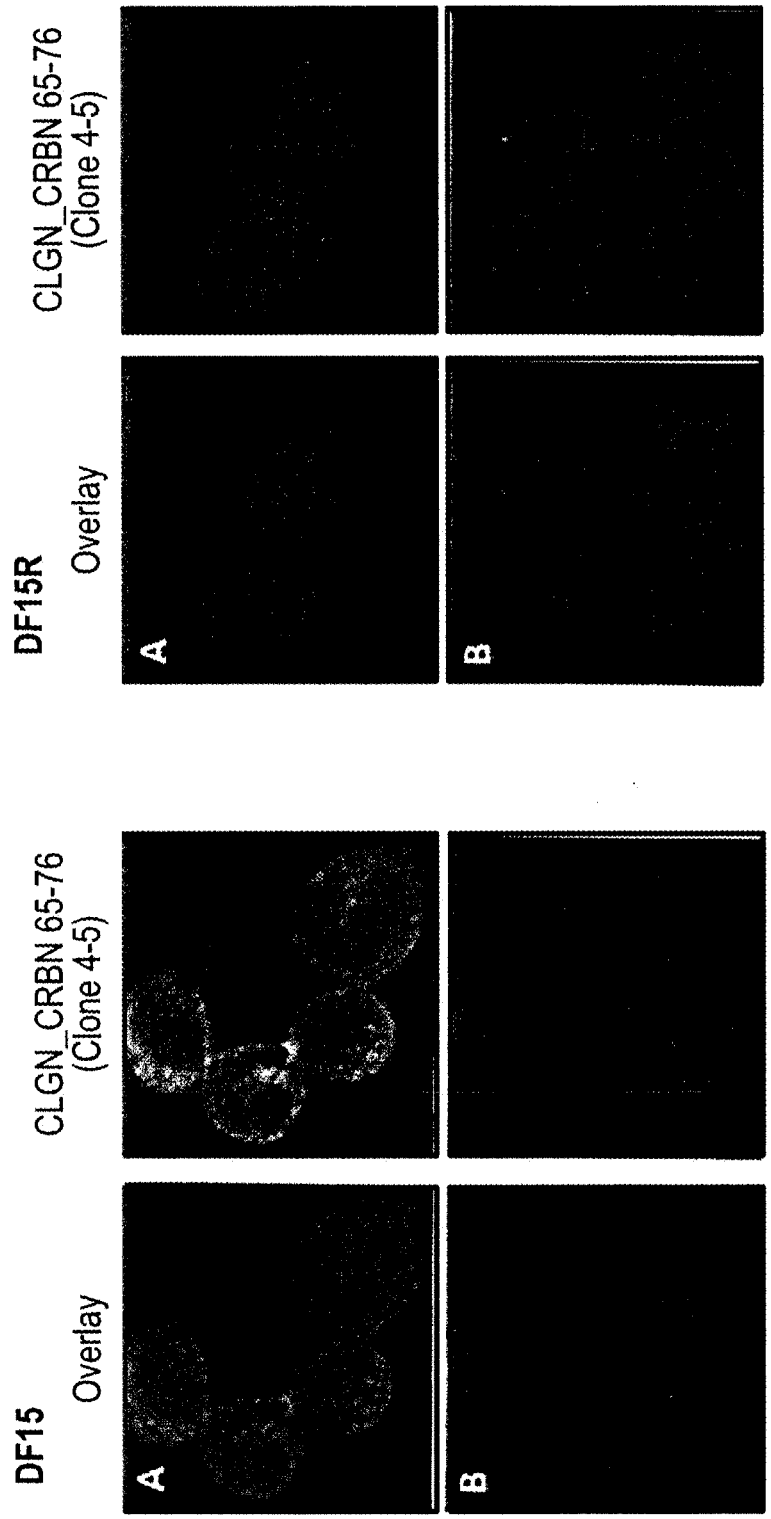

FIGS. 37A & 37B: Confocal immunofluorescent analysis of DF15 (left panel) and DF15R cells (right panel) using 1 μg/ml CGN-6-4-5 antibody (green) (A) or CGN-6-4-5 antibody/CRBN blocking peptide mix (1:5 excess ratio) (B). Nuclear staining performed with Dapi (blue).

FIG. 38: Immunoblot with myeloma cells containing endogenous CRBN (DF15), DF15R with no CRBN and HEK293 cells expressing recombinant flag-tagged CRBN.

Figure 39B:
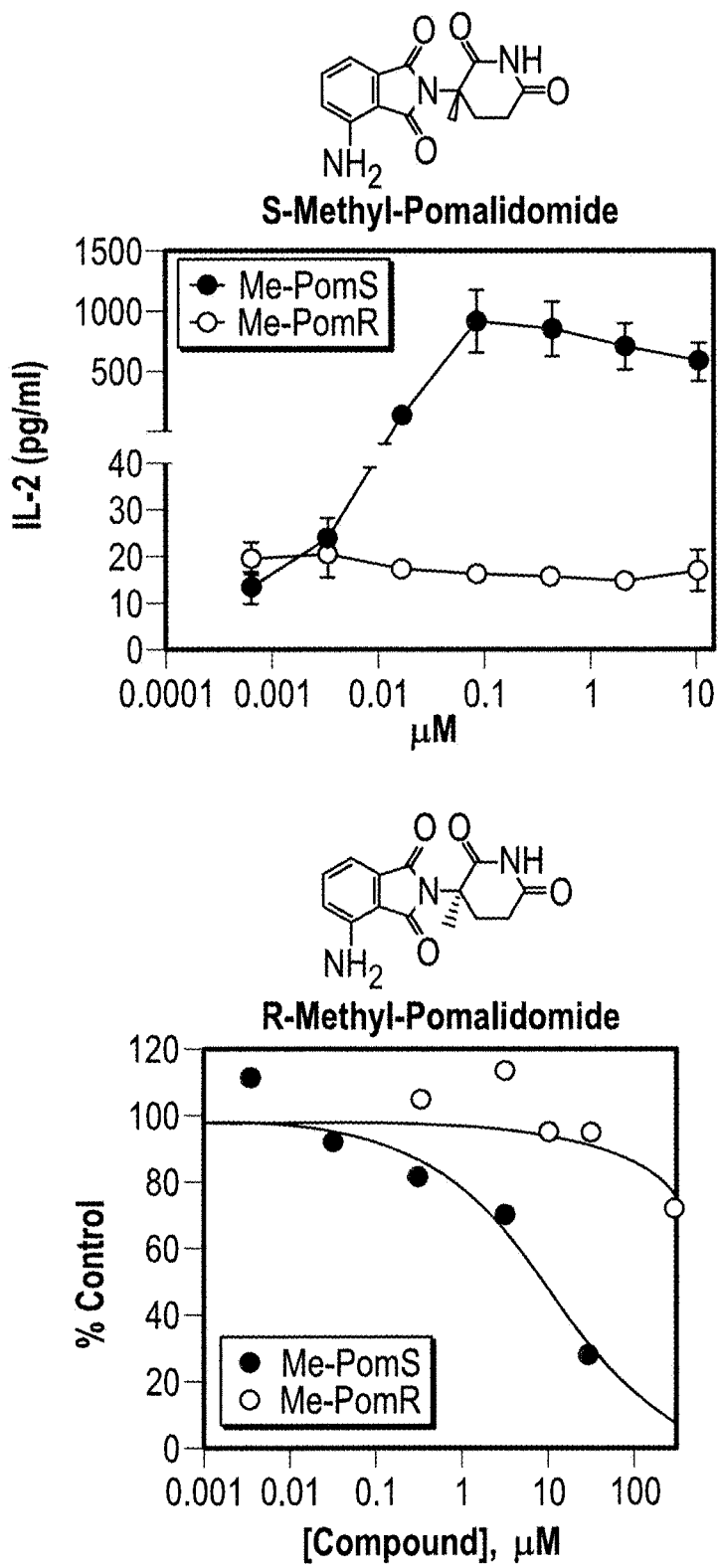

FIGS. 39A & 39B: Binding of thalidomide and other compounds to CRBN

5. DETAILED DESCRIPTION OF THE INVENTION

The methods provided herein are based, in part, on the discovery that cereblon is associated with the anti-proliferative activities of certain drugs, such as the compounds provided herein. In some embodiments, Cereblon (CRBN) may be utilized as a biomarker to indicate the effectiveness or progress of a disease treatment with a compound provided herein.

Without being bound to a particular theory, CRBN binding may contribute to or even be required for anti-proliferative or other activities of certain compounds, such as the compounds provided herein. In certain embodiments, the compounds provided herein bind directly to CRBN-DDB1 and/or the CRBN E3 ubiquitin-ligase complex. Mutations in CRBN could be associated with resistance to the compounds provided herein.

For example, the levels of CRBN were significantly lower in the pomalidomide-resistant cells line DF15R and the lenalidomide-resistant cells, H929 R10-1, H929 R10-2, H929 R10-3, H929 R10-4 and MM1/R compared to the matched parental lines. Furthermore, an interesting mutation was found in CRBN gene of one of the myeloma lines that had acquired resistance to lenalidomide while in the parental line the CRBN gene was wild type. This mutation mapped to the DDB1 binding domain in CRBN. Thus, in certain embodiments, the sensitivity of a cancer cell, e.g., a myeloma cell, or a patient having cancer, to therapy with a compound provided herein is related to CRBN expression.

In relapsed or refractory diffuse large B-cell lymphoma (DLBCL), higher responses were seen in the activated B-cell-like (ABC) subtype than the germinal center B-cell-like subtype. As provided herein using DLBCL cell lines, it was shown that lenalidomide treatment preferentially suppressed proliferation of ABC-DLBCL cells in vitro and delayed tumor growth in a human tumor xenograft model, with minimal effect on non-ABC-DLBCL cells. This tumoricidal effect was associated with downregulation of interferon regulatory factor 4 (IRF4), a hallmark of ABC-DLBCL cells.

IRF4 inhibition by lenalidomide caused downregulation of B cell receptor (BCR)-dependent NF-κB activation. While IRF4-specific siRNA mimicked effects of lenalidomide reducing NF-κB activation, IRF4 overexpression enhanced NF-κB activation and conferred resistance to lenalidomide. Furthermore, lenalidomide-induced IRF4 downregulation required the expression of CRBN. Without being bound to a particular theory, these data show that lenalidomide may have direct antitumor activity against DLBCL cells, preferentially ABC-DLBCL cells, by blocking IRF4 expression and the BCR-NF-κB signaling pathway in a CRBN-dependent manner.

It has been proposed that CRBN protein functions as a substrate receptor for Cul4-E3-ligase complexes through its interaction with DDB1. As provided herein, whether in vivo ubiquitination is associated with drug responses in multiple myeloma cells has been investigated. In H929 cells, compounds provided herein decrease total K48-linked polyubiquitination but not K-63-linked ubiquitination after 30 minutes treatment. At present, nearly two dozen proteins are reported to be degraded by a Cul4-DDB1 ligase2. Several studies have shown Cul4/DDB1-dependent ubiquitination of core histones, DNA repair proteins, cell cycle regulators and key signaling pathways molecules. mTORC1 signaling requires proteasomal function and the involvement of CUL4-DDB1 ubiquitin E3 ligase. Using CST Ubiscan technology, 162 unique ubiquitin-peptides were identified which were significantly modulated by the compounds provided herein after short treatments (1-4 h). The corresponding proteins participate in nucleasome and chromatin function, protein-DNA assembly and histone H2A. The relevance of this early modification in the mode of action of compounds provided herein, and the relationship with CRBN and CUL4/DDB1 activities are under investigation.

Provided herein are methods for the treatment or management of cancer and inflammatory diseases using CRBN as a predictive or prognostic factor for the compounds provided herein. In certain embodiments, provided herein are methods for screening or identifying cancer patients, e.g., lymphoma, leukemia, multiple myeloma, solid tumor, non-Hodgkin's lymphoma, DLBCL, mantle cell lymphoma, follicular lymphoma, acute myeloblastic leukemia, chronic lymphocytic leukemia, MDS or melanoma patients, for treatment with thalidomide, lenalidomide and/or pomalidomide, using CRBN levels as a predictive or prognostic factor. In some embodiments, provided herein are methods for selecting patients having a higher response rate to therapy with thalidomide, lenalidomide and/or pomalidomide, using CRBN levels as a predictive or prognostic factor.

In one embodiment, provided herein is a method of predicting patient response to treatment of cancer or an inflammatory disease with thalidomide, lenalidomide and/or pomalidomide, the method comprising obtaining biological material from the patient, and measuring the presence or absence of CRBN.

In one embodiment, the mRNA or protein is purified from the tumor and the presence or absence of a biomarker is measured by gene or protein expression analysis. In certain embodiments, the presence or absence of a biomarker is measured by quantitative real-time PCR (QRT-PCR), microarray, flow cytometry or immunofluorescence. In other embodiments, the presence or absence of a biomarker is measured by enzyme-linked immunosorbent assay-based methodologies (ELISA) or other similar methods known in the art.

In another embodiment, provided herein is a method of predicting the sensitivity to compound (e.g., drug) treatment in a cancer patient, such as, a multiple myeloma or non-Hodgkin's lymphoma patient. The method comprises obtaining a biological sample from the patient, optionally isolating or purifying mRNA from the biological sample, amplifying the mRNA transcripts by, e.g., RT-PCR, where a higher baseline level of a specific biomarker indicates a higher likelihood that the cancer will be sensitive to treatment with a compound (e.g., drug). In certain embodiments, the biomarker is a gene or protein associated with multiple myeloma or non-Hodgkin's lymphoma (e.g., DLBCL). In one embodiment, the genes are selected from the group consisting of DDB1, DDB2, GSK3B, CUL4A, CUL4B, XBP-1, FAS1, RANBP6, DUS3L, PHGDH, AMPK, IRF4 and NFκB.

In one embodiment, identifying a patient having lymphoma, leukemia, multiple myeloma, a solid tumor, non-Hodgkin's lymphoma, diffuse large B-cell lymphoma, mantle cell lymphoma, follicular lymphoma, acute myeloblastic leukemia, chronic lymphocytic leukemia, MDS or melanoma sensitive to treatment with thalidomide, lenalidomide, pomalidomide and/or 3-(5-amino-2-methyl-4-oxo-4H-quinazolin-3-yl)-piperidine-2,6-dione, comprises identifying a gene or protein associated with CRBN. In one embodiment, the gene or protein associated with CRBN is selected from the group consisting of DDB1, DDB2, GSK3B, CUL4A, CUL4B, XBP-1, FAS1, RANBP6, DUS3L, PHGDH, AMPK, IRF4 and NFκB.

In one embodiment, identifying a patient having lymphoma, leukemia, multiple myeloma, solid tumor, non-Hodgkin's lymphoma, DLBCL, mantle cell lymphoma, follicular lymphoma, acute myeloblastic leukemia, chronic lymphocytic leukemia, MDS or melanoma sensitive to treatment with thalidomide, lenalidomide, pomalidomide and/or 3-(5-amino-2-methyl-4-oxo-4H-quinazolin-3-yl)-piperidine-2,6-dione comprises measuring the level of CRBN activity in the patient. In another embodiment, measuring the level of CRBN activity in the patient comprises measuring DDB1, DDB2, GSK3B, CUL4A, CUL4B, XBP-1, FAS1, RANBP6, DUS3L, PHGDH, AMPK, IRF4 and/or NFκB in cells obtained from the patient.

In one embodiment, the compound is thalidomide.

In another embodiment, the compound is lenalidomide.

In another embodiment, the compound is pomalidomide.

In another embodiment, the compound is 3-(5-amino-2-methyl-4-oxo-4H-quinazolin-3-yl)-piperidine-2,6-dione, or an enantiomer thereof, or a pharmaceutically acceptable salt, polymorph, solvate or hydrate thereof.

In one embodiment, the cancer is multiple myeloma.

In another embodiment, the cancer is non-Hodgkin's lymphoma. In one embodiment, the non-Hodgkin's lymphoma is of the activated B-cell phenotype.

In another embodiment, the cancer is diffuse large B-cell lymphoma. In one embodiment, the diffuse large B-cell lymphoma is of the activated B-cell phenotype.

In another embodiment, the cancer is mantle cell lymphoma.

In another embodiment, the cancer is follicular lymphoma.

In another embodiment, the cancer is acute myeloblastic leukemia.

In another embodiment, the cancer is chronic lymphocytic leukemia.

In another embodiment, the cancer is myelodysplastic syndrome.

In another embodiment, the cancer is melanoma.

In still other embodiments, provided herein are methods of predicting the sensitivity to compound (e.g., drug) treatment in a patient having a disease or disorder selected from systemic lupus erythematosus, ANCA-induced vasculitis, glomerulonephritis, acute Wegener's granulomatosis, Myasthenia Gravis, Sjogren Syndrome, anti-phospholipid syndrome, rheumatoid arthritis and fibrotic conditions such as systemic sclerosis. The method comprises obtaining a biological sample from the patient, optionally isolating or purifying mRNA from the biological sample, amplifying the mRNA transcripts by, e.g., RT-PCR, where a higher baseline level of a specific biomarker indicates a higher likelihood that the disease or disorder will be sensitive to treatment with a compound (e.g., drug). In certain embodiments, the biomarker is a gene or protein selected from the group consisting of DDB1, DDB2, GSK3B, CUL4A, CUL4B, XBP-1, FAS1, RANBP6, DUS3L, PHGDH, AMPK, IRF4 and NFκB.

In one embodiment, identifying a patient having selected from systemic lupus erythematosus, ANCA-induced vasculitis, glomerulonephritis, acute Wegener's granulomatosis, Myasthenia Gravis, Sjogren Syndrome, anti-phospholipid syndrome, rheumatoid arthritis or systemic sclerosis sensitive to treatment with thalidomide, lenalidomide, pomalidomide and/or 3-(5-amino-2-methyl-4-oxo-4H-quinazolin-3-yl)-piperidine-2,6-dione comprises identification of a gene or protein associated with CRBN. In one embodiment, the gene or protein associated with CRBN is selected from the group consisting of DDB1, DDB2, GSK3B, CUL4A, CUL4B, XBP-1, FAS1, RANBP6, DUS3L, PHGDH, AMPK, IRF4 and NFκB.

In one embodiment, identifying a patient having systemic lupus erythematosus, ANCA-induced vasculitis, glomerulonephritis, acute Wegener's granulomatosis, Myasthenia Gravis, Sjogren Syndrome, anti-phospholipid syndrome, rheumatoid arthritis or systemic sclerosis sensitive to treatment with thalidomide, lenalidomide, pomalidomide and/or 3-(5-amino-2-methyl-4-oxo-4H-quinazolin-3-yl)-piperidine-2,6-dione comprises measuring the level of CRBN activity in the patient. In another embodiment, measuring the level of CRBN activity in the patient comprises measuring DDB1, DDB2, GSK3B, CUL4A, CUL4B, XBP-1, FAS1, RANBP6, DUS3L, PHGDH, AMPK, IRF4 and/or NFκB in cells obtained from the patient.

In one embodiment, the compound is thalidomide.

In another embodiment, the compound is lenalidomide.

In another embodiment, the compound is pomalidomide.

In another embodiment, the compound is 3-(5-amino-2-methyl-4-oxo-4H-quinazolin-3-yl)-piperidine-2,6-dione, or an enantiomer thereof, or a pharmaceutically acceptable salt, polymorph, solvate or hydrate thereof.

Also provided herein are kits useful for predicting the likelihood of an effective lymphoma, leukemia, multiple myeloma, a solid tumor, non-Hodgkin's lymphoma, diffuse large B-cell lymphoma, mantle cell lymphoma, follicular lymphoma, acute myeloblastic leukemia, chronic lymphocytic leukemia, myelodysplastic syndrome or melanoma treatment or for monitoring the effectiveness of a treatment with one or more compounds (e.g., drugs). The kit comprises a solid support, and a means for detecting the protein expression of at least one biomarker in a biological sample. Such a kit may employ, for example, a dipstick, a membrane, a chip, a disk, a test strip, a filter, a microsphere, a slide, a multiwell plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an oral tissue, gastrointestinal tissue, an organ, an organelle, a biological fluid, a blood sample, a urine sample, or a skin sample. The biological sample can be, for example, a lymph node biopsy, a bone marrow biopsy, or a sample of peripheral blood tumor cells.

In another embodiment, the kit comprises a solid support, nucleic acids contacting the support, where the nucleic acids are complementary to at least 20, 50, 100, 200, 350, or more bases of mRNA, and a means for detecting the expression of the mRNA in a biological sample.

In certain embodiments, the kits provided herein employ means for detecting the expression of a biomarker by quantitative real-time PCR (QRT-PCR), microarray, flow cytometry or immunofluorescence. In other embodiments, the expression of the biomarker is measured by ELISA-based methodologies or other similar methods known in the art.

In still other embodiments, the kits provided herein are useful for predicting the likelihood of an effective treatment of a disease or disorder selected from systemic lupus erythematosus, ANCA-induced vasculitis, glomerulonephritis, acute Wegener's granulomatosis, Myasthenia Gravis, Sjogren Syndrome, anti-phospholipid syndrome, rheumatoid arthritis and fibrotic conditions such as systemic sclerosis.

Provided herein is a method of selecting a group of cancer patients based on the level of CRBN expression, or the levels of DDB1, DDB2, GSK3B, CUL4A, CUL4B, XBP-1, FAS1, RANBP6, DUS3L, PHGDH, AMPK, IRF4 or NFκB expression within the cancer, for the purposes of predicting clinical response, monitoring clinical response, or monitoring patient compliance to dosing by thalidomide, lenalidomide, pomalidomide or 3-(5-amino-2-methyl-4-oxo-4H-quinazolin-3-yl)-piperidine-2,6-dione, a stereoisomer thereof, or a pharmaceutically acceptable salt, solvate, hydrate, co-crystal, clathrate, or polymorph thereof; wherein the cancer patients are selected from multiple myeloma, non-Hodgkin's lymphoma, diffuse large B-cell lymphoma, melanoma and solid tumor patients.

In one embodiment, the cancer patients are multiple myeloma patients.

In one embodiment, cancer patients are non-Hodgkin's lymphoma patients. In one embodiment, the non-Hodgkin's lymphoma is of the activated B-cell phenotype.

In one embodiment, cancer patients are diffuse large B-cell lymphoma patients. In one embodiment, the diffuse large B-cell lymphoma is of the activated B-cell phenotype.

In one embodiment, method of selecting a group of cancer patients is based on the level of DDB1 expression within the cancer.

In one embodiment, the method of selecting a group of cancer patients is based on the level of DDB2 expression within the cancer.

In one embodiment, the method of selecting a group of cancer patients is based on the level of GSK3B expression within the cancer.

In one embodiment, the method of selecting a group of cancer patients is based on the level of CUL4A expression within the cancer.

In one embodiment, the method of selecting a group of cancer patients is based on the level of CUL4B expression within the cancer.

In one embodiment, the method of selecting a group of cancer patients is based on the level of XBP-1 expression within the cancer.

In one embodiment, the method of selecting a group of cancer patients is based on the level of FAS1 expression within the cancer.

In one embodiment, the method of selecting a group of cancer patients is based on the level of RANBP6 expression within the cancer.

In one embodiment, the method of selecting a group of cancer patients is based on the level of DUS3L expression within the cancer.

In one embodiment, the method of selecting a group of cancer patients is based on the level of PHGDH expression within the cancer.

In one embodiment, the method of selecting a group of cancer patients is based on the level of AMPK expression within the cancer.

In one embodiment, the method of selecting a group of cancer patients is based on the level of IRF4 expression within the cancer.

In one embodiment, the method of selecting a group of cancer patients is based on the level of NFκB expression within the cancer.

Also provided herein is a method of identifying or monitoring multiple myeloma patient resistance to thalidomide, lenalidomide, pomalidomide or 3-(5-amino-2-methyl-4-oxo-4H-quinazolin-3-yl)-piperidine-2,6-dione therapy, based on the presence or appearance of mutations within a CRBN gene.

In one embodiment, the mutation with the CRBN gene is a single-nucleotide polymorphism in the coding region c.745C>CA causing an amino acid change 249D>YD in the protein within the DDB1 binding domain of CRBN.

In another embodiment, provided herein is a method of selecting a group of patients responsive to treatment with thalidomide, lenalidomide, pomalidomide or 3-(5-amino-2-methyl-4-oxo-4H-quinazolin-3-yl)-piperidine-2,6-dione, a stereoisomer thereof, or a pharmaceutically acceptable salt, solvate, hydrate, co-crystal, clathrate, or polymorph thereof; based on the level of CRBN expression, or the levels of DDB1, DDB2, GSK3B, CUL4A, CUL4B, XBP-1, FAS1, RANBP6, DUS3L, PHGDH, AMPK, IRF4 or NFκB expression within the patient's T cells, B cells, or plasma cells, for the purposes of predicting clinical response, monitoring clinical response, or monitoring patient compliance to dosing by thalidomide, lenalidomide, pomalidomide or 3-(5-amino-2-methyl-4-oxo-4H-quinazolin-3-yl)-piperidine-2,6-dione, a stereoisomer thereof, or a pharmaceutically acceptable salt, solvate, hydrate, co-crystal, clathrate, or polymorph thereof.

Also provided herein is an isolated CRBN antibody, for example, "CRBN70," as prepared according to Example 6.20 or 6.21 below. In one embodiment, the antibody is a polyclonal antibody. In another embodiment, the antibody is a monoclonal antibody. In some embodiments, the antibody is a rabbit polyclonal antibody. In other embodiments, the antibody is a rabbit monoclonal antibody.

In another embodiment, provided herein is an isolated antibody which immunospecifically binds to the epitope having an amino acid sequence EEFHGRTLHDDDC (SEQ ID:1). In another embodiment, the antibody immunospecifically binds to the epitope having an amino acid sequence EEFHGRTLHDDDC (SEQ ID:1), wherein the peptide is coupled to Keyhole Limpet Hemocyanin (KLH). In one embodiment, the antibody is a polyclonal antibody. In another embodiment, the antibody is a monoclonal antibody. In some embodiments, the antibody is a rabbit polyclonal antibody. In other embodiments, the antibody is a rabbit monoclonal antibody. In certain embodiments, the antibody immunospecifically binds peptide 65-76 (SEQ ID NO:1) of human CRBN (SEQ ID NO:12).

In certain embodiments, provided herein is an antibody that immunospecifically binds CRBN and comprises a heavy chain having the amino acid sequence depicted in SEQ ID NO:5. In other embodiment, the antibody immunospecifically binds CRBN and comprises a light chain having the amino acid sequence depicted in SEQ ID NO:7. In some embodiments, the antibody comprises a heavy chain having the amino acid sequence depicted in SEQ ID NO:5 and a light chain having the amino acid sequence depicted in SEQ ID NO:7. In certain embodiments, the antibody immunospecifically binds CRBN and comprises a heavy chain having the amino acid sequence depicted in SEQ ID NO:9. In other embodiment, the antibody immunospecifically binds CRBN and comprises a light chain having the amino acid sequence depicted in SEQ ID NO:11. In some embodiments, the antibody comprises a heavy chain having the amino acid sequence depicted in SEQ ID NO:9 and a light chain having the amino acid sequence depicted in SEQ ID NO:11. In certain embodiments, the antibody immunospecifically binds peptide 65-76 (SEQ ID NO:1) of human CRBN (SEQ ID NO:12).

Also provided herein is a method of utilizing a CRBN antibody (e.g., a rabbit polyclonal or monoclonal antibody CRBN70, or a rabbit polyclonal or monoclonal antibody that binds peptide 65-76 (SEQ ID NO:1) of human CRBN (SEQ ID NO:12) to measure expression levels of CRBN in patient tumor or host cells, to predict clinical response, monitor clinical response, monitor patient compliance to dosing, or monitor development of resistance to therapy with thalidomide, lenalidomide, pomalidomide, or 3-(5-amino-2-methyl-4-oxo-4H-quinazolin-3-yl)-piperidine-2,6-dione, a stereoisomer thereof, or a pharmaceutically acceptable salt, solvate, hydrate, co-crystal, clathrate, or polymorph thereof. In one embodiment, the CRBN antibody immunospecifically binds to the epitope having an amino acid sequence EEFHGRTLHDDD (residues 1-12 of SEQ ID NO:1). In an embodiment, the CRBN antibody specifically binds to EEFHGRTLHDDD (residues 1-12 of SEQ ID NO:1), which is coupled to Keyhole Limpet Hemocyanin (KLH). In one embodiment, the CRBN antibody is a polyclonal antibody, such as a rabbit polyclonal antibody. In another embodiment, the CRBN antibody is a monoclonal antibody, such as a rabbit monoclonal antibody.

5.1 Definitions

As used herein, and unless otherwise specified, the terms "treat," "treating" and "treatment" refer to an action that occurs while a patient is suffering from the specified cancer, which reduces the severity of the cancer, or retards or slows the progression of the cancer.

The term "sensitivity" and "sensitive" when made in reference to treatment with compound is a relative term which refers to the degree of effectiveness of the compound in lessening or decreasing the progress of a tumor or the disease being treated. For example, the term "increased sensitivity" when used in reference to treatment of a cell or tumor in connection with a compound refers to an increase of, at least a 5%, or more, in the effectiveness of the tumor treatment.

As used herein, and unless otherwise specified, the term "therapeutically effective amount" of a compound is an amount sufficient to provide a therapeutic benefit in the treatment or management of a cancer, or to delay or minimize one or more symptoms associated with the presence of the cancer. A therapeutically effective amount of a compound means an amount of therapeutic agent, alone or in combination with other therapies, which provides a therapeutic benefit in the treatment or management of the cancer. The term "therapeutically effective amount" can encompass an amount that improves overall therapy, reduces or avoids symptoms or causes of cancer, or enhances the therapeutic efficacy of another therapeutic agent.

As used herein, an "effective patient tumor response" refers to any increase in the therapeutic benefit to the patient. An "effective patient tumor response" can be, for example, a 5%, 10%, 25%, 50%, or 100% decrease in the rate of progress of the tumor. An "effective patient tumor response" can be, for example, a 5%, 10%, 25%, 50%, or 100% decrease in the physical symptoms of a cancer. An "effective patient tumor response" can also be, for example, a 5%, 10%, 25%, 50%, 100%, 200%, or more increase in the response of the patient, as measured by any suitable means, such as gene expression, cell counts, assay results, etc.

The term "likelihood" generally refers to an increase in the probability of an event. The term "likelihood" when used in reference to the effectiveness of a patient tumor response generally contemplates an increased probability that the rate of tumor progress or tumor cell growth will decrease. The term "likelihood" when used in reference to the effectiveness of a patient tumor response can also generally mean the increase of indicators, such as mRNA or protein expression, that may evidence an increase in the progress in treating the tumor.

The term "predict" generally means to determine or tell in advance. When used to "predict" the effectiveness of a cancer treatment, for example, the term "predict" can mean that the likelihood of the outcome of the cancer treatment can be determined at the outset, before the treatment has begun, or before the treatment period has progressed substantially.

The term "monitor," as used herein, generally refers to the overseeing, supervision, regulation, watching, tracking, or surveillance of an activity. For example, the term "monitoring the effectiveness of a compound" refers to tracking the effectiveness in treating a cancer in a patient or in a tumor cell culture. Similarly, the "monitoring," when used in connection with patient compliance, either individually, or in a clinical trial, refers to the tracking or confirming that the patient is actually taking a drug being tested as prescribed. The monitoring can be performed, for example, by following the expression of mRNA or protein biomarkers.

An improvement in the cancer or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about a 10%, 20%, 30%, 40%, 50%, 60%, 70%, 80%, or 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

"Tumor," as used herein, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

The terms "cancer" and "cancerous" refer to or describe the physiological condition in mammals that is typically characterized by unregulated cell growth. Examples of cancer include, but are not limited to, blood-borne tumors (e.g., multiple myeloma, lymphoma and leukemia), and solid tumors.

The term "refractory or resistant" refers to a circumstance where patients, even after intensive treatment, have residual cancer cells (e.g., leukemia or lymphoma cells) in their lymphatic system, blood and/or blood forming tissues (e.g., marrow).

As used herein the terms "polypeptide" and "protein" as used interchangeably herein, refer to a polymer of amino acids of three or more amino acids in a serial array, linked through peptide bonds. The term "polypeptide" includes proteins, protein fragments, protein analogues, oligopeptides and the like. The term polypeptide as used herein can also refer to a peptide. The amino acids making up the polypeptide may be naturally derived, or may be synthetic. The polypeptide can be purified from a biological sample.

The term "antibody" is used herein in the broadest sense and covers fully assembled antibodies, antibody fragments which retain the ability to specifically bind to the antigen (e.g., Fab, F(ab')2, Fv, and other fragments), single chain antibodies, diabodies, antibody chimeras, hybrid antibodies, bispecific antibodies, humanized antibodies, and the like. The term "antibody" covers both polyclonal and monoclonal antibodies.

The term "antibody" and "immunoglobulin" or "Ig" may be used interchangeably herein. The terms "antibodies that immunospecifically bind to a CRBN antigen," "antibodies that immunospecifically bind to a CRBN epitope," "CRBN antibodies," "anti-CRBN antibodies" and analogous terms are also used interchangeably herein and refer to antibodies and fragments thereof, that specifically bind to a CRBN polypeptide, such as a CRBN antigen or epitope (e.g., EEF-HGRTLHDDD (residues 1-12 of SEQ ID NO:1) or peptide 65-76 human CRBN (SEQ ID NO:12)). The antibodies, including both modified antibodies (i.e., antibodies that comprise a modified IgG (e.g., IgG1) constant domain and unmodified antibodies (i.e., antibodies that do not comprise a modified IgG (e.g., IgG1) constant domain that specifically bind to a CRBN polypeptide. An antibody or a fragment thereof that immunospecifically binds to a CRBN antigen may be cross-reactive with related antigens. In certain embodiments, an antibody or a fragment thereof that immunospecifically binds to a CRBN antigen does not cross-react with other antigens. An antibody or a fragment thereof that immunospecifically binds to a CRBN antigen can be identified, for example, by immunoassays, BIAcore, or other techniques known to those of skill in the art. An antibody or a fragment thereof binds specifically to a CRBN antigen when it binds to a CRBN antigen with higher affinity than to any cross-reactive antigen as determined using experimental techniques, such as radioimmunoassays (RIA) and enzyme-linked immunosorbent assays (ELISAs). Typically a specific or selective reaction will be at least twice background signal or noise and more typically more than 10 times background. See, e.g., Paul, ed., 1989, Fundamental Immunology Second Edition, Raven Press, New York at pages 332-336 for a discussion regarding antibody specificity.

Antibodies provided herein include, but are not limited to, synthetic antibodies, monoclonal antibodies, recombinantly produced antibodies, multispecific antibodies (including bispecific antibodies), human antibodies, humanized antibodies, chimeric antibodies, intrabodies, single-chain Fvs (scFv) (e.g., including monospecific, bispecific, etc.), camelized antibodies, Fab fragments, F(ab") fragments, disulfide-linked Fvs (sdFv), anti-idiotypic (anti-Id) antibodies, and epitope-binding fragments of any of the above. In particular, antibodies provided herein include immunoglobulin molecules and immunologically active portions of immunoglobulin molecules, i.e., antigen binding domains or molecules that contain an antigen-binding site that immunospecifically binds to a CRBN antigen (e.g., one or more complementarity determining regions (CDRs) of an anti-CRBN antibody). The antibodies provided herein can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. In some embodiments, the anti-CRBN antibodies are fully human, such as fully human monoclonal CRBN antibodies. In certain embodiments, antibodies provided herein are IgG antibodies, or a class (e.g., human IgG1 or IgG4) or subclass thereof.

The term "antigen binding domain," "antigen binding region," "antigen binding fragment," and similar terms refer to that portion of an antibody which comprises the amino acid residues that interact with an antigen and confer on the binding agent its specificity and affinity for the antigen (e.g., the CDR). The antigen binding region can be derived from any animal species, such as rodents (e.g., rabbit, rat or hamster) and humans. In some embodiments, the antigen binding region will be of human origin.

The term "constant region" or "constant domain" of an antibody refers to a carboxy terminal portion of the light and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CL domain of the light chain.

The term "epitope" as used herein refers to a localized region on the surface of an antigen, such as CRBN polypeptide or CRBN polypeptide fragment, that is capable of being bound to one or more antigen binding regions of an antibody, and that has antigenic or immunogenic activity in an animal, such as a mammal (e.g., a human), that is capable of eliciting an immune response. An epitope having immunogenic activity is a portion of a polypeptide that elicits a antibody response in an animal. An epitope having antigenic activity is a portion of a polypeptide to which an antibody immunospecifically binds as determined by any method well known in the art, for example, by the immunoassays described herein. Antigenic epitopes need not necessarily be immunogenic. Epitopes usually consist of chemically active surface groupings of molecules such as amino acids or sugar side chains and have specific three dimensional structural characteristics as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen. An exemplary epitope of CRBN provided herein is EEFHGRTLHDDD (residues 1-12 of SEQ ID NO:1) or peptide 65-60 of CRBN (SEQ ID NO:13).

The terms "fully human antibody" or "human antibody" are used interchangeably herein and refer to an antibody that comprises a human variable region and, in some embodiments, a human constant region. In specific embodiments, the terms refer to an antibody that comprises a variable region and constant region of human origin. "Fully human" anti-CRBN antibodies, in certain embodiments, can also encompass antibodies which bind CRBN polypeptides and are encoded by nucleic acid sequences which are naturally occurring somatic variants of human germline immunoglobulin nucleic acid sequence. In a specific embodiment, the anti-CRBN antibodies provided herein are fully human antibodies. The term "fully human antibody" includes antibodies having variable and constant regions corresponding to human germline immunoglobulin sequences as described by Kabat et al., Sequences of Proteins of Immunological Interest, Fifth Edition, U.S. Department of Health and Human Services, NIH Publication No. 91-3242, 1991. Exemplary methods of producing fully human antibodies are provided, e.g., in the Examples herein, but any method known in the art may be used.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see, e.g., Taylor, L. D. et al. (1992) Nucl. Acids Res. 20:6287-6295) or antibodies prepared, expressed, created or isolated by any other means that involves splicing of human immunoglobulin gene sequences to other DNA sequences. Such recombinant human antibodies can have variable and constant regions derived from human germline immunoglobulin sequences. See Kabat, E. A. et al. (1991) Sequences of Proteins of Immunological Interest, Fifth Edition, U.S. Department of Health and Human Services, NIH Publication No. 91-3242. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "heavy chain" when used in reference to an antibody refers to five distinct types, called alpha (α), delta (δ), epsilon (ε), gamma (γ) and mu (μ), based on the amino acid sequence of the heavy chain constant domain. These distinct types of heavy chains are well known and give rise to five classes of antibodies, IgA, IgD, IgE, IgG and IgM, respectively, including four subclasses of IgG, namely IgG1, IgG1, IgG3 and IgG4. In some embodiments the heavy chain is a human heavy chain.

The terms "Kabat numbering," and like terms are recognized in the art and refer to a system of numbering amino acid residues which are more variable (i.e. hypervariable) than other amino acid residues in the heavy and light chain variable regions of an antibody, or an antigen binding portion thereof. Kabat et al. (1971) Ann. any Acad. Sci. 190:382-391 and, Kabat et cd. (1991) Sequences of Proteins of Immunological Interest, Fifth Edition, U.S. Department of Health and Human Services, NIH Publication No. 91-3242. For the heavy chain variable region, the hypervariable region typically ranges from amino acid positions 31 to 35 for CDR1, amino acid positions 50 to 65 for CDR2, and amino acid positions 95 to 102 for CDR3. For the light chain variable region, the hypervariable region typically ranges from amino acid positions 24 to 34 for CDR1, amino acid positions 50 to 56 for CDR2, and amino acid positions 89 to 97 for CDR3. Other numbering schemes will be readily understood by those skilled in the art.

The term "light chain" when used in reference to an antibody refers to two distinct types, called kappa (κ) of lambda (λ) based on the amino acid sequence of the constant domains. Light chain amino acid sequences are well known in the art. In certain embodiments, the light chain is a human light chain.

The term "monoclonal antibody" refers to an antibody obtained from a population of homogenous or substantially homogeneous antibodies, and each monoclonal antibody will typically recognize a single epitope on the antigen. In some embodiments, a "monoclonal antibody," as used herein, is an antibody produced by a single hybridoma or other cell, wherein the antibody immunospecifically binds to only a CRBN epitope as determined, e.g., by ELISA or other antigen-binding or competitive binding assay known in the art or in the Examples provided herein. The term "monoclonal" is not limited to any particular method for making the antibody. For example, monoclonal antibodies provided herein may be made by the hybridoma method as described in Kohler et al.; Nature, 256:495 (1975) or may be isolated from phage libraries using the techniques as described herein, for example. Other methods for the preparation of clonal cell lines and of monoclonal antibodies expressed thereby are well known in the art. See, e.g., Chapter 11 in: Short Protocols in Molecular Biology, (2002) 5th Ed., Ausubel et al., eds., John Wiley and Sons, New York. Other exemplary methods of producing other monoclonal antibodies are provided in the Examples herein.

"Polyclonal antibodies" as used herein refers to an antibody population generated in an immunogenic response to a protein having many epitopes and thus includes a variety of different antibodies directed to the same and to different epitopes within the protein. Methods for producing polyclonal antibodies are known in the art. See, e.g., Chapter 11 in: Short Protocols in Molecular Biology, (2002) 5th Ed., Ausubel et al., eds., John Wiley and Sons, New York.

The terms "cereblon" or "CRBN" and similar terms refers to the polypeptides ("polypeptides," "peptides" and "proteins" are used interchangeably herein) comprising the amino acid sequence any CRBN, such as a human CRBN protein (e.g., human CRBN isoform 1, GenBank Accession No. NP_057386 (SEQ ID NO:12); or human CRBN isoforms 2, GenBank Accession No. NP_001166953 (SEQ ID NO:13), each of which is herein incorporated by reference in its entirety), and related polypeptides, including SNP variants thereof. Related CRBN polypeptides include allelic variants (e.g., SNP variants); splice variants; fragments; derivatives; substitution, deletion, and insertion variants; fusion polypeptides; and interspecies homologs, which, in certain embodiments, retain CRBN activity and/or are sufficient to generate an anti-CRBN immune response.

The term "CRBN antigen" refers to that portion of a CRBN polypeptide to which an antibody immunospecifically binds. A CRBN antigen also refers to an analog or derivative of a CRBN polypeptide or fragment thereof to which an antibody immunospecifically binds. A localized region on the surface of a CRBN antigen that is capable of eliciting an immune response is an CRBN "epitope." A region of a CRBN polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, the CRBN epitope is EEFHGRTLHDDD (residues 1-12 of SEQ ID NO:1) or peptide 65-76 of human CRBN (SEQ ID NO:12).

The term "variable region" or "variable domain" refers to a portion of the light and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complimentarily determining regions (CDRs) while the more highly conserved regions in the variable domain are called framework regions (FR). The CDRs of the light and heavy chains are primarily responsible for the interaction of the antibody with antigen. Numbering of amino acid positions used herein is according to the EU Index, as in See Kabat, E. A. et al. (1991) Sequences of Proteins of Immunological Interest, Fifth Edition, U.S. Department of Health and Human Services, NIH Publication No. 91-3242. In some embodiments, the variable region is a human variable region.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to give a protein, a polypeptide or a portion thereof.

An mRNA that is "upregulated" is generally increased upon a given treatment or condition. An mRNA that is "downregulated" generally refers to a decrease in the level of expression of the mRNA in response to a given treatment or condition. In some situations, the mRNA level can remain unchanged upon a given treatment or condition.

An mRNA from a patient sample can be "upregulated" when treated with a drug, as compared to a non-treated control. This upregulation can be, for example, an increase of about 5%, 10%, 20%, 30%, 40%, 50%, 60%, 70%, 90%, 100%, 200%, 300%, 500%, 1,000%, 5,000% or more of the comparative control mRNA level.

Alternatively, an mRNA can be "downregulated", or expressed at a lower level, in response to administration of certain compounds or other agents. A downregulated mRNA can be, for example, present at a level of about 99%, 95%, 90%, 80%, 70%, 60%, 50%, 40%, 30%, 20%, 10%, 1% or less of the comparative control mRNA level.

Similarly, the level of a polypeptide or protein biomarker from a patient sample can be increased when treated with a drug, as compared to a non-treated control. This increase can be about 5%, 10%, 20%, 30%, 40%, 50%, 60%, 70%, 90%, 100%, 200%, 300%, 500%, 1,000%, 5,000% or more of the comparative control protein level.

Alternatively, the level of a protein biomarker can be decreased in response to administration of certain compounds or other agents. This decrease can be, for example, present at a level of about 99%, 95%, 90%, 80%, 70%, 60%, 50%, 40%, 30%, 20%, 10%, 1% or less of the comparative control protein level.

The terms "determining", "measuring", "evaluating", "assessing" and "assaying" as used herein generally refer to any form of measurement, and include determining if an element is present or not. These terms include both quantitative and/or qualitative determinations. Assessing may be relative or absolute. "Assessing the presence of" can include determining the amount of something present, as well as determining whether it is present or absent.

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural nucleotides, nucleotide mimetics such as 2'-modified nucleosides, peptide nucleic acids, oligomeric nucleoside phosphonates, and any polynucleotide that has added substituent groups, such as protecting groups or linking moieties.

The term "complementary" refers to specific binding between polynucleotides based on the sequences of the polynucleotides. As used herein, a first polynucleotide and a second polynucleotide are complementary if they bind to each other in a hybridization assay under stringent conditions, e.g. if they produce a given or detectable level of signal in a hybridization assay. Portions of polynucleotides are complementary to each other if they follow conventional base-pairing rules, e.g. A pairs with T (or U) and G pairs with C, although small regions (e.g. less than about 3 bases) of mismatch, insertion, or deleted sequence may be present.

"Sequence identity" or "identity" in the context of two nucleic acid sequences refers to the residues in the two sequences which are the same when aligned for maximum correspondence over a specified comparison window, and can take into consideration additions, deletions and substitutions.

The term "substantial identity" or "homologous" in their various grammatical forms in the context of polynucleotides generally means that a polynucleotide comprises a sequence that has a desired identity, for example, at least 60% identity, preferably at least 70% sequence identity, more preferably at least 80%, still more preferably at least 90% and even more preferably at least 95%, compared to a reference sequence. Another indication that nucleotide sequences are substantially identical is if two molecules hybridize to each other under stringent conditions.

The terms "isolated" and "purified" refer to isolation of a substance (such as mRNA, antibody or protein) such that the substance comprises a substantial portion of the sample in which it resides, i.e. greater than the substance is typically found in its natural or un-isolated state. Typically, a substantial portion of the sample comprises, e.g., greater than 1%, greater than 2%, greater than 5%, greater than 10%, greater than 20%, greater than 50%, or more, usually up to about 90%-100% of the sample. For example, a sample of isolated mRNA can typically comprise at least about 1% total mRNA. Techniques for purifying polynucleotides are well known in the art and include, for example, gel electrophoresis, ion-exchange chromatography, affinity chromatography, flow sorting, and sedimentation according to density.

The term "sample" as used herein relates to a material or mixture of materials, typically, although not necessarily, in fluid form, containing one or more components of interest.

"Biological sample" as used herein refers to a sample obtained from a biological subject, including sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, fractions and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Preferred biological samples include but are not limited to whole blood, partially purified blood, PBMCs, tissue biopsies, and the like.

The term "capture agent," as used herein, refers to an agent that binds an mRNA or protein through an interaction that is sufficient to permit the agent to bind and concentrate the mRNA or protein from a homogeneous mixture.

The term "probe" as used herein, refers to a capture agent that is directed to a specific target mRNA biomarker sequence. Accordingly, each probe of a probe set has a respective target mRNA biomarker. A probe/target mRNA duplex is a structure formed by hybridizing a probe to its target mRNA biomarker.

The term "nucleic acid" or "oligonucleotide probe" refers to a nucleic acid capable of binding to a target nucleic acid of complementary sequence, such as the mRNA biomarkers provided herein, through one or more types of chemical bonds, usually through complementary base pairing, usually through hydrogen bond formation. As used herein, a probe may include natural (e.g., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with isotopes, for example, chromophores, lumiphores, chromogens, or indirectly labeled with biotin to which a streptavidin complex may later bind. By assaying for the presence or absence of the probe, one can detect the presence or absence of a target mRNA biomarker of interest.

The term "stringent assay conditions" refers to conditions that are compatible to produce binding pairs of nucleic acids, e.g., probes and target mRNAs, of sufficient complementarity to provide for the desired level of specificity in the assay while being generally incompatible to the formation of binding pairs between binding members of insufficient complementarity to provide for the desired specificity. The term stringent assay conditions generally refers to the combination of hybridization and wash conditions.

A "label" or a "detectable moiety" in reference to a nucleic acid, refers to a composition that, when linked with a nucleic acid, renders the nucleic acid detectable, for example, by spectroscopic, photochemical, biochemical, immunochemical, or chemical means. Exemplary labels include, but are not limited to, radioactive isotopes, magnetic beads, metallic beads, colloidal particles, fluorescent dyes, enzymes, biotin, digoxigenin, haptens, and the like. A "labeled nucleic acid or oligonucleotide probe" is generally one that is bound, either covalently, through a linker or a chemical bond, or noncovalently, through ionic bonds, van der Waals forces, electrostatic attractions, hydrophobic interactions, or hydrogen bonds, to a label such that the presence of the nucleic acid or probe can be detected by detecting the presence of the label bound to the nucleic acid or probe.

The terms "Polymerase chain reaction," or "PCR," as used herein generally refers to a procedure wherein small amounts of a nucleic acid, RNA and/or DNA, are amplified as described, for example, in U.S. Pat. No. 4,683,195 to Mullis. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., Cold Spring Harbor Symp. Quant. Biol., 51: 263 (1987); Erlich, ed., PCR Technology, (Stockton Press, NY, 1989).

The term "cycle number" or "CT" when used herein in reference to PCR methods, refers to the PCR cycle number at which the fluorescence level passes a given set threshold level. The CT measurement can be used, for example, to approximate levels of mRNA in an original sample. The CT measurement is often used in terms of "dCT" or the "difference in the CT" score, when the CT of one nucleic acid is subtracted from the CT of another nucleic acid.

As used herein, and unless otherwise indicated, the term "optically pure" means a composition that comprises one optical isomer of a compound and is substantially free of other isomers of that compound. For example, an optically pure composition of a compound having one chiral center will be substantially free of the opposite enantiomer of the compound. An optically pure composition of a compound having two chiral centers will be substantially free of other diastereomers of the compound. A typical optically pure compound comprises greater than about 80% by weight of one enantiomer of the compound and less than about 20% by weight of other enantiomers of the compound, more preferably greater than about 90% by weight of one enantiomer of the compound and less than about 10% by weight of the other enantiomers of the compound, even more preferably greater than about 95% by weight of one enantiomer of the compound and less than about 5% by weight of the other enantiomers of the compound, more preferably greater than about 97% by weight of one enantiomer of the compound and less than about 3% by weight of the other enantiomers of the compound, and most preferably greater than about 99% by weight of one enantiomer of the compound and less than about 1% by weight of the other enantiomers of the compound.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "solvate" means a compound provided herein or a salt thereof, that further includes a stoichiometric or non-stoichiometric amount of solvent bound by non-covalent intermolecular forces. Where the solvent is water, the solvate is a hydrate.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

As used herein and unless otherwise indicated, the term "co-crystal" means a crystalline form that contains more than one compound in a crystal lattice. Co-crystals include crystalline molecular complexes of two or more non-volatile compounds bound together in a crystal lattice through non-ionic interactions. As used herein, co-crystals include pharmaceutical cocrystals wherein the crystalline molecular complexes containing a therapeutic compound and one or more additional non-volatile compound(s) (referred to herein as counter-molecule(s)). A counter-molecule in a pharmaceutical cocrystal is typically a non-toxic pharmaceutically acceptable molecule, such as, for example, food additives, preservatives, pharmaceutical excipients, or other APIs. In some embodiments, pharmaceutical cocrystals enhance certain physicochemical properties of drug products (e.g., solubility, dissolution rate, bioavailability and/or stability). without compromising the chemical structural integrity of the active pharmaceutical ingredient (API). See, e.g., Jones et al., "Pharmaceutical Cocrystals: An Emerging Approach to Physical Property Enhancement," *MRS Bulletin,* 2006, 31, 875-879; Trask, "An Overview of Pharmaceutical Cocrystals as Intellectual Property," *Molecular Pharmaceutics*, 2007, 4(3), 301-309; Schultheiss & Newman, "Pharmaceutical Cocrystals and Their Physicochemical Properties," *Crystal Growth & Design*, 2009, 9(6), 2950-2967; Shan & Zaworotko, "The Role of Cocrystals in Pharmaceutical Science," *Drug Discovery Today*, 2008, 13(9/10), 440-446; and Vishweshwar et al., "Pharmaceutical Co-Crystals," *J. Pharm. Sci.*, 2006, 95(3), 499-516.

A biological marker or "biomarker" is a substance whose detection indicates a particular biological state, such as, for example, the presence of cancer. In some embodiments, biomarkers can either be determined individually, or several biomarkers can be measured simultaneously.

In some embodiments, a "biomarker" indicates a change in the level of mRNA expression that may correlate with the risk or progression of a disease, or with the susceptibility of the disease to a given treatment. In some embodiments, the biomarker is a nucleic acid, such as a mRNA or cDNA.

In additional embodiments, a "biomarker" indicates a change in the level of polypeptide or protein expression that may correlate with the risk, susceptibility to treatment, or progression of a disease. In some embodiments, the biomarker can be a polypeptide or protein, or a fragment thereof. The relative level of specific proteins can be determined by methods known in the art. For example, antibody based methods, such as an immunoblot, enzyme-linked immunosorbent assay (ELISA), or other methods can be used.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al. (1989) *Molecular Cloning; A Laboratory Manual* (2d ed.); D. N Glover, ed. (1985) *DNA Cloning*, Volumes I and II; M. J. Gait, ed. (1984) *Oligonucleotide Synthesis*; B. D. Hames & S J. Higgins, eds. (1984) *Nucleic Acid Hybridization*; B. D. Hames & S. J. Higgins, eds. (1984) *Transcription and Translation*; R. I. Freshney, ed. (1986) *Animal Cell Culture; Immobilized Cells and Enzymes* (IRL Press, 1986); *Immunochemical Methods in Cell and Molecular Biology* (Academic Press, London); Scopes (1987) *Protein Purification: Principles and Practice* (2d ed.; Springer Verlag, N.Y.); and D. M. Weir and C. C. Blackwell, eds. (1986) *Handbook of Experimental Immunology*, Volumes I-IV.

5.2 Clinical Trial Endpoints

"Overall survival" is defined as the time from randomization until death from any cause, and is measured in the intent-to-treat population. Overall survival should be evaluated in randomized controlled studies. Demonstration of a statistically significant improvement in overall survival can be considered to be clinically significant if the toxicity profile is acceptable, and has often supported new drug approval.

Several endpoints are based on cancer assessments. These endpoints include disease free survival (DFS), objective response rate (ORR), time to progression (TTP), progression-free survival (PFS), and time-to-treatment failure (TTF). The collection and analysis of data on these time-dependent endpoints are based on indirect assessments, calculations, and estimates (e.g., tumor measurements).

Generally, "disease free survival" (DFS) is defined as the time from randomization until recurrence of cancer or death from any cause. Although overall survival is a conventional endpoint for most adjuvant settings, DFS can be an important endpoint in situations where survival may be prolonged, making a survival endpoint impractical. DFS can be a surrogate for clinical benefit or it can provide direct evidence of clinical benefit. This determination is based on the magnitude of the effect, its risk-benefit relationship, and the disease setting. The definition of DFS can be complicated, particularly when deaths are noted without prior cancer progression documentation. These events can be scored either as disease recurrences or as censored events. Although all methods for statistical analysis of deaths have some limitations, considering all deaths (deaths from all causes) as recurrences can minimize bias. DFS can be overestimated using this definition, especially in patients who die after a long period without observation. Bias can be introduced if the frequency of long-term follow-up visits is dissimilar between the study arms or if dropouts are not random because of toxicity.

"Objective response rate" (ORR) is defined as the proportion of patients with cancer reduction of a predefined amount and for a minimum time period. Response duration usually is measured from the time of initial response until documented cancer progression. Generally, the FDA has defined ORR as the sum of partial responses plus complete responses. When defined in this manner, ORR is a direct measure of drug anticancer activity, which can be evaluated in a single-arm study. If available, standardized criteria should be used to ascertain response. A variety of response criteria have been considered appropriate (e.g., RECIST criteria) (Therasse et al., (2000) J. Natl. Cancer Inst, 92: 205-16). The significance of ORR is assessed by its magnitude and duration, and the percentage of complete responses (no detectable evidence of cancer).

"Time to progression" (TTP) and "progression-free survival" (PFS) have served as primary endpoints for drug approval. TTP is defined as the time from randomization until objective cancer progression; TTP does not include deaths. PFS is defined as the time from randomization until objective cancer progression or death. Compared with TTP, PFS is the preferred regulatory endpoint. PFS includes deaths and thus can be a better correlate to overall survival. PFS assumes patient deaths are randomly related to cancer progression. However, in situations where the majority of deaths are unrelated to cancer, TTP can be an acceptable endpoint.

As an endpoint to support drug approval, PFS can reflect cancer growth and be assessed before the determination of a survival benefit. Its determination is not confounded by subsequent therapy. For a given sample size, the magnitude of effect on PFS can be larger than the effect on overall survival. However, the formal validation of PFS as a surrogate for survival for the many different malignancies that exist can be difficult. Data are sometimes insufficient to allow a robust evaluation of the correlation between effects on survival and PFS. Cancer trials are often small, and proven survival benefits of existing drugs are generally modest. The role of PFS as an endpoint to support licensing approval varies in different cancer settings. Whether an improvement in PFS represents a direct clinical benefit or a surrogate for clinical benefit depends on the magnitude of the effect and the risk-benefit of the new treatment compared to available therapies.

"Time-to-treatment failure" (TTF) is defined as a composite endpoint measuring time from randomization to discontinuation of treatment for any reason, including disease progression, treatment toxicity, and death. TTF is not recommended as a regulatory endpoint for drug approval. TTF does not adequately distinguish efficacy from these additional variables. A regulatory endpoint should clearly distinguish the efficacy of the drug from toxicity, patient or physician withdrawal, or patient intolerance.

5.3 Second Active Agents

The compounds provided herein may be combined with other pharmacologically active compounds ("second active agents") in methods and compositions provided herein. It is believed that certain combinations work synergistically in the treatment of particular types of cancer, and certain diseases and conditions associated with or characterized by undesired angiogenesis and/or inflammation. The compounds provided herein provided herein can also work to alleviate adverse effects associated with certain second active agents, and some second active agents can be used to alleviate adverse effects associated with the compounds provided herein provided herein.

One or more second active ingredients or agents can be used in the methods and compositions provided herein with the compounds provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. In certain embodiments, large molecule active agents are biological molecules, such as naturally occurring or artificially made proteins. Proteins that are particularly useful in this disclosure include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and compositions of the disclosure include, but are not limited to: filgrastim, which is sold in the United States under the trade name NEUPOGEN® (Amgen, Thousand Oaks, Calif.); sargramostim, which is sold in the United States under the trade name LEUKINE® (Immunex, Seattle, Wash.); and recombinant EPO, which is sold in the United States under the trade name EPGEN® (Amgen, Thousand Oaks, Calif.).

Recombinant and mutated forms of GM-CSF can be prepared as described in U.S. Pat. Nos. 5,391,485; 5,393,870; and 5,229,496; the disclosure of each of which is incorporated herein by reference in its entirety. Recombinant and mutated forms of G-CSF can be prepared as described in U.S. Pat. Nos. 4,810,643; 4,999,291; 5,528,823; and 5,580,755; the disclosure of each of which is incorporated herein by reference in its entirety.

This disclosure encompasses the use of native, naturally occurring, and recombinant proteins. The disclosure further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated finals). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with the compound of Formula I provided herein include monoclonal and polyclonal antibodies. Examples of antibodies include, but are not limited to, trastuzumab (HERCEPTIN®), rituximab (RITUXAN®), bevacizumab (AVASTIN™), pertuzumab (OMNITARG™), tositumomab (BEXXAR®), edrecolomab (PANOREX®), panitumumab and G250. The compound of Formula I provided herein can also be combined with or used in combination with anti-TNF-α antibodies.

Large molecule active agents may be administered in the form of anti-cancer vaccines. For example, vaccines that secrete, or cause the secretion of, cytokines such as IL-2, SCF, CXC14 (platelet factor 4), G-CSF, and GM-CSF can be used in the methods, pharmaceutical compositions, and kits of the disclosure. See, e.g., Emens, L. A., et al., *Curr. Opinion Mol. Ther.* 3(1):77-84 (2001).

Second active agents that are small molecules can also be used to alleviate adverse effects associated with the administration of the compound of Formula I provided herein. However, like some large molecules, many are believed to be capable of providing a synergistic effect when administered with (e.g., before, after or simultaneously) the compound of Formula I. Examples of small molecule second active agents include, but are not limited to, anti-cancer agents, antibiotics, immunosuppressive agents, and steroids.

Examples of anti-cancer agents include, but are not limited to: abraxane; ace-11; acivicin; aclarubicin; acodazole hydrochloride; acronine; adozelesin; aldesleukin; altretamine; ambomycin; ametantrone acetate; amrubicin; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; herceptin; hydroxyurea; idarubicin hydrochloride; ifosfamide; ilmofosine; iproplatin; irinotecan; irinotecan hydrochloride; lanreotide acetate; lapatinib; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; romidepsin; safingol; safingol hydrochloride; semustine; simtrazene; sparfosate sodium; sparsomycin; spirogermanium hydrochloride; spiromustine; spiroplatin; stem cell treatments such as PDA-001; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinzolidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; amsacrine; atamestane; atrimustine; axinastatin 1; axinastatin 2; axinastatin 3; azasetron; azatoxin; azatyrosine; baccatin III derivatives; balani; batimastat; BCR/ABL antagonists; benzochlorins; benzoylstaurosporine; beta lactam derivatives; beta-alethine; betaclamycin B; betulinic acid; b-FGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., GLEEVEC®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (GENASENSE®); O$^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine;

thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, oblimersen (GENASENSE®), remicade, docetaxel, celecoxib, melphalan, dexamethasone (DECADRON®), steroids, gemcitabine, cisplatinum, temozolomide, etoposide, cyclophosphamide, temodar, carboplatin, procarbazine, gliadel, tamoxifen, topotecan, methotrexate, ARISA®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (DOXIL®), paclitaxel, ganciclovir, adriamycin, estramustine sodium phosphate (EMCYT®), sulindac, and etoposide.

5.4 Methods of Treatment and Prevention

In one embodiment, provided herein is a method of treating and preventing cancer, which comprises administering to a patient a compound provided herein, or an enantiomer or a mixture of enantiomers thereof, or a pharmaceutically acceptable salt, solvate, hydrate, co-crystal, clathrate, or polymorph thereof.

In another embodiment, provided herein is method of managing cancer, which comprises administering to a patient a compound provided herein, or an enantiomer or a mixture of enantiomers thereof, or a pharmaceutically acceptable salt, solvate, hydrate, co-crystal, clathrate, or polymorph thereof.

Also provided herein are methods of treating patients who have been previously treated for cancer but are non-responsive to standard therapies, as well as those who have not previously been treated. The invention also encompasses methods of treating patients regardless of patient's age, although some diseases or disorders are more common in certain age groups. The invention further encompasses methods of treating patients who have undergone surgery in an attempt to treat the disease or condition at issue, as well as those who have not. Because patients with cancer have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

In yet another embodiment, provided herein is a method of treating, managing, or preventing diseases and disorders other than cancer that are associated with or characterized by undesired angiogenesis, which comprises administering to a patient a compound provided herein, or an enantiomer or a mixture of enantiomers thereof, or a pharmaceutically acceptable salt, solvate, hydrate, co-crystal, clathrate, or polymorph thereof.

As used herein, the term "cancer" includes, but is not limited to, solid tumors and blood born tumors. The term "cancer" refers to disease of skin tissues, organs, blood, and vessels, including, but not limited to, cancers of the bladder, bone, blood, brain, breast, cervix, chest, colon, endrometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant giolma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma In certain embodiments, the cancer is a blood borne tumor. In certain embodiments, the blood borne tumor is metastatic. In certain embodiments, the blood borne tumor is drug resistant. In certain embodiments, the cancer is myeloma or lymphoma.

In certain embodiments, the cancer is a solid tumor. In certain embodiments, the solid tumor is metastatic. In certain embodiments, the solid tumor is drug-resistant. In certain embodiments, the solid tumor is hepatocellular carcinoma, prostate cancer, ovarian cancer, or glioblastoma.

As used herein to refer to diseases and conditions other than cancer, the terms "diseases or disorders associated with or characterized by undesired angiogenesis," "diseases or disorders associated with undesired angiogenesis," and "diseases or disorders characterized by undesired angiogenesis" refer to diseases, disorders, and conditions that are caused, mediated, or attended by undesired, unwanted, or uncontrolled angiogenesis, including, but not limited to, inflammatory diseases, autoimmune diseases, genetic diseases, allergic diseases, bacterial diseases, ocular neovascular diseases, choroidal neovascular diseases, and retina neovascular diseases.

Examples of such diseases or disorders associated with undesired angiogenesis include, but are not limited to, diabetic retinopathy, retinopathy of prematurity, corneal graft rejection, neovascular glaucoma, retrolental fibroplasia, proliferative vitreoretinopathy, trachoma, myopia, optic pits, epidermic keratoconjunctivitis, atopic keratitis, superior limbic keratitis, pterygium keratitis sicca, sjogrens, acne rosacea, phylectenulosis, syphilis, lipid degeneration, bacterial ulcer, fungal ulcer, Herpes simplex infection, Herpes zoster infection, protozoan infection, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, sickle cell anemia, sarcoid, pseudoxanthoma elasticum, Pagets disease, vein occlusion, artery occlusion, carotid obstructive disease, chronic uveitis, chronic vitritis, Lyme's disease, Eales disease, Behcet's disease, retinitis, choroiditis, presumed ocular histoplasmosis, Bests disease, Stargarts disease, pars planitis, chronic retinal detachment, hyperviscosity syndromes, toxoplasmosis, rubeosis, sarcodisis, sclerosis, soriatis, psoriasis, primary sclerosing cholangitis, proctitis, primary biliary srosis, idiopathic pulmonary fibrosis, and alcoholic hepatitis.

In certain embodiments, a therapeutically or prophylactically effective amount of the compound is from about 0.005 to about 1,000 mg per day, from about 0.01 to about 500 mg per day, from about 0.01 to about 250 mg per day, from about 0.01 to about 100 mg per day, from about 0.1 to about 100 mg per day, from about 0.5 to about 100 mg per day, from about 1 to about 100 mg per day, from about 0.01 to about 50 mg per day, from about 0.1 to about 50 mg per day, from about 0.5 to about 50 mg per day, from about 1 to about 50 mg per day, from about 0.02 to about 25 mg per day, or from about 0.05 to about 10 mg per day.

In certain embodiments, the therapeutically or prophylactically effective amount is about 1, about 2, about 5, about 10, about 15, about 20, about 25, about 30, about 40, about 45, about 50, about 60, about 70, about 80, about 90, about 100, or about 150 mg per day.

In one embodiment, the recommended daily dose range of the compound for the conditions described herein lie within the range of from about 0.5 mg to about 50 mg per day, preferably given as a single once-a-day dose, or in divided doses throughout a day. In some embodiments, the dosage ranges from about 1 mg to about 50 mg per day. In other embodiments, the dosage ranges from about 0.5 to about 5 mg per day. Specific doses per day include 0.5, 1, 1.5, 2, 2.5, 3, 3.5, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day. In other embodiments, specific doses per day include 0.5, 1, 1.5, 2, 2.5, 3, 3.5 or 4 mg per day. In a specific embodiment, the recommended starting dosage may be 0.5, 1, 1.5, 2, 2.5, 3, 3.5, 4, 5, 10, 15, 20, 25 or 50 mg per day. In another embodiment, the recommended starting dosage may be 0.5, 1, 1.5, 2, 2.5, 3, 3.5 or 4 mg per day. The dose may be escalated to 15, 20, 25, 30, 35, 40, 45 and 50 mg/day. In a specific embodiment, the compound can be administered in an amount of about 25 mg/day to patients with cancer. In a particular embodiment, the compound can be administered in an amount of about 10 mg/day to patients with cancer.

In certain embodiments, the therapeutically or prophylactically effective amount is from about 0.001 to about 100 mg/kg/day, from about 0.01 to about 50 mg/kg/day, from about 0.01 to about 25 mg/kg/day, from about 0.01 to about 10 mg/kg/day, from about 0.01 to about 9 mg/kg/day, 0.01 to about 8 mg/kg/day, from about 0.01 to about 7 mg/kg/day, from about 0.01 to about 6 mg/kg/day, from about 0.01 to about 5 mg/kg/day, from about 0.01 to about 4 mg/kg/day, from about 0.01 to about 3 mg/kg/day, from about 0.01 to about 2 mg/kg/day, or from about 0.01 to about 1 mg/kg/day.

The administered dose can also be expressed in units other than mg/kg/day. For example, doses for parenteral administration can be expressed as $mg/m^2/day$. One of ordinary skill in the art would readily know how to convert doses from mg/kg/day to $mg/m^2/day$ to given either the height or weight of a subject or both (see, www.fda.gov/cder/cancer/animalframe.htm). For example, a dose of 1 mg/kg/day for a 65 kg human is approximately equal to 38 $mg/m^2/day$.

In certain embodiments, the amount of the compound administered is sufficient to provide a plasma concentration of the compound at steady state, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In other embodiments, the amount of the compound administered is sufficient to provide a plasma concentration of the compound at steady state, ranging from about 5 to about 100 nM, about 5 to about 50 nM, about 10 to about 100 nM, about 10 to about 50 nM or from about 50 to about 100 nM.

As used herein, the term "plasma concentration at steady state" is the concentration reached after a period of administration of a compound provided herein, e.g., the compound of Formula I, or an enantiomer or a mixture of enantiomers thereof, or a pharmaceutically acceptable salt, solvate, hydrate, co-crystal, clathrate, or polymorph thereof. Once steady state is reached, there are minor peaks and troughs on the time dependent curve of the plasma concentration of the compound.

In certain embodiments, the amount of the compound administered is sufficient to provide a maximum plasma concentration (peak concentration) of the compound, ranging from about 0.001 to about 500 μM, about 0.002 to about 200 μM, about 0.005 to about 100 μM, about 0.01 to about 50 μM, from about 1 to about 50 μM, about 0.02 to about 25 μM, from about 0.05 to about 20 μM, from about 0.1 to about 20 μM, from about 0.5 to about 20 μM, or from about 1 to about 20 μM.

In certain embodiments, the amount of the compound administered is sufficient to provide a minimum plasma concentration (trough concentration) of the compound, ranging from about 0.001 to about 500 μM, about 0.002 to about 200 μM, about 0.005 to about 100 μM, about 0.01 to about 50 μM, from about 1 to about 50 μM, about 0.01 to about 25 μM, from about 0.01 to about 20 μM, from about 0.02 to about 20 μM, from about 0.02 to about 20 μM, or from about 0.01 to about 20 μM.

In certain embodiments, the amount of the compound administered is sufficient to provide an area under the curve (AUC) of the compound, ranging from about 100 to about 100,000 ng*hr/mL, from about 1,000 to about 50,000 ng*hr/mL, from about 5,000 to about 25,000 ng*hr/mL, or from about 5,000 to about 10,000 ng*hr/mL.

In certain embodiments, the patient to be treated with one of the methods provided herein has not been treated with anticancer therapy prior to the administration of the drug. In certain embodiments, the patient to be treated with one of the methods provided herein has been treated with anticancer therapy prior to the administration of the drug. In certain embodiments, the patient to be treated with one of the methods provided herein has developed drug resistance to the anticancer therapy.

The methods provided herein encompass treating a patient regardless of patient's age, although some diseases or disorders are more common in certain age groups. Further provided herein is a method for treating a patient who has undergone surgery in an attempt to treat the disease or condition at issue, as well in one who has not. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

Depending on the disease to be treated and the subject's condition, the compound provided herein, or an enantiomer or a mixture of enantiomers thereof; or a pharmaceutically acceptable salt, solvate, hydrate, co-crystal, clathrate, or polymorph thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The compound, or an enantiomer or a mixture of enantiomers thereof; or a pharmaceutically acceptable salt, solvate, hydrate, co-crystal, clathrate, or polymorph thereof, may be formulated, alone or together, in suitable dosage unit with pharmaceutically acceptable excipients, carriers, adjuvants and vehicles, appropriate for each route of administration.

In one embodiment, the compound provided herein, or an enantiomer or a mixture of enantiomers thereof; or a pharmaceutically acceptable salt, solvate, hydrate, co-crystal, clathrate, or polymorph thereof, is administered orally. In another embodiment, the compound, or an enantiomer or a mixture of enantiomers thereof; or a pharmaceutically acceptable salt, solvate, hydrate, co-crystal, clathrate, or polymorph thereof, is administered parenterally. In yet another embodiment, the compound, or an enantiomer or a mixture of enantiomers thereof; or a pharmaceutically acceptable salt, solvate, hydrate, co-crystal, clathrate, or polymorph thereof, is administered intravenously.

The compound, or an enantiomer or a mixture of enantiomers thereof; or a pharmaceutically acceptable salt, solvate, hydrate, co-crystal, clathrate, or polymorph thereof, can be delivered as a single dose such as, e.g., a single bolus injection, or oral tablets or pills; or over time, such as, e.g., continuous infusion over time or divided bolus doses over time. The compound can be administered repeatedly if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The compound, or an enantiomer or a mixture of enantiomers thereof; or a pharmaceutically acceptable salt, solvate, hydrate, co-crystal, clathrate, or polymorph thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound is administered once or more than once each day, for example, for a period of time. The term "continuous" is intended to mean that a therapeutic compound is administered daily for an uninterrupted period of at least 10 days to 52 weeks. The term "intermittent" or "intermittently" as used herein is intended to mean stopping and starting at either regular or irregular intervals. For example, intermittent administration of a compound is administration for one to six days per week, administration in cycles (e.g., daily administration for two to eight consecutive weeks, then a rest period with no administration for up to one week), or administration on alternate days. The term "cycling" as used herein is intended to mean that a therapeutic compound is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound, or an enantiomer or a mixture of enantiomers thereof; or a pharmaceutically acceptable salt, solvate, hydrate, co-crystal, clathrate, or polymorph thereof, is administered once a day. In another embodiment, the compound, or an enantiomer or a mixture of enantiomers thereof; or a pharmaceutically acceptable salt, solvate, hydrate, co-crystal, clathrate, or polymorph thereof, is administered twice a day. In yet another embodiment, the compound, or an enantiomer or a mixture of enantiomers thereof; or a pharmaceutically acceptable salt, solvate, hydrate, co-crystal, clathrate, or polymorph thereof, is administered three times a day. In still another embodiment, the compound, or an enantiomer or a mixture of enantiomers thereof; or a pharmaceutically acceptable salt, solvate, hydrate, co-crystal, clathrate, or polymorph thereof, is administered four times a day.

In certain embodiments, the compound, or an enantiomer or a mixture of enantiomers thereof; or a pharmaceutically acceptable salt, solvate, hydrate, co-crystal, clathrate, or polymorph thereof, is administered once per day from one day to six months, from one week to three months, from one week to four weeks, from one week to three weeks, or from one week to two weeks. In certain embodiments, the compound, or a pharmaceutically acceptable salt or solvate thereof, is administered once per day for one week, two weeks, three weeks, or four weeks. In one embodiment, the compound, or an enantiomer or a mixture of enantiomers thereof; or a pharmaceutically acceptable salt, solvate, hydrate, co-crystal, clathrate, or polymorph thereof, is administered once per day for one week. In another embodiment, the compound, or an enantiomer or a mixture of enantiomers thereof; or a pharmaceutically acceptable salt, solvate, hydrate, co-crystal, clathrate, or polymorph thereof, is administered once per day for two weeks. In yet another embodiment, the compound, or an enantiomer or a mixture of enantiomers thereof; or a pharmaceutically acceptable salt, solvate, hydrate, co-crystal, clathrate, or polymorph thereof, is administered once per day for three weeks. In still another embodiment, the compound, or an enantiomer or a mixture of enantiomers thereof; or a pharmaceutically acceptable salt, solvate, hydrate, co-crystal, clathrate, or polymorph thereof, is administered once per day for four weeks.

5.5 Combination Therapy with a Second Active Agent

A compound provided herein, or an enantiomer or a mixture of enantiomers thereof; or a pharmaceutically acceptable salt, solvate, hydrate, co-crystal, clathrate, or polymorph thereof, can also be combined or used in combination with other therapeutic agents useful in the treatment and/or prevention of a disease described herein.

In one embodiment, provided herein is a method of treating, preventing, or managing cancer, comprising administering to a patient compound provided herein, or an enantiomer or a mixture of enantiomers thereof; or a pharmaceutically acceptable salt, solvate, hydrate, co-crystal, clathrate, or polymorph thereof; in combination with one or more second active agents, and optionally in combination with radiation therapy, blood transfusions, or surgery. Examples of second active agents are disclosed herein (see, e.g., section 5.3).

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a patient with a disease or disorder. A first therapy (e.g., a prophylactic or therapeutic agent such as a compound provided herein, a compound provided herein, or an enantiomer or a mixture of enantiomers thereof, or a pharmaceutically acceptable salt, solvate, hydrate, co-crystal, clathrate, or polymorph thereof) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

Administration of the compound and one or more second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the cancer being treated.

The route of administration of the compound is independent of the route of administration of a second therapy. In one embodiment, the compound is administered orally. In another embodiment, the compound is administered intravenously. Thus, in accordance with these embodiments, the compound is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, the compound and a second therapy are administered by the same mode of administration, orally or by IV. In another embodiment, the compound is administered by one mode of administration, e.g., by IV, whereas the second agent (an anticancer agent) is administered by another mode of administration, e.g., orally.

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount of the drug provided herein and any optional additional active agents concurrently administered to the patient. In certain embodiments, the second active agent is oblimersen (GENASENSE®), GM-CSF, G-CSF, SCF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine, or a combination thereof.

In certain embodiments, GM-CSF, G-CSF, SCF or EPO is administered subcutaneously during about five days in a four or six week cycle in an amount ranging from about 1 to about 750 mg/m$^2$/day, from about 25 to about 500 mg/m$^2$/day, from about 50 to about 250 mg/m$^2$/day, or from about 50 to about 200 mg/m$^2$/day. In certain embodiments, GM-CSF may be administered in an amount of from about 60 to about 500 mcg/m$^2$ intravenously over 2 hours or from about 5 to about 12 mcg/m$^2$/day subcutaneously. In certain embodiments, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In certain embodiments, EPO may be administered subcutaneously in an amount of 10,000 Unit 3 times per week.

In certain embodiments, a compound provided herein, or an enantiomer or a mixture of enantiomers thereof, or a pharmaceutically acceptable salt, solvate, hydrate, co-crystal, clathrate, or polymorph thereof, is administered with melphalan and dexamethasone to patients with amyloidosis. In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, and steroids can be administered to patients with amyloidosis.

In certain embodiments, a compound provided herein, or an enantiomer or a mixture of enantiomers thereof, or a pharmaceutically acceptable salt, solvate, hydrate, co-crystal, clathrate, or polymorph thereof, is administered with gemcitabine and cisplatinum to patients with locally advanced or metastatic transitional cell bladder cancer.

In certain embodiments, a compound provided herein, or an enantiomer or a mixture of enantiomers thereof, or a pharmaceutically acceptable salt, solvate, hydrate, co-crystal, clathrate, or polymorph thereof, is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapsed brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In certain embodiments, a compound provided herein, or an enantiomer or a mixture of enantiomers thereof, or a pharmaceutically acceptable salt, solvate, hydrate, co-crystal, clathrate, or polymorph thereof, is administered with methotrexate, cyclophosphamide, taxane, abraxane, lapatinib, herceptin, aromatase inhibitors, selective estrogen modulators, estrogen receptor antagonists, and/or PLX3397 (Plexxikon) to patients with metastatic breast cancer.

In certain embodiments, a compound provided herein, or an enantiomer or a mixture of enantiomers thereof, or a pharmaceutically acceptable salt, solvate, hydrate, co-crystal, clathrate, or polymorph thereof, is administered with temozolomide to patients with neuroendocrine tumors.

In certain embodiments, a compound provided herein, or an enantiomer or a mixture of enantiomers thereof, or a pharmaceutically acceptable salt, solvate, hydrate, co-crystal, clathrate, or polymorph thereof, is administered with gemcitabine to patients with recurrent or metastatic head or neck cancer.

In certain embodiments, a compound provided herein, or an enantiomer or a mixture of enantiomers thereof, or a pharmaceutically acceptable salt, solvate, hydrate, co-crystal, clathrate, or polymorph thereof, is administered with gemcitabine to patients with pancreatic cancer.

In certain embodiments, a compound provided herein, or an enantiomer or a mixture of enantiomers thereof, or a pharmaceutically acceptable salt, solvate, hydrate, co-crystal, clathrate, or polymorph thereof, is administered to patients with colon cancer in combination with ARISA®, avastatin, taxol, and/or taxotere.

In certain embodiments, a compound provided herein, or an enantiomer or a mixture of enantiomers thereof, or a pharmaceutically acceptable salt, solvate, hydrate, co-crystal, clathrate, or polymorph thereof, is administered with capecitabine and/or PLX4032 (Plexxikon) to patients with refractory colorectal cancer or patients who fail first line therapy or have poor performance in colon or rectal adenocarcinoma.

In certain embodiments, a compound provided herein, or an enantiomer or a mixture of enantiomers thereof, or a pharmaceutically acceptable salt, solvate, hydrate, co-crystal, clathrate, or polymorph thereof, is administered in combination with fluorouracil, leucovorin, and irinotecan to patients with Dukes C & D colorectal cancer or to patients who have been previously treated for metastatic colorectal cancer.

In certain embodiments, a compound provided herein, or an enantiomer or a mixture of enantiomers thereof, or a pharmaceutically acceptable salt, solvate, hydrate, co-crystal, clathrate, or polymorph thereof, is administered to patients with refractory colorectal cancer in combination with capecitabine, xeloda, and/or CPT-11.

In certain embodiments, a compound provided herein, or an enantiomer or a mixture of enantiomers thereof, or a pharmaceutically acceptable salt, solvate, hydrate, co-crystal, clathrate, or polymorph thereof, is administered with capecitabine and irinotecan to patients with refractory colorectal cancer or to patients with unresectable or metastatic colorectal carcinoma.

In certain embodiments, a compound provided herein, or an enantiomer or a mixture of enantiomers thereof, or a pharmaceutically acceptable salt, solvate, hydrate, co-crystal, clathrate, or polymorph thereof, is administered alone or in combination with interferon alpha or capecitabine to patients with unresectable or metastatic hepatocellular carcinoma; or with cisplatin and thiotepa to patients with primary or metastatic liver cancer.

In certain embodiments, a compound provided herein, or an enantiomer or a mixture of enantiomers thereof, or a pharmaceutically acceptable salt, solvate, hydrate, co-crystal, clathrate, or polymorph thereof, is administered in combination with pegylated interferon alpha to patients with Kaposi's sarcoma.

In certain embodiments, a compound provided herein, or an enantiomer or a mixture of enantiomers thereof, or a pharmaceutically acceptable salt, solvate, hydrate, co-crystal, clathrate, or polymorph thereof, is administered in combination with fludarabine, carboplatin, and/or topotecan to patients with refractory or relapsed or high-risk acuted myelogenous leukemia.

In certain embodiments, a compound provided herein, or an enantiomer or a mixture of enantiomers thereof, or a pharmaceutically acceptable salt, solvate, hydrate, co-crystal, clathrate, or polymorph thereof, is administered in combination with liposomal daunorubicin, topotecan and/or cytarabine to patients with unfavorable karotype acute myeloblastic leukemia.

In certain embodiments, a compound provided herein, or an enantiomer or a mixture of enantiomers thereof, or a pharmaceutically acceptable salt, solvate, hydrate, co-crystal, clathrate, or polymorph thereof, is administered in combination with gemcitabine, abraxane, erlotinib, geftinib, and/or irinotecan to patients with non-small cell lung cancer.

In certain embodiments, a compound provided herein, or an enantiomer or a mixture of enantiomers thereof, or a pharmaceutically acceptable salt, solvate, hydrate, co-crystal, clathrate, or polymorph thereof, is administered in combination with carboplatin and irinotecan to patients with non-small cell lung cancer.

In certain embodiments, a compound provided herein, or an enantiomer or a mixture of enantiomers thereof, or a pharmaceutically acceptable salt, solvate, hydrate, co-crystal, clathrate, or polymorph thereof, is administered with doxetaxol to patients with non-small cell lung cancer who have been previously treated with carbo/VP 16 and radiotherapy.

In certain embodiments, a compound provided herein, or an enantiomer or a mixture of enantiomers thereof, or a pharmaceutically acceptable salt, solvate, hydrate, co-crystal, clathrate, or polymorph thereof, is administered in combination with carboplatin and/or taxotere, or in combination with carboplatin, paclitaxel and/or thoracic radiotherapy to patients with non-small cell lung cancer.

In certain embodiments, a compound provided herein, or an enantiomer or a mixture of enantiomers thereof, or a pharmaceutically acceptable salt, solvate, hydrate, co-crystal, clathrate, or polymorph thereof, is administered in combination with taxotere to patients with stage IIIB or IV non-small cell lung cancer.

In certain embodiments, a compound provided herein, or an enantiomer or a mixture of enantiomers thereof, or a pharmaceutically acceptable salt, solvate, hydrate, co-crystal, clathrate, or polymorph thereof, is administered in combination with oblimersen (Genasense®) to patients with small cell lung cancer.

In certain embodiments, a compound provided herein, e.g., the compound of Formula I, or an enantiomer or a mixture of enantiomers thereof, or a pharmaceutically acceptable salt, solvate, hydrate, co-crystal, clathrate, or polymorph thereof, is administered in combination with ABT-737 (Abbott Laboratories) and/or obatoclax (GX15-070) to patients with lymphoma and other blood cancers.

In certain embodiments, a compound provided herein, or an enantiomer or a mixture of enantiomers thereof, or a pharmaceutically acceptable salt, solvate, hydrate, co-crystal, clathrate, or polymorph thereof, is administered alone or in combination with a second active ingredient such as vinblastine or fludarabine to patients with various types of lymphoma, including, but not limited to, Hodgkin's lymphoma, non-Hodgkin's lymphoma, cutaneous T-Cell lymphoma, cutaneous B-Cell lymphoma, diffuse large B-Cell lymphoma or relapsed or refractory low grade follicular lymphoma.

In certain embodiments, a compound provided herein, or an enantiomer or a mixture of enantiomers thereof, or a pharmaceutically acceptable salt, solvate, hydrate, co-crystal, clathrate, or polymorph thereof, is administered in combination with taxotere, IL-2, IFN, GM-CSF, PLX4032 (Plexxikon) and/or dacarbazine to patients with various types or stages of melanoma.

In certain embodiments, a compound provided herein, or an enantiomer or a mixture of enantiomers thereof, or a pharmaceutically acceptable salt, solvate, hydrate, co-crystal, clathrate, or polymorph thereof, is administered alone or in combination with vinorelbine to patients with malignant mesothelioma, or stage IIIB non-small cell lung cancer with pleural implants or malignant pleural effusion mesothelioma syndrome.

In certain embodiments, a compound provided herein, or an enantiomer or a mixture of enantiomers thereof, or a pharmaceutically acceptable salt, solvate, hydrate, co-crystal, clathrate, or polymorph thereof, is administered to patients with various types or stages of multiple myeloma in combination with dexamethasone, zoledronic acid, palmitronate, GM-CSF, biaxin, vinblastine, melphalan, busulphan, cyclophosphamide, IFN, palmidronate, prednisone, bisphosphonate, celecoxib, arsenic trioxide, PEG INTRON-A, vincristine, or a combination thereof.

In certain embodiments, a compound provided herein, or an enantiomer or a mixture of enantiomers thereof, or a pharmaceutically acceptable salt, solvate, hydrate, co-crystal, clathrate, or polymorph thereof, is administered to patients with relapsed or refractory multiple myeloma in combination with doxorubicin (Doxil®), vincristine and/or dexamethasone (Decadron®).

In certain embodiments, a compound provided herein, or an enantiomer or a mixture of enantiomers thereof, or a pharmaceutically acceptable salt, solvate, hydrate, co-crystal, clathrate, or polymorph thereof, is administered to patients with various types or stages of ovarian cancer such as peritoneal carcinoma, papillary serous carcinoma, refractory ovarian cancer or recurrent ovarian cancer, in combination with taxol, carboplatin, doxorubicin, gemcitabine, cisplatin, xeloda, paclitaxel, dexamethasone, or a combination thereof.

In certain embodiments, a compound provided herein, or an enantiomer or a mixture of enantiomers thereof, or a pharmaceutically acceptable salt, solvate, hydrate, co-crystal, clathrate, or polymorph thereof, is administered to patients with various types or stages of prostate cancer, in combination with xeloda, 5 FU/LV, gemcitabine, irinotecan plus gemcitabine, cyclophosphamide, vincristine, dexamethasone, GM-CSF, celecoxib, taxotere, ganciclovir, paclitaxel, adriamycin, docetaxel, estramustine, Emcyt, denderon or a combination thereof.

In certain embodiments, a compound provided herein, or an enantiomer or a mixture of enantiomers thereof, or a pharmaceutically acceptable salt, solvate, hydrate, co-crystal, clathrate, or polymorph thereof, is administered to patients with various types or stages of renal cell cancer, in combination with capecitabine, IFN, tamoxifen, IL-2, GM-CSF, Celebrex®, or a combination thereof.

In certain embodiments, a compound provided herein, or an enantiomer or a mixture of enantiomers thereof, or a pharmaceutically acceptable salt, solvate, hydrate, co-crystal, clathrate, or polymorph thereof, is administered to patients with various types or stages of gynecologic, uterus or soft tissue sarcoma cancer in combination with IFN, a COX-2 inhibitor such as Celebrex®, and/or sulindac.

In certain embodiments, a compound provided herein, or an enantiomer or a mixture of enantiomers thereof, or a pharmaceutically acceptable salt, solvate, hydrate, co-crystal, clathrate, or polymorph thereof, is administered to patients with various types or stages of solid tumors in combination with celebrex, etoposide, cyclophosphamide, docetaxel, apecitabine, IFN, tamoxifen, IL-2, GM-CSF, or a combination thereof.

In certain embodiments, a compound provided herein, or an enantiomer or a mixture of enantiomers thereof, or a pharmaceutically acceptable salt, solvate, hydrate, co-crystal, clathrate, or polymorph thereof, is administered to patients with scleroderma or cutaneous vasculitis in combination with celebrex, etoposide, cyclophosphamide, docetaxel, apecitabine, IFN, tamoxifen, IL-2, GM-CSF, or a combination thereof.

Also encompassed herein is a method of increasing the dosage of an anti-cancer drug or agent that can be safely and effectively administered to a patient, which comprises administering to the patient (e.g., a human) or an enantiomer or a mixture of enantiomers thereof, or a pharmaceutically acceptable salt, solvate, hydrate, co-crystal, clathrate, or polymorph thereof. Patients that can benefit by this method are those likely to suffer from an adverse effect associated with anti-cancer drugs for treating a specific cancer of the skin, subcutaneous tissue, lymph nodes, brain, lung, liver, bone, intestine, colon, heart, pancreas, adrenal, kidney, prostate, breast, colorectal, or combinations thereof. The administration of a compound provided herein, or an enantiomer or a mixture of enantiomers thereof, or a pharmaceutically acceptable salt, solvate, hydrate, co-crystal, clathrate, or polymorph thereof, alleviates or reduces adverse effects which are of such severity that it would otherwise limit the amount of anti-cancer drug.

In one embodiment, a compound provided herein, or an enantiomer or a mixture of enantiomers thereof, or a pharmaceutically acceptable salt, solvate, hydrate, co-crystal, clathrate, or polymorph thereof, is administered orally and daily in an amount ranging from about 0.1 to about 150 mg, from about 1 to about 50 mg, or from about 2 to about 25 mg, prior to, during, or after the occurrence of the adverse effect associated with the administration of an anti-cancer drug to a patient. In certain embodiments, a compound provided herein, or an enantiomer or a mixture of enantiomers thereof, or a pharmaceutically acceptable salt, solvate, hydrate, co-crystal, clathrate, or polymorph thereof, is administered in combination with specific agents such as heparin, aspirin, coumadin, or G-CSF to avoid adverse effects that are associated with anti-cancer drugs such as but not limited to neutropenia or thrombocytopenia.

In one embodiment, a compound provided herein, or an enantiomer or a mixture of enantiomers thereof, or a pharmaceutically acceptable salt, solvate, hydrate, co-crystal, clathrate, or polymorph thereof, is administered to patients with diseases and disorders associated with or characterized by, undesired angiogenesis in combination with additional active ingredients, including, but not limited to, anti-cancer drugs, anti-inflammatories, antihistamines, antibiotics, and steroids.

In another embodiment, encompassed herein is a method of treating, preventing and/or managing cancer, which comprises administering the compound, or an enantiomer or a mixture of enantiomers thereof, or a pharmaceutically acceptable salt, solvate, hydrate, co-crystal, clathrate, or polymorph thereof, in conjunction with (e.g. before, during, or after) conventional therapy including, but not limited to, surgery, immunotherapy, biological therapy, radiation therapy, or other non-drug based therapy presently used to treat, prevent or manage cancer. The combined use of the compound provided herein and conventional therapy may provide a unique treatment regimen that is unexpectedly effective in certain patients. Without being limited by theory, it is believed that the compound of Formula I may provide additive or synergistic effects when given concurrently with conventional therapy.

As discussed elsewhere herein, encompassed herein is a method of reducing, treating and/or preventing adverse or undesired effects associated with conventional therapy including, but not limited to, surgery, chemotherapy, radiation therapy, hormonal therapy, biological therapy and immunotherapy. A compound provided herein, or an enantiomer or a mixture of enantiomers thereof, or a pharmaceutically acceptable salt, solvate, hydrate, co-crystal, clathrate, or polymorph thereof, and other active ingredient can be administered to a patient prior to, during, or after the occurrence of the adverse effect associated with conventional therapy.

In one embodiment, the compound can be administered in an amount ranging from about 0.1 to about 150 mg, from about 1 to about 25 mg, from about 2 to about 10 mg, or about 0.5 to about 4 mg orally and daily alone, or in combination with a second active agent disclosed herein (see, e.g., section 4.3), prior to, during, or after the use of conventional therapy.

In certain embodiments, a compound provided herein, or an enantiomer or a mixture of enantiomers thereof, or a pharmaceutically acceptable salt, solvate, hydrate, co-crystal, clathrate, or polymorph thereof, and doxetaxol are administered to patients with non-small cell lung cancer who were previously treated with carbo/VP 16 and radiotherapy.

5.6 Pharmaceutical Compositions

Pharmaceutical compositions can be used in the preparation of individual, single unit dosage forms. Pharmaceutical compositions and dosage forms provided herein comprise a compound, or a pharmaceutically acceptable salt, solvate, hydrate, stereoisomer, clathrate, or prodrug thereof. Pharmaceutical compositions and dosage forms provided herein may further comprise one or more excipients.

Pharmaceutical compositions and dosage forms provided herein may also comprise one or more additional active ingredients. Examples of optional second, or additional, active ingredients are disclosed herein.

Single unit dosage forms are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms provided herein will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms provided herein will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided herein are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions provided herein can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms may be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

5.7 Oral Dosage Forms

Pharmaceutical compositions that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

In one embodiment, a solid oral dosage form of the invention comprises a compound provided herein, anhydrous lactose, microcrystalline cellulose, polyvinylpyrrolidone, stearic acid, colloidal anhydrous silica, and gelatin.

5.8 Delayed Release Dosage Forms

Active ingredients may be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein. Thus, provided herein are single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.9 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms provided herein. For example, cyclodextrin and its derivatives can be used to increase the solubility of a compound and its derivatives. See, e.g., U.S. Pat. No. 5,134,127, which is incorporated herein by reference.

5.10 Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., *Remington's Pharmaceutical Sciences*, $16^{th}$ and $18^{th}$ eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, $16^{th}$ and $18^{th}$ eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

5.11 Kits

In some embodiments provided herein, active ingredients are preferably not administered to a patient at the same time or by the same route of administration. Thus, provided herein are kits which, when used by the medical practitioner, can simplify the administration of appropriate amounts of active ingredients to a patient.

In one embodiment a kit provided herein comprises a compound provided herein, or a pharmaceutically acceptable salt, solvate or hydrate thereof. Kits may further comprise additional active agents, including but not limited to those disclosed herein.

Kits provided herein may further comprise devices that are used to administer the active ingredients. Examples of such devices include, but are not limited to, syringes, drip bags, patches, and inhalers.

Kits may further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5.12 Antibodies

Antibodies that immunospecifically bind to CRBN (anti-CRBN antibodies) provided herein include, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and antigen- or epitope-binding fragments of any of the above.

In particular, antibodies provided herein include immunoglobulin molecules and immunologically active portions of immunoglobulin molecules, i.e., molecules that contain an antigen binding site that immunospecifically binds to a CRBN antigen. The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule. In a specific embodiment, an antibody provided herein is an IgG antibody, and, in certain embodiments, an IgG1 or IgG4.

Also provided herein is an isolated CRBN antibody, for example, "CRBN70," as prepared according to Example 6.20 or 6.21 below. In one embodiment, the antibody is a polyclonal antibody. In another embodiment, the antibody is a monoclonal antibody. In some embodiments, the antibody is a rabbit polyclonal antibody. In other embodiments, the antibody is a rabbit monoclonal antibody.

In another embodiment, provided herein is an isolated antibody which immunospecifically binds to the epitope having an amino acid sequence EEFHGRTLHDDDC (SEQ ID:1). In another embodiment, the antibody immunospecifically binds to the epitope having an amino acid sequence EEFHGRTLHDDDC (SEQ ID:1), wherein the peptide is coupled to Keyhole Limpet Hemocyanin (KLH). In one embodiment, the antibody is a polyclonal antibody. In another embodiment, the antibody is a monoclonal antibody. In some embodiments, the antibody is a rabbit polyclonal antibody. In other embodiments, the antibody is a rabbit monoclonal antibody. In certain embodiments, the antibody immunospecifically binds peptide 65-76 (SEQ ID NO:1) of human CRBN (SEQ ID NO:12).

In certain embodiments, provided herein is an antibody that immunospecifically binds CRBN and comprises a heavy chain having the amino acid sequence depicted in SEQ ID NO:5, or the VH domain, VH CDR1, VH CDR2, and/or VH CDR3 thereof. In other embodiment, the antibody immunospecifically binds CRBN and comprises a light chain having the amino acid sequence depicted in SEQ ID NO:7, or the VL domain, VL CDR1, VL CDR2, and/or VL CDR3 thereof. In some embodiments, the antibody comprises a heavy chain having the amino acid sequence depicted in SEQ ID NO:5, or the VH domain, VH CDR1, VH CDR2, and/or VH CDR3 thereof; and a light chain having the amino acid sequence depicted in SEQ ID NO:7, or the VL domain, VL CDR1, VL CDR2, and/or VL CDR3 thereof. In certain embodiments, the antibody immunospecifically binds CRBN and comprises a heavy chain having the amino acid sequence depicted in SEQ ID NO:9, or the VH domain, VH CDR1, VH CDR2, and/or VH CDR3 thereof. In other embodiment, the antibody immunospecifically binds CRBN and comprises a light chain having the amino acid sequence depicted in SEQ ID NO:11, or the VL domain, VL CDR1, VL CDR2, and/or VL CDR3 thereof. In some embodiments, the antibody comprises a heavy chain having the amino acid sequence depicted in SEQ ID NO:9, or the VH domain, VH CDR1, VH CDR2, and/or VH CDR3 thereof; and a light chain having the amino acid sequence depicted in SEQ ID NO:11, or the VL domain, VL CDR1, VL CDR2, and/or VL CDR3 thereof. In certain embodiments, the antibody immunospecifically binds peptide 65-76 (SEQ ID NO:1) of human CRBN (SEQ ID NO:12).

Any of the CRBN antibodies provided herein can be used in any of the methods provided herein Variants and derivatives of antibodies include antibody fragments that retain the ability to specifically bind to an epitope. Exemplary fragments include Fab fragments (an antibody fragment that contains the antigen-binding domain and comprises a light chain and part of a heavy chain bridged by a disulfide bond); Fab' (an antibody fragment containing a single anti-binding domain comprising an Fab and an additional portion of the heavy chain through the hinge region); F(ab')$_2$ (two Fab' molecules joined by interchain disulfide bonds in the hinge regions of the heavy chains; the Fab' molecules may be directed toward the same or different epitopes); a bispecific Fab (a Fab molecule having two antigen binding domains, each of which may be directed to a different epitope); a single chain Fab chain comprising a variable region, also known as, a sFv (the variable, antigen-binding determinative region of a single light and heavy chain of an antibody linked together by a chain of 10-25 amino acids); a disulfide-linked Fv, or dsFv (the variable, antigen-binding determinative region of a single light and heavy chain of an antibody linked together by a disulfide bond); a camelized VH (the variable, antigen-binding determinative region of a single heavy chain of an antibody in which some amino acids at the VH interface are those found in the heavy chain of naturally occurring camel antibodies); a bispecific sFv (a sFv or a dsFv molecule having two antigen-binding domains, each of which may be directed to a different epitope); a diabody (a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes). Derivatives of antibodies also include one or more CDR sequences of an antibody combining site. The CDR sequences may be linked together on a scaffold when two or more CDR sequences are present. In certain embodiments, the anti-CRBN antibody comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs see Pluckthun in The Pharmacology of Monoclonal Antibodies, vol. 113, Rosenburg and Moore eds. Springer-Verlag, New York, pp. 269-315 (1994).

Provided herein are antibodies that immunospecifically bind to a CRBN epitope, the antibodies comprising derivatives of the VH and VL chains described herein that immunospecifically bind to a CRBN antigen or a CRBN epitope. Standard techniques known to those of skill in the art can be used to introduce mutations in the nucleotide sequence encoding a molecule of the invention, including, for example, site-directed mutagenesis and PCR-mediated mutagenesis which results in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a preferred embodiment, the derivatives have conservative amino acid substitutions are made at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

In another embodiment, an antibody that immunospecifically binds to a CRBN epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of CGN-6-1-110R CGN-6-1-11, or an antigen-binding fragment thereof, such as a VH domain, VL domain, VH chain, or VL chain. In one embodiment, an antibody that immunospecifically binds to a CRBN epitope comprises an amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to an amino acid sequence depicted in SEQ ID NOS:5, 7, 9 or 11.

In a specific embodiment, an antibody that immunospecifically binds a CRBN antigen comprises an amino acid sequence of a VH chain and/or an amino acid sequence a VL chain encoded by a nucleotide sequence that hybridizes to (1) the complement of a nucleotide sequence encoding any one of the VH and/or VL chains depicted in SEQ ID NOS:5 or 9 (H chain) and/or SEQ ID NOS:7 or 11 (L chain) under stringent conditions (e.g., hybridization to filter-bound DNA in 6× sodium chloride/sodium citrate (SSC) at about 45° C. followed by one or more washes in 0.2×SSC/0.1% SDS at about 50-65° C.) under highly stringent conditions (e.g., hybridization to filter-bound nucleic acid in 6×SSC at about 45° C. followed by one or more washes in 0.1×SSC/0.2% SDS at about 68° C.), or under other stringent hybridization conditions which are known to those of skill in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3).

The anti-CRBN antibodies may be from any animal origin including birds and mammals (e.g., human, murine, donkey, sheep, rabbit, goat, guinea pig, camel, horse, or chicken). In certain embodiments, the anti-CRBN antibodies are human or humanized monoclonal antibodies. As used herein, "human" antibodies include antibodies having the amino acid sequence of a human immunoglobulin and include antibodies isolated from human immunoglobulin libraries or from mice that express antibodies from human genes.

In certain embodiments, the anti-CRBN antibodies are fully human antibodies, such as fully human antibodies that immunospecifically bind a CRBN polypeptide, a CRBN polypeptide fragment, or a CRBN epitope. Such fully human antibodies would be advantageous over fully mouse (or other full or partial non-human species antibodies), humanized antibodies, or chimeric antibodies to minimize the development of unwanted or unneeded side effects, such as immune responses directed toward non-fully human antibodies (e.g., anti-CRBN antibodies derived from other species) when administered to the subject.

Anti-CRBN antibodies provided herein may be monospecific, bispecific, trispecific or of greater multispecificity. Multispecific antibodies may be specific for different epitopes of a CRBN polypeptide or may be specific for both a CRBN polypeptide as well as for a heterologous epitope, such as a heterologous polypeptide or solid support material. In certain embodiments, the antibodies provided herein are monospecific for a given epitope of a CRBN polypeptide and do not immunospecifically bind to other epitopes.

In certain embodiments, provided herein are anti-CRBN antibodies that immunospecifically bind to a CRBN epitope (e.g., EEFHGRTLHDDD (residues 1-12 of SEQ ID NO:1) or peptide 65-76 of human CRBN (SEQ ID NO:12)) or a CRBN antigen, as well as methods of use thereof.

Standard techniques known to those of skill in the art can be used to introduce mutations in the nucleotide sequence encoding an anti-CRBN provided herein, including, for example, site-directed mutagenesis and PCR-mediated mutagenesis which results in amino acid substitutions. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

In some embodiments, the antibody is a fully human anti-human CRBN antibody, such as a fully human monoclonal antibody. Fully human antibodies may be produced by any method known in the art. Exemplary methods include immunization with a CRBN antigen (any CRBN polypeptide capable of eliciting an immune response, and optionally conjugated to a carrier) of transgenic animals (e.g., mice) that are capable of producing a repertoire of human antibodies in the absence of endogenous immunoglobulin production; see, e.g., Jakobovits et al., (1993) *Proc. Natl. Acad. Sci.,* 90:2551; Jakobovits et al., (1993) *Nature,* 362:255 258 (1993); Bruggermann et al., (1993) *Year in Immunol.,* 7:33. Other methods of producing anti-CRBN antibodies can be found in the Examples provided herein.

Alternatively, fully human antibodies may be generated through the in vitro screening of phage display antibody libraries; see e.g., Hoogenboom et al., J. Mol. Biol., 227:381 (1991); Marks et al., J. Mol. Biol., 222:581 (1991), incorporated herein by reference. Various antibody-containing phage display libraries have been described and may be readily prepared by one skilled in the art. Libraries may contain a diversity of human antibody sequences, such as human Fab, Fv, and scFv fragments, that may be screened against an appropriate target.

The anti-CRBN antibodies include antibodies that are chemically modified, i.e., by the covalent attachment of any type of molecule to the antibody. For example, but not by way of limitation, the antibody derivatives include antibodies that have been chemically modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formulation, metabolic synthesis of tunicamycin, etc. Additionally, the antibody may contain one or more non-classical amino acids.

In certain embodiments, anti-CRBN antibodies that immunospecifically bind to a CRBN antigen comprise a framework region known to those of skill in the art (e.g., a human or non-human fragment). The framework region may, for example, be naturally occurring or consensus framework regions. In some embodiments, the framework region of an anti-CRBN antibody is human (see, e.g., Chothia et al., 1998, *J. Mol. Biol.* 278:457-479 for a listing of human framework regions, which is incorporated by reference herein in its entirety). See also Kabat et al. (1991) *Sequences of Proteins of Immunological Interest* (U.S. Department of Health and Human Services, Washington, D.C.) 5th ed.

In certain embodiments, the anti-CRBN antibodies provided herein are chimeric or humanized antibodies. In some embodiments, the antibodies provided herein comprise human framework regions with one or more amino acid substitutions at one, two, three or more of the following residues: (a) rare framework residues that differ between the murine antibody framework (i.e., donor antibody framework) and the human antibody framework (i.e., acceptor antibody framework); (b) Venier zone residues when differing between donor antibody framework and acceptor antibody framework; (c) interchain packing residues at the VH/VL interface that differ between the donor antibody framework and the acceptor antibody framework; (d) canonical residues which differ between the donor antibody framework and the acceptor antibody framework sequences, particularly the framework regions crucial for the definition of the canonical class of the murine antibody CDR loops; (e) residues that are adjacent to a CDR; (g) residues capable of interacting with the antigen; (h) residues capable of interacting with the CDR; and (i) contact residues between the VH domain and the VL domain. In certain embodiments, antibodies that immunospecifically bind to a CRBN antigen comprising the human framework regions with one or more amino acid substitutions at one, two, three or more of the above-identified residues are antagonistic CRBN antibodies.

In other embodiments, fusion proteins comprising an anti-CRBN antibody are provided herein that immunospecifically binds to a CRBN antigen and a heterologous polypeptide.

5.13 Diagnostic Use of Antibodies

Labeled CRBN antibodies provided herein and derivatives and analogs thereof, which immunospecifically bind to a CRBN antigen can be used for diagnostic purposes to detect, diagnose, or monitor CRBN expression levels or a CRBN-mediated disease in a patient.

In some embodiments, provided herein are methods of utilizing a CRBN antibody to measure expression levels of CRBN in patient tumor or host cells, to predict clinical response to therapy with thalidomide, lenalidomide, pomalidomide, or 3-(5-amino-2-methyl-4-oxo-4H-quinazolin-3-yl)-piperidine-2,6-dione, a stereoisomer thereof, or a pharmaceutically acceptable salt, solvate, hydrate, co-crystal, clathrate, or polymorph thereof. Also provided herein are methods of utilizing a CRBN antibody provided herein to measure expression levels of CRBN in patient tumor or host cells, to monitor clinical response to therapy with thalidomide, lenalidomide, pomalidomide, or 3-(5-amino-2-methyl-4-oxo-4H-quinazolin-3-yl)-piperidine-2,6-dione, a stereoisomer thereof, or a pharmaceutically acceptable salt, solvate, hydrate, co-crystal, clathrate, or polymorph thereof. Also provided herein are methods of utilizing a CRBN antibody provided herein to measure expression levels of CRBN in patient tumor or host cells, to monitor patient compliance to dosing to therapy with thalidomide, lenalidomide, pomalidomide, or 3-(5-amino-2-methyl-4-oxo-4H-quinazolin-3-yl)-piperidine-2,6-dione, a stereoisomer thereof, or a pharmaceutically acceptable salt, solvate, hydrate, co-crystal, clathrate, or polymorph thereof. Also provided herein are methods of utilizing a CRBN antibody provided herein to measure expression levels of CRBN in patient tumor or host cells, to monitor development of resistance to therapy with thalidomide, lenalidomide, pomalidomide, or 3-(5-amino-2-methyl-4-oxo-4H-quinazolin-3-yl)-piperidine-2,6-dione, a stereoisomer thereof, or a pharmaceutically acceptable salt, solvate, hydrate, co-crystal, clathrate, or polymorph thereof.

Provided herein are diagnostic assays for diagnosing a CRBN-mediated disease comprising: (a) assaying for the level of a CRBN antigen in cells or a tissue sample of an individual using one or more antibodies of the invention that immunospecifically bind to a CRBN antigen; and (b) comparing the level of the CRBN antigen with a control level, e.g., levels in normal tissue samples, whereby an increase in the assayed CRBN antigen level compared to the control level of the CRBN antigen is indicative of a CRBN-mediated disease.

Antibodies provided herein can be used to assay CRBN antigen levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin.

Provided herein are methods for the detection or CRBN in a patient. In one embodiment, the method comprises: a) administering (for example, parenterally, subcutaneously, or intraperitoneally) to a subject an effective amount of a labeled antibody that immunospecifically binds to a CRBN antigen; b) waiting for a time interval following the administering for permitting the labeled antibody to preferentially concentrate at sites in the subject where the CRBN antigen is expressed (and for unbound labeled molecule to be cleared to background level); c) determining background level; and d) detecting the labeled antibody in the subject, such that detection of labeled antibody above the background level indicates that the subject has increased CRBN expression. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled antibody to preferentially concentrate at sites in the subject and for unbound labeled antibody to be cleared to background level is 6 to 48 hours or 6 to 24 hours or 6 to 12 hours. In another embodiment the time interval following administration is 5 to 20 days or 5 to 10 days.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

6. EXAMPLES

Certain embodiments of the invention are illustrated by the following non-limiting examples.

6.1 Preparation of 3-(4-amino-1-oxo-1,3-dihydro-isoindol-2-yl)-piperidine-2,6-dione (lenalidomide)

Methyl 2-bromomethyl-3-nitrobenzoate

A stirred mixture of methyl 2-methyl-3-nitrobenzoate (14.0 g, 71.7 mmol) and N-bromosuccinimide (15.3 g, 86.1 mmol) in carbon tetrachloride (200 mL) was heated under gentle reflux for 15 hours while a 100 W bulb situated 2 cm away was shining on the flask. The mixture was filtered and the solid was washed with methylene chloride (50 mL). The filtrate was washed with water (2×100 mL), brine (100 mL) and dried. The solvent was removed in vacuo and the residue was purified by flash chromatography (hexane/ethyl acetate, 8/2) to afford 19 g (96%) of the product as a yellow solid: mp 70.0-71.5° C.; 1H NMR (CDCl$_3$) δ 8.12-8.09 (dd, J=1.3 and 7.8 Hz, 1H), 7.97-7.94 (dd, J=1.3 and 8.2 Hz, 1H), 7.54 (t, J=8.0 Hz, 1H). 5.15 (s, 2H), 4.00 (s, 3H); $^{13}$C NMR (CDCl$_3$) δ 165.85, 150.58, 134.68, 132.38, 129.08, 127.80, 53.06, 22.69; HPLC, Water Nove-Pak/C18, 3.9×150 mm, 4 micron, 1 mL/min, 240 nm, 40/60 CH$_3$CN/0.1% H$_3$PO$_4$(aq) 7.27 min(98.92%); Anal. Calcd for C$_9$H$_8$NO$_4$Br: C, 39.44; H, 2.94; N, 5.11; Br, 29.15. Found: C, 39.46; H, 3.00; N, 5.00; Br, 29.11.

t-Butyl N-(1-oxo-4-nitroisoindolin-2-yl)-L-glutamine

Triethylamine (2.9 g, 28.6 mmol) was added dropwise to a stirred mixture of methyl 2-bromomethyl-3-nitrobenzoate (3.5 g, 13.0 mmol) and L-glutamine t-butyl ester hydrochloride (3.1 g, 13.0 mmol) in tetrahydrofuran (90 mL). The mixture was heated to reflux for 24 hours. To the cooled mixture was added methylene chloride (150 mL) and the mixture was washed with water (2×40 mL), brine (40 mL) and dried. The solvent was removed in vacuo and the residue was purified by flash chromatography (3% CH$_3$OH in methylene chloride) to afford 2.84 g (60%) of crude product which was used directly in the next reaction: 1H NMR (CDCl$_3$) δ 8.40 (d, J=8.1 Hz, 1H), 8.15 (d, J=7.5 Hz, 1H), 7.71 (t, J=7.8 Hz, 1H), 5.83 (s, 1H), 5.61 (s, 1H), 5.12 (d, J=19.4 Hz, 1H), 5.04-4.98 (m, 1H), 4.92 (d, J=19.4 Hz, 1H), 2.49-2.22 (m, 4H). 1.46 (s, 9H); HPLC, Waters Nova-Pak C18, 3.9×150 mm, 4 micron, 1 mL/min, 240 nm, 25/75 CH$_3$CN/0.1% H$_3$PO$_4$(aq) 6.75 min(99.94%).

N-(1-oxo-4-nitroisoindolin-2-yl)-L-glutamine

Hydrogen chloride gas was bubbled into a stirred 5° C. solution of t-butyl N-(1-oxo-4-nitro-isoindolin-2-yl)-L-glutamine (3.6 g, 9.9 mmol) in methylene chloride (60 mL) for 1 hour. The mixture was then stirred at room temperature for another hour. Ether (40 mL) was added and the resulting mixture was stirred for 30 minutes. The slurry was filtered, washed with ether and dried to afford 3.3 g of the product: 1H NMR (DMSO-d$_6$) δ 8.45 (d, J=8.1 Hz, 1H), 8.15 (d, J=7.5 Hz, 1H), 7.83 (t, J=7.9 Hz. 1H), 7.24 (s, 1H), 6.76 (s, 1H), 4.93 (s, 2H), 4.84-4.78 (dd, J=4.8 amd 10.4 Hz, 1H), 2.34-2.10 (m, 4H); $^{13}$C NMR (DMSO-d$_6$) δ 173.03, 171.88, 165.96, 143.35, 137.49, 134.77, 130.10, 129.61, 126.95, 53.65, 48.13, 31.50, 24.69; Anal. Calcd for C$_{13}$H$_{13}$N$_3$O$_6$: C, 50.82; H, 4.26; N, 13.68. Found: C, 50.53; H, 4.37; N, 13.22.

(S)-3-(1-oxo-4-nitroisoindolin-2-yl)piperidine-2,6-dione

A stirred suspension mixture of N-(1-oxo-4-nitroisoindolin-2-yl)-L-glutamine (3.2 g, 10.5 mmol) in anhydrous methylene chloride (150 mL) was cooled to −40° C. with isopropanol/dry ice bath. Thionyl chloride (0.82 mL, 11.3 mmol) was added dropwise to the cooled mixture followed by pyridine (0.9 g. 11.3 mmol). After 30 min, triethylamine (1.2 g, 11.5 mmol) was added and the mixture was stirred at −30 to −40° C. for 3 hours. The mixture was poured into ice water (200 mL) and the aqueous layer was extracted with methylene chloride (40 mL). The methylene chloride solution was washed with water (2×60 mL), brine (60 mL) and dried. The solvent was removed in vacuo and the solid residue was slurried with ethyl acetate (20 mL) to give 2.2 g (75%) of the product as a white solid: mp 285° C.; 1H NMR (DMSO-$d_6$) δ: 1.04 (s, 1H), 8.49-8.45 (dd, J=0.8 and 8.2 Hz, 1H), 8.21-8.17 (dd, J=7.3 Hz, 1H), 7.84 (t, J=7.6 Hz, 1H), 5.23-5.15 (dd, J=4.9 and 13.0 Hz, 1H), 4.96 (dd, J=19.3 and 32.4 Hz, 2H), 3.00-2.85 (m, 1H), 2.64-2.49 (m, 2H), 2.08-1.98 (m, 1H); $^{13}$C NMR (DMSO-$d_6$) δ 172.79, 170.69, 165.93, 143.33, 137.40, 134.68, 130.15, 129.60, 127.02, 51.82, 48.43, 31.16. 22.23; HPLC, Waters Nove-Pak/C18, 3.9×150 mm, 4 micron, 1 mL/min, 240 nm, 20/80 $CH_3CN$/0.1% $H_3PO_4$(aq) 3.67 min (100%); Anal. Calcd for $C_{13}H_nN_3O_5$: C, 53.98; H, 3.83; N, 14.53. Found: C, 53.92; H, 3.70; N, 14.10.

3-(4-amino-1-oxo-1,3-dihydro-isoindol-2-yl)-piperidine-2,6-dione

A mixture of (S)-3-(1-oxo-4-nitroisoindolin-2-yl)piperidine-2,6-dione (1.0 g, 3.5 mmol) and 10% Pd/C (0.3 g) in methanol (600 mL) was hydrogenated in a Parr-Shaker apparatus at 50 psi of hydrogen for 5 hours. The mixture was filtered through Celite and the filtrate was concentrated in vacuo. The solid was slurried in hot ethyl acetate for 30 min, filtered and dried to afford 0.46 g (51%) of the product as a white solid: mp 235.5-239° C.; 1H NMR (DMSO-$d_6$) δ 11.01 (s, 1H). 7.19 (t, J=7.6 Hz, 1H). 6.90 (d. J=7.3 Hz, 1H), 6.78 (d, J=7.8 Hz, 1H), 5.42 (s, 2H). 5.12 (dd. J=5.1 and 13.1 Hz, 1H), 4.17 (dd, J=17.0 and 28.8 Hz, 2H), 2.92-2.85 (m, 1H). 2.64-2.49 (m, 1H). 2.34-2.27 (m, 1H), 2.06-1.99 (m, 1H); $^{13}$C NMR (DMSO-$d_6$) δ 172.85, 171.19, 168.84, 143.58, 132.22. 128.79, 125.56, 116.37, 110.39, 51.48, 45.49, 31.20, 22.74; HPLC. Waters Nova-Pak/C18, 3.9×150 mm, 4 micron, 1 mL/min, 240 nm, 10/90 $CH_3CN$/0.1% $H_3PO_4$(aq) 0.96 min (100%); Chiral analysis, Daicel Chiral Pak AD, 40/60 Hexane/IPA, 6.60 min (99.42%); Anal. Calcd for $C_{13}H_{13}N_3O_3$: C, 60.23; H, 5.05; N, 16.21. Found: C, 59.96; H, 4.98; N, 15.84. 3-(4-Amino-1-oxo-1,3-dihydro-isoindol-2-yl)-piperidine-2,6-dione may also be prepared by methods known in the art, for example, as provided in *Drugs of the Future*, 2003, 28(5): 425-431, the entirety of which is incorporated by reference.

6.2 Preparation of 4-amino-2-(2,6-dioxopiperidin-3-yl)-1H-isoindole-1,3-dione (pomalidomide)

The preparation of 4-amino-2-(2,6-dioxopiperidin-3-yl)-1H-isoindole-1,3-dione is described, for example, in U.S. Pat. Nos. 7,812,169 and 7,709,502, the entirety of each of which is incorporated by reference.
Into a stirring solution of carboxybenzyloxy-L-glutamine (2.8 g, 10 mmols) in 40 mL anhydrous THF, 1,1-carbonyldiimidazole (1.92 g, 12 mmols) were added. The reaction mixture was heated under reflux for 18 hours. The THF was evaporated and the product was dissolved in chloroform. The chloroform layer was washed with water and brine and dried over anhydrous $CaSO_4$, filtered and evaporated to give white solid. The solid product was crystallized from ethyl ether to give 2.4 grams crystalline powder (90%). (Alternatively, carboxybenzyloxy-L-glutamine can be cyclized by treating with $SOCl_2$ in N,N-dimethylformamide at −70° C. to 0° C. for 1 hour to form the product). The reaction mixture was diluted with $CHCl_3$ and washed with 5% $Na_2CO_3$, dried over anhydrous $Na_2SO_4$, filtered, and evaporated to give 2.5 g (90% yield) S(−)-(3-benzyloxycarbonylamino)-glutarimide). $^1$H NMR ($CDCl_3$) δ 8.2 (1H, s broad), 7.4 (5H, s, aromatic), 5.8 (1H, d), 5.15 (2H, s), 4.4 (1H, dd, J=4.5, 3), 2.95-2.4 (3H, m), 1.86 (1H, d, t, J=11.5, 6.5). m.p. 122-124° C. (lit. 122-124° C.).

Into a solution of S(−)-(2-benzyloxycarbonylamino)glutarimide (1.2 g, 4.6 mmols) in 15 mL acetic acid glacial, 8 mL of 30% HBr/acetic acid solution was added at 20° C. The temperature of reaction mixture was raised to RT and stirred for 1 hour. White solid powder of S-(−)-2-amino-glutarimide HBr started appearing in reaction mixture. The solid was filtered and washed with 5 mL acetic acid glacial and then with ether to give 1.8 g (80%) product. Analysis on polarimeter of product showed (−) rotation, $[α]^{25}_D$ (c=1, water)= −37.5° and confirmed the product as S-(−)-2-amino-glutarimide. $^1$H NMR in DMSO-$D_6$ confirmed the product as 2-amino-L-glutarimide HBr.

Into a solution of (4.18 g, 20 mmols S-(−)-2-amino-glutarimide HBr in 50 mL of anhydrous DMF, 3.8 g (20 mmols) of 3-nitrophthalic anhydride was added. After adding 100 mL acetic acid (glacial), the reaction mixture was heated at about 70° C. to about 80° C. for about 24 hours. Thereafter, the solvents were evaporated under vacuum to yield an off-white solid. On adding 10 mL ethyl alcohol to the solid, an off-white powder product was formed. The product was separated and washed with 20 mL ethyl alcohol. $^1$H NMR (DMSO-$D_6$) δ 11.25 (1H, broad), 8.35 (1H, d, J=7.2), 8.25 (1H, d, J=7.0), 8.15 (1H, t, J=8.0), 5.2 (1H, dd, J=5.5, 7.2), 3.00-2.85 (1H, m), 2.65-2.4 (2H, m), 2.15-2.05 (1H, m). m.p.: 228-229° C. (lit. 228.5-229.5° C.).

4-Nitro-thalidomide (1 g, 3.3 mmols) was dissolved in 50 mL dioxane/methanol 4:1 mixture and hydrogenated in a Parr hydrogenater at 40 psi of hydrogen in the presence of a Pd/C 5% catalyst for about 4 hours. After filtering the reaction mixture through a Celite filtering agent, the solvents were evaporated under vacuum to yield a yellow powder. The product was recrystallized from ethyl acetate/dioxane to yield 800 mg (85% purity) of S(−)-4-amino-thalidomide. $^1$H NMR in DMSO-$D_6$: 11.10 (1H, s broad), 7.45 (1H, t, J=7.5), 7.05 (1H, d, J=5.2), 6.95 (1H, d, J=5.2), 6.5 (2H, s broad), 5.05 (1H, dd, J=5.0, 13.42), 2.95-2.80 (1H, m), 2.65-2.5 (2H, m), 2.05-1.95 (1H, m). m.p. 318.2-319.5° C. Absolute configuration was determined by comparison of specific rotation $[α]^{25}_D$ of (R)- and (S)-4-amino-2-(2,6-dioxopiperidin-3-yl)-1H-isoindole-1,3-dione to the analogous compounds R(+)- and S(−)-thalidomide. Analysis on polarimeter of product showed (−) rotation, $[α]^{25}_D$ (C=0.5, dioxane)=−27.70° and confirmed the product as S(−)-4-amino-2-(2,6-dioxopiperidin-3-yl)-1H-isoindole-1,3-dione.

The two enantiomers were resolved by chiral HPLC column Welk-01 (10 mm×750 mm) and eluted with CH3CN/MeOH/H20 1:1:5 mixture. The retention time for the S(−) enantiomer was 33.74 minutes and for the R(+) enantiomer 35.62 minutes at a flow rate of 2 mL/min at 240 nm, respectively.

6.3 Preparation of 3-(5-amino-2-methyl-4-oxo-4H-quinazolin-3-yl)-piperidine-2,6-dione (Compound B)

To a solution of potassium hydroxide (16.1 g, 286 mmol) in water (500 mL), was added 3-nitrophthalimide (25.0 g, 130 mmol) in portion at 0° C. The suspension was stirred at 0° C.

for 3 hrs, and then heated to 30° C. for 3 hrs. To the solution, was added HCl (100 mL, 6N). The resulting suspension was cooled to 0° C. for 1 hr. The suspension was filtered and washed with cold water (2×10 mL) to give 3-nitro-phthalamic acid as a white solid (24.6 g, 90% yield): $^1$H NMR (DMSO-$d_6$) δ 7.69 (brs, 1H, NHH), 7.74 (t, J=8 Hz, 1H, Ar), 7.92 (dd, J=1, 8 Hz, 1H, Ar), 8.13 (dd, J=1, 8 Hz, 1H, Ar), 8.15 (brs, 1H, NHH), 13.59 (s, 1H, OH); $^{13}$C NMR (DMSO-$d_6$) δ 125.33, 129.15, 130.25, 132.54, 136.72, 147.03, 165.90, 167.31.

To a mixture of 3-nitro-phthalamic acid (24.6 g, 117 mmol) and potassium hydroxide (6.56 g, 117 mmol) in water (118 mL), was added a mixture of bromine (6 mL), potassium hydroxide (13.2 g, 234 mmol) in water (240 mL) at 0° C., followed by addition of a solution of potassium hydroxide (19.8 g, 351 mmol) in water (350 mL). After 5 minutes at 0° C., the mixture was heated in a 100° C. oil bath for 1 hr. The reaction solution was cooled to room temperature, and then, in an ice-water bath for 30 minutes. To the mixture, a solution of HCl (240 mL, 2N) was added dropwise at 0° C., and the resulting mixture was kept for 1 hr. The suspension was filtered and washed with water (5 mL) to give 2-amino-6-nitro-benzoic acid as yellow solid (15.6 g, 73% yield): HPLC: Waters Symmetry $C_{18}$, 5 μm, 3.9×150 mm, 1 mL/min, 240 nm, $CH_3CN$/0.1% $H_3PO_4$, 5% grad to 95% over 5 min, 5.83 min (85%); $^1$H NMR (DMSO-$d_6$) δ 6.90 (dd, J=1, 8 Hz, 1H, Ar), 7.01 (dd, J=1, 9 Hz, 1H, Ar), 7.31 (t, J=8 Hz, 1H, Ar), 8.5-9.5 (brs, 3H, OH, $NH_2$); $^{13}$C NMR (DMSO-$d_6$) δ 105.58, 110.14, 120.07, 131.74, 149.80, 151.36, 166.30; LCMS: MH=183.

A mixture of 2-amino-6-nitro-benzoic acid (1.5 g, 8.2 mmol) in acetic anhydride (15 mL) was heated at 200° C. for 30 minutes in a microwave oven. The mixture was filtered and washed with ethyl acetate (20 mL). The filtrate was concentrated in vacuo. The solid was stirred in ether (20 mL) for 2 hrs. The suspension was filtered and washed with ether (20 mL) to give 2-methyl-5-nitro-benzo[d][1,3]oxazin-4-one as a light brown solid (1.4 g, 85% yield): HPLC: Waters Symmetry $C_{18}$, 5 μm, 3.9×150 mm, 1 mL/min, 240 nm, $CH_3CN$/0.1% $H_3PO_4$, 5% grad 95% in 5 min, 5.36 min (92%); $^1$H NMR (DMSO-$d_6$) δ 2.42 (s, 3H, $CH_3$), 7.79 (dd, J=1, 8 Hz, 1H, Ar), 7.93 (dd, J=1, 8 Hz, 1H, Ar), 8.06 (t, J=8 Hz, 1H, Ar); $^{13}$C NMR (DMSO-$d_6$) δ 20.87, 107.79, 121.54, 128.87, 137.19, 147.12, 148.46, 155.18, 161.78; LCMS: MH=207.

Two vials each with a suspension of 5-nitro-2-methyl-benzo[d][1,3]oxazin-4-one (0.60 g, 2.91 mmol) and 3-amino-piperidine-2,6-dione hydrogen chloride (0.48 g, 2.91 mmol) in pyridine (15 mL) were heated at 170° C. for 10 minutes in a microwave oven. The suspension was filtered and washed with pyridine (5 mL). The filtrate was concentrated in vacuo. The resulting mixture was stirred in HCl (30 mL, 1N), ethyl acetate (15 mL) and ether (15 mL) for 2 hrs. The suspension was filtered and washed with water (30 mL) and ethyl acetate (30 mL) to give a dark brown solid, which was stirred with methanol (50 mL) at room temperature overnight. The suspension was filtered and washed with methanol to give 3-(2-methyl-5-nitro-4-oxo-4H-quinazolin-3-yl)-piperidine-2,6-dione as a black solid (490 mg, 27% yield). The solid was used in the next step without further purification.

A mixture of 3-(2-methyl-5-nitro-4-oxo-4H-quinazolin-3-yl)-piperidine-2,6-dione (250 mg) and Pd(OH)$_2$ on carbon (110 mg) in DMF (40 mL) was shaken under hydrogen (50 psi) for 12 hrs. The suspension was filtered through a pad of Celite and washed with DMF (10 mL). The filtrate was concentrated in vacuo and the resulting oil was purified by flash column chromatography (silica gel, methanol/methylene chloride) to give 3-(5-amino-2-methyl-4-oxo-4H-quinazolin-3-yl)-piperidine-2,6-dione as a white solid (156 mg, 69% yield): HPLC: Waters Symmetry $C_{18}$, 5 μm, 3.9×150 mm, 1 mL/min, 240 nm, 10/90 $CH_3CN$/0.1% $H_3PO_4$, 3.52 min (99.9%); mp: 293-295° C.; $^1$H NMR (DMSO-$d_6$) δ 2.10-2.17 (m, 1H, CHH), 2.53 (s, 3H, $CH_3$), 2.59-2.69 (m, 2H, $CH_2$), 2.76-2.89 (m, 1H, CHH), 5.14 (dd, J=6, 11 Hz, 1H, NCH), 6.56 (d, J=8 Hz, 1H, Ar), 6.59 (d, J=8 Hz, 1H, Ar), 7.02 (s, 2H, $NH_2$), 7.36 (t, J=8 Hz, 1H, Ar), 10.98 (s, 1H, NH); $^{13}$C NMR (DMSO-$d_6$) δ 20.98, 23.14, 30.52, 55.92, 104.15, 110.48, 111.37, 134.92, 148.17, 150.55, 153.62, 162.59, 169.65, 172.57; LCMS: MH=287; Anal. Calcd. for $C_{14}H_{14}N_4O_3$+ 0.3$H_2O$: C, 57.65; H, 5.05; N, 19.21. Found: C, 57.50; H, 4.73; N, 19.00.

6.4 Identification of Direct Compound Targets

To identify the direct target of thalidomide and other related drugs, we develop an affinity purification technique. A compound control ("Compound A") coupled to Affigel-10 (10 μmol drug per mg Affigel) was used for affinity purification experiments.

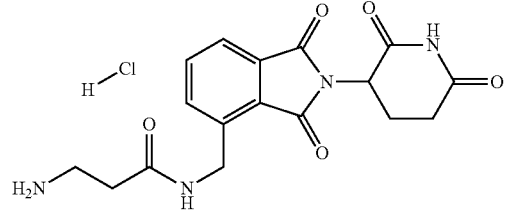 [SMILES: NCCC(=O)NCc1cccc2c1C(=O)N(C1CCC(=O)NC1=O)C2=O ; Cl]

Compound A (TNF IC$_{50}$=622 nM; Jurkat IL-2 EC$_{200}$=3.47 μM)

Proteins were isolated from Jurkat T cell lysates by binding to the Compound A-Affigel followed by elution using free Compound A. Coomassie stained bands were excised and sent to Harvard Microchemistry Facility for sequence analysis. The proteins were proteolytically digested and analyzed by microcapillary reverse-phase HPLC nano-electrospray tandem mass spectrometry on a Finnigan LCQ DECA quadrupole ion trap mass spectrometer. The MS/MS spectra were correlated with known sequences using the algorithm Sequest and other programs, then the peptide sequences were reviewed by a scientist for consensus with known proteins and the results manually confirmed for fidelity.

Summary of Results:

DDB1 (DNA damage binding protein 1 (XPCE, human) was affinity purified from Jurkat extracts using Compound A-immobilized beads. DDB1 was highly represented in the eluted fractions (108 peptides) compare with for example with the second proteins most represented Glycogen branching enzyme (55 peptides). DDB1 directly interacts with CRBN and could had been pull-down by virtue of its binding to CRBN.

6.5 CRBN siRNAs Knocked Down CRBN in Sensitive Multiple Myeloma Cell Lines

The role of cereblon (CRBN) in lenalidomide MOA was confirmed using knock-down experiments in two lenalidomide sensitive multiple myeloma cell lines, H929 and U266B1. It was found that down regulation of CRBN abrogates drug-induced cell cycle arrest, activation of tumor suppressors, inhibition of oncogenes and global changes in gene expression profiles and ubiquitination.

10 different single and pool siRNAs against CRBN were evaluated in H929 and U266B1 cells. RT-PCR was used to test the knockdown efficiency after 24 and 48 hour transfection. The results showed that the CRBN-siRNA-1, CRBN-siRNA-7, CRBN-siRNA-9, CRBN-siRNA-10, and CRBN-siRNA-11 significantly reduced the expression of CRBN mRNA as compared with other siRNAs and mock siRNA (Table 1).

TABLE 1

Effect of CRBN-siRNAs on CRBN gene expression

| siRNA | % inhibition of CRBN mRNA relative to CRBN mRNA levels in Mock control siRNA conc | | |
|---|---|---|---|
| | 10 nM | 25 nM | 50 nM |
| Invitrogen siRNAs | | | |
| Low GC Neg ctrl | 88/100 | 85.5/77.5 | 85/77 |
| CRBN-7 | 22/25 | 14/17.5 | 16.5/17 |
| CRBN-8 | 47.5/61 | 29.5/41 | 33/37.5 |
| CRBN-9 | 67.5/66.4 | 61.5/52 | 42/37 |
| Dharmacon siRNAs | | | |
| Smart pool neg ctrl | 87/78 | 72.5/84 | 98.5/88.5 |
| CRBN Smartpool | 28/34.5 | 19.3/28.5 | 18/17 |
| CRBN-9 | 55/50 | 28.5/33 | 17.5/23 |
| CRBN-10 | 23/35 | 20.5/29 | 20/22.5 |
| J-021086-11 | 22/27 | 20/17 | 16.3/15.3 |
| J-021086-12 | 55/53 | 37/39 | 21/25 |

6.6 Knockdown of CRBN Abrogates the Anti-Proliferative Effect of Drugs in Multiple Myeloma Cells Drugs such as lenalidomide and pomalidomide have direct anti-proliferative activity against MM cells by inducing cell cycle arrest in G1 phase, followed by a decrease in viability. To study the role of CRBN in lenalidomide and other drugs anti-proliferative activities, H929 and U266B1 cells, two sensitive myeloma lines, were transfected with CRBN-siRNAs or control siRNAs for 24, 48, 72 and 96 hours. Cells were treated 24 h after transfection with DMSO (0.1%), pomalidomide (1 µM) and lenalidomide (10 µM) for 1, 2, 3 days to evaluated the compound effect on CRBN protein, mRNA expression and the effect on cell cycle and proliferation. RT-PCR and western blot assays showed that CRBN siRNAs knocked down CRBN. CRBN down regulation was confirmed by RT-PCR and Western blot using the CRBN70 antibody (FIG. 1). Treatment with lenalidomide and pomalidomide affected neither mRNA nor protein expression of CRBN significantly.

Lenalidomide and pomalidomide induced a delay of cell cycle progression, measured as the decrease of the number of cells in S phase, of 40% and 50% respectively in control mock and negative control siRNA-transfected cells (average inhibition of 3 days of treatment) (FIGS. 2A & 2B). Knockdown of CRBN markedly abrogated the lenalidomide and pomalidomide-induced delay in cell cycle progression in U266B1 cells. Id.

The effect of CRBN in H929 cells was also evaluated. H929 cells were transfected with mock, negative control siRNA and CRBN-siRNA-7 for 24, 48, 72 and 96 h. Cells were treated 24 h after transfection with DMSO (0.1%), pomalidomide (1 µM), lenalidomide (10 µM) or 3-(5-amino-2-methyl-4-oxo-4H-quinazolin-3-yl)-piperidine-2,6-dione ("Compound B") for 1, 2, 3 days and the effect on cell cycle and proliferation investigated. Lenalidomide, pomalidomide and Compound B induced a delay of cell cycle progression, measured as the decrease of the number of cells in S phase, in control mock and negative control siRNA-transfected cells after 72 h treatment (FIG. 2C). Knockdown of CRBN markedly abrogated immunomodulatory drugs-induced delay in cell cycle progression in H929 cells (FIG. 2C) from of 50 to 4% for lenalidomide, from 70 to 15% for pomalidomide, and from 65 to 22% for Compound B.

6.7 Knockdown of CRBN Abrogated Effect of Drugs on Cell Cycle, Tumor Suppressor and Apoptotic Proteins To further investigate the effects of CRBN on the cell cycle arrest induced by drugs we used RT-PCR and Western blot analysis to measure the levels of key cell cycle and apoptotic regulators. U266B1 cells were transfected with mock, negative control siRNA, CRBN-siRNA-7 and CRBN-siRNA-11 for 24, 48, 72 and 96 h (FIG. 3A). Cells were treated 24 h after transfection with DMSO (0.1%), pomalidomide (1 µM) and lenalidomide (10 µM) for 1, 2, 3 days and the effect on mRNA and protein levels of the cyclin-dependent kinase (CDK) inhibitor $p21^{WAF-1}$ were evaluated. It has been shown that lenalidomide- and pomalidomide-induced cell cycle arrest is dependent on up-regulation of $p21^{WAF-1}$ in U2669. Our results showed that p21 was up-regulated by lenalidomide and pomalidomide in control mock and negative control siRNA-transfected cells (FIG. 3C) indicating a decrease of S phase cells resulted from lenalidomide and pomalidomide G1 arrest (FIG. 3B). However, knockdown of CRBN prevents the induction of $p21^{WAF-1}$ indicating the successful abrogation of G1 arrest and renewal of S phase progression (FIGS. 3C & 3D).

Figure 4C:
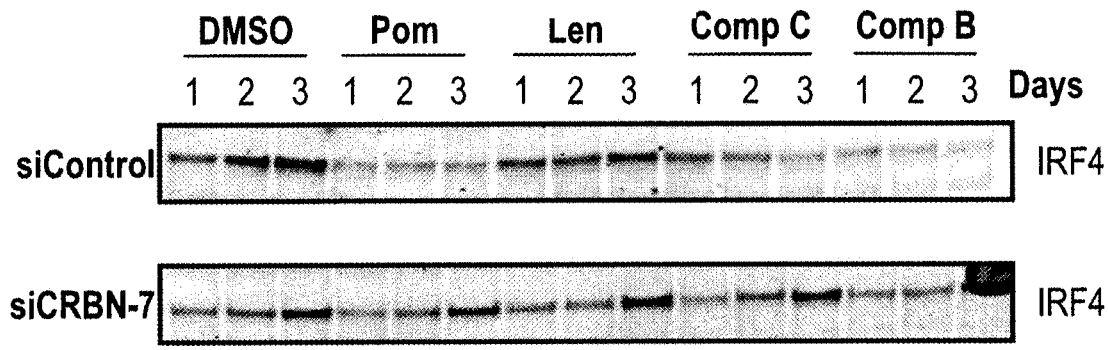
Figure 4D:
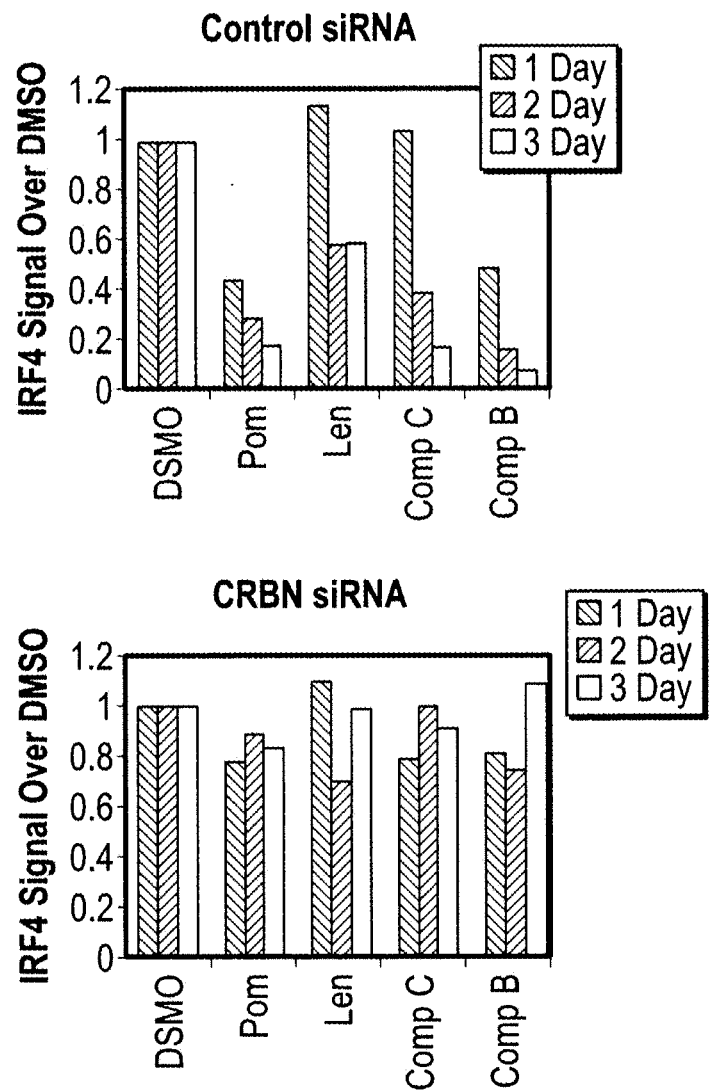

In H929 cells, the cell cycle arrest in G1 phase by the drugs coincides with a reduction of tumor suppressor, pRb, phosphorylation and the oncogene and myeloma survival factor IRF4. Western blot analysis showed that lenalidomide, pomalidomide and Compound B decreased phosphorylation of pRB (FIGS. 4A & 4B) and total level of protein IRF4 (FIGS. 4C & 4D). The effect of the drugs was reduced by knockdown of CRBN suggesting that inhibition of cell cycle progression by the drugs requires CRBN protein.

6.8 Knockdown of CRBN Inhibits Lenalidomide and Pomalidomide Effects on Gene Expression Gene expression profile using microarray technology identified 759 or 609 genes differentially modulated in negative control siRNA-transfected U266B1 cells treated with pomalidomide (1 µM) or lenalidomide (10 µM) compared to DMSO treated control (±1.7 fold; P<0.05 ANOVA p-value) (FIGS. 5A & 5B).

Representative significant Gene Ontology (GO) classes of down regulated genes in pomalidomide include: cell cycle (87 genes; P=5.2E-56), mitosis (43 genes; P=1.2E-39), cytoskeleton (58 genes; P=2.6E-16) and response to DNA damage stimulus (36 genes; P=1.8E-21). Representative significant Gene Ontology (GO) classes of up regulated genes include: antigen processing and presentation (12 genes; P=2.8E-17), immune response (35 genes; P=5.70E-14) and cell death (50 genes; P=1.7E-10).

Representative significant Gene Ontology (GO) classes of up regulated genes in lenalidomide include: antigen processing and presentation (11 genes; P=1.9E-16), immune response (37 genes; P=3.9E-13) and cell death (55 genes; P=1.0E-10) (Tables 4 and 5). Lenalidomide and pomalidomide effects on cell cycle and gene expression profiles in U266 were abrogated by knockdown of CRBN using 4 different siRNAs (FIGS. 5A-5C).

6.9 CRBN Levels are Decreased in Multiple Myeloma Cells Resistant to Lenalidomide or Pomalidomide Although the development of lenalidomide-based therapies has improved significantly clinical responses, most multiple myeloma patients eventually relapse or become refractory to their therapeutic regimens. Multiple myeloma cell lines resistant to the anti-proliferative effects of lenalidomide have been developed in order to evaluate the potential mechanisms responsible for lenalidomide resistance.

Due to the relevance of CRBN for the anti-proliferative response of lenalidomide, pomalidomide and other immunomodulatory the levels of CRBN protein was compared in matched pairs of parental sensitive lines with acquired lenalidomide- or pomalidomide-resistance cells. Consistent with CRBN being required for the anti-proliferative activity of lenalidomide and pomalidomide, the levels of CRBN protein were significantly lower in the pomalidomide-resistant cells line DF15R and the lenalidomide-resistant cells, H929 R10-1, H929 R10-2, H929 R10-3, H929 R10-4 and MM1/R compared to the matched parental lines (Table 2).

TABLE 2

Fold difference of CRBN protein level between lenalidomide- or pomalidomide-resistant cells and the matched parental cells

|  | CRBN protein fold decrease relative to matched parental lines |
|---|---|
| DF15R | 7.16E-07 |
| H929 R10-1 | 0.503989 |
| H929 R10-2 | 0.295482 |
| H929 R10-3 | 0.459599 |
| H929 R10-4 | 0.659341 |
| MM1/R | 0.172249 |

6.10 Genomic DNA Sequencing of CRBN, DDB1 and GSK3 from Human Cell Lines and Primary Cells The target genes CRBN, DDB1, and GSK3B were sequenced from a variety of human cell lines and primary cells. Sequencing of the CRBN gene identified mutations in lenalidomide resistant human cell lines which are absent in parental cells.

Sequence enrichment, NexGen sequencing, and data analysis yielded the results shown in Tables 3-6 below. Each table lists the cell lines from which the data are derived. The reference nucleotide refers to the wild type nucleotide at that position. "Coverage" refers to the total number of reads at that position. The overall mutation score ("Score") is based on the concept of Phred scores with a maximum value of 30, meaning the probability that the mutations call is wrong is 1/1000; 20, 1/100; and 10, 1/10. A Score, however, does not necessarily mean that the mutation is more than likely a false mutation. A low Score implies only that the mutation cannot be called a true mutation with absolute certainty. "Mutation Call" denotes the nucleotide change. For example, T>TG indicates a heterozygous change from reference T to T and G. T>G indicates a homozygous change from reference T to G. The term "c." refers to the coding sequence while "IVS" refers to an intron variant. The "Amino Acid Change" column uses similar notation to the "Mutation Call" column.

Results

In the large-scale sequence analysis of 27 cell lines, more intronic mutations were found than exonic mutations. The multiple myeloma cell line, ANBL-6, showed a mutation in CRBN of the lenalidomide-resistant line that was not seen in the wild type. ANBL-6.wt was treated only with DMSO and the CRBN coding sequence exactly matched the reference. However, in the ANBL-6.R10R which has resistance to 10 μM lenalidomide, a SNP in the coding region c.745C>CA caused an amino acid change 249D>YD in the protein. This amino acid change mapped to the DDB1 binding domain of CRBN.

A silent mutation found in the CRBN coding region of HepG2 and JeKo-1 was heterozygous c.735A>AG with KMS-12-BM as homozygous c.735A>G. The cell line, OPM2, had a different silent mutation in the coding region of CRBN, c.1209C>CT. No amino acid changes resulted from these SNPs.

The sequencing results for DDB1 uncovered a SNP in the coding region c.909T>TA which resulted in an amino acid change 303E>ED in both ANBL-6.wt and ANBL-6.R10R cell lines. A different SNP was found in the Jurkat cell line, with a mutation c.2143C>CT in the DDB1 coding region that changed the amino acid sequence 715V>VI.

A silent mutation found in the DDB1 coding region of ANBL-6.wt, ANBL-6.R10R, and SH-SY5Y at c.153G>GA did not change the amino acid sequence. A sample of PBMC from a healthy donor also had a silent mutation in the DDB1 coding region c.2265G>GA that did not change the amino acid sequence.

One GSK3β mutation was found in the PMBC sample. The mutation in the coding region c.1187C>CT resulted in an amino acid change 396R>RQ. This mutation did not map to the kinase domain. Other mutations are shown in Table 11. Most of these have low coverage. This could be due to primers targeting these regions and/or sequencing error.

While no consistent mutations in CRBN, DDB1 and GSK3-β were found to correlate with resistance to lenalidomide or pomalidomide in these MM cell lines, sporadic mutations such as the 249D>YD CRBN mutation observed in lenalidomide-resistant ANBL-6 MM cells exemplify the type of polymorphism which might occur in such genes within the clinical setting, and which might constitute a mechanism of resistance. Further studies would be needed to confirm or refute this hypothesis.

TABLE 3

CRBN Mutations

| Cell line | Mutation Call | Amino Acid Change |
|---|---|---|
| OPM2 | c.1209C > CT | 403T > TT[a] |
| HepG2 | c.735A > AG | 245Y > YY[a] |
| JeKo-1 | c.735A > AG | 245Y > YY[a] |
| KMS-12-BM | c.735A > G | 245Y > Y[a] |
| ANBL-6.R10R | c.745C > AC | 249D > YD[b] |
| KMS-12-BM | IVS1148 + 21__1148 + 22insA | |
| SH-SY5Y | IVS1148 + 21__1148 + 22insA | |
| SKMM2 | IVS1148 + 21__1148 + 22insA | |
| Jurkat | IVS1148 + 23delA | |
| EJM | IVS1329 + 18__1329 + 19insAACT | |
| H929__R10-4 | IVS1329 + 18 1329 + 19insAACT | |

TABLE 3-continued

CRBN Mutations

| Cell line | Mutation Call | Amino Acid Change |
|---|---|---|
| JJN-3 | IVS1329 + 18_1329 + 19insAACT | |
| OPM2 | IVS1329 + 18_1329 + 19insAACT | |
| SH-SY5Y | IVS1329 + 18_1329 + 19insAACT | |
| MM.1S.R10R | IVS175-9A > AG | |
| MM.1S.wt | IVS175-9A > AG | |
| PBMC | IVS175-9A > AG | |
| HepG2 | IVS175-9A > AG, IVS1148 + 21_1148 + 22insA | |
| ANBL-6.wt | IVS175-9A > G | |
| EJM | IVS175-9A > G | |
| H929_D1 | IVS175-9A > G | |
| H929_R10-1 | IVS175-9A > G | |
| H929_R10-2 | IVS175-9A > G | |
| H929_R10-3 | IVS175-9A > G | |
| H929_R10-4 | IVS175-9A > G | |
| H929-1uM-CC5013 | IVS175-9A > G | |
| JeKo-1 | IVS175-9A > G | |
| JJN-3 | IVS175-9A > G | |
| Jurkat | IVS175-9A > G | |
| KMS-12-BM | IVS175-9A > G | |
| OPM2 | IVS175-9A > G | |
| RPMI-8226 | IVS175-9A > G | |
| SH-SY5Y | IVS175-9A > G | |
| SK-Hep1 | IVS175-9A > G | |
| SKMM2 | IVS175-9A > G | |
| U266_B1 | IVS175-9A > G | |
| ANBL-6.R10R | IVS175-9A > G, IVS1148 + 21 1148 + 22insA | |
| U87 | IVS175-9A > G, IVS1148 + 21 1148 + 22insA, IVS528-29 528-28insCT | |
| H929 | IVS175-9A > G, IVS1329 + 18 1329 + 19insAACT | |
| H929-0.1uM-CC4047 | IVS175-9A > G, IVS1329 + 18_1329 + 19insAACT | |
| H929-DMSO | IVS175-9A > G, IVS528-29_528-28insCT | |
| KMS-12-BM | IVS528-29_528-28insCT | |
| SKMM2 | IVS528-29_528-28insCT | |
| U266_B1 | IVS528-29 528-28insCT | |

[a] = silent mutation;
[b] = region required for DDB1 interaction

TABLE 4

DDB1 Mutations

| Cell line | Mutation Call | Amino Acid Change |
|---|---|---|
| ANBL-6.R10R | c.153G > AG | 51P > PP[a] |
| ANBL-6.wt | c.153G > AG | 51P > PP[a] |
| SH-SY5Y | c.153G > AG | 51P > PP[a] |
| Jurkat | c.2143C > CT | 715V > VI |
| PBMC | c.2265G > AG | 755S > SS[a] |
| ANBL-6.R10R | c.909T > AT | 303E > DE |
| ANBL-6.wt | c.909T > AT | 303E > DE |
| ANBL-6.wt | IVS1123-29A > G | |
| EJM | IVS1123-29A > G | |
| H929 | IVS1123-29A > G | |
| H929_R10-3 | IVS1123-29A > G | |
| H929-1uM-CC5013 | IVS1123-29A > G | |
| HepG2 | IVS1123-29A > G | |
| JeKo-1 | IVS1123-29A > G | |
| MM.1S.wt | IVS1123-29A > G | |
| OPM2 | IVS1123-29A > G | |
| SK-Hep1 | IVS1123-29A > G | |
| U266_B1 | IVS1123-29A > G | |
| ANBL-6.wt | IVS1123-30C > T | |

TABLE 4-continued

DDB1 Mutations

| Cell line | Mutation Call | Amino Acid Change |
|---|---|---|
| EJM | IVS1123-30C > T | |
| H929 | IVS1123-30C > T | |
| H929_R10-3 | IVS1123-30C > T | |
| H929-1uM-CC5013 | IVS1123-30C > T | |
| HepG2 | IVS1123-30C > T | |
| JeKo-1 | IVS1123-30C > T | |
| MM.1S.wt | IVS1123-30C > T | |
| OPM2 | IVS1123-30C > T | |
| SK-Hep1 | IVS1123-30C > T | |
| U266_B1 | IVS1123-30C > T | |
| PBMC | IVS1225 + 30T > C | |
| MM.1S.R10R | IVS1225 + 30T > CT | |
| MM.1S.wt | IVS1225 + 30T > CT | |
| RPMI-8226 | IVS1225 + 30T > CT | |
| JJN-3 | IVS1862-26A > AT | |
| OPM2 | IVS1862-26A > AT | |
| H929-0.1uM-CC4047 | IVS1862-27A > AC | |
| JJN-3 | IVS1862-27A > AC | |
| OPM2 | IVS1862-27A > AC | |
| SH-SY5Y | IVS1862-27A > AC | |
| H929 | IVS2278-26T > GT | |
| H929-1uM-CC5013 | IVS2278-26T > GT | |
| Jurkat | IVS2278-26T > GT | |
| KMS-12-BM | IVS2278-26T > GT | |
| OPM2 | IVS2278-26T > GT | |
| ANBL-6.wt | IVS2278-27C > CT | |
| EJM | IVS2278-27C > CT | |
| H929 | IVS2278-27C > CT | |
| H929_R10-2 | IVS2278-27C > CT | |
| H929-1uM-CC5013 | IVS2278-27C > CT | |
| JJN-3 | IVS2278-27C > CT | |
| Jurkat | IVS2278-27C > CT | |
| KMS-12-BM | IVS2278-27C > CT | |
| OPM2 | IVS2278-27C > CT | |
| PBMC | IVS2278-27C > CT | |
| SH-SY5Y | IVS2278-27C > CT | |
| SK-Hep1 | IVS2278-27C > CT | |
| SKMM2 | IVS2278-27C > CT | |
| U266_B1 | IVS2278-27C > CT | |
| U87 | IVS2278-27C > CT | |
| ANBL-6.wt | IVS2278-28C > T | |
| H929 | IVS2278-28C > T | |
| H929_R10-2 | IVS2278-28C > T | |
| H929_R10-3 | IVS2278-28C > T | |
| H929-1uM-CC5013 | IVS2278-28C > T | |
| Jurkat | IVS2278-28C > T | |
| KMS-12-BM | IVS2278-28C > T | |
| OPM2 | IVS2278-28C > T | |
| PBMC | IVS2278-28C > T | |
| SH-SY5Y | IVS2278-28C > T | |
| SKMM2 | IVS2278-28C > T | |
| U266_B1 | IVS2278-28C > T | |
| U87 | IVS2278-28C > T | |
| JJN-3 | IVS2661 + 6C > CT | |
| PBMC | IVS2832 + 6C > CT | |
| RPMI-8226 | IVS2832 + 6C > CT | |

[a] = silent mutation

TABLE 5

GSK3β Mutations

| Cell line | Mutation Call | Amino Acid Change |
|---|---|---|
| PBMC | c.1187C > CT | 396R > RQ |
| Jurkat | IVS282 + 3delT | |

TABLE 5-continued

GSK3β Mutations

| Cell line | Mutation Call | Amino Acid Change |
|---|---|---|
| U266_B1 | IVS366 + 29A > AG | |
| H929 | IVS366 + 29A > G | |
| Jurkat | IVS909 + 11delA | |

TABLE 6

Other Mutations

Chr Y: LOC100288025
Chr M: ATP6, COX1, CYTB, ND1, ND4, ND4L, ND5
Chr 2: C2orf67
Chr 1: ITLN1
Chr 19: KLK10
Chr 17: KRT15
Chr 14: PRMT5, FMNL1
Chr 9: NOTCH1

6.11 Study of the Relationship Between Drugs and the Ubiquitin Proteasome System Specific antibodies for poly-ubiquitin chains were used to study the effect of immunomodulatory drugs on global levels of ubiquitination. H929 cells were treated with lenalidomide (1 µM), pomalidomide (1 µM) or proteasome inhibitor MG132. After 30 minutes cells were process for immunofluorescence. Global levels of K63-linked polyubiquitination were quantified by Cellomics. As shown in FIGS. 7A & 7B, immunomodulatory drugs decrease total K48-linked polyubiquitination but not K-63-linked ubiquitination in H929.

6.12 Study of the Effect of Drugs on Global Changes of Ubiquination and Protein Abundance The effects of lenalidomide and pomalidomide on protein ubiquination were investigated using CST Ubiscan technology. Treated samples were sent to Cell Signaling Technology for ubiquinated peptide enrichment and quantification by LC/MS/MS. Raw intensity was used for this analysis to identify peptides that are significantly regulated by the drugs, or the drugs with proteasome inhibitor MG132. Analysis showed that compared with MG132, the effects of lenalidomide and pomalidomide on ubiquitinated peptides are small. In the MG132 combo, more ubiquinated peptides are observed (compared with their controls). 162 unique ubiquitinated peptides were significantly up-regulated by lenalidomide and pomalidomide alone, or with MG132 at 1 hour or 4 hours. These peptides correspond to 176 unique proteins. Top few groups are: nucleosome, chromatin, protein-DNA complex assembly, Histone H2A. Among the 176 proteins, we found five proteins that belong to "ubiquitin-protein ligase activity" category, they are MDM2, HERC2, UBE2D3 (only by pomalidomide), UBE2N (lenalidomide only), UBE2M (both). Results for hits categorized by conditions are shown in FIGS. 8 & 9 (without MG132) and FIGS. 10 & 11 (with MG132).

6.13 CRBN Knockdown Effect on Drug Induced TNFα and IL-2 in Primary T-Cells

In these studies, human T cells were isolated from blood and treated with 1 µg/ml PHA-L at 37° C. After 24 hr stimulation T cells were subjected to siRNA transfection with the indicated siRNAs. Knockdown efficiencies were analyzed by qRT-PCR after 24 h transfections and the remaining transfected cells seeded in 96-well plate s pre-bound with OKT3 and treated with DMSO or 1 and 10 µM thalidomide, lenalidomide, pomalidomide and phthalimide in duplicate at 37° C. for 48 hours. After 48 hours, the supernatants were collected and tested for TNFα and IL-2 production by ELISA (FIGS. 12A-12D). This data indicates that siRNA knockdown of CRBN abrogates drug-induced TNFα and IL-2 production in anti-CD3-stimulated primary human T cells.

6.14 Knocking Down Cul4A and Cul4B Together Partially Abrogates Lenalidomide, Pomalidomide, or Compound B-Induced TNFα and IL-2 Induction in T Cells Cul4A knockdown efficiency prior to drug treatment was measured. Cul4A gene expression was knocked down by 82% and 76% by Cul4A siRNA-1 and Cul4A+Cul4B siRNA, respectively (FIG. 13A). Cul4B gene expression was suppressed by 70% and 63% by Cul4B and Cul4A+Cul4B siRNA, respectively. The individual knock down of Cul4A or Cul4B had no effect on T cell TNF-α or IL-2 production induced by 10 µM lenalidomide, pomalidomide or Compound B (FIGS. 13 B & C). However, the double knockdown of Cul4A and Cul4B together resulted in a significant but partial reversal of the compound-induced elevation of TNF- production due to lenalidomide, pomalidomide, and Compound B (FIG. 13B). There was a trend of a reversal of IL-2 induction when Cul4A and Cul4B were knocked down (FIG. 13C). These data suggest that lenalidomide, pomalidomide, and Compound B-mediated T cell costimulation is dependent on the expression of Cul4A and Cul4B, and that these proteins serve redundant functions in the T cell.

6.15 CRBN Expression and Sensitivity to Lenalidomide in Lymphoma Cells

The antiproliferative activity of lenalidomide versus baseline CRBN expression was studied in diffuse large B-cell lymphoma (DLBCL) cell lines. The following DLBCL cell lines were evaluated for sensitivity to lenalidomide: OCI-Ly10-NCI, U2932, OCI-Ly-3, DB, RIVA, TMD8, Toledo, OCI-Ly-19, Pfeiffer, WSU-DLCL2, Karpas-1106P and SU-DHL-4. Results are shown in FIG. 14.

6.16 Preparation of CRBN-DDB1 Complex

Primers were designed for cloning of CRBN into pBV-ZZ-HT-LIC and pBV-notag-LIC. Two primers were prepared, "CRBN_For" (SEQ ID NO: 14) and CRBN_Rev. (SEQ ID NO: 15)

```
CRBN_For:  GTGCCGCGTGGCTCCATGATGGCCGGCGAAGGAGATCA

CRBN_Rev:  GCTTCCTTTCGGGCTTATTACAAGCAAAGTATTACTT
```

The primers were used to amplify the CRBN gene from a cDNA library. The product was gel purified and treated with T4 DNA polymerase in the presence of TTP only to make single-stranded ends compatible for ligation independent cloning. The CRBN DNA was then annealed to pBV-ZZ-HT-LIC to create CRBN_034 (FIG. 15A).

For DDB1, two primers were prepared, "DDB1_For" and "DDB1_Rev."

```
                                                            (SEQ ID NO: 2)
DDB1_For:  TCGGGCGCGGCTCTCGGTCCGAAAAGGATGTCGTACAACTACGTGGTAAC (SEQ ID NO: 3)
DDB1_Rev:  GCTTCCTTTCGGGCTTATTTTTCGAACTGCGGGTGGCTCCAATGGATCCGAGTTAGCTCCT
```

The DDB1_Rev adds a StrepTag at the C-termini of DDB1. The DDB1 gene was amplified from a cDNA library, gel purified, and treated with T4 polymerase in the presence of TTP. The DDB1 gene was then annealed to pBV-notag-LIC to create the plasmid DDB1004 (FIG. 15B).

Expression of Constructs in Baculovirus and Purification

The constructs could were tested for expression in insect cells. Recombinants pBV-HT-LIC and pBV-GST-LIC plasmids were transformed into DH10Bac to produced bacmids. Integrity of the recombination was followed by a blue-white screen and PCR. The recombinant bacmids were used to transfect 9×105 Sf9 adherent cells per well in serum free-Grace media. After the transfection, fresh Grace media containing antibiotics and glutamine was added.

Infection was followed by observation of the cell monolayers under microscope. After 5 to 7 days, the supernatants were saved (P1 virus) and the pellets were analyzed for recombinant protein expression. Virus amplification was in 24 deep well plates with 4 ml of 2×106 Sf9 cells/ml per well. Aliquots were removed to assess the kinetics of protein expression. After 4 days, the plate was centrifuged, the supernatant were saved (P2 virus) and the pellets were analyzed by mini scale purification of the tagged proteins. The viruses were finally amplified in 750 ml of Grace media containing antibiotics and glutamine and the supernatants saved as P3 virus. Pellets were saved and purified using either the AKATxpress or the AKTA purifier from Amersham Biosciences.

Purification

Cell pastes containing CRBN-DDB1 were lysed in a buffer containing 50 mM Tris pH 8.0, 500 mM NaCl, 20 mM Imidazole, 10% Glycerol, and 2 mM DTT and protease inhibitors. The lysate was then cleared by centrifugation. The tagged proteins were then purified from the supernatants using the AKTA Express from Amersham Biosciences. Five ml HisTrap HP columns were used for the affinity step while a 16 mm×60 cm Sephacryl S-200 HR was used for the size exclusion steps. After loading the column, was column was washed with 20 volumes of lysis buffer, then 10 column volumes of 50 mM Tris pH 8.0, 1000 mM NaCl, 40 mM Imidazole, 10% Glycerol, and 2 mM DTT. Elution of the bound proteins was performed with lysis buffer containing 500 mM Imidazole. Eluted proteins were directly injected into the gel filtration column equilibrated in 25 mM Tris pH 8.0, 200 mM NaCl, 5% Glycerol, and 2 mM DTT. Fractions were analyzed by 4-20% SDS polyacrylamide gel electrophoresis.

Fractions containing both CRBN and DDB1 were pooled and digested with Thrombin to remove the ZZ-HT tag from CRBN. Digestion was carried at 4° C. for 5-6 hours with 1:2000 (weight/weight) of thrombin and CRBN-DDB1. Cleaved CRBN-DDB1 was diluted in 25 mM Tris pH 8.0, 5% Glycerol, and 2 mM DTT, and loaded onto an 8 ml MonoQ column (Amersham-Pharmacia) equilibrated in 25 mM Tris pH 8.0, 75 mM NaCL, 5% Glycerol, and 2 mM DTT. After loading the column was wash with 2 volumes of 25 mM Tris pH 8.0, 75 mM NaCl, 5% Glycerol and 2 mM DTT, and the bound proteins were eluted with a gradient from 75 mM to 400 mM in 25 mM Tris pH 8.0, 5% Glycerol and 2 mM DTT A final gel filtration was done to polish the CRBN-DDB1 complex. The fraction pooled from the MonoQ were loaded onto a 140 ml S200HR Gel filtration column and ran in 25 mM Tris pH 8.0, 200 mM NaC, 5% Glycerol, and 2 mM DTT. Fractions were analyzed and positive fractions were pooled and concentrated to approximately 15 mg/ml. Aliquots were stored at −80° C.

6.17 Ubiscan Ubiquitination Experiments

The results of 1 hour and 4 hour ubiquitination experiments are shown in FIGS. 17-22, which demonstrate that certain peptides are regulated by lenalidomide and/or pomalidomide.

The tables of FIG. 23 show Ubiscan data results for lenalidomide, pomalidomide and Compound B. Ub-proteins IKZF3, RPL19, PCM1 and NEDD8 were commonly increased in abundance by Rev and Pom in U266 and Compound B in T cells. Proteins GNB2L1 and HNRNPR were commonly decreased in abundance by Rev and Pom in U266 and Compound B in T cells.

Treatment of T cells with Compound B resulted in a greater abundance of two ubiquitinated peptides (vs. DMSO control), SECTM1 and ZC3H15.

Proteins in common with lenalidomide, pomalidomide and Compound B: IKZF3, RPL19, PCM1, NEDD8, GNB2L1, and HNRNPR.

TABLE 7

Final Ubiscan hits for lenalidomide and pomalidomide (1 hr)

| ID | Gene Name | Peptide Sequence | SEQ ID NO: |
|---|---|---|---|
| 1 | 147 G3BP2 | QYYTLLNK*APEYLHR | 16 |
| 2 | 904 COPS6 | QVCEIIESPLFLK*LNPM#TK | 17 |
| 3 | 905 COPS6 | QVCEIIESPLFLKLNPM#TK* | 18 |
| 5 | 1137 VCPIP1 | VGDVQGQESESQLPTKIILT-GQK* | 19 |
| 9 | 1582 HYOU1 | FFGDSAASM#AIK*NPK | 20 |
| 10 | 2541 MCM7 | FLQEFYQDDELGK*K | 21 |
| 13 | 3043 CCT3 | SM#M#K*MLLDPMGGIVM#TNDGNAILR | 22 |
| 14 | 3226 LMNB2 | LSSDQNDK*AASAAR 278 | 23 |
| 16 | 3910 C12orf51 | LSPYLEDVSGGMWPVVHIQK*KNTK | 24 |
| 18 | 3992 EDEM3 | ATGDPYYLEVGK*TLIENLNK | 25 |
| 25 | 4982 RAB28 | VVK*ADIVNYNQEPM#SR | 26 |
| 33 | 7093 HNRNPUL1 | IGWSLDSCSTQLGEEPFSYGYGGTGK*K | 27 |
| 35 | 7556 ABCF2 | YGLTGK*QQVSPIR | 28 |
| 37 | 7740 DNAJC1 | ALPHLIQDAGQFYAKYK* | 29 |

TABLE 7-continued

Final Ubiscan hits for lenalidomide and pomalidomide (1 hr)

| ID | Gene Name | Peptide Sequence | SEQ ID NO: |
|---|---|---|---|
| 38 | 7798GNAS | VLTSGIFETKFQVDK*VNFHM#FDVGGQRDER | 30 |
| 39 | 8193SLC16A1 | ASLEK*AGK | 31 |
| 42 | 10418RPL19 | HMGIGK*R | 32 |
| 43 | 10556RPL36 | AMELLKVSK* | 33 |
| 44 | 10565RPL4 | MFAPTK*TWR | 34 |
| 46 | 11831UBE2Q1 | ELK*LLESIFHR | 35 |
| 47 | 12009ARMC6 | NLVAHGQAFSK*PILDLGAEALIM#QAR | 36 |
| 50 | 12698KLHL7 | ISVNSNNVQSLLDAANQYQIEPVK*K | 37 |
| 51 | 12891NUP37 | FCTSAADMK*IR | 38 |
| 52 | 12942POC5 | VVTSAQQK*AGR | 39 |
| 54 | 13152SNRPE | IM#LK*GDNITLLQSVSN | 40 |

TABLE 8

Final Ubiscan hits for lenalidomide and pomalidomide (MG 1 hr)

| ID | Gene Name | Peptide Sequence | SEQ ID NO: |
|---|---|---|---|
| 1 | 105 DOK5 | K*ASSKGPK | 41 |
| 2 | 324 SHCBP1 | AYQDYILADCK*ASEVQEFTAEFLEK | 42 |
| 4 | 389 YWHAE | MK*GDYHR | 43 |
| 5 | 512 FERMT3 | ETTLSYYK*SQDEAPGDPIQQLNLK | 44 |
| 6 | 904 COPS6 | QVCEIIESPLFLK*LNPM#TK | 45 |
| 7 | 905 COPS6 | QVCEIIESPLFLKLNPM#TK* | 46 |
| 8 | 1010 PCM1 | LMAAK*QK | 47 |
| 9 | 1112 SMC4 | SVAVNPK*EIASK | 48 |
| 10 | 1114 TOPORS | K*IQEQDIINFR | 49 |
| 11 | 1323 HSPA1A | SAVEDEGLK*GK | 50 |
| 12 | 1323 HSPA1B | SAVEDEGLK*GK | 50 |
| 13 | 1452 HSPA8 | DISENK*R | 51 |
| 14 | 1623 ATRX | DNRGGIKSK* | 52 |
| 15 | 1679 DUT | IFYPEIEEVQALDDTERGSGGFGSTGK*N | 53 |
| 16 | 1773 H2AFJ | K*GNYAER | 54 |
| 17 | 1773 HIST1H2AA | 17 | |
| 18 | 1773 HIST1H2AC | K*GNYAER | 54 |

TABLE 8-continued

Final Ubiscan hits for lenalidomide and pomalidomide (MG 1 hr)

| ID | Gene Name | Peptide Sequence | SEQ ID NO: |
|---|---|---|---|
| 19 | 1773 HIST1H2AI | K*GNYAER | 54 |
| 20 | 1773 HIST1H2AK | K*GNYAER | 54 |
| 21 | 1773 HIST2H2AA3 | K*GNYAER | 54 |
| 22 | 1773 HIST2H2AB | K*GNYAER | 54 |
| 23 | 1773 HIST2H2AC | K*GNYAER | 54 |
| 24 | 1863 H2AFX | K*TSATVGPK | 55 |
| 25 | 3146 LMNA | TLEGELHDLRGQVAK*LEAALGEAK | 56 |
| 26 | 3192 LMNA | K*LESTESR | 57 |
| 27 | 3377 TUBA1A | DVNAAIATIK*TK | 58 |
| 28 | 3377 TUBA1B | DVNAAIATIK*TK | 58 |
| 29 | 3377 TUBA1C | DVNAAIATIK*TK | 58 |
| 30 | 3377 TUBA3C | DVNAAIATIK*TK | 58 |
| 31 | 3377 TUBA3D | DVNAAIATIK*TK | 58 |
| 32 | 3377 TUBA3E | DVNAAIATIK*TK | 58 |
| 33 | 3963 DHFR | LTEQPELANK*VDM#VWIVGGSSVYK | 59 |
| 34 | 3984 DHX15 | EVDDLGPEVGDIK*IIPLYSTLPPQQQQR | 60 |
| 37 | 4111 GBA | LLLPHWAK*VVLTDPEAAK | 61 |
| 41 | 4199 IDH3G | NTGK*SIANK | 62 |
| 43 | 4471 PPAT | CGLPYVEVLCK*NR | 63 |
| 44 | 4938 GNB3 | GQQK*TV | 64 |
| 45 | 4938 H2AFZ | GQQK*TV | 64 |
| 46 | 5121 VAV1 | VLK*YHLLLQELVK | 65 |
| 47 | 5121 VAV3 | VLK*YHLLLQELVK | 65 |
| 48 | 5126 VAV1 | IDGELK*ITSVER | 66 |
| 49 | 5252 UCK2 | VLTSEQKAK* | 67 |
| 50 | 5377 ALDOA | ADDGRPFPQVIK*SK | 68 |
| 54 | 5582 SDHA | AFGGQSLKFGK* | 69 |
| 59 | 6046 PSMA7 | AITVFSPDGHLFQVEYAQEAVK*K | 70 |
| 60 | 6046 PSMA8 | AITVFSPDGHLFQVEYAQEAVK*K | 70 |
| 61 | 6049 PSMA7 | AITVFSPDGHLFQVEYAQEAVKK* | 71 |
| 62 | 6049 PSMA8 | AITVFSPDGHLFQVEYAQEAVKK* | 71 |

TABLE 8-continued

Final Ubiscan hits for lenalidomide and pomalidomide (MG 1 hr)

| ID | Gene Name | Peptide Sequence | SEQ ID NO: |
|---|---|---|---|
| 64 | 6567 IRAK2 | CPIPAFPDSVK*PEKPLAASVR | 72 |
| 65 | 6662 PRKDC | NILEESLCELVAKQLK* | 73 |
| 66 | 6662 LOC731751 | NILEESLCELVAKQLK* | 73 |
| 67 | 6741 PRKDC | GHDEREHPFLVK*GGEDLR | 74 |
| 68 | 6741 LOC731751 | GHDEREHPFLVK*GGEDLR | 74 |
| 70 | 7093 HNRNPUL1 | IGWSLDSCSTQLGEEPFSYGYGGTGK*K | 75 |
| 72 | 7306 PCBP2 | LVVPASQCGSLIGK*GGCK | 76 |
| 75 | 7542 ABCE1 | VAETANEEEVKK* | 77 |
| 78 | 7783 GNAL | VLAGK*SK | 78 |
| 79 | 7783 GNAS | VLAGK*SK | 78 |
| 80 | 7939 KCNAB2 | IGVGAM#TWSPLACGIVSGK*YDSGIPPYSR | 79 |
| 81 | 8156 PTCH1 | DKPIDISQLTK*QR | 80 |
| 82 | 8173 SEMA4A | VCK*NDVGGEK | 81 |
| 84 | 8478 ASCC3 | FQALQDNCK*K | 82 |
| 85 | 8779 HMGB2 | IK*SEHPGLSIGDTAK | 83 |
| 86 | 8808 IFI16 | KK*EVDATSPAPSTSSTVK | 84 |
| 88 | 8973 ILF2 | K*ILGQEGDASYLASEISTWDGVIVTPSEK | 85 |
| 89 | 9023 IRF4 | QWLIDQIDSGK*YPGLVWENEEK | 86 |
| 91 | 9082 NACA | NILFVITKPDVYK*SPASDTYIVFGEAK | 87 |
| 92 | 9465 SUPT5H | SSVGETVYGGSDELSDDITQQQLLPGVK*DPNLWTVK | 88 |
| 93 | 9525 TRIP4 | GK*DVEFPNDYPSGCLLGCVDLIDCLSQK | 89 |
| 94 | 9764 EEF1A1 | IGYNPDTVAFVPISGWNGDNM#LEPSANM#PWFK*GWK | 90 |
| 95 | 9764 eEF1AL3 | IGYNPDTVAFVPISGWNGDNM#LEPSANM#PWFK*GWK | 90 |
| 96 | 9766 EEF1A1 | IGYNPDTVAFVPISGWNGDNM#LEPSANM#PWFKGWK* | 91 |
| 97 | 9766 eEF1AL3 | IGYNPDTVAFVPISGWNGDNM#LEPSANM#PWFKGWK* | 91 |
| 98 | 9794 EEF1A1 | AAGAGK*VTK | 92 |
| 99 | 9794 eEF1AL3 | AAGAGK*VTK | 92 |
| 106 | 10407 RPL19 | TLSK*EEETKK | 93 |
| 107 | 10409 RPL19 | TLSKEEETK*K | 94 |
| 108 | 10411 RPL19 | TLSKEEETKK* | 95 |
| 111 | 11082 RPS25 | LVSK*HR | 96 |
| 112 | 11397 COPS3 | LKAM#DQEITVNPQFVQK*SM#GSQEDDSGNKPSSYS | 97 |
| 113 | 11426 CUL9 | ILK*AHGEK | 98 |
| 115 | 11794 UBAP2L | IDLAVLLGK*TPSTMENDSSNLDPSQAPSLAQPLVFSNSK | 99 |
| 116 | 11931 ADRM1 | GTTVTPDK*R | 100 |
| 120 | 12423 FAM10A4 | AK*SEENTKEEKPDSK | 101 |
| 121 | 12423 FAM10A5 | AK*SEENTKEEKPDSK | 101 |
| 122 | 12423 ST13 | AK*SEENTKEEKPDSK | 101 |
| 123 | 12447 FAM129A | VLK*QYDYDSSTIR | 102 |
| 125 | 12609 IGJ | FVYHLSDLCK*K | 103 |
| 126 | 12627 IKZF3 | SHTVEKPYK*CEFCGR | 104 |
| 131 | 13060 S100A6 | EGDKHTLSK*K | 105 |
| 132 | 13212 SSR2 | KYDTPK*TK | 106 |
| 133 | 13250 SSX1 | SK*AFDDIATYFSK | 107 |
| 134 | 13306 TIPRL | LK*VVPTTDHIDTEKLK | 108 |
| 136 | 13598 AMBRA1 | REPFAVVK*TASEM#ER | 109 |
| 137 | 13676 COPG | ALQQYTLEPSEKPFDLK*SVPLATAPM#AEQR | 110 |
| 138 | 13280 TBCC | GK*DAASSTKVDAAPGIPPAVESIQDSPLPK | 111 |
| 139 | 13281 TBCC | GKDAASSTK*VDAAPGIPPAVESIQDSPLPK | 112 |

TABLE 9

Final Ubiscan hits for lenalidomide and pomalidomide (4 hr)

| ID | Gene Name | Peptide Sequence | SEQ ID NO: |
|---|---|---|---|
| 1 | 236 GNB2L1 | LK*TNHIGHTGYLNTVTVSPDGSLCASGGK | 113 |
| 2 | 487 CTNNB1 | LLHPPSHWPLIK*ATVGLIR | 114 |
| 3 | 512 FERMT3 | ETTLSYYK*SQDEAPGDPIQQLNLK | 44 |
| 5 | 663 PKP2 | TYDMLK*AGTTATYEGR | 115 |

TABLE 9-continued

Final Ubiscan hits for lenalidomide and pomalidomide (4 hr)

| ID | Gene | Name | Peptide Sequence | SEQ ID NO: |
|---|---|---|---|---|
| 6 | 732 | HSP90B1 | NLGTIAK*SGTSEFLNK | 116 |
| 9 | 1112 | SMC4 | SVAVNPK*EIASK | 48 |
| 10 | 1863 | H2AFX | K*TSATVGPK | 55 |
| 11 | 2508 | HIST2H2AB | KTESHKPGK*NK | 117 |
| 12 | 2512 | HIST2H2AB | KTESHKPGKNK* | 118 |
| 13 | 2579 | NAP1L2 | GLIGYVLDTDFVESLPVKVK* | 119 |
| 15 | 3712 | TPD52 | SFEEK*VENLK | 120 |
| 16 | 3742 | VAPA | RYCVRPNSGIIDPGSTVTVSVM#LQPFDYDPNEKSK* | 121 |
| 17 | 3799 | AKR1B1 | LLLNNGAK*M#PILGLGTWK | 122 |
| 18 | 3916 | CHPF | SALTAHPVRDPVHMYQLHK*AFAR | 123 |
| 19 | 3955 | DDX24 | ATNEGLSLM#LIGPEDVINFKK* | 124 |
| 20 | 4035 | FASN | DGLLENQTPEFFQDVCKPK* | 125 |
| 23 | 4181 | HMOX1 | K*AALEQDLAFWYGPR | 126 |
| 25 | 4347 | NANS | QLLPCEMACNEK*LGK | 127 |
| 27 | 4938 | GNB3 | GQQK*TV | 64 |
| 28 | 4938 | H2AFZ | GQQK*TV | 64 |
| 29 | 4968 | NET1 | IGEATK*PDGTVEQIGHILVSWLPR | 128 |
| 31 | 5672 | ANP32E | KLELSDNIISGGLEVLAEK*CPNLTYLNLSGNK | 129 |
| 32 | 5676 | CDC25C | SLNQYPALYYPELYILK*GGYR | 130 |
| 33 | 5732 | PPP1CB | AK*YQYGGLNSGRPVTPPR | 131 |
| 35 | 6543 | CHEK1 | M#CGTLPYVAPELLK*R | 132 |
| 36 | 6546 | CSNK1A1 | LFLIDFGLAK*K | 133 |
| 37 | 6546 | CSNK1A1L | LFLIDFGLAK*K | 133 |
| 38 | 6563 | IRAK1 | GTLAYLPEEYIK*TGR | 134 |
| 40 | 6843 | PRKAG2 | KK*DVSSPGGSGGK*K*NASQK* | 135 |
| 41 | 6858 | CPSF3L | VNCYM#PANGETVTLPTSPSIPVGISLGLLK*R | 136 |
| 42 | 7344 | RARS | SDGGYTYDTSDLAAIK*QR | 137 |
| 43 | 7672 | C7orf42 | QSNPEFCPEK*VALAEA | 138 |
| 44 | 7717 | CPNE1 | SEVIK*NNLNPTWK | 139 |
| 46 | 8137 | NUP88 | IYSLREPQTPTNVIILSEAEEESLVLNK*GR | 140 |
| 47 | 8331 | TCIRG1 | QEENK*AGLLDLPDASVNGWSSDEEK | 141 |
| 48 | 8723 | FAF1 | K*SPM#M#PENAENEGDALLQFTAEFSSR | 142 |
| 49 | 8734 | FUBP3 | ITGDAFK*VQQAR | 143 |
| 54 | 9253 | PSMC3 | LAGPQLVQM#FIGDGAK*LVR | 144 |
| 55 | 9526 | TSG101 | ASLISAVSDK*LR | 145 |
| 56 | 9794 | EEF1A1 | AAGAGK*VTK | 92 |
| 57 | 9794 | eEF1AL3 | AAGAGK*VTK | 92 |

TABLE 9-continued

Final Ubiscan hits for lenalidomide and pomalidomide (4 hr)

| ID | Gene Name | Peptide Sequence | SEQ ID NO: |
|---|---|---|---|
| 58 | 9933EIF2S1 | ADIEVACYGYEGIDAVK*EALR | 146 |
| 62 | 10690RPL9 | K*FLDGIYVSEK | 147 |
| 64 | 11010RPS2 | AEDK*EWMPVTK | 148 |
| 65 | 11010LOC645018 | AEDK*EWMPVTK | 148 |
| 66 | 11585NAE1 | CINITK*QTPSFWILAR | 149 |
| 67 | 11831UBE2Q1 | ELK*LLESIFHR | 35 |
| 68 | 12110C13orf40 | KPDLRIIEQEEK* | 150 |
| 70 | 12242COMMD4 | LEVAAAPGTPAQPVAM#SLSADK*FQVLLAELK | 151 |
| 71 | 12320DDIT4 | GALLDVCVEQGK*SCHSVGQLALDPSLVPTF | 152 |
| 72 | 12458FAM60A | TPVFSFLDLTYWK*R | 153 |
| 73 | 12545HLA-E | GYEQFAYDGK*DYLTLNEDLR | 154 |
| 74 | 12758MAGEA3 | AREPVTK*AEM#LGSVVGNWQYFFPVIFSK | 155 |
| 75 | 12758MAGEA6 | AREPVTK*AEM#LGSVVGNWQYFFPVIFSK | 155 |
| 76 | 12865NHP2 | IK*ADPDGPEAQAEACSGER | 156 |
| 78 | 13290TBL3 | LWTIK*NNECVR | 157 |
| 79 | 13930NEDD8 | QMNDEK*TAADYK | 158 |
| 80 | 403YWHAZ | YLAEVAAGDDK*K | 159 |
| 81 | 805SHISA5 | SQPPYNPAYM#DAPK*AAL | 160 |
| 82 | 2089HIST1H1A | GTLVQTK*GTGASGSFK | 161 |
| 83 | 2089HIST1H1B | GTLVQTK*GTGASGSFK | 161 |
| 84 | 2089HIST1H1C | GTLVQTK*GTGASGSFK | 161 |
| 85 | 2089HIST1H1D | GTLVQTK*GTGASGSFK | 161 |
| 86 | 2089HIST1H1E | GTLVQTK*GTGASGSFK | 161 |
| 87 | 13902NEDD8 | LIYSGK*QMNDEK | 162 |
| 88 | 14057RPS27A | K*IQDK*EGIPPDQQR | 163 |
| 89 | 14057RPS27AP5 | K*IQDK*EGIPPDQQR | 163 |
| 90 | 14057UBA52 | K*IQDK*EGIPPDQQR | 163 |
| 91 | 14057UBB | K*IQDK*EGIPPDQQR | 163 |
| 92 | 14057UBC | K*IQDK*EGIPPDQQR | 163 |

TABLE 10

Final Ubiscan hits for lenalidomide and pomalidomide (MG 4 hr)

| ID | Gene Name | Peptide Site | SEQ ID NO: |
|---|---|---|---|
| 1 | 11 PLAA | FIIDNTK*GQM#LGLGNPSFSDPFTGGGR | 164 |
| 2 | 259 HGS | ACGQIFCGK*CSSK | 165 |
| 3 | 260 HGS | ACGQIFCGKCSSK* | 166 |
| 4 | 358 UBE2M | VGQGYPHDPPK*VK | 167 |

TABLE 10-continued

Final Ubiscan hits for lenalidomide and pomalidomide (MG 4 hr)

| ID | Gene | Name | Peptide Site | SEQ ID NO: |
|---|---|---|---|---|
| 5 | 361 | UBE2M | VGQGYPHDPPKVK* | 168 |
| 6 | 533 | IL32 | GDK*EELTPQK | 169 |
| 7 | 826 | ANXA7 | AM#K*GFGTDEQAIVDVVANR | 170 |
| 8 | 917 | CP110 | NKMLGTSSKESEELLK*SK* | 171 |
| 9 | 1112 | SMC4 | SVAVNPK*EIASK | 48 |
| 10 | 1146 | ANP32B | IFGGLDM#LAEKLPNLTHLNLSGNKLK* | 172 |
| 11 | 2579 | NAP1L2 | GLIGYVLDTDFVESLPVKVK* | 119 |
| 12 | 2591 | PURA | FFFDVGSNK*YGVFM#R | 173 |
| 13 | 2768 | VCP | KAFEEAEK*NAPAIIFIDELDAIAPKR | 174 |
| 14 | 2791 | VCP | ELQELVQYPVEHPDKFLK* | 175 |
| 15 | 2929 | ACTB | DIK*EKLCYVALDFEQEMATAASSSSLEK | 176 |
| 16 | 2929 | ACTG1 | DIK*EKLCYVALDFEQEMATAASSSSLEK | 176 |
| 17 | 2929 | POTEE | DIK*EKLCYVALDFEQEMATAASSSSLEK | 176 |
| 18 | 3231 | LSP1 | QEM#LLSLK*PSEAPELDEDEGFGDWSQRPEQR | 177 |
| 19 | 3281 | NES | TSLSFQDPK*LELQFPR | 178 |
| 20 | 3575 | AUP1 | FPSSGPVTPQPTALTFAK*SSWAR | 179 |
| 21 | 3588 | MAN1A1 | GYAWGLNELK*PISK | 180 |
| 22 | 3589 | MAN1A1 | K*GSGPAALR | 181 |
| 23 | 3712 | TPD52 | SFEEK*VENLK | 120 |
| 24 | 3740 | VAPA | YCVRPNSGIIDPGSTVTVSVM#LQPFDYDPNEK*SK | 182 |
| 27 | 4483 | PPIA | VSFELFADK*VPK | 183 |
| 29 | 4655 | TPI1 | ELASQPDVDGFLVGGASLK*PEFVDIINAKQ | 184 |
| 30 | 4656 | TPI1 | KQSLGELIGTLNAAK*VPADTEVVCAPPTAYIDFAR | 185 |
| 31 | 4938 | GNB3 | GQQK*TV | 64 |
| 32 | 4938 | H2AFZ | GQQK*TV | 64 |
| 33 | 5308 | ALDOA | VDK*GVVPLAGTNGETTTQGLDGLSER | 186 |
| 34 | 5459 | MTX1 | FTGAPLK*VHKISNPWQSPSGTLPALR | 187 |
| 35 | 5573 | PTRH2 | TQIAPGSQTVLGIGPGPADLIDKVTGHLK*LY | 188 |
| 36 | 5640 | MYL6 | VFDK*EGNGTVMGAEIR | 189 |
| 37 | 5792 | PPP3CA | HLTEYFTFK*QECK | 190 |
| 38 | 5792 | PPP3CB | HLTEYFTFK*QECK | 190 |
| 39 | 5810 | PPP3CC | SQATGFPSLITIFSAPNYLDVYNNK*AAVLK | 191 |
| 40 | 6427 | UCHL5 | TLAEHQQLIPLVEKAK* | 192 |
| 41 | 6449 | USP15 | GPSTPNVK*NSNYCLPSYTAYK | 193 |
| 42 | 6558 | HUNK | K*PEPHQPGPGSTGIPHK*EDPLMLDM#VR | 194 |
| 45 | 6861 | CPSF6 | KTTQSGQMSGEGK*AGPPGGSSR | 195 |
| 46 | 7088 | HNRNPR | IK*ALLER | 196 |
| 47 | 7088 | SYNCRIP | IK*ALLER | 196 |

TABLE 10-continued

Final Ubiscan hits for lenalidomide and pomalidomide (MG 4 hr)

| ID | Gene Name | Peptide Site | SEQ ID NO: |
|---|---|---|---|
| 48 | 7186MORC3 | STNQQTATDVSTSSNIEESVNHM#DGESLK*LR | 197 |
| 49 | 7240PABPC1 | VVCDENGSK*GYGFVHFETQEAAER | 198 |
| 50 | 7522ABCE1 | STALK*ILAGK | 199 |
| 51 | 7672C7orf42 | QSNPEFCPEK*VALAEA | 138 |
| 52 | 8030MLC1 | K*GSMSDSANILDEVPFPAR | 200 |
| 53 | 8239SLC35F2 | TAEPAESSVPPVTSIGIDNLGLK*LEENLQETHSAVL | 201 |
| 54 | 8370TMEM57 | KHNLGINNNNILQPVDSKIQEIEYM#ENHINSK* | 202 |
| 56 | 9215POLR2L | CFTCGKIVGNK*WEAYLGLLQAEYTEGDALDALGLKR | 203 |
| 57 | 9354RSF1 | AQIDPVLLK*NSSQQDNSSR | 204 |
| 58 | 9398SP140 | MK*ESPGSQQCCQESEVLER | 205 |
| 59 | 9468TBL1XR1 | DK*LAQQQAAAAAAAAAAASQQGSAK | 206 |
| 61 | 10524RPL30 | KSEIEYYAM#LAK*TGVHHYSGNNIELGTACGK*YYR | 207 |
| 62 | 11010RPS2 | AEDK*EWMPVTK | 148 |
| 63 | 1101LOC645018 | AEDK*EWMPVTK | 148 |
| 64 | 11435DCUN1D1 | QFM#IFTQSSEK*TAVSCLSQNDWK | 208 |
| 65 | 11510MDM2 | ENWLPEDKGKDKGEISEK* | 209 |
| 66 | 11580MIB1 | SSEDATDDISSGNIPVLQK*DKDNTNVNADVQK | 210 |
| 67 | 11581MIB1 | SSEDATDDISSGNIPVLQKDK*DNTNVNADVQK | 211 |
| 68 | 11830UBE2O | STDSQCGTVIDVNIDCAVK*LIGTNCIIYPVNSK | 212 |
| 69 | 11969ANKRD13A | LTLDLM#KPK* | 213 |
| 71 | 12110C13orf40 | KPDLRIIEQEEK* | 150 |
| 72 | 12127C19orf43 | QKTEDEVLTSK*GDAWAK | 214 |
| 73 | 12129C19orf43 | QKTEDEVLTSKGDAWAK* | 215 |
| 74 | 12171CAPN8 | LAGKDSEITANALK* | 216 |
| 75 | 12259COPS8 | K*PVAGALDVSFNKFIPLSEPAPVPPIPNEQQLAR | 217 |
| 76 | 12322DDIT4 | K*LYSSEQLLIEEC | 218 |
| 77 | 12432FAM114A1 | SVLTGGLDALEFIGK* | 219 |
| 78 | 12564HSPBP1 | AMQQQVQK*LK | 220 |
| 79 | 12929PLIN2 | GAVTGSVEK*TK | 221 |
| 80 | 12930PLIN2 | GAVTGSVEKTK* | 222 |
| 81 | 13264STRBP | M#VLLPVM#K*FPTYPVPHYSFF | 223 |
| 82 | 13561WDR6 | MVK*VDPETR | 224 |
| 83 | 13849VAMP8 | NLQSEVEGVK*NIMTQNVER | 225 |
| 84 | 2097HIST1H1A | K*ALAAAGYDVEKNNSR | 226 |
| 85 | 2097HIST1H1C | K*ALAAAGYDVEKNNSR | 226 |
| 86 | 2097HIST1H1D | K*ALAAAGYDVEKNNSR | 226 |
| 87 | 2097HIST1H1E | K*ALAAAGYDVEKNNSR | 226 |
| 88 | 2097HIST1H1T | K*ALAAAGYDVEKNNSR | 226 |

TABLE 10-continued

Final Ubiscan hits for lenalidomide and pomalidomide (MG 4 hr)

| ID | Gene Name | Peptide Site | SEQ ID NO: |
|---|---|---|---|
| 89 | 3242 MYO18A | INSLQDMVTK*YQKR | 227 |
| 90 | 4677 UAP1 | LTLSK*AGQEHLLR | 228 |
| 91 | 8262 SLC3A2 | IK*VAEDEAEAAAAAK | 229 |

6.18 Efficacy of Lenalidomide in Activated B-Cell Like Subtype DLBCL is Dependent Upon Expression of IRF4 and CRBN Cell Proliferation Assay Cell proliferation was assessed using the $^3$H-thymidine incorporation assay. Briefly, logarithmically growing DLBCL cells were cultured in 96-well culture plates in complete media with the indicated concentration of lenalidomide or DMSO control. Following incubation at 37° C. for 5 days, 1 μCi $^3$H-thymidine (GE Healthcare Biosciences, Piscataway, N.J.) was added to each well for the final 5 hours of incubation. Cells were then harvested onto UniFilter GF/C filter plates (PerkinElmer, Waltham, Mass.) using a cell harvester (Tomtec, Hamden, Conn.) and the plates were allowed to dry overnight. The $^3$H-thymidine incorporation of each well was then measured using a TopCount NXT Microplate Scintillation and Luminescence Counter (Packard Bio-Science, Meriden, Conn.). The percent inhibition of cell proliferation was calculated and normalized to DMSO control.

Protein Expression Analysis

Cells were treated with test compounds or 0.1% DMSO for indicated times. Following incubation, cells were collected, pelleted with centrifugation, and immediately lysed in 0.1 ml lysis buffer containing 10 mM Tris-HCl pH 8.0, 10 mM EDTA, 150 mM NaCl, 1% NP-40, 0.5% SDS, 1 mM DTT, 1 mM Na$_3$VO$_4$, plus Complete protease inhibitor cocktail (Roche Applied Science, Indianapolis, Ind.), then processed with a Qiashredder™ (Qiagen, Valencia, Calif.) for 1 minute and frozen on dry ice. Samples were diluted with 6×SDS sample buffer and then boiled for 5 min. Approximately 30 μl of this mixture was loaded per lane on a Criterion Precast 4-12% Tris-HCl gel (Bio-Rad, Hercules, Calif.), electrophoresed, and transferred to nitrocellulose membranes (Bio-Rad, Hercules, Calif.). The membranes were blocked for 1 hour at room temperature using blocking buffer (LI-COR Biosciences, Lincoln, Nebr.), then incubated overnight at 4° C. with antibodies against either BCL-10, IRF4, CRBN or β-actin. Membranes were washed and incubated with IRDye Secondary Antibodies (1:30,000) for 1 hour at room temperature. A standard protocol was then followed for signal detection, using the Odyssey® Infrared Imaging System and software (LI-COR Biosciences, Lincoln, Nebr.).

NF-κB Activity Assays

Logarithmically growing DLBCL cells were treated with test agents as indicated. Nuclear extracts were prepared using a Nuclear Extract Kit (Active Motif, Carlsbad, Calif.) and protein concentration was determined by the bicinchoninic acid assay (Thermo Scientific, Rockford, Ill.). Detection of NF-κB activity was performed using a sensitive oligo-based colorimetric enzyme-linked immunosorbent assay (ELISA) method, according to the instructions of the manufacturer (Active Motif). Briefly, nuclear extracts of DLBCL cells were hybridized to 96-well plates coated with wild-type DNA oligonucleotides containing a single copy of the NF-κB consensus binding sequence. Bound NF-κB protein was then detected with antibodies specific for p50, p65 (Rel A) or p70 subunits. A secondary antibody conjugated to horseradish peroxidase was added and plates were then read by spectrophotometry at 450 nm with a reference wavelength of 655 nm. NF-κB activity was calculated based on OD450/655 nm.

For the NF-κB-driven luciferase reporter gene assay, cells were transfected with the pGL4.32 [luc2P/NF-κB-RE/Hygro] plasmid (Promega, Madison, Wis.) using Nucleofector kit V and program 013 according to the manufacturer's protocol (Amaxa Biosystems, Gaithersburg, Md.). After 24 hours of transfection, cells were treated with test agents for 2 days and lysates were prepared using the Dual-Glo® Luciferase Assay System (Promega). Luciferase activities of each sample were measured using a TopCount NXT Microplate Scintillation and Luminescence Counter (Packard Bio-Science).

Real-Time Quantitative Reverse Transcriptase-PCR Analysis

After 48 hours of cell treatment, total RNA was purified with RNeasy® Mini Kits using QiaCube™ system (Qiagen Inc., Valencia, Calif.). Real-time quantitative RT-PCR with 25-100 ng of total RNA was performed using the reverse transcription kit and Taqman® PCR probes specific for the genes of interest according to standard methods (Applied Biosystems Inc.). The quantity of product was normalized to glyceraldehyde-3-phosphate dehydrogenase as the endogenous housekeeping gene. Fold increase of gene expression was calculated using comparative Ct method ($2^{-\Delta\Delta Ct}$).

Electroporation for Overexpression and Knockdown of IRF4

To knockdown IRF4, cells were transfected with Silencer® Select siRNA (small interfering RNA, Applied Biosystems) directed against IRF4, CRBN, or Silencer® Select Negative Control siRNAs at a final concentration of 0.2-1 μM using Nucleofector® Kit V for transfection. For IRF4 overexpression, cells were transfected with IRF4- or green fluorescent protein (GFP)-cytomegalovirus (CMV) expression plasmids (OriGene Technologies, Rockville, Md.) for 24 h using the Cell Line Nucleofector kit V as above-mentioned. After 24 hours of transfection, cells were treated with lenalidomide for 2 days before luciferase assay, RT-PCR gene expression analysis and Western blot.

Human Tumor Xenograft Model

Female CB17 severe combined immunodeficiency (SCID) mice (6-12 weeks old) were obtained from the Charles River Laboratory (Wilmington, Mass.) and maintained in microisolator cages under sterile conditions. A total of 10×10$^6$ OCI-Ly10 DLBCL cells in 100% Matrigel (Becton Dickinson, San Jose, Calif.) were injected subcutaneously into the right flank of mice. Mice were monitored 2 or 3 times a week for the appearance of tumors. Once the tumors reached an average size of 100-150 mg, 10 mice in each group were treated with either vehicle (0.5% carboxymethyl cellulose: 0.25% Tween 80 in deionized H$_2$O) or indicated doses of lenalidomide (qd×28, p.o.) or the positive control vincristine (q4d×4, i.v.). Mice were monitored daily for health status as well as tumor growth. Tumors of all mice were measured with a digital caliper and volumes calculated with the following formula: tumor volume (mm$^3$)=length (mm)×width (mm)$^2$. Mice were killed when tumor size exceeded 1000 mm$^3$.

Statistical Analysis

Analyses for multiple group comparisons were performed with one-way analysis of variance, followed by Dunnett's post-test, and correlation analyses were carried out using the two-tailed P-value Pearson test using GraphPad Prism® version 5.01 (San Diego, Calif.). A value of P<0.05 was considered significant in all analyses.

Results

6.18.1 ABC-DLBCL Cells are More Sensitive to Lenalidomide than Non-ABC-DLBCL Cells In order to define the place of lenalidomide for DLBCL therapy in specific patient populations and to understand the molecular mechanisms of efficacy, a panel of DLBCL cell lines was collected in this study. The DLBCL subtypes of the cell lines were confirmed based on literature information (Lenz G, et al., *Proc Natl Acad Sci USA* 2008; 105: 13520-5) and molecular analysis, including intracellular NF-κB activity or IRF4 expression, as well as gene expression profiling of key signature genes of activated B cells. See FIGS. 24A-24C. Cell proliferation of DLBCL cell lines was found to be inhibited to various degrees by treatment with lenalidomide at a concentration range of 0.01-100 μM. Lenalidomide had minimal effects on proliferation of PBML and GCB-DLBCL cells, but significantly inhibited proliferation of ABC-DLBCL cell lines, except for OCI-Ly3. See FIG. 24. Lenalidomide treatment also induced apoptosis of sensitive cell lines such as OCI-Ly10. See FIG. 26.

6.18.2 Lenalidomide Reduces IRF4 Expression in ABC-DLBCL Cells

To understand the molecular mechanism of lenalidomide on ABC-DLBCL cells, the effects of lenalidomide on IRF4 expression in these cells were investigated. Lenalidomide treatment for 1-3 days was found to significantly downregulate IRF4 protein levels in sensitive cell lines such as U2932 and OCI-Ly10, but not the insensitive line OCI-Ly3 cells. See FIGS. 27A-C. Lenalidomide-induced decrease of IRF4 expression occurred as early as 1 day of drug treatment, with similar kinetics to that of the inhibitors (zVRPR-fmk and LY-333,531, respectively) of MALT1 and PKCβ, two key enzymes involved in NF-κB activation upon BCR engagement in B cells. In OCI-Ly3 cells, neither lenalidomide nor the PKCβ inhibitor had any appreciable effect on IRF4 levels during 1-3 day treatments. However, the MALT1 inhibitor suppressed IRF4 expression in OCI-Ly3 cells, with complete inhibition observed after 2-3 days of treatment. Taken together, these data suggest that lenalidomide-mediated inhibition of IRF4 expression may be an important mechanism and appears to be related to cell sensitivity to the drug.

6.18.3 Lenalidomide Reduces CARD11-BCL-10-MALT1 Complex Activity of ABC-DLBCL Cells Our DNA sequencing data confirmed previous reports (Lenz, G., et al., *Science* 2008, 319: 1676-9) that the lenalidomide-insensitive ABC-DLBCL line OCI-Ly3 has a unique point mutation in CARD11 within the exons encoding the coiled-coil domain, while lenalidomide-sensitive ABC-DLBCL lines OCI-Ly10, U2932, TMD8, and Riva do not. See FIG. 28. This mutation has been reported to cause constitutive formation and activation of CARD11-BCL-10-MALT1 (CBM) complex of BCR signaling pathway, leading to NF-κB overactivation in lymphoma cells. See Lenz, G., et al., *Science* 2008, 319: 1676-9; Thome, M. et al., *Cold Spring Harb Perspect Biol.* 2010; 2: a003004. To investigate the potential involvement of CBM complex in lenalidomide-induced IRF4 inhibition in these cells, the effect of lenalidomide on the complex activity was examined by measuring MALT1 paracaspase enzymatic activity. MALT1 is activated upon association with BCL-10 and CARD11 to form active CBM complex and then cleaves its binding partners, such as BCL-10. See FIGS. 29A-C.

Similar to the effect of the specific MALT1 inhibitor and PKCβ inhibitor, lenalidomide inhibited MALT1-induced BCL-10 cleavage in a concentration-dependent manner in the sensitive ABC-DLBCL cell lines OCI-Ly10 and U2932. Time-kinetic studies revealed that while MALT1- and PKCβ-inhibitors affected BCL-10 cleavage within 1 day of treatment, significant inhibition of BCL-10 cleavage by lenalidomide occurred after 2 days of treatment. See FIGS. 29A and 29B. Unlike the MALT1 inhibitor, neither the PKCβ inhibitor nor lenalidomide had any effect on BCL-10 cleavage in OCI-Ly3 cells, presumably due to CARD11 mutation which causes over-activation of CBM complex. See FIG. 29C. These data suggest that lenalidomide, similar to the PKCβ inhibitor, can significantly block CBM complex formation/activation or other upstream events in sensitive ABC-DLBCL cells.

6.18.4 Lenalidomide Reduces NF-κB Activity of ABC-DLBCL Cells but not Non-ABC Subtype Cells The effect of lenalidomide on NF-κB activity in various DLBCL cells was examined by measuring the level of NF-κB subunit proteins binding to consensus sequences and the NF-κB-driven luciferase activity. As expected, NF-κB in ABC-DLBCL cells demonstrated increased NF-κB DNA binding compared to non-ABC-DLBCL. See FIG. 24B. An NF-κB-driven luciferase assay demonstrated that lenalidomide inhibited transcriptional activity of NF-κB by 32-56% in the lenalidomide-sensitive ABC-DLBCL cell lines OCI-Ly10 and U2932 after 2 day drug treatment. See FIG. 30A. Lenalidomide also partially inhibited DNA binding by Rel A/p65, p50 and c-rel/p70 NF-κB subunits in a concentration-dependent manner in several ABC-DLBCL cell lines, although the effect was not as potent as the control IKKα/β inhibitor CC-415501. See FIGS. 30B and 30C. In contrast, lenalidomide had no effect on NF-κB DNA binding in GCB-DLBCL lines nor in normal peripheral blood mononuclear cells. The lenalidomide-insensitive ABC-DLBCL OCI-Ly3 line containing the CARD11 mutation showed significant NF-κB inhibition only by the IKKα/β inhibitor, and not by lenalidomide. See FIGS. 30B and 30C. These data suggest that lenalidomide inhibits NF-κB signaling at CBM complex or upstream events in sensitive ABC-DLBCL cells.

6.18.5 Alteration of IRF4 Expression in Sensitive ABC-DLBCL Cells Confers Resistance to Lenalidomide The dependency role of IRF4 expression in BCR-NF-κB signal transduction and the sequent effects of lenalidomide treatment upon IRF4 were investigated. Lenalidomide-sensitive ABC-DLBCL cells were transfected with IRF4-specific siRNA or IRF4-CMV-based expression plasmid to modulate IRF4 expression. When U2932 or OCI-Ly10 cells were transfected with IRF4 siRNA to knock down the expression of IRF4, NF-κB transcriptional activity was diminished by 36-53%. See FIG. 31A. Thus IRF4 siRNA mimicked the effects of lenalidomide on NF-κB in these cells. The addition of lenalidomide to the IRF4 siRNA-transfected cells led to even further downregulation of NF-κB transcriptional activity.

In contrast to IRF4 siRNA transfection, over-expressing IRF4 in these cells for 24 h significantly increased NF-κB activity by 3.6-7.9 fold. See FIG. 31B. Furthermore, IRF4 overexpression decreased protein expression levels of the CBM-component BCL-10. See FIG. 31C. In addition, IRF4 overexpression antagonized the effect of lenalidomide and the PKCβ inhibitor but not the IKK inhibitor on NF-κB-driven luciferase expression in both U2932 and OCI-Ly10 cells. See FIG. 31D. Therefore, the positive feedback effect of IRF4 on the BCR-NFκB pathway appeared to be at a point somewhere between PKCβ and IKK.

6.18.6 Cereblon is Required for Lenalidomide Effect on ABC-DLBCL Cells

Cereblon has been shown to be a primary mediator of the teratogenicity of thalidomide. Due to its critical role in the anti-myeloma and immunomodulatory activities of lenalidomide and pomalidomide, the role of cereblon in lenalidomide sensitivity of DLBCL was investigated. In ABC-DLBCL cells, knockdown of CRBN with siRNA conferred resistance to lenalidomide as demonstrated by the abrogation of the inhibitory effects of lenalidomide on IRF4 expression, BCL-10 cleavage, NF-κB activity and proliferation of these cells, while the activity of inhibitors to PKCβ and IKK remained unaffected. See FIGS. 32A-32D. These data indicate that antitumor effects of lenalidomide on ABC-DLBCL cells require the presence of cereblon.

6.18.7 Lenalidomide Down-Regulates IRF4/NF-κB Signaling in OCI-Ly10 Mouse Xenograft Model To confirm the relevance of lenalidomide-mediated inhibition of NF-κB/IRF4 signaling in vivo in ABC-DLBCL, a subcutaneous OCI-Ly10 xenograft model was established. Lenalidomide at 3-30 mg/kg (po, qdX28) significantly decreased tumor size in this model (p<0.01). See FIG. 33A. No pronounced toxicity of lenalidomide was observed based upon mouse weight throughout study. Compared with vehicle control group, lenalidomide treatment for 7 days reduced IRF4 expression and BCL-10 cleavage by 15-35% (p<0.05). See FIG. 33B. These data demonstrate that lenalidomide can reduce IRF4 expression in vivo and delays tumor growth in an ABC-DLBCL model, supporting the potential value of lenalidomide as a therapeutic in the treatment of ABC-DLBCL in clinical studies.

6.18.8 IRF4 and CRBN Baseline mRNA Levels and "ABC scores" of DLBCL Cells Correlate with Sensitivity to Lenalidomide As multiple studies have demonstrated greater lenalidomide sensitivity of ABC-DLBCL cells versus non-ABC-subytpes, potential biomarkers predictive for a therapeutic response to lenalidomide were studied. Pooled in vitro data from eleven DLBCL cell lines of various subtypes showed that lenalidomide sensitivity of DLBCL subtypes highly correlated to the baseline level of IRF4 and CRBN mRNA expression. Additionally, the overall "ABC score," calculated based on baseline levels of signature genes of ABC-DLBCL cells proposed by Staudt, et al. (*Ann. Rev. Med.*, 2002, 53: 303-18), correlated to lenalidomide activity and further confirms the unique sensitivity of this subtype. See FIGS. 34A and 25. Lenalidomide-sensitive ABC-DLBCL cell lines tended to express higher CRBN and IRF4 protein levels than GCB-DLBCL cell lines. See FIG. 34B. Notably, the lenalidomide-resistant OCI-Ly3 ABC-DLBCL cell line was devoid of CRBN protein expression. These data support the preferential efficacy of lenalidomide in ABC-DLBCL seen in clinical studies, and suggest that the "ABC score," or the expression of IRF4 or CRBN itself, may serve as potential biomarkers for the prediction of lenalidomide efficacy.

6.19 Polyclonal CRBN70 Antibody

Rabbit polyclonal antibody CRBN70 was generated by inoculating rabbits with the CRBN peptide sequence EEFHGRTLHDDD (residues 1-12 of SEQ ID NO:1), wherein a C-terminal cysteine EEFHGRTLHDDDC (SEQ ID NO: 1) (underlined) is further used to couple the peptide to Keyhole Limpet Hemocyanin (KLH).

| Seq. | Mod. |
|---|---|
| EEFHGRTLHDDDC-KLH | KLH-Peptide Cys |

The peptide depicted in SEQ ID NO:1 used to make the antibody corresponds to amino acids 65-76 (bolded) of CRBN isoform 1 (NP_057386) (SEQ ID NO:12):

```
  1   magegdqqda ahnmgnhlpl lpaeseeede mevedqdske akkpniinfd tslptshtyl
 61   gadmeefhgr tlhdddscqv ipvlpqvmmi lipgqtlplq lfhpqevsmv rnliqkdrtf
121   avlaysnvqe reaqfgttae iyayreeqdf gieivkvkai grqrfkvlel rtqsdgiqqa
181   kvqilpecvl pstmsavqle slnkcqifps kpvsredqcs ykwwqkyqkr kfhcanltsw
241   prwlyslyda etlmdrikkq lrewdenlkd dslpsnpidf syrvaaclpi ddvlriqllk
301   igsaiqrlrc eldimnkcts lcckqcqete ittkneifsl slcgpmaayv nphgyvhetl
361   tvykacnlnl igrpstehsw fpgyawtvaq ckicashigw kftatkkdms pqkfwgltrs
421   allptipdte deispdkvil cl
```

It is noted that isoform 2 of CRBN (GenBank Accession No. NP_001166953; SEQ ID NO:13) uses an alternate in frame splice site that results in the elimination of the alanine (underlined), but has no other changes:

```
  1  magegdqqda ahnmgnhlpl lpeseeedem evedqdskea kkpniinfdt slptshtylg 61  admeefhgrt lhdddscqvi pvlpqvmmil ipgqtlplql fhpqevsmvr nliqkdrtfa 121  vlaysnvqer eaqfgttaei yayreeqdfg ieivkvkaig rqrfkvlelr tqsdgiqqak 181  vqilpecvlp stmsavqles lnkcqifpsk pvsredqcsy kwwqkyqkrk fhcanltswp 241  rwlyslydae tlmdrikkql rewdenlkdd slpsnpidfs yrvaaclpid dvlriqllki 301  gsaiqrlrce ldimnkctsl cckqcqetei ttkneifsls lcgpmaayvn phgyvhetlt 361  vykacnlnli grpstehswf pgyawtvaqc kicashigwk ftatkkdmsp qkfwgltrsa 421  llptipdted eispdkvilc l
```

The polyclonal CRBN70 antibody was purified. Purified antibody was then titered by indirect ELISA against the peptide or protein bound to a solid-phase to measure the reactivity of the antibodies after elution and the amount of antibody remaining in serum (the flow-through).

| Sample | Volume (mL) | Conc. (mg/mL) | Total (mg) | Titer (ng) | Flow-through |
|---|---|---|---|---|---|
| CRBN70 | 6 | 0.414 | 2.484 | 5 | 2048 |

The eluent "titer" indicates the minimum concentration at which the CRBN70 antibody can effectively detect the CRBN antigen. The "flow-through" titer represents the reactivity of the antibodies remaining in the serum after it has been passed through the column.

6.20 Sequences of VH and VL of Anti-CRBN Antibodies

Rabbits were primed with amino acid sequence 65-76 (SEQ ID NO:1) of human CRBN (SEQ ID NO:12), and the spleen was removed for IgG subtyping and monoclonal antibody creation.

The IgG heavy and light chains from two CGN-6 hybridoma clones were sequenced by Epitomics. The two clones were CGN-6-1-11 and CGN-6-4-5.

Brief Methods Description of RabMAb IgG Molecular Cloning:

Messenger RNA (mRNA) from hybridoma cells was isolated using TURBOCAPTURE Kit (Qiagen: Catalog #72232) following the manufacturer's suggested protocol, and then reverse transcribed into cDNA using oligo-dT primer. The variable region of heavy chain (VH) was PCR amplified using proprietary primers OYZ64-2 and OYZvh3. The entire light chain (LC) was PCR amplified using proprietary primers OYZ62 and OYZ71. The PCR products were resolved on 1% argrose gel followed by purification using Qiagen gel purification kit (Qiagen: Catalog #28704), and the purified DNA fragments were subjected to sequencing.

```
CGN-6-1-11-Heavy chain nucleotide sequence (SEQ ID NO: 4):
ATGGAGACTGGGCTGCGCTGGCTTCTCCTGGTCGCTGTGCTCAAAGGTGTCCACTGTCAGTCAGTGGAGGAGTCCGG

GGGTCGCCTGGTCACGCCTGGGACACCCCTGACACTCACCTGTACAGTCTCTGGATTCTCCCTCAGTTACTATGGAG

TGAGCTGGGTCCGCCAGGCTCCAGGGAAGGGGCTAGAATACATCGGATACATTTATAGTGATAGTGATAAGACATAC

TACGCGACCTGGGCGAAAGGCCGATTCACCATCTCCAAAACCTCGACCACGGTGGATTTGAAAATCACCAGTCCGAC

AATCGAGGACACGGCCACCTATTTCTGTGCCAGAGGTACTCCGCTTGCTAGTTATAGCATCTGGGGCCCAGGCACCC

TGGTCACCGTCTCCTTAGGGCAACCTAAGGCTCCATCAGTCTTCCCACTGGCCCCCTGCTGCGGGGACACACCCAGC

TCCACGGTGACCCTGGGCTGCCTGGTCAAAGGGTACCTCCCGGAGCCAGTGACCGTGACCTGGAACTCGGGCACCCT

CACCAATGGGGTACGCACCTTCCCGTCCGTCCGGCAGTCCTCAGGCCTCTACTCGCTGAGCAGCGTGGTGAGCGTGA

CCTCAAGCAGCCAGCCCGTCACCTGCAACGTGGCCCACCCAGCCACCAACACCAAAGTGGACAAGACCGTTGCGCCC

TCGACATGCAGCAAGCCCACGTGCCCACCCCCTGAACTCCTGGGGGGACCGTCTGTCTTCATCTTCCCCCCAAAACC

CAAGGACACCCTCATGATCTCACGCACCCCCGAGGTCACATGCGTGGTGGTGGACGTGAGCCAGGATGACCCCGAGG

TGCAGTTCACATGGTACATAAACAACGAGCAGGTGCGCACCGCCCGGCCGCCGCTACGGGAGCAGCAGTTCAACAGC

ACGATCCGCGTGGTCAGCACCCTCCCCATCGCGCACCAGGACTGGCTGAGGGGCAAGGAGTTCAAGTGCAAAGTCCA

CAACAAGGCACTCCCGGCCCCCATCGAGAAAACCATCTCCAAAGCCAGAGGGCAGCCCCTGGAGCCGAAGGTCTACA

CCATGGGCCCTCCCCGGGAGGAGCTGAGCAGCAGGTCGGTCAGCCTGACCTGCATGATCAACGGCTTCTACCCTTCC

GACATCTCGGTGGAGTGGGAGAAGAACGGGAAGGCAGAGGACAACTACAAGACCACGCCGGCCGTGCTGGACAGCGA
```

CGGCTCCTACTTCCTCTACAGCAAGCTCTCAGTGCCCACGAGTGAGTGGCAGCGGGGCGACGTCTTCACCTGCTCCG

TGATGCACGAGGCCTTGCACAACCACTACACGCAGAAGTCCATCTCCCGCTCTCCGGGTAAATGA

CGN-6-1-11-Heavy chain protein sequence (SEQ ID NO: 5):
METGLRWLLLVAVLKGVHCQSVEESGGRLVTPGTPLTLTCTVSGFSLSYYGVSWVRQAPG

KGLEYIGYIYSDSDKTYYATWAKGRFTISKTSTTVDLKITSPTIEDTATYFCARGTPLAS

YSIWGPGTLVTVSLGQPKAPSVFPLAPCCGDTPSSTVTLGCLVKGYLPEPVTVTWNSGTL

TNGVRTFPSVRQSSGLYSLSSVVSVTSSSQPVTCNVAHPATNTKVDKTVAPSTCSKPTCP

PPELLGGPSVFIFPPKPKDTLMISRTPEVTCVVVDVSQDDPEVQFTWYINNEQVRTARPP

LREQQFNSTIRVVSTLPIAHQDWLRGKEFKCKVHNKALPAPIEKTISKARGQPLEPKVYT

MGPPREELSSRSVSLTCMINGFYPSDISVEWEKNGKAEDNYKTTPAVLDSDGSYFLYSKL

SVPTSEWQRGDVFTCSVMHEALHNHYTQKSISRSPGK-

CGN-6-1-11-Light chain nucleotide sequence (SEQ ID NO: 6):
ATGGACACGAGGGCCCCCACTCAGCTGCTGGGGCTCCTGCTGCTCTGGCTCCCAGGTGCCACATTTGCCCAGGTGCT

GACCCAGACTCCAGCCTCGGTGTCTGCAGCTGTGGGAGGCACAGTCACCATCAATTGCCAGGCCAGTCAGAGTGTTT

ATAAGAATAACTATTTATCCTGGTTTCAGCAGAAACCAGGGCAGCCTCCCAAGCTCCTGATTTACGAAGCGTCCAAA

CTGGCATCTGGGGTCCCCCCGCGGTTCAAAGGCAGTGGATTTGGGACACAGTTCACTTTCACCATTAGCGACCTGGA

GTGTGACGATGCTGCCTTTTACTACTGTGCAGGCGGTTATTATGGTAATATTTTTTTTTTCGGCGGAGGGACCGAGG

TGGTGGTCAAAGGTGATCCAGTTGCACCTACTGTCCTCATCTTCCCACCAGCTGCTGATCAGGTGGCAACTGGAACA

GTCACCATCGTGTGTGTGGCGAATAAATACTTTCCCGATGTCACCGTCACCTGGGAGGTGGATGGCACCACCCAAAC

AACTGGCATCGAGAACAGTAAAACACCGCAGAATTCTGCAGATTGTACCTACAACCTCAGCAGCACTCTGACACTGA

CCAGCACACAGTACAACAGCCACAAAGAGTACACCTGCAAGGTGACCCAGGGCACGACCTCAGTCGTCCAGAGCTTC

AATAGGGGTGACTGTTAG

CGN-6-1-11-Light chain protein sequence (SEQ ID NO: 7):
MDTRAPTQLLGLLLLWLPGATFAQVLTQTPASVSAAVGGTVTINCQASQSVYKNNYLSWF

QQKPGQPPKLLIYEASKLASGVPPRFKGSGFGTQFTFTISDLECDDAAFYYCAGGYYGNI

FFFGGGTEVVVKGDPVAPTVLIFPPAADQVATGTVTIVCVANKYFPDVTVTWEVDGTTQT

TGIENSKTPQNSADCTYNLSSTLTLTSTQYNSHKEYTCKVTQGTTSVVQSFNRGDC-

CGN-6-4-5-Heavy chain nucleotide sequence (SEQ ID NO: 8):
ATGGAGACTGGGCTGCGCTGGCTTCTCCTGGTCGCTGTGCTCAAAGGTGTCCAGTGTCAGTCGGTGGAGGAGTCCGG

GGGTCGCCTGGTCACGCCTGGGACACCCCTGACACTCACCTGCACAGTCTCTGGATTCTCCCTCAGTAGGTATGGAG

TGAGCTGGGTCCGCCAGGCTCCAGGGAAGGGGCTGGAACACATCGGATACATTTATAGTGATCCTGGTATGACATTC

TACGCGACCTGGGCGAAAGGCCGATTCACCATCTCCAAAACCTCGTCGACCACGGTGGATTTGAAAATGACCAGTCC

GACAATCGAGGACACGGCCACCTATTTCTGTGCCAGAGGTACTCCGCTTGCTAGTTATAGCACCTGGGGCCCAGGCA

CCCTGGTCACCATCTCCTTAGGGCAACCTAAGGCTCCATCAGTCTTCCCACTGGCCCCCTGCTGCGGGGACACACCC

AGCTCCACGGTGACCCTGGGCTGCCTGGTCAAAGGGTACCTCCCGGAGCCAGTGACCGTGACCTGGAACTCGGGCAC

CCTCACCAATGGGGTACGCACCTTCCCGTCCGTCCGGCAGTCCTCAGGCCTCTACTCGCTGAGCAGCGTGGTGAGCG

TGACCTCAAGCAGCCAGCCCGTCACCTGCAACGTGGCCCACCCAGCCACCAACACCAAAGTGGACAAGACCGTTGCG

CCCTCGACATGCAGCAAGCCCACGTGCCCACCCCCTGAACTCCTGGGGGGACCGTCTGTCTTCATCTTCCCCCCAAA

ACCCAAGGACACCCTCATGATCTCACGCACCCCCGAGGTCACATGCGTGGTGGTGGACGTGAGCCAGGATGACCCCG

AGGTGCAGTTCACATGGTACATAAACAACGAGCAGGTGCGCACCGCCCGGCCGCCGCTACGGGAGCAGCAGTTCAAC

AGCACGATCCGCGTGGTCAGCACCCTCCCCATCGCGCACCAGGACTGGCTGAGGGGCAAGGAGTTCAAGTGCAAAGT

CCACAACAAGGCACTCCCGGCCCCCATCGAGAAAACCATCTCCAAAGCCAGAGGGCAGCCCCTGGAGCCGAAGGTCT

```
                              -continued
ACACCATGGGCCCTCCCCGGGAGGAGCTGAGCAGCAGGTCGGTCAGCCTGACCTGCATGATCAACGGCTTCTACCCT

TCCGACATCTCGGTGGAGTGGGAGAAGAACGGGAAGGCAGAGGACAACTACAAGACCACGCCGGCCGTGCTGGACAG

CGACGGCTCCTACTTCCTCTACAGCAAGCTCTCAGTGCCCACGAGTGAGTGGCAGCGGGGCGACGTCTTCACCTGCT

CCGTGATGCACGAGGCCTTGCACAACCACTACACGCAGAAGTCCATCTCCCGCTCTCCGGGTAAATGA

CGN-6-4-5-Heavy chain protein sequence (450 amino acids) (SEQ ID NO: 9):
METGLRWLLLVAVLKGVQCQSVEESGGRLVTPGTPLTLTCTVSGFSLSRYGVSWVRQAPG

KGLEHIGYIYSDPGMTFYATWAKGRFTISKTSSTTVDLKMTSPTIEDTATYFCARGTPLA

SYSTWGPGTLVTISLGQPKAPSVFPLAPCCGDTPSSTVTLGCLVKGYLPEPVTVTWNSGT

LTNGVRTFPSVRQSSGLYSLSSVVSVTSSSQPVTCNVAHPATNTKVDKTVAPSTCSKPTC

PPPPELLGGPSVFIFPPKPKDTLMISRTPEVTCVVVDVSQDDPEVQFTWYINNEQVRTARP

PLREQQFNSTIRVVSTLPIAHQDWLRGKEFKCKVHNKALPAPIEKTISKARGQPLEPKVY

TMGPPREELSSRSVSLTCMINGFYPSDISVEWEKNGKAEDNYKTTPAVLDSDGSYFLYSK

LSVPTSEWQRGDVFTCSVMHEALHNHYTQKSISRSPGK-

CGN-6-4-5-Light chain nucleotide sequence (SEQ ID NO: 10):
ATGGACACGAGGGCCCCCACTCAGCTGCTGGGGCTCCTGCTGCTCTGGCTCCCAGGTGCCACATTTGCTCAAGTGCT

GACCCAGACTCCAGCCTCCGTGTCTGCAGCTGTGGGAGGCACAGTCACCATCAATTGCCAGTCCAGTGAGAATATTT

ATAAGAACAACTACTTATCCTGGTTTCAGCAGAAACCAGGGCAGCCTCCCAAGCTCCTGATCTATCAGGCATCCACT

CTGGCATCTGGGGTCCCATCGCGGTTCAAAGGCAGTGGATCTGGGACACGATTCAGTCTCACCATCAGCGACCTGGA

GTGTGACGATGCTGCCACTTACTACTGTGCAGGCGGTTATAGTGGTAATATTTTTACTTTCGGCGGAGGGACCGAGG

TGGTGGTCAAAGGTGATCCAGTTGCACCTACTGTCCTCATCTTCCCACCAGCTGCTGATCAGGTGGCAACTGGAACA

GTCACCATCGTGTGTGTGGCGAATAAATACTTTCCCGATGTCACCGTCACCTGGGAGGTGGATGGCACCACCCAAAC

AACTGGCATCGAGAACAGTAAAACACCGCAGAATTCTGCAGATTGTACCTACAACCTCAGCAGCACTCTGACACTGA

CCAGCACACAGTACAACAGCCACAAAGAGTACACCTGCAAGGTGACCCAGGGCACGACCTCAGTCGTCCAGAGCTTC

AATAGGGGTGACTGTTAG

CGN-6-4-5-Light chain protein sequence (SEQ ID NO: 11):
MDTRAPTQLLGLLLLWLPGATFAQVLTQTPASVSAAVGGTVTINCQSSENIYKNNYLSWF

QQKPGQPPKLLIYQASTLASGVPSRFKGSGSGTRFSLTISDLECDDAATYYCAGGYSGNI

FTFGGGTEVVVKGDPVAPTVLIFPPAADQVATGTVTIVCVANKYFPDVTVTWEVDGTTQT

TGIENSKTPQNSADCTYNLSSTLTLTSTQYNSHKEYTCKVTQGTTSVVQSFNRGDC-
```

Amino acid sequence alignments of the heavy and light chains of the CGN6-1-11 and CGN 6-4-5 antibodies are provided in FIG. 35 (heavy chains) and 36 (light chains).

6.21 Immunoblot and Immunofluorescnce with Monoclonal Anti-CRBN Antibody, CGN-6-4-5

Rabbit monoclonal antibody CGN-6-4-5 specifically recognizes the full-length 51 kDa human CRBN protein on denaturing immunoblots.

Confocal Microscopic Immunofluorescence:

CGN-6-4-5 was diluted 1:1000. Exemplary sell staining of DF15 and DF15R cells is shown in FIG. 37. In particular, FIGS. 37A and 37B depict confocal immunofluorescent analysis of DF15 (left panel) and DF15R cells (right panel) using 1 μg/ml CGN-6-4-5 antibody (green) (A) or CGN-6-4-5 antibody/CRBN blocking peptide mix (1:5 excess ratio) (B). Nuclear staining was performed with Dapi (blue).

Immunoblot

CGN-6-4-5 was diluted 1:10,000 dilution in 0.1% Tween PBS buffer. An exemplary immunoblot with myeloma cells containing endogenous CRBN (DF15), DF15R with no CRBN and HEK293 cells expressing recombinant flag-tagged CRBN is shown in FIG. 38. Peptide neutralization was performed by combining antibody with a five-fold (by weight) excess of blocking peptide in 500 μl PBS and incubating with constant rotation at room temperature for 2 hours.

6.22 Thalidomide, Lenalidomide and Pomalidomide Bind to CRBN Via the Glutarimide Moiety The binding of pthalimide and glutarimide to CRBN was investigated in order to elucidate the mechanism of CRBN binding of thalidomide, lenalidomide, pomalidomide and structurally similar compounds. Glutarimide bound to CRBN while pthalimide did not. Thus, these results support the hypothesis that thalidomide, lenalidomide and pomalidomide bind to CRBN via the glutarimide moiety. See FIG. 39A.

6.23 CRBN Binding of Methyl-Pomalidomide is Enantioselective

The binding of S-methyl-pomalidomide and R-methyl-pomalidomide was investigated in order to determine whether CRBN binding is enantioselective. S-methyl-pomalidomide had greater affinity for CRBN than R-methyl-pomalidomide limide. See FIG. 39B.

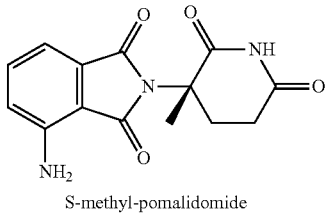

S-methyl-pomalidomide

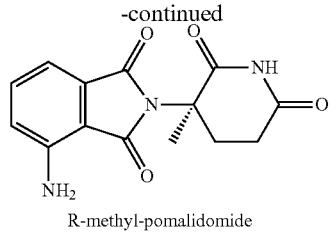

R-methyl-pomalidomide

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

---

What is claimed is:

1. A method of selecting the group of cancer patients based on the level of CRBN expression within the cancer, wherein said method comprises:
   obtaining a biological sample of the cancer from the patient;
   determining whether CRBN is present in the sample, wherein said determining is performed by contacting the cancer with an isolated antibody that immunospecifically binds to an epitope in CRBN, wherein the epitope has the amino acid sequence SEQ ID NO:1, and wherein the antibody comprises: (i) a heavy chain having the amino acid sequence depicted in SEQ ID NO:5 or 9, or (ii) a light chain having the amino acid sequence depicted in SEQ ID NO:7 or 11;
   diagnosing the patient as having a drug-sensitive cancer if a higher than baseline level of the CRBN is determined to be present in the sample; and
   administering a therapeutically effective amount of the drug to a patient diagnosed as having a drug-sensitive cancer;
   wherein the cancer patients are multiple myeloma, non-Hodgkin's lymphoma, diffuse large B-cell lymphoma, melanoma or solid tumor patients; and
   wherein the drug is thalidomide, lenalidomide, pomalidomide or 3-(5-amino-2-methyl-4-oxo-4H-quinazolin-3-yl)-piperidine-2,6-dione, a stereoisomer thereof, or a pharmaceutically acceptable salt, solvate, hydrate, co-crystal, clathrate, or polymorph thereof.

2. The method of claim 1, wherein the antibody is polyclonal.

3. The method of claim 1, wherein the antibody comprises: a heavy chain having the amino acid sequence depicted in SEQ ID NO:5 or 9.

4. The method of claim 1, wherein the antibody comprises a light chain having the amino acid sequence depicted in SEQ ID NO:7 or 11.

5. The method of claim 1, wherein the antibody comprises a heavy chain having the amino acid sequence depicted in SEQ ID NO:5 and a light chain having the amino acid sequence depicted in SEQ ID NO:7.

6. The method of claim 1, wherein the antibody comprises a heavy chain having the amino acid sequence depicted in SEQ ID NO:9 and a light chain having the amino acid sequence depicted in SEQ ID NO:11.

7. The method of claim 1, wherein the cancer patients are non-Hodgkin's lymphoma patients.

8. The method of claim 1, wherein the level of CRBN expression is within the patient's T cells, B cells, or plasma cells of the patient.

9. The method of claim 8, wherein the cancer patients are multiple myeloma patients.

10. The method of claim 8, wherein the cancer patients are diffuse large B-cell lymphoma patients.

11. The method of claim 10, wherein the diffuse large B-cell lymphoma is of the activated B-cell-like subtype.

12. The method of claim 1, wherein the drug is thalidomide.

13. The method of claim 1, wherein the drug is a stereoisomer of thalidomide, or a pharmaceutically acceptable salt, solvate, hydrate, co-crystal, clathrate, or polymorph of thalidomide.

14. The method of claim 1, wherein the drug is pomalidomide.

15. The method of claim 1, wherein is a stereoisomer of pomalidomide, or a pharmaceutically acceptable salt, solvate, hydrate, co-crystal, clathrate, or polymorph of pomalidomide.

16. The method of claim 1, wherein the drug is lenalidomide.

17. The method of claim 1, wherein is a stereoisomer of lenalidomide, or a pharmaceutically acceptable salt, solvate, hydrate, co-crystal, clathrate, or polymorph of lenalidomide.

18. The method of claim 1, wherein the drug is 3-(5-amino-2-methyl-4-oxo-4H-quinazolin-3-yl)-piperidine-2,6-dione.

19. The method of claim 1, wherein is a stereoisomer of 3-(5-amino-2-methyl-4-oxo-4H-quinazolin-3-yl)-piperidine-2,6-dione, or a pharmaceutically acceptable salt, solvate, hydrate, co-crystal, clathrate, or polymorph of 3-(5-amino-2-methyl-4-oxo-4H-quinazolin-3-yl)-piperidine-2,6-dione.

* * * * *